US012692223B2

(12) United States Patent
Quibell et al.

(10) Patent No.: US 12,692,223 B2
(45) Date of Patent: Jul. 28, 2026

(54) PHENYL-SULFAMOYL-BENZOIC ACID DERIVATIVES AS ERAP1-MODULATORS

(71) Applicant: GREY WOLF THERAPEUTICS LIMITED, Abingdon (GB)

(72) Inventors: Martin Quibell, Oxford (GB); Jason John Shiers, Oxford (GB); John Feutrill, Oxford (GB)

(73) Assignee: Grey Wolf Therapeutics Limited, Abingdon (GB)

( * ) Notice: Subject to any disclaimer, the term of this patent is extended or adjusted under 35 U.S.C. 154(b) by 308 days.

(21) Appl. No.: 18/291,714

(22) PCT Filed: Jul. 29, 2022

(86) PCT No.: PCT/GB2022/052013

§ 371 (c)(1),
(2) Date: Jan. 24, 2024

(87) PCT Pub. No.: WO2023/007188

PCT Pub. Date: Feb. 2, 2023

(65) Prior Publication Data

US 2024/0376046 A1 Nov. 14, 2024

(30) Foreign Application Priority Data

Jul. 30, 2021 (GB) .................................... 2111029
Feb. 15, 2022 (GB) .................................... 2201996

(51) Int. Cl.
*C07C 311/21* (2006.01)
*A61K 31/196* (2006.01)
(Continued)

(52) U.S. Cl.
CPC .......... *C07C 311/21* (2013.01); *A61K 31/196* (2013.01); *A61K 31/275* (2013.01); *A61K 31/337* (2013.01); *A61K 31/341* (2013.01); *A61K 31/397* (2013.01); *A61K 31/41* (2013.01); *A61K 31/42* (2013.01); *A61K 31/425* (2013.01); *A61K 45/06* (2013.01); *C07D 205/04* (2013.01); *C07D 257/04* (2013.01); *C07D 261/08* (2013.01); *C07D 275/02* (2013.01); *C07D 305/06* (2013.01); *C07D 305/14* (2013.01); *C07D 307/12* (2013.01); *C07D 309/12* (2013.01); *C07D 493/08* (2013.01); *C07C 2601/02* (2017.05); *C07C 2601/04* (2017.05); *C07C 2601/08* (2017.05); *C07C 2601/14* (2017.05); *C07C 2602/18* (2017.05); *C07C 2602/50* (2017.05)

(58) Field of Classification Search
CPC ............... C07C 311/21; C07C 2601/02; C07C 2601/04; C07C 2601/08; C07C 2601/14;
(Continued)

(56) References Cited

U.S. PATENT DOCUMENTS

2006/0025594 A1 2/2006 De Bethune et al.
2010/0105686 A1 4/2010 Beke et al.
2017/0183315 A1 6/2017 Tjulandin et al.

FOREIGN PATENT DOCUMENTS

CN 101817767 A 9/2010
WO WO 2008/008374 A2 1/2008
(Continued)

OTHER PUBLICATIONS

CAS Registry No. 1808453-32-8 (which entered the STN database on Sep. 29, 2015). (Year: 2015).*
(Continued)

*Primary Examiner* — Kamal A Saeed
*Assistant Examiner* — Meghan C Heasley
(74) *Attorney, Agent, or Firm* — Lathrop GPM LLP; Brian C. Trinque

(57) ABSTRACT

The present invention relates to a compound of formula (I), or a pharmaceutically acceptable salt or hydrate thereof, Formula (I), wherein, the group X—Y is —$NHSO_2$—; Z is a monocyclic or polycyclic cycloalkyl group or a monocyclic or polycyclic heterocycloalkyl group, each of which is optionally substituted by one or more groups selected from haloalkyl, alkyl, alkenyl, alkynyl and —$(CR_{16}R_{17})_mR_{18}$, where m is 0 to 6; L is a direct bond or a group $(CR_{14}R_{15})_n$, where n is 1 or 2; $R_1$ is H, CN, Cl or F or alkyl; $R_2$ is selected from COOH and a tetrazolyl group; $R_3$ is selected from H, halo, alkoxy and alkyl; $R_4$ is selected from H and halo; $R_5$ is selected from H, alkyl, haloalkyl, $SO_2$-alkyl, Cl, alkoxy, OH, CN, hydroxyalkyl, alkylthio, heteroaryl, cycloalkyl, heterocycloalkyl and haloalkoxy; $R_6$ is H; $R_7$ is selected from H, CN, haloalkyl, halo, $SO_2$-alkyl, $SO_2NR_{12}R_{13}$, heteroaryl, $CONR_{10}R_{11}$ and alkyl, wherein said heteroaryl group is optionally substituted by one or more substituents selected from alkyl, halo, alkoxy, CN, haloalkyl and OH; $R_9$ is selected from H, alkyl and halo; $R_{10}$, $R_{11}$, $R_{12}$ and $R_{13}$ are each independently H or alkyl; $R_{14}$ and $R_{15}$ are each independently H, halo or alkyl; $R_{16}$ and $R_{17}$ are each independently H, halo, haloalkyl or alkyl; and each $R_{18}$ is independently selected from OH, CN, alkoxy and halo. Further aspects of the invention relate to such compounds for use in the field of immune-oncology and related applications.

(I)

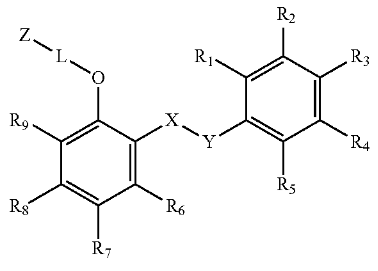

34 Claims, No Drawings

(51) Int. Cl.

| | |
|---|---|
| ***A61K 31/275*** | (2006.01) |
| ***A61K 31/337*** | (2006.01) |
| ***A61K 31/341*** | (2006.01) |
| ***A61K 31/397*** | (2006.01) |
| ***A61K 31/41*** | (2006.01) |
| ***A61K 31/42*** | (2006.01) |
| ***A61K 31/425*** | (2006.01) |
| ***A61K 45/06*** | (2006.01) |
| ***C07D 205/04*** | (2006.01) |
| ***C07D 257/04*** | (2006.01) |
| ***C07D 261/08*** | (2006.01) |
| ***C07D 275/02*** | (2006.01) |
| ***C07D 305/06*** | (2006.01) |
| ***C07D 305/14*** | (2006.01) |
| ***C07D 307/12*** | (2006.01) |
| ***C07D 309/12*** | (2006.01) |
| ***C07D 493/08*** | (2006.01) |

(58) Field of Classification Search

CPC ............ C07C 2602/18; C07C 2602/50; C07C 2603/62; C07C 2603/90; A61K 31/196; A61K 31/275; A61K 31/337; A61K 31/341; A61K 31/397; A61K 31/41; A61K 31/42; A61K 31/425; A61K 45/06; A61K 31/18; A61K 31/277; A61K 40/19; A61K 40/24; A61K 40/4201; A61K 2039/585; A61K 2239/46; C07D 205/04; C07D 257/04; C07D 261/08; C07D 275/02; C07D 305/06; C07D 305/14; C07D 307/12; C07D 309/12; C07D 493/08; C07D 307/20; C07D 257/06; A61P 29/00; A61P 31/12; A61P 31/18; A61P 35/00; A61P 37/00; A61P 35/02

See application file for complete search history.

(56) References Cited

FOREIGN PATENT DOCUMENTS

| | | | |
|---|---|---|---|
| WO | WO 2016/001452 | A1 | 1/2016 |
| WO | WO 2019/139869 | A1 | 7/2019 |
| WO | WO 2020/104822 | A1 | 5/2020 |
| WO | WO 2020/225569 | A1 | 11/2020 |
| WO | WO 2021/007474 | A1 | 1/2021 |
| WO | WO 2021/007478 | A1 | 1/2021 |
| WO | WO 2021/021951 | A1 | 2/2021 |
| WO | WO 2021/094763 | A1 | 5/2021 |
| WO | WO 2022/064187 | A1 | 3/2022 |

OTHER PUBLICATIONS

Aurora Building Blocks 7, Apr. 19, 2021, CAS Registry No. 1808835-54-2. See Chemcats Accession No. 0240181050.

Aurora Building Blocks 7, Apr. 19, 2021, CAS Registry No. 1808673-43-9. See Chemcats Accession No. 0291036135.

Aurora Building Blocks 7, Apr. 19, 2021, CAS Registry No. 1808453-32-8. See Chemcats Accession No. 1769003737.

Berge et al., "Pharmaceutical Salts", *Journal of Pharmaceutical Sciences*, 66(1):1-19 (1977).

Chen et al., "Silencing or inhibition of endoplasmic reticulum aminopeptidase 1 (ERAP1) suppresses free heavy chain expression and Th17 responses in ankylosing spondylitis", *Annals of the Rheumatic Diseases* 75:916 (2014).

Cifaldi et al., "ERAP1 Regulates Natural Killer Cell Function by Controlling the Engagement of Inhibitory Receptors", *Cancer Research* 75:824 (2015).

Conde-Jaldon et al., "Epistatic interaction of ERAP1 and HLA-B in Behçet disease: a replication study in the Spanish population", *PLoS One* 14;9(7) (2014).

Evans et al., "Interaction between ERAP1 and HLA-B27 in ankylosing spondylitis implicates peptide handling in the mechanism for HLA-B27 in disease susceptibility", *Nature Genetics* 10:43(8):761-767 (2011).

Fingl et al., "The Pharmacological Basis of Therapeutics", Chapter 1—General Principles, pp. 1-46 (1975).

Gennaro (editor), Remington's Pharmaceutical Sciences, Mack Publishing Co. (1985).

Greene, Protective Groups in Organic Synthesis, Chapter 1, J. Wiley & Sons, Inc. (1991), pp. 10-142.

James et al., "Induction of Protective Antitumor Immunity through Attenuation of ERAAP Function", *Journal of Immunology* 190:5839 (2013).

Karttunen et al., "Detection of rare antigen-presenting cells by the lacZ T-cell activation assay suggests an expression cloning strategy for T-cell antigens", *PNAS USA* 89:6020-6024 (1992).

Kim et al., "Human cytomegalovirus microRNA miR-US4-1 inhibits CD8+T cell responses by targeting the aminopeptidase ERAP1", *Nature Immunology* 12:984 (2011).

Kuiper et al., "Intraocular interleukin-17 and proinflammatory cytokines in HLA-A29-associated birdshot chorioretinopathy", *American Journal of Ophthalmology* 152(2):177-182 (2011).

Kuiper et al., "Interleukin-17 production and T helper 17 cells in peripheral blood mononuclear cells in response to ocular lysate in patients with birdshot chorioretinopathy", *Molecular Vision* 19:2606-2614 (2013).

Kuiper et al., "A genome-wide association study identifies a functional ERAP2 haplotype associated with birdshot chorioretinopathy", *Human Molecular Genetics* 23(22):6081-6087 (2014).

Kuiper et al., "Functionally distinct ERAP1 and ERAP2 are a hallmark of HLA-A29-(Birdshot) Uveitis", *Human Molecular Genetics* doi: 10.1093/hmg/ddy319 (2018).

Maben et al., "Discover of selective inhibitors of endoplasmic reticulum aminopeptidase 1", *J Med Chem* 63(1): 103-121 (2020).

March (editor), Advanced Organic Chemistry, 3rd Edition, John Wiley and Sons, New York (1985).

Nagarajan et al., "ERAAP Shapes the Peptidome Associated with Classical and Nonclassical MHC Class I Molecules"; *Journal of Immunology* 197(4)1035-1043 (2016).

Nicolaou et al., "Calicheamicin θ: A Rationally Designed Molecule with Extremely Potent and Selective DNA Cleaving Properties and Apoptosis Inducing Activity", Angewandte Chemie Intl. Ed. Engl., 33:183-186 (1994).

Pepelyayeva et al., "ERAP1 deficient mice have reduced Type 1 regulatory T cells and develop skeletal and intestinal features of Ankylosing Spondylitis", *Science Reports* 8:12464 (2018).

Purcell et al., "Mass spectrometry-based identification of MHC-bound peptides for immunopeptidomics", *Nature Protocols* 14:1687-1707 (2019).

Reeves et al., "Functionally distinct ERAP1 allotype combinations distinguish individuals with Ankylosing Spondylitis", *PNAS USA* 111:17594-17599 (2014).

Reeves et al., "The role of polymorphic ERAP1 in autoinflammatory disease", *Bioscience Reports* 29, p. 38 (2018).

Serwold et al., "ERAAP customizes peptides for MHC class I molecules in the endoplasmic reticulum" *Nature* 419:480 (2002).

Sheehan, "The ramifications of HLA-B27", *Journal of the Royal Society of Medicine* 97(1):10-14 (Jan. 2004).

Smith, "Update on ankylosing spondylitis: current concepts in pathogenesis", *Current Allergy and Asthma Reports* 15(1):489 (Jan. 2015).

Snyder et al., "Genetic Basis for Clinical Response to CTLA-4 Blockade in Melanoma", *The New England Journal of Medicine* 371:2189 (2014).

Steinbach et al., "ERAP1 overexpression in HPV-induced malignancies: A possible novel immune evasion mechanism", *Oncoimmunology* 6:e1336594 (2017).

Strange et al., "Genome-wide association study identifies new psoriasis susceptibility loci and an interaction between HLA-C and ERAP1", *Nature Genetics* 42(11):985-990 (2010).

Tenzer et al., "Antigen processing influences HIV-specific cytotoxic T lymphocyte immunodominance", *Nature Immunology* 10:636 (2009).

(56) References Cited

OTHER PUBLICATIONS

Uniprot ID Q9NZ08, Jun. 2, 2021.
Van Allen et al., "Genomic correlates of response to CTLA-4 blockade in metastatic melanoma", *Science* 348:124 (2015)—correction 350:6257:207-211.
Wade and Weller (editors), Handbook of Pharmaceutical Excipients, 2nd Edition, (1994).
Bastin et al., "Salt Selection and Optimisation Procedures for Pharmaceutical New Chemical Entities", *Organic Process Research & Development* 4(5):427-435 (2000).
Belikov, Pharmaceutical Chemistry textbook, Moscow, MEDpress-inform, pp. 27-29 (2007).
Kümmerer, "Pharmaceuticals in the Environment", *Annual Review of Environment and Resources* 35:57-75 (2010).
Mashkovsky, Medicines Manual for Physicians, pp. 10-11 (2005).
International Search Report and Written Opinion for International Application No. PCT/GB2022/052013 mailed Oct. 21, 2022, 9 pages.
Maben et al., "Discovery of Selective Inhibitors of Endoplasmic Reticulum Aminopeptidase 1", *Journal of Medicinal Chemistry* 63:103-121 (2020).
CAS Registry Database No. 1241218-16-5, retrieved Feb. 24, 2026.
CAS Registry Database No. 1316419-39-2, retrieved Feb. 24, 2026.

* cited by examiner

PHENYL-SULFAMOYL-BENZOIC ACID DERIVATIVES AS ERAP1-MODULATORS

The present invention relates to compounds that are capable of modulating ERAP1. The compounds have potential therapeutic applications in the treatment of a variety of disorders, including proliferative, viral, immune and inflammatory disorders.

BACKGROUND TO THE INVENTION

ERAP1 (Endoplasmic Reticulum Aminopeptidase 1; also referred to as APPILS or ARTS1) is an aminopeptidase important in the generation of a proportion of antigens and neoantigens as part of the antigen presentation pathway[1]. The antigen presentation pathway starts with the breakdown of proteins by the proteasome into peptides. These peptides are transported into the endoplasmic reticulum where a proportion are processed by ERAP1 before binding to the Major Histocompatibility Complex Class I (MHC Class 1)[1]. Antigens bound to MHC Class I are then transported to the surface of a cell and presented to $CD8^+$ T-cells and recognised as either self or non-self. Neoantigens are antigens that are specific to cancer and can be recognised as foreign by the immune system leading to destruction of cancer cells. Neoantigens are created either as a direct result of somatic mutations in the DNA of cancer cells, leading to the generation of mutated proteins, or through the indirect consequences of somatic mutations on protein processing and expression. Those cancers with higher rates of mutation and correspondingly higher levels of neoantigens have much greater response rates to the checkpoint inhibitor immunotherapies anti-PD-1 (e.g. pembrolizumab, nivolumab), anti-PD-L1 (e.g. atezolizumab, avelumab, durvalumab) and anti-CTLA4 antibodies (e.g. ipilimumab, tremelimuab) compared with cancers harbouring lower numbers of neoantigens[23].

The role of ERAP1 in the antigen presentation pathway is to trim a proportion of peptides, via its aminopeptidase activity, to create antigens and neoantigens of the optimal length for binding to MHC Class 1. ERAP1 also over-trims some neoantigens, preventing their binding to MHC Class I and presentation at the cell surface[4]. Ablation of ERAP1 activity has been shown to change the antigen and neoantigen repertoire, leading to an increase in presentation of certain antigens/neoantigens and the presentation of entirely novel antigens/neoantigens[5]. In addition, ERAP1 ablation causes $CD8^+$ T cell dependent tumour rejection in mouse cancer models[4].

Accordingly, modulators of ERAP1 activity may be useful for cancer treatment, either used alone or in combination with current cancer immunotherapy agents, including checkpoint inhibitors, because they change the antigens and neoantigens presented on the surface of cancer cells and make them more visible to the immune system, leading to tumour attack and destruction.

Knockdown of ERAP1 is also shown to reduce the levels of regulatory-like T cells and enhance the killing of cancer cells by natural killer cells[6, 7]. This suggests that modulators of ERAP1 activity might be effective cancer treatments by both modulating cancer cell visibility and creating a more anti-tumourogenic immune response. ERAP1's peptide processing role in antigen presentation is also applicable in infectious viral disease.

Maben et al (J. Med. Chem. 2020; 63, 103-121) disclose compounds that selectively inhibit ERAP1 over its paralogues ERAP2 and IRAP. WO 2020/104822, WO 2020/225569, WO 2021/094763 and WO2022/064187 (Grey Wolf Therapeutics Limited) disclose a series of aryl sulfonamide compounds that are capable of modulating ERAP1.

The present invention seeks to provide further compounds that are capable of modulating ERAP1. Such compounds have potential therapeutic applications in the treatment of a variety of disorders, including proliferative disorders, immune disorders and inflammatory disorders.

STATEMENT OF INVENTION

A first aspect of the invention relates to a compound of formula (I), or a pharmaceutically acceptable salt or hydrate thereof, (I)

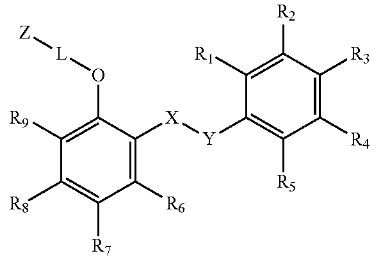

wherein:

the group X—Y is —$NHSO_2$—;

Z is a monocyclic or polycyclic cycloalkyl group or a monocyclic or polycyclic heterocycloalkyl group, each of which is optionally substituted by one or more groups selected from haloalkyl, alkyl, alkenyl, alkynyl and —$(CR_{16}R_{17})_mR_{18}$, where m is 0 to 6;

L is a direct bond or a group $(CR_{14}R_{15})_n$, where n is 1 or 2;

$R_1$ is selected from H, CN, Cl, F and alkyl;

$R_2$ is selected from COOH and a tetrazolyl group;

$R_3$ is selected from H, halo, alkoxy and alkyl;

$R_4$ is selected from H and halo;

$R_5$ is selected from H, alkyl, haloalkyl, $SO_2$-alkyl, Cl, alkoxy, OH, CN, hydroxyalkyl, alkylthio, heteroaryl, cycloalkyl, heterocycloalkyl and haloalkoxy;

$R_6$ is H;

$R_7$ is selected from H, CN, haloalkyl, halo, $SO_2$-alkyl, $SO_2NR_{12}R_{13}$, heteroaryl, $CONR_{10}R_{11}$ and alkyl, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is selected from H, alkyl and halo;

$R_{10}$, $R_{11}$, $R_{12}$ and $R_{13}$ are each independently selected from H and alkyl;

$R_{14}$ and $R_{15}$ are each independently selected from H, halo and alkyl;

$R_{16}$ and $R_{17}$ are each independently selected from H, halo, haloalkyl and alkyl; and each $R_{18}$ is independently selected from OH, CN, alkoxy and halo.

The invention also encompasses enantiomers of compounds of formula (I), and mixtures of enantiomers, including racemic mixtures.

Advantageously, the presently claimed compounds are capable of modulating ERAP 1, thereby rendering the compounds of therapeutic interest in the treatment of various disorders, for example, in the field of oncology and immunooncology. In particular, compounds according to the present invention exhibit excellent potency against ERAP1.

A second aspect of the invention relates to a pharmaceutical composition comprising at least one compound as described above and a pharmaceutically acceptable carrier, diluent or excipient.

A third aspect of the invention relates to a compound as described above for use in medicine.

A fourth aspect of the invention relates to a compound as described above for use in treating or preventing a disorder selected from a proliferative disorder, an immune disorder, a viral disorder and an inflammatory disorder.

A fifth aspect of the invention relates to the use of a compound as described above in the preparation of a medicament for treating or preventing a disorder selected from a proliferative disorder, an immune disorder, a viral disorder and an inflammatory disorder.

A sixth aspect of the invention relates to a compound as described above for use in the prevention or treatment of a disorder caused by, associated with or accompanied by any abnormal ERAP1 activity.

A seventh aspect of the invention relates to the use of a compound as described above in the preparation of a medicament for the prevention or treatment of a disorder caused by, associated with or accompanied by abnormal ERAP1 activity.

An eighth aspect of the invention relates to a method of treating a mammal having a disease state alleviated by modulation of ERAP1, wherein the method comprises administering to a mammal a therapeutically effective amount of a compound as described above.

A ninth aspect of the invention relates to a compound as described above for use in treating or preventing a disease state alleviated by modulation of ERAP1.

A tenth aspect of the invention relates to the use of a compound as described above in the preparation of a medicament for treating or preventing a disease state alleviated by modulation of ERAP1.

An eleventh aspect of the invention relates to a method of treating or preventing a disorder selected from a proliferative disorder, an immune disorder, a viral disorder and an inflammatory disorder in a subject, wherein the method comprises administering to the subject a therapeutically effective amount of a compound as described above.

DETAILED DESCRIPTION

The present invention relates to bis-aryl sulfonamide compounds that are capable of modulating ERAP1.

"Alkyl" is defined herein as a straight-chain or branched alkyl radical, preferably $C_{1-20}$ alkyl, more preferably $C_{1-12}$ alkyl, even more preferably $C_{1-10}$ alkyl or $C_{1-6}$ alkyl, for example, methyl, ethyl, propyl, isopropyl, butyl, isobutyl, tert-butyl, pentyl, hexyl. Preferably, the alkyl group is a $C_{1-4}$-alkyl group.

"Cycloalkyl" is defined herein as a cyclic alkyl ring, preferably, $C_{3-7}$cycloalkyl, more preferably $C_{3-6}$-cycloalkyl. Preferred examples include cyclopropyl, cyclobutyl, cyclopentyl, cyclohexyl or cycloheptyl, or a fused bicyclic ring system such as norbornane.

"Halogen" is defined herein as chloro, fluoro, bromo or iodo.

Haloalkyl" is defined herein as a straight-chain or branched alkyl radical as defined above, for example, methyl, ethyl, propyl, isopropyl, butyl, isobutyl, tert-butyl, pentyl, hexyl, that is substituted with one or more halogen atoms (that may be the same or different), such as fluorine, chlorine, bromine, and iodine. Preferably, the haloalkyl is a $C_{1-20}$ haloalkyl, more preferably a $C_{1-12}$ haloalkyl, even more preferably a $C_{1-10}$ haloalkyl or a $C_{1-6}$ haloalkyl, or a $C_{1-3}$ haloalkyl. Preferred examples are $CF_3$ and $CHF_2$, with $CF_3$ being particularly preferred.

"Alkoxy" is defined herein as an oxygen atom bonded to an alkyl group as defined above, for example methoxy, ethoxy, propoxy, isopropoxy, butoxy, isobutoxy, tert-butoxy, pentoxy and hexoxy. Preferably, the alkoxy is a $C_{1-20}$ alkoxy, more preferably a $C_{1-12}$ alkoxy, even more preferably $C_{1-10}$ alkoxy or a $C_{1-6}$ alkoxy, or a $C_{1-3}$ alkoxy. A particularly preferred example is methoxy ($-OCH_3$).

As used herein, the term "alkenyl" refers to both straight and branched carbon chains which have at least one carbon-carbon double bond. In some embodiments, alkenyl groups may include $C_2$-$C_{12}$ alkenyl groups. In other embodiments, alkenyl includes $C_2$-$C_1$, $C_2$-$C_8$, $C_2$-$C_6$ or $C_2$-$C_4$ alkenyl groups. In one embodiment of alkenyl, the number of double bonds is 1-3; in another embodiment of alkenyl, the number of double bonds is one. Other ranges of carbon-carbon double bonds and carbon numbers are also contemplated depending on the location of the alkenyl moiety on the molecule. "$C_2$-$C_{10}$-alkenyl" groups may include more than one double bond in the chain.

As used herein, the term "alkynyl" refers to both straight and branched carbon chains which have at least one carbon-carbon triple bond. In some embodiments, alkynyl groups may include $C_2$-$C_{12}$ alkynyl groups. In other embodiments, alkynyl includes $C_2$-$C_{10}$, $C_2$-$C_8$, $C_2$-$C_6$ or $C_2$-$C_4$ alkynyl groups. In one embodiment of alkynyl, the number of triple bonds is 1-3; in another embodiment of alkenyl, the number of triple bonds is one. A particularly preferred alkynyl group is $-C{\equiv}CH$.

As used herein, the term "polycyclic group" means a group comprising two or more cyclic groups which may be fused, unfused, bridged or spirocyclic.

As used herein, the term "aryl" refers to a $C_{6-12}$ aromatic group, which may be benzocondensed, for example, phenyl or naphthyl.

"Heteroaryl" is defined herein as a monocyclic or bicyclic $C_{2-12}$ aromatic ring comprising one or more heteroatoms (that may be the same or different), such as oxygen, nitrogen or sulphur. Examples of suitable heteroaryl groups include thienyl, furanyl, pyrrolyl, pyridinyl, oxazolyl, thiazolyl, imidazolyl, pyrazolyl, isoxazolyl, isothiazolyl, oxadiazolyl, triazolyl, thiadiazolyl etc and benzo derivatives thereof, such as benzofuranyl, benzothienyl, benzimidazolyl, indolyl, isoindolyl, indazolyl etc.; or pyridyl, pyrazinyl, pyrimidinyl, pyridazinyl, triazinyl, tetrazolyl, etc. and benzo derivatives thereof, such as quinolinyl, isoquinolinyl, cinnolinyl, phthalazinyl, quinazolinyl, quinoxalinyl, naphthyridinyl etc. Particularly preferred heteroaryl groups include 1H-imidazol-5-yl, 1H-imidazol-4-yl, 1H-imidazol-2-yl, 1H-pyrrol-1-yl, 1H-pyrrol-2-yl, 1H-pyrrol-3-yl, 1H-pyrrol-4-yl, 1H-pyrrol-5-yl, 1H-pyrazol-1-yl, 1H-pyrazol-5-yl, 1H-pyrazol-3-yl, 1H-pyrazol-4-yl, oxazol-2-yl, oxazol-4-yl, oxazol-5-yl, 1H-1,2,4-triazol-3-yl, 1H-1,2,4-triazol-5-yl, 1H-1,2,4-triazol-1-yl, 1H-1,2,3-triazol-4-yl, 1H-1,2,3-triazol-5-yl, 1H-1,2,3-triazol-1-yl, thiazol-5-yl, thiazol-4-yl, 1H-1,2,3,4-tetrazol-4-yl, 2H-1,2,3,4-tetrazol-5-yl, oxazol-5-yl, oxazol-4-yl, oxazol-2-yl, isoxazol-3-yl, isoxazol-4-yl, isoxazol-5-yl, isothiazol-3-yl, isothiazol-4-yl, isothiazol-5-yl, pyradizin-3-yl, pyradizin-4-yl, pyrazinyl, 1,3,4-oxadizol-2-yl, 1,3,4-oxadizol-5-yl, 1,2,5-oxadiazol-3-yl, 1,2,5-oxadiazol-4-yl, 1,2,3-oxadiazol-4-yl, 1,2,3-oxadiazol-5-yl, 1,2,4-oxadiazol-3-yl, 1,2,4-oxadiazol-5-yl, isoxazol-5-yl, isoxazol-4-yl and isoxazol-3-yl.

"Heterocycloalkyl" refers to a cyclic aliphatic group containing one or more heteroatoms selected from nitrogen, oxygen and sulphur, which is optionally interrupted by one or more —(CO)— groups in the ring and/or which optionally contains one or more double bonds in the ring. Preferably, the heterocycloalkyl group is monocyclic or bicyclic. Preferably, the heterocycloalkyl group is a $C_{3-7}$-heterocycloalkyl, more preferably a $C_{3-6}$-heterocycloalkyl. Alternatively, the heterocycloalkyl group is a $C_{4-7}$-heterocycloalkyl, more preferably a $C_{4-6}$-heterocycloalkyl. Preferred heterocycloalkyl groups include, but are not limited to, piperazinyl, piperidinyl, morpholinyl, thiomorpholinyl, pyrrolidinyl, tetrahydrofuranyl and tetrahydropyranyl.

Where the compound of the invention contains one or more chiral centres, the invention encompasses all enantiomers and diastereomers thereof, as well as mixtures thereof.

By way of example, the point of attachment to the Z group (here shown for illustrative purposes as a simple 5-membered monocycloalkyl group, but equally applicable to Z groups in general) can exist in one of the following configurations:

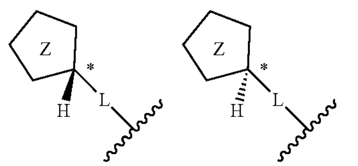

The invention encompasses the compounds in either of the above configurations, as well as mixtures thereof, including racemic mixtures. The skilled person will understand that the absolute stereochemistry (R- and S-) at the chiral centre denoted * will depend on the nature of group Z, and the nature and position of any substituent(s) on the Z group.

In one preferred embodiment, the compound is in the form of a mixture of the R- and S-enantiomers. In one preferred embodiment, the mixture is a racemic mixture, i.e. a 50:50 mixture of a compound of the R- and S-enantiomers.

Racemic mixtures can be used to prepare enantiomerically pure R- and S-forms by separating the enantiomers using standard methods, for example by chemical resolution using optically active acid or by the use of column chromatography or reverse-phase column chromatography using a substantially optically active (or "chiral") stationary phase as known to those skilled in the art. Racemic mixtures can also be used to prepare enantiomerically enriched mixtures of the S- and R-forms. Mixtures enriched with either the R- or S-enantiomer can also be obtained from the appropriate enantiomerically enriched precursors.

In one preferred embodiment of the invention, the compound is in the form of a mixture comprising enantiomers wherein the weight:weight ratio is at least approximately 2:1 or greater, preferably at least approximately 5:1 or greater, most preferably at least approximately 10:1 or greater in favour of the enantiomer that displays significant in vitro and/or in vivo activity (the eutomer).

In one embodiment, the compound is in the form of a mixture comprising the S-enantiomer and the R-enantiomer, wherein the weight:weight ratio of R-enantiomer to S-enantiomer is greater than 1.05:1, more preferably, greater than 2:1, even more preferably greater than 5:1, even more preferably greater than 10:1.

In one embodiment, the compound is in the form of a mixture comprising the S-enantiomer and the R-enantiomer, which is substantially enriched with the R-enantiomer.

In one embodiment, the compound is in the form of a mixture comprising the S-enantiomer and the R-enantiomer, wherein the weight:weight ratio of S-enantiomer to R-enantiomer is greater than 1.05:1, more preferably, greater than 2:1, even more preferably greater than 5:1, even more preferably greater than 10:1.

In one embodiment, the compound is in the form of a mixture comprising the S-enantiomer and the R-enantiomer, which is substantially enriched with the S-enantiomer.

Compounds of Formula (I)

One aspect of the invention relates to compounds of formula (I), and pharmaceutically acceptable salts and hydrates thereof:

(I)

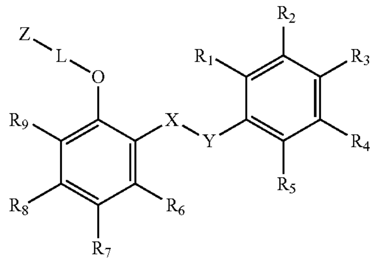

wherein:

the group X—Y is $—NHSO_2—$ or $—SO_2NH—$;

Z is a monocyclic or polycyclic cycloalkyl group or a monocyclic or polycyclic heterocycloalkyl group, each of which is optionally substituted by one or more groups selected from haloalkyl, alkyl, alkenyl, alkynyl and $—(CR_{16}R_{17})_mR_{18}$, where m is 0 to 6;

L is a direct bond or a group $(CR_{14}R_{15})_n$, where n is 1 or 2;

$R_1$ is selected from H, CN, Cl, F and alkyl;

$R_2$ is selected from COOH and a tetrazolyl group;

$R_3$ is selected from H, halo, alkoxy and alkyl;

$R_4$ is selected from H and halo;

$R_5$ is selected from H, alkyl, haloalkyl, $SO_2$-alkyl, Cl, alkoxy, OH, CN, hydroxyalkyl, alkylthio, heteroaryl, cycloalkyl, heterocycloalkyl and haloalkoxy;

$R_6$ is H;

$R_7$ is selected from H, CN, haloalkyl, halo, $SO_2$-alkyl, $SO_2NR_{12}R_{13}$, heteroaryl, $CONR_{10}R_{11}$ and alkyl, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is selected from H, alkyl and halo;

$R_{10}$, $R_{11}$, $R_{12}$ and $R_{13}$ are each independently selected from H and alkyl;

$R_{14}$ and $R_{15}$ are each independently selected from H, halo and alkyl;

$R_{16}$ and $R_{17}$ are each independently selected from H, halo, haloalkyl and alkyl; and each $R_{18}$ is independently selected from OH, CN, alkoxy and halo.

In one preferred embodiment, X—Y is —$NHSO_2$—, i.e. the compound is of the formula:

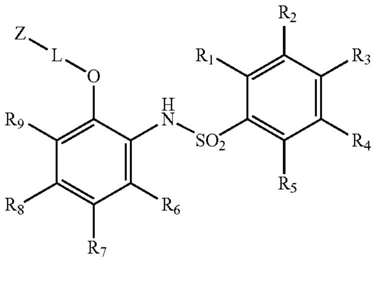

In one preferred embodiment, L is a direct bond.

In another preferred embodiment, L is $(CR_{14}R_{15})_n$ and n is 1 or 2. More preferably, n is 1.

In one preferred embodiment, $R_{14}$ and $R_{15}$ are each independently selected from H, Cl and Me. More preferably, $R_{14}$ and $R_{15}$ are both H.

In another preferred embodiment, L is $(CH_2)_n$ and n is 1 or 2, more preferably n is 1.

In one highly preferred embodiment, L is $CH_2$ or CH(Me), even more preferably $CH_2$.

In the following embodiments, where Z is a heterocycloalkyl group, the heterocycloalkyl group contains one or more heteroatoms selected from O, S and N, more preferably one or more heteroatoms selected from O and N. More preferably still, the heterocycloalkyl group contains one or more O atoms. Even more preferably, the heterocycloalkyl group contains one O atom.

In one preferred embodiment, Z is a monocyclic cycloalkyl or monocyclic heterocycloalkyl group, each of which is optionally substituted. Preferably, Z is a 3-, 4-, 5-, 6- or 7-membered monocyclic cycloalkyl or monocyclic heterocycloalkyl group, each of which is optionally substituted. More preferably, Z is a 4-, 5- or 6-membered monocyclic cycloalkyl or monocyclic heterocycloalkyl group, even more preferably, a 4- or 5-membered monocyclic cycloalkyl or monocyclic heterocycloalkyl group, each of which is optionally substituted. More preferably, Z is a monocyclic cycloalkyl or monocyclic heterocycloalkyl group selected from cyclobutyl, cyclopentyl, cyclohexyl, oxetanyl, tetrahydro-2H-pyranyl, azetidinyl and tetrahydrofuranyl. More preferably still, Z is a monocyclic cycloalkyl or monocyclic heterocycloalkyl group selected from cyclobutyl, cyclopentyl, oxetanyl, azetidinyl and tetrahydrofuranyl.

In one preferred embodiment, Z is a 4-membered monocyclic cycloalkyl or a 4-membered monocyclic heterocycloalkyl group, each of which is optionally substituted. In one preferred embodiment, Z is a 4-membered monocyclic cycloalkyl group which is optionally substituted. In one preferred embodiment, Z is a cyclobutyl group optionally substituted by one or more substituents selected from CN, halo, alkyl, haloalkyl, OH and alkoxy. More preferably, Z is a cyclobutyl group optionally substituted by one or more substituents selected from CN, F, Me, OH, OMe and $CF_3$. In one highly preferred embodiment, Z is an unsubstituted cyclobutyl group.

In one preferred embodiment, Z is a 4-membered monocyclic heterocycloalkyl group which is optionally substituted. In one preferred embodiment, Z is an oxetanyl or azetidinyl group, each of which is optionally substituted by one or more substituents selected from alkyl and halo. More preferably, Z is an oxetanyl or azetidinyl group, each of which is optionally substituted by one or more substituents selected from Me and F.

In one preferred embodiment, Z is a 5-membered monocyclic cycloalkyl or a 5-membered monocyclic heterocycloalkyl group, each of which is optionally substituted.

In one preferred embodiment, Z is a 5-membered monocyclic cycloalkyl group which is optionally substituted. In one preferred embodiment, Z is a cyclopentyl group optionally substituted by one or more substituents selected from CN, alkynyl, halo, alkyl, OH and alkoxy. More preferably, Z is a cyclopentyl group optionally substituted by one or more substituents selected from CN, F, —C≡CH, Me, OH, OMe.

In one preferred embodiment, Z is a 5-membered monocyclic heterocycloalkyl group which is optionally substituted.

In one preferred embodiment, Z is an optionally substituted polycyclic cycloalkyl group or an optionally substituted polycyclic heterocycloalkyl group, wherein said polycyclic group is fused, unfused, bridged or spirocyclic.

In one preferred embodiment, Z is an optionally substituted spirocyclic group. As used herein, a spirocyclic group refers to a polycyclic group in which two rings are connected through a common atom. The spirocyclic group may be fully carbocyclic (all carbon) or heterocyclic (having one or more non-carbon atoms). Preferably, each ring is independently a 3-, 4-, 5-, 6- or 7-membered ring, optionally containing one or more heteroatoms selected from O, N and S. More preferably, each ring is independently a 3-, 4-, 5- or 6-membered ring, optionally containing one or more heteroatoms selected from O and N. Even more preferably, each ring is independently a 3-, 4- or 5-membered ring, optionally containing one or more heteroatoms selected from O and N.

In one preferred embodiment, Z is an optionally substituted bicyclic spirocyclic group, for example, an an optionally substituted carbocyclic bicyclic spirocyclic group or an optionally substituted heterocyclic bicyclic spirocyclic group. More preferably, the bicyclic spirocyclic group is selected from the following: spiro[3,3]heptane, spiro[2,4]heptane, spiro[2,3]hexane, 1-oxaspiro[2,3]hexane, 4-oxaspiro[2,3]hexane, 2-oxaspiro[3,3]heptane, 1-oxaspiro[3,3]heptane, 4-oxaspiro[2,4]heptane, 5-oxaspiro[2,4]heptane and 1-oxaspiro[2,4]heptane. Even more preferably, the bicyclic spirocyclic group is selected from spiro[3,3]heptane, spiro[2,4]heptane, spiro[2,3]hexane and 2-oxaspiro[3,3]heptane.

In another preferred embodiment, Z is a polycyclic group which is a fused cycloalkyl or fused heterocycloalkyl group, each of which is optionally substituted. As used herein, a fused cycloalkyl or fused heterocycloalkyl group refers to a polycyclic group in which two or more rings are linked by two adjacent atoms. Preferably, each ring is independently a 3-, 4-, 5-, 6- or 7-membered ring optionally containing one or more heteroatoms selected from O, N and S. More preferably, each ring is independently a 3-, 4- or 5-membered ring optionally containing one or more heteroatoms selected from O and N.

In another preferred embodiment, Z is polycyclic group which is an unfused polycyclic cycloalkyl or an unfused polycyclic heterocycloalkyl group, each of which is optionally substituted. As used herein, an unfused cycloalkyl or unfused heterocycloalkyl group refers to a polycyclic group in which two or more rings are linked by a direct bond. Preferably, each ring is independently a 3-, 4-, 5-, 6- or 7-membered ring optionally containing one or more heteroatoms selected from O, N and S. More preferably, each ring is independently a 3-, 4- or 5-membered ring optionally containing one or more heteroatoms selected from O and N. Preferably, for this embodiment Z is an unfused bicyclic cycloalkyl or unfused bicyclic heterocycloalkyl group, or an unfused cycloalkyl-heterocycloalkyl group, each of which is optionally substituted. In one particularly preferred embodiment, Z is selected from cyclopropyl-cyclobutyl, cyclopentyl-cyclobutyl, cyclopentyl-cyclopropyl, cyclobutyl-cyclobutyl, cyclopropyl-cyclopropyl and cyclopentyl-cyclopentyl. More preferably, Z is 2-cyclopropyl-cyclobutyl or 3-cyclopropyl-cyclobutyl, even more preferably, 2-cyclopropyl-cyclobutyl.

In one preferred embodiment, Z is a fused cycloalkyl or fused heterocycloalkyl group selected from bicyclo[3.1.0]hexane, bicyclo[4.2.0]octane, decahydronaphthalene, bicyclo[4.1.0]heptane, bicyclo[3.2.0]heptane, octahydropentalene, octahydro-1H-indene and (1s,2s,3s,4s,6s,7s)-cubane, each of which is optionally substituted.

In another preferred embodiment, Z is a polycyclic group which is a bridged cycloalkyl or bridged heterocycloalkyl group, each of which is optionally substituted. As used herein, a bridged cycloalkyl or bridged heterocycloalkyl group refers to a polycyclic group in which two (or more) rings are linked by two non-adjacent atoms. Preferably, each ring is independently a 3-, 4-, 5-, 6- or 7-membered ring optionally containing one or more heteroatoms selected from O, N and S. More preferably, each ring is independently a 4-, 5- or 6-membered ring optionally containing one or more heteroatoms selected from O and N.

In one preferred embodiment, Z is a bridged cycloalkyl or bridged heterocycloalkyl group selected from bicyclo[1.1.1]pentane, bicyclo[2.1.1]hexane, 2-oxabicyclo[2.1.1]hexane, 5-oxabicyclo[2.1.1]hexane, bicyclo[2.2.1]heptane, bicyclo[3.2.1]octane, bicyclo[2.2.2]octane, 2-oxabicyclo[2.2.2]octane, 7-oxabicyclo[2.2.1]heptane, 2-oxabicyclo[2.2.1]heptane, each of which is optionally substituted. More preferably, Z is a bridged cycloalkyl group selected from bicyclo[1.1.1]pentane and 2-oxabicyclo[2.1.1]hexane, each of which is optionally substituted.

In one preferred embodiment, Z is a bicyclic cycloalkyl or bicyclic heterocycloalkyl group, each of which is fused, bridged or spirocyclic, and each of which is optionally substituted.

Throughout this disclosure, the Z group is optionally substituted by one or more substituents selected from halogen, haloalkyl, alkyl, alkenyl, alkynyl and $-(CR_{16}R_{17})_m R_{18}$, where m is 0 to 6. Preferably m is 0, 1, 2 or 3, more preferably 0 or 1, even more preferably, 0.

In one preferred embodiment, $R_{16}$ and $R_{17}$ are each independently selected from H, Cl, F, $C_1$-$C_4$-alkyl and $C_1$-$C_1$-haloalkyl. More preferably, $R_{16}$ and $R_{17}$ are each independently selected from H, Cl, F, $CF_3$ and Me. Even more preferably, $R_{16}$ and $R_{17}$ are both H.

In one preferred embodiment, the Z group is substituted by one or more groups selected from halogen, $C_{1-4}$-haloalkyl, $C_{1-4}$-alkyl, $C_{1-4}$-alkenyl, $C_{1-4}$-alkynyl and $-(CR_{16}R_{17})_m R_{18}$, where m is 0, 1, 2 or 3. More preferably, m is 0.

In one preferred embodiment, $R_{18}$ is selected from OH, CN, OMe, Cl, Br and F.

In one preferred embodiment, the Z group is substituted by one or more groups selected from Me, $CF_3$, OH, CN, F, OMe, $-C{\equiv}CH$, $-CH_2-C{\equiv}CH$ and $-CH_2CN$.

In one preferred embodiment, Z is selected from:

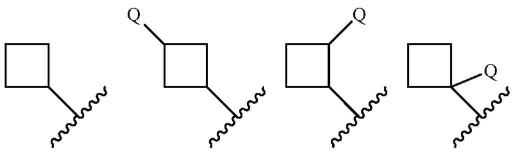

-continued

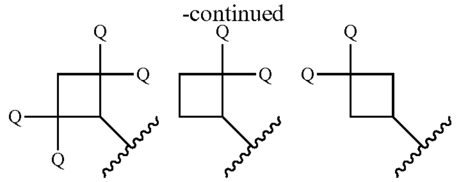

wherein each Q is independently selected from alkyl, alkoxy, haloalkyl, alkynyl, halo, OH and CN. More preferably, each Q is independently selected from Me, OMe, $CF_3$, F, OH, $C{\equiv}CH$ and CN.

In one preferred embodiment, Z is selected from:

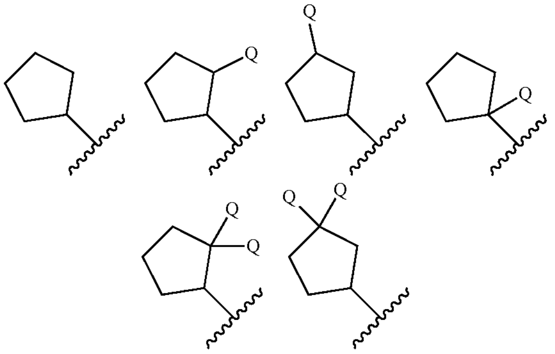

wherein each Q is independently selected from alkyl, alkoxy, haloalkyl, alkynyl, halo, OH and CN. More preferably, each Q is independently selected from Me, OMe, $CF_3$, F, OH, $C{\equiv}CH$ and CN.

In one preferred embodiment, L-Z is selected from:

Z-4

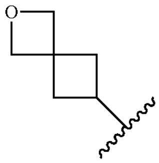

Z-5

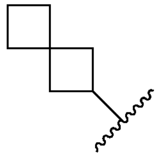

Z-11

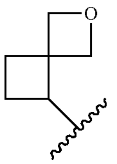

Z-18

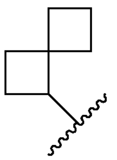

-continued
Z-20
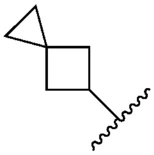
Z-21
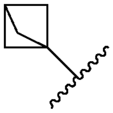
Z-22
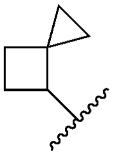
Z-36
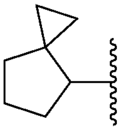
Z-37
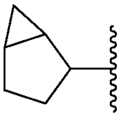
Z-40
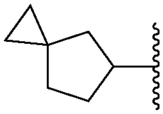
Z-41
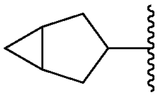
Z-124
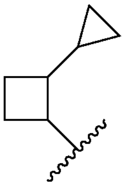
Z-125
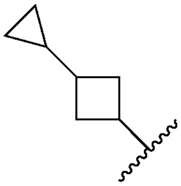
In one preferred embodiment, Z is selected from:
Z-1
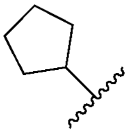
-continued
Z-2
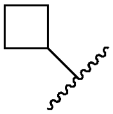
Z-3
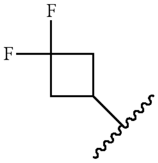
Z-4
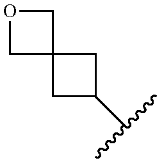
Z-5
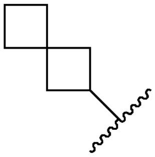
Z-6
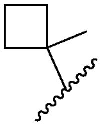
Z-7
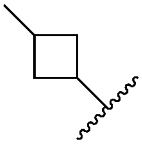
Z-8
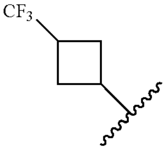
Z-9
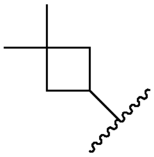
Z-10
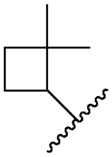
Z-11
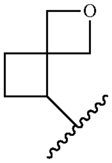

-continued
Z-12
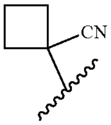
Z-13
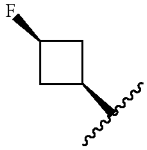
Z-14
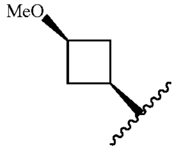
Z-15
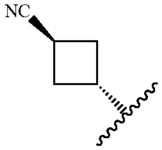
Z-16
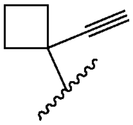
Z-17
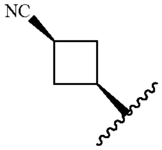
Z-18
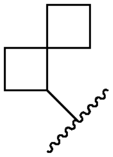
Z-19
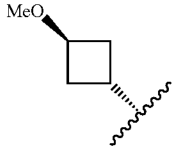
Z-20
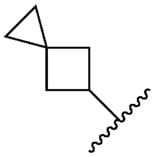
Z-21
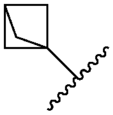
-continued
Z-22
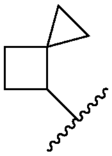
Z-23
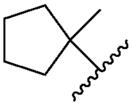
Z-24
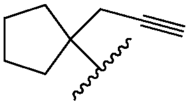
Z-25
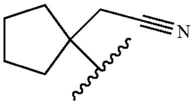
Z-26
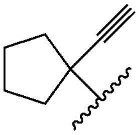
Z-27
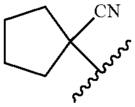
Z-28
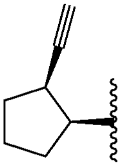
Z-29
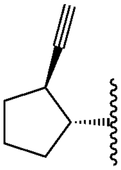
Z-30
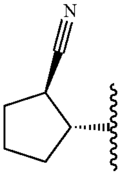
Z-31
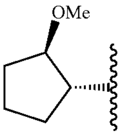

-continued
Z-32
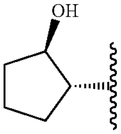
Z-33
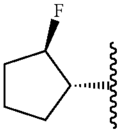
Z-34
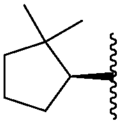
Z-35
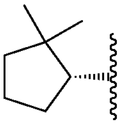
Z-36
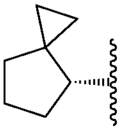
Z-37
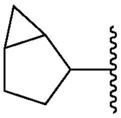
Z-38
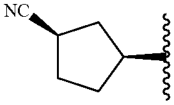
Z-39
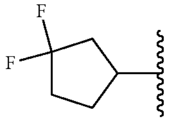
Z-40
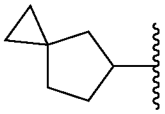
Z-41
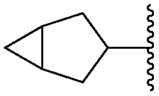
Z-42
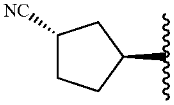
Z-63
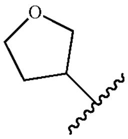
-continued
Z-64
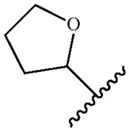
Z-65
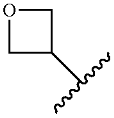
Z-66
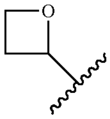
Z-67
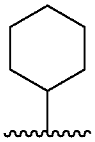
Z-72
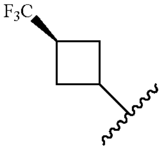
Z-75
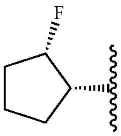
Z-76
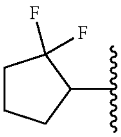
Z-77
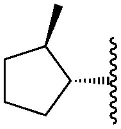
Z-78
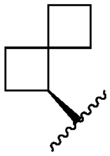
Z-79
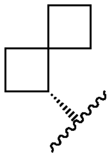

-continued
Z-80
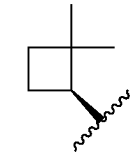
Z-81
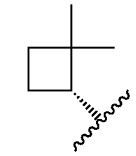
Z-82
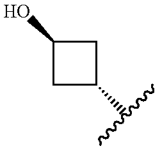
Z-83
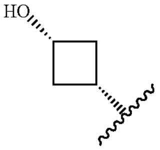
Z-84
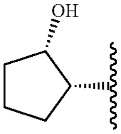
Z-85
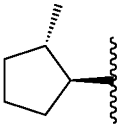
Z-86
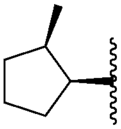
Z-87
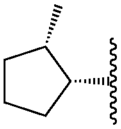
Z-88
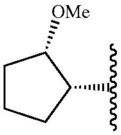
Z-89
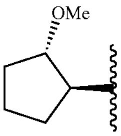
-continued
Z-90
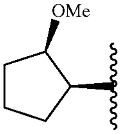
Z-91
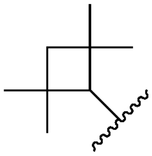
Z-92
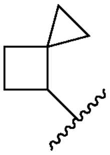
Z-93
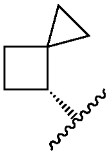
Z-94
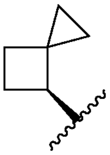
Z-95
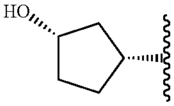
Z-96
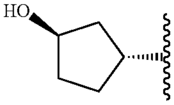
Z-97
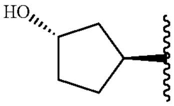
Z-98
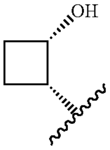
Z-99
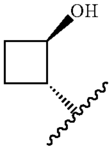

-continued
Z-100
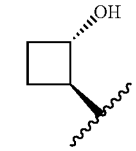
Z-101
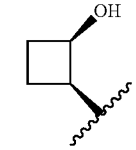
Z-102
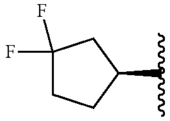
Z-103
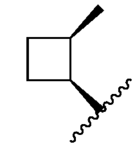
Z-104
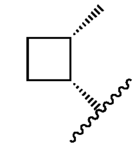
Z-105
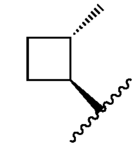
Z-106
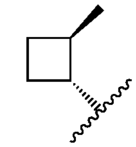
Z-107
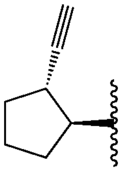
Z-108
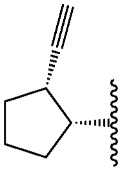
Z-109
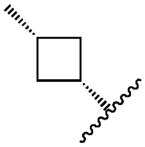
-continued
Z-110
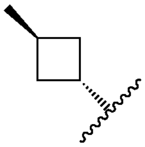
Z-111
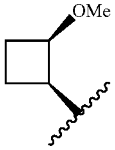
Z-112
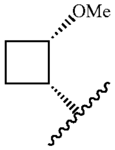
Z-113
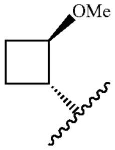
Z-114
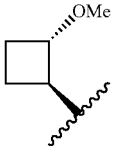
Z-115
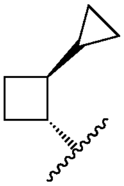
Z-116
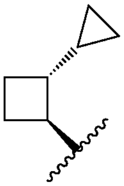
Z-117
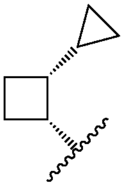
Z-118
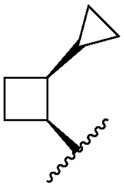

-continued
Z-119
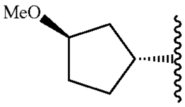
Z-120
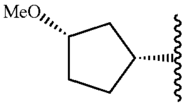
Z-121
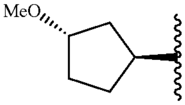
Z-122
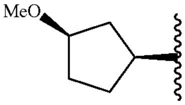
Z-123
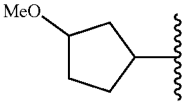
Z-124
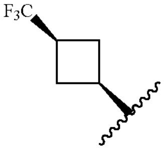
Z-125
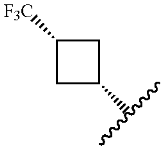
Z-126
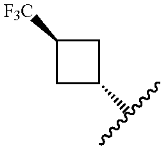
Z-127
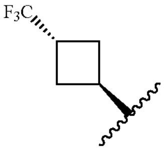
Z-128
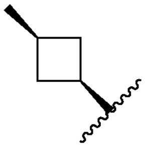
Z-129
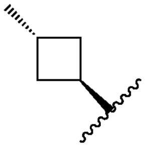
-continued
Z-130
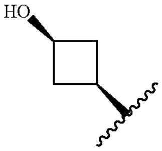
Z-131
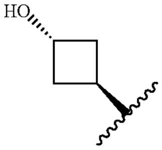
Z-132
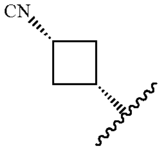
Z-133
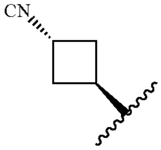
Z-134
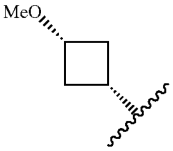
Z-135
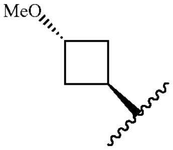
Z-136
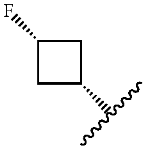
Z-137
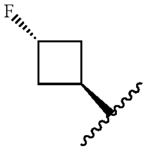
Z-138
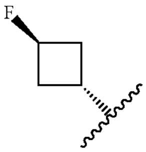
Z-139
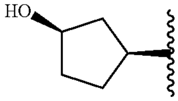

-continued
Z-140
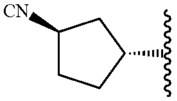
Z-141
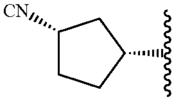
Z-142
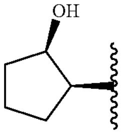
Z-143
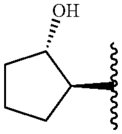
Z-144
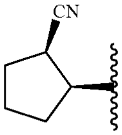
Z-145
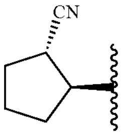
Z-146
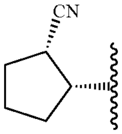
Z-147
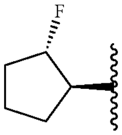
Z-148
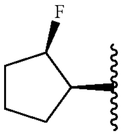
Z-149
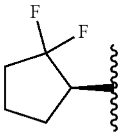
Z-150
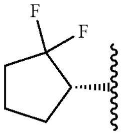
-continued
Z-151
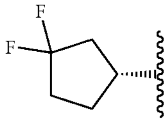
Z-152
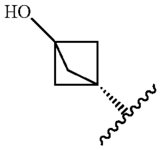
Z-153
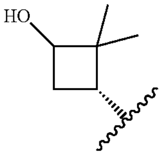
Preferably for the above embodiment, L is a direct bond. In one preferred embodiment, L is a direct bond, and Z is a group selected from Z1-Z-72 above.
In another preferred embodiment, L is a group $(CR_{14}R_{15})_n$, and L-Z is selected from the following:
Z-43
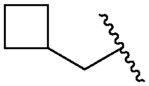
Z-44
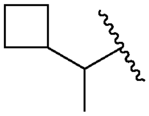
Z-45
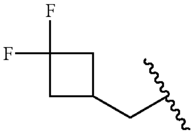
Z-46
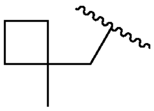
Z-47
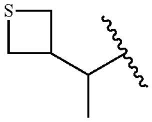
Z-48
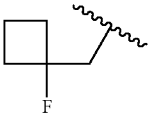
Z-49
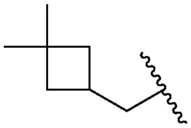

-continued
Z-50
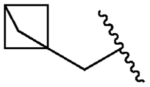
Z-51
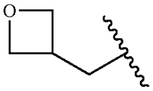
Z-52
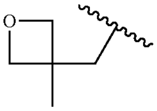
Z-53
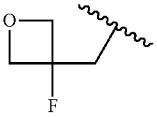
Z-54
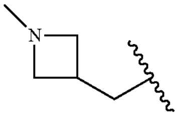
Z-55
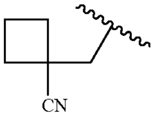
Z-56
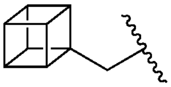
Z-57
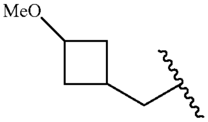
Z-58
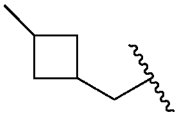
Z-59
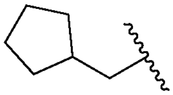
Z-60
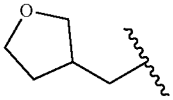
Z-61
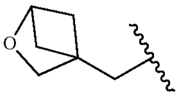
Z-62
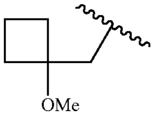
-continued
Z-68
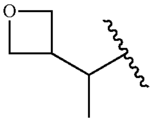
Z-69
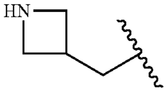
Z-70
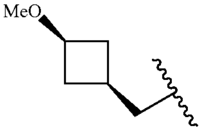
Z-71
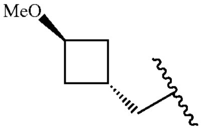
Z-73
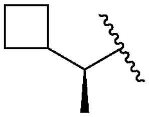
Z-74
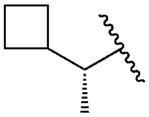
In one highly preferred embodiment, Z is selected from:
Z-1
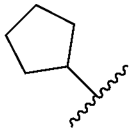
Z-2
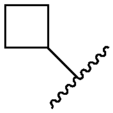
Z-3
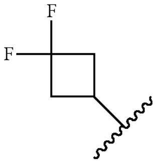
Z-67
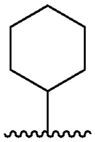
In one preferred embodiment, $R_1$ is selected from H, CN, F and alkyl
In one preferred embodiment, $R_1$ is selected from H, CN and alkyl.
In one preferred embodiment, $R_1$ is H.

In one preferred embodiment, $R_2$ is COOH.

In one particularly preferred embodiment, X is NH and Y is $SO_2$. In another preferred embodiment, X is $SO_2$ and Y is NH. Preferably, X is NH and Y is $SO_2$.

In one preferred embodiment, $R_3$ is selected from H, Cl, F, OMe and Me. More preferably, $R_3$ is selected from H and F. Even more preferably, $R_3$ is H.

In one preferred embodiment, $R_4$ is selected from H, Cl and F. More preferably, $R_4$ is selected from H and F.

In one preferred embodiment, $R_5$ is selected from alkyl, haloalkyl, $SO_2$-alkyl, Cl, alkoxy, OH, CN, hydroxyalkyl, alkylthio, heteroaryl, cycloalkyl, heterocycloalkyl and haloalkoxy.

In one preferred embodiment, $R_5$ is selected from alkyl, alkoxy and cycloalkyl. More preferably, $R_5$ is cycloalkyl, more preferably, cyclopropyl, cyclobutyl or cyclopentyl.

In one particularly preferred embodiment, $R_5$ is selected from OMe, OEt, Me, Et, and cyclopropyl.

In another preferred embodiment, $R_5$ is selected from H, Me, $CF_3$, $CHF_2$, $SO_2$-Me, Cl, MeO, OH, $CH_2OH$, SMe, cyclopropyl, triazolyl, oxetanyl and CN. More preferably, $R_5$ is selected from H, CN, Me, $SO_2$-Me, $CF_3$ and $CHF_2$, $CH_2OH$, SMe, cyclopropyl, 3,4-triazol-1-yl, oxetan-3-yl. More preferably, $R_5$ is selected from H, CN, Me, $SO_2$-Me, $CF_3$ and $CHF_2$.

In another preferred embodiment, $R_5$ is selected from OMe, Me, Et, Pr and Cl, and is more preferably OMe or Et.

In one particularly preferred embodiment, $R_5$ is selected from OMe, Et, and cyclopropyl.

In one especially preferred embodiment, $R_5$ is cyclopropyl.

In another preferred embodiment, $R_5$ is OMe.

In another preferred embodiment, $R_5$ is Et.

In one preferred embodiment, $R_7$ is selected from H, CN, haloalkyl, Cl, F, $SO_2$-alkyl, $CONR_{10}R_{11}$, $SO_2NR_{16}R_{17}$, heteroaryl and alkyl, wherein said heteroaryl group is optionally substituted by one or more substituents selected from alkyl, halo, alkoxy, CN, haloalkyl and OH.

In one preferred embodiment, $R_7$ is selected from H, CN, haloalkyl, Cl, F, $SO_2$-alkyl, $CONR_{10}R_{11}$, $SO_2NR_{12}R_{13}$, heteroaryl and alkyl, wherein said heteroaryl group is optionally substituted by one or more substituents selected from alkyl, halo, alkoxy, CN, haloalkyl and OH.

In one preferred embodiment, $R_7$ is a heteroaryl group optionally substituted by one or more substituents selected from alkyl, halo, alkoxy, CN, haloalkyl and OH.

In one preferred embodiment, $R^7$ is a heteroaryl group selected from pyridinyl, thienyl, imidazolyl, pyrimidinyl, pyrazolyl, pyrazinyl, pyradizinyl, thiazolyl, isothiazolyl, triazinyl, pyrrolyl, furanyl, oxazolyl, isoxazolyl, oxadiazolyl, tetrazolyl and triazolyl, each of which is optionally substituted by one or more substituents selected from alkyl, halo, alkoxy, CN, haloalkyl and OH.

In one preferred embodiment, $R^7$ is a heteroaryl group selected from imidazolyl, pyrazolyl, pyrazinyl, pyradizinyl, thiazolyl, isothiazolyl, oxazolyl, isoxazolyl, oxadiazolyl, tetrazolyl and triazolyl, each of which is optionally substituted by one or more substituents selected from alkyl, halo, alkoxy, CN, haloalkyl and OH.

In one preferred embodiment, $R^7$ is a heteroaryl group selected from 1H-imidazol-5-yl, 1H-imidazol-4-yl, 1H-imidazol-2-yl, 1H-pyrrol-1-yl, 1H-pyrrol-2-yl, 1H-pyrrol-3-yl, 1H-pyrrol-4-yl, 1H-pyrrol-5-yl, 1H-pyrazol-1-yl, 1H-pyrazol-5-yl, 1H-pyrazol-3-yl, 1H-pyrazol-4-yl, oxazol-2-yl, oxazol-4-yl, oxazol-5-yl, 1H-1,2,4-triazol-3-yl, 1H-1,2,4-triazol-5-yl, 1H-1,2,4-triazol-1-yl, 1H-1,2,3-triazol-4-yl, 1H-1,2,3-triazol-5-yl, 1H-1,2,3-triazol-1-yl, thiazol-5-yl, thiazol-4-yl, 1H-1,2,3,4-tetrazol-4-yl, 2H-1,2,3,4-tetrazol-5-yl, tetrazol-1-yl, oxazol-5-yl, oxazol-4-yl, oxazol-2-yl, isoxazol-3-yl, isoxazol-4-yl, isoxazol-5-yl, isothiazol-3-yl, isothiazol-4-yl, isothiazol-5-yl, pyradizin-3-yl, pyradizin-4-yl, pyrazinyl, 1,3,4-oxadizol-2-yl, 1,3,4-oxadizol-5-yl, 1,2,5-oxadiazol-3-yl, 1,2,5-oxadiazol-4-yl, 1,2,3-oxadiazol-4-yl, 1,2,3-oxadiazol-5-yl, 1,2,4-oxadiazol-3-yl, 1,2,4-oxadiazol-5-yl, isoxazol-5-yl, isoxazol-4-yl and isoxazol-3-yl, each of which is optionally substituted by one or more substituents selected from alkyl, halo, CN, alkoxy, haloalkyl and OH.

In one highly preferred embodiment, $R^7$ is a heteroaryl group selected from 1H-pyrazol-5-yl, 1H-pyrazol-3-yl, 1H-pyrazol-4-yl, oxazol-2-yl, 1H-1,2,3-triazol-4-yl, 1H-1,2,3-triazol-5-yl, thiazol-5-yl, 1H-1,2,3,4-tetrazol-4-yl, 2H-1,2,3,4-tetrazol-5-yl, tetrazol-1-yl, isoxazol-4-yl, isoxazol-5-yl, isothiazol-5-yl, pyradizin-3-yl, pyradizin-4-yl, pyrazinyl and 1,3,4-oxadizol-2-yl, each of which is optionally substituted by one or more substituents selected from Me, F, Cl, CN and MeO.

In one highly preferred embodiment, $R^7$ is a heteroaryl group selected from 1H-1,2,3,4-tetrazol-4-yl, tetrazol-1-yl and 2H-1,2,3,4-tetrazol-5-yl, each of which is optionally substituted by one or more substituents selected from Me, F, Cl, CN and MeO.

In one preferred embodiment, $R_7$ is selected from H, CN, haloalkyl, Cl, F, $SO_2$-alkyl, $CONR_{10}R_{11}$, heteroaryl and alkyl, wherein the heteroaryl group is selected from pyrazol-3-yl, pyrazol-4-yl, pyrazol-5-yl, isothiazol-3-yl, isothiazol-4-yl, isothiazol-5-yl, 1,2,4-triazol-5-yl, tetrazol-1-yl, tetrazol-5-yl, isoxazol-3-yl, isoxazol-4-yl and isoxazol-5-yl, each of which is optionally substituted by one or more substituents selected from alkyl, halo, alkoxy, CN, haloalkyl and OH.

In one preferred embodiment, $R_7$ is selected from CN, haloalkyl, $SO_2$-alkyl, $SO_2NR_{16}R_{17}$, $CONR_{10}R_{11}$ and tetrazolyl.

In one preferred embodiment, $R_7$ is selected from CN, haloalkyl, $SO_2$-alkyl, $SO_2NR_{12}R_{13}$, $CONR_{10}R_{11}$ and tetrazolyl.

In one preferred embodiment, $R_7$ is selected from $CF_3$, CN, $CONH_2$, 1H-1,2,3,4-tetrazol-1-yl, $SO_2NH_2$ and $SO_2Me$.

In one preferred embodiment, $R_7$ is selected from H, CN, $CF_3$, $CHF_2$, Cl, F, $SO_2$-Me, $CONH_2$, $SO_2NH_2$, heteroaryl and Me. More preferably, $R_7$ is selected from H, CN, Me, $SO_2$-Me, $CONH_2$, $SO_2NH_2$, tetrazolyl, $CF_3$ and $CHF_2$.

In another preferred embodiment, $R_7$ is selected from CN, haloalkyl, $SO_2$-alkyl, $SO_2NH_2$, $CONR_{10}R_{11}$ and tetrazolyl. More preferably for this embodiment, $R_7$ is selected from $CF_3$, CN, $SO_2NH_2$, 1H-1,2,3,4-tetrazol-1-yl, $CONH_2$ and $SO_2Me$, more preferably from $CF_3$, CN, 1H-1,2,3,4-tetrazol-1-yl and $SO_2Me$.

In one preferred embodiment, $R_7$ is haloalkyl or heteroaryl, more preferably tetrazolyl, isothiazolyl or isoxazolyl, each of which is optionally substituted.

In one preferred embodiment, $R_7$ is selected from tetrazol-1-yl, isothiazol-5-yl and isoxazol-4-yl, each of which is optionally substituted by one or more substituents selected from alkyl, halo, alkoxy, CN, haloalkyl and OH.

In one preferred embodiment, $R_7$ is selected from CN, $CF_3$, tetrazol-1-yl, isothiazol-5-yl and 5-methyl-isoxazol-4-yl.

In another preferred embodiment, $R_7$ is haloalkyl, more preferably, $CF_3$.

In one particularly preferred embodiment, $R_7$ is CN.

In another preferred embodiment, $R_7$ is $SO_2$-alkyl, more preferably $SO_2Me$.

In another preferred embodiment, $R_7$ is $SO_2NR_{16}R_{17}$, more preferably $SO_2NH_2$.

In another preferred embodiment, $R_7$ is $SO_2NR_{12}R_{13}$, more preferably $SO_2NH_2$.

In one preferred embodiment, $R_8$ is selected from H, alkyl, haloalkyl and Cl.

In another preferred embodiment, $R_8$ is selected from H, alkyl and halo.

In one preferred embodiment, $R_8$ is selected from H, Cl, F and Me. More preferably, Ra is selected from H, Cl and F.

In another preferred embodiment, $R_8$ is selected from alkyl and halo. More preferably, $R_8$ is selected from Me, Cl and F.

In one preferred embodiment, $R_8$ is H or haloalkyl, more preferably H or $CF_3$, even more preferably H.

In one particularly preferred embodiment, $R_8$ is Cl.

In one preferred embodiment, $R_9$ is selected from H, F, Cl and Me, more preferably, H and F. Even more preferably, $R_9$ is H.

In one preferred embodiment, $R_1$, $R_3$, $R_4$, $R_6$, $R_3$ and $R_9$ are all H.

In one preferred embodiment, $R_{10}$ and $R_{11}$ are each independently H or Me. More preferably, $R_{10}$ and $R_{11}$ are both H.

In one preferred embodiment, $R_{12}$ and $R_{13}$ are each independently H or Me. More preferably, $R_{12}$ and $R_{13}$ are both H.

In one particularly preferred embodiment:

X—Y is NH—$SO_2$;

$R_1$ is H;

$R_2$ is COOH;

$R_3$ is H or F;

$R_4$ is H or F;

$R_5$ is selected from OMe, OEt, Me, Et, and cyclopropyl, and is more preferably selected from OMe, cyclopropyl and Et;

$R_6$ is H;

$R_7$ is selected from CN, tetrazol-1-yl, isothiazol-5-yl and 5-methyl-isoxazol-4-yl;

$R_8$ is selected from H, Cl and F;

$R_9$ is selected from H, Me, Cl and F; and

L and Z are as defined above.

In one particularly preferred embodiment:

X—Y is NH—$SO_2$;

L is selected from a direct bond, $CH_2$ and CHMe;

$R_1$ is H;

$R_2$ is COOH;

$R_3$ is H or F;

$R_4$ is H or F;

$R_5$ is selected from OMe, OEt, Me, Et, and cyclopropyl, and is more preferably selected from OMe, cyclopropyl and Et;

$R_6$ is H;

$R_7$ is selected from CN, tetrazol-1-yl, isothiazol-5-yl and 5-methyl-isoxazol-4-yl;

$R_8$ is selected from H, C and F;

$R_9$ is selected from H, Me, C and F; and

Z is as defined above, and is more preferably selected from Z-1, Z-2 and Z-3.

In one preferred embodiment, the compound of the invention is of formula (Ia):

(Ia)

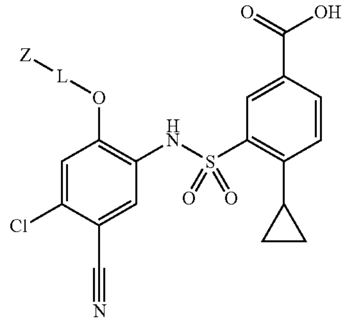

wherein L and Z are as defined according to any one of the embodiments described above.

In one preferred embodiment, the compound of formula (I) is selected from the following. In the structures depicted herein, where the absolute stereochemistry of a bond is known (for example, derived from a bona fide chiral starting material), then the assignment is denoted by (R) or (S) in the conventional manner. Where the absolute configuration is unknown, the bonds are drawn in the plane (flat), and the descriptor adds what is known, for example, "trans racemate", "trans relative", "trans diastereomer D1" and the like:

(1)

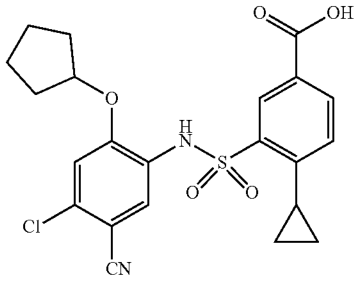

(2)

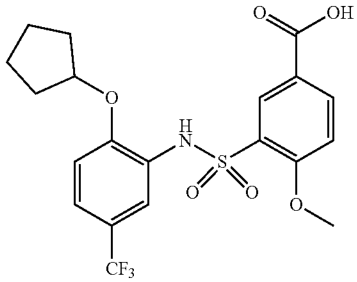 [SMILES: COc1ccc(C(=O)O)cc1S(=O)(=O)Nc1cc(C(F)(F)F)ccc1OC1CCCC1]

(3)

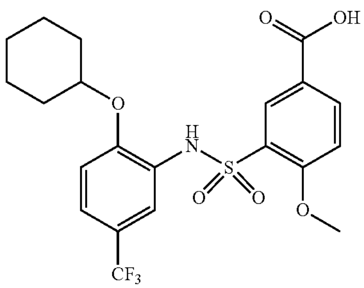 [SMILES: COc1ccc(C(=O)O)cc1S(=O)(=O)Nc1cc(C(F)(F)F)ccc1OC1CCCCC1]

-continued
(4)
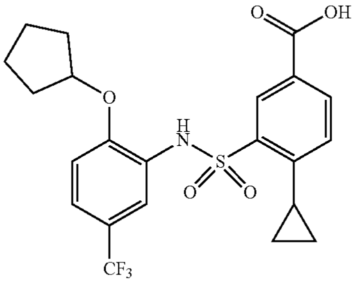 [SMILES: O=C(O)c1ccc(C2CC2)c(S(=O)(=O)Nc2cc(C(F)(F)F)ccc2OC2CCCC2)c1]
(5)
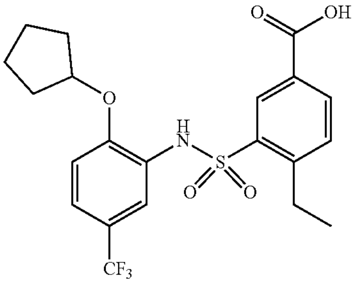
(6)
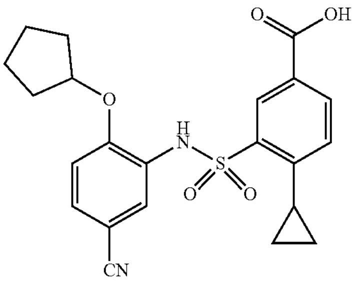 [SMILES: N#Cc1ccc(OC2CCCC2)c(NS(=O)(=O)c2cc(C(=O)O)ccc2C2CC2)c1]
(7)
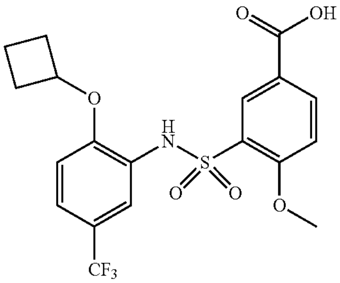 [SMILES: CCc1ccc(C(=O)O)cc1S(=O)(=O)Nc1cc(C(F)(F)F)ccc1OC1CCC1]
(8)
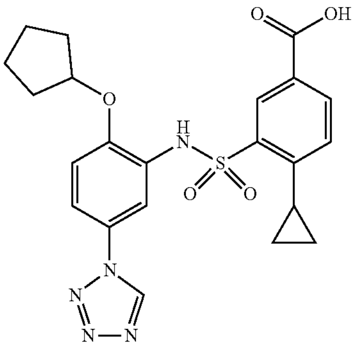
-continued
(9)
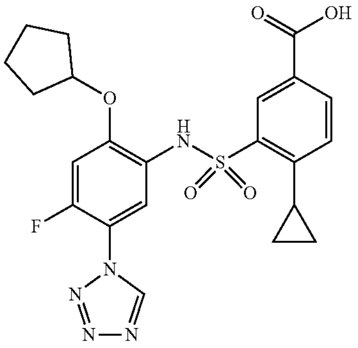
(10)
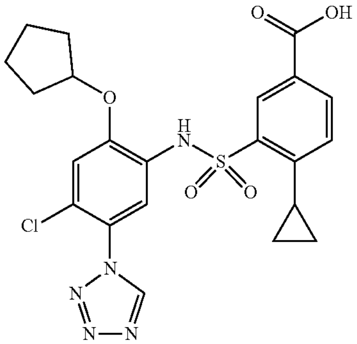
(11)
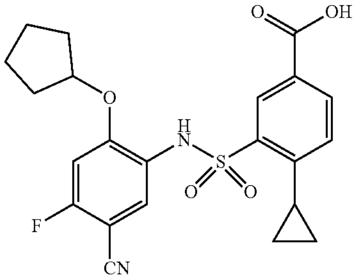 [SMILES: N#Cc1cc(NS(=O)(=O)c2cc(C(=O)O)ccc2C2CC2)c(OC2CCCC2)cc1F]
(12)
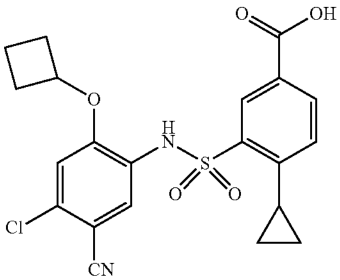 [SMILES: N#Cc1cc(NS(=O)(=O)c2cc(C(=O)O)ccc2C2CC2)c(OC2CCC2)cc1Cl]
(13)
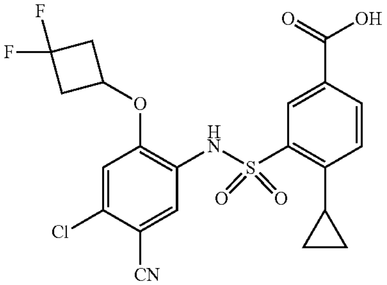

-continued
(14)
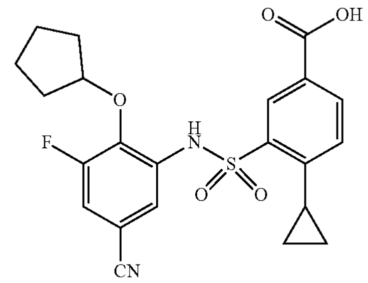
(15)
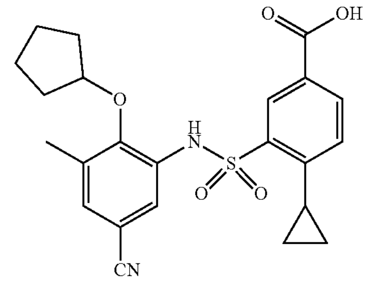
(16)
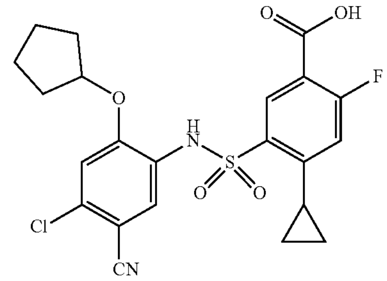
(17)
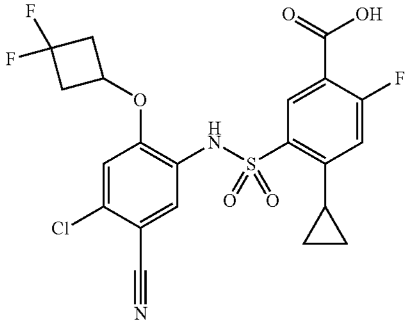
(18)
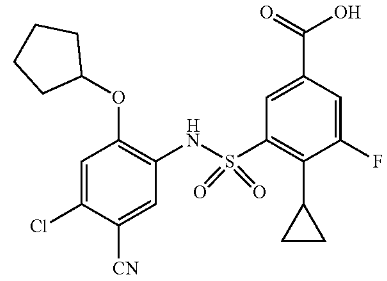
-continued
(19)
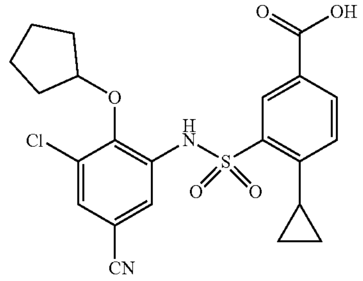
(20)
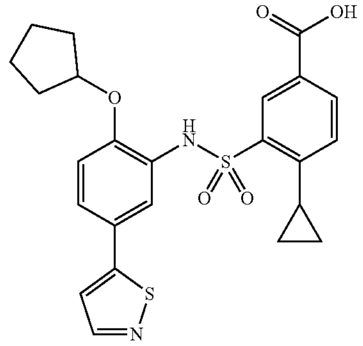
(21)
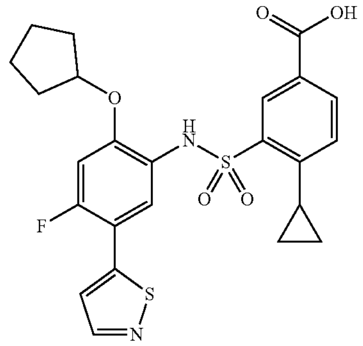
(22)
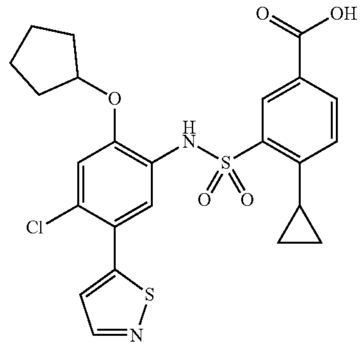

-continued
(23)
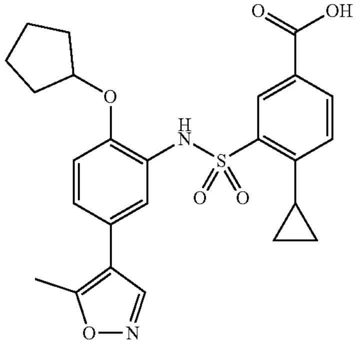
(24)
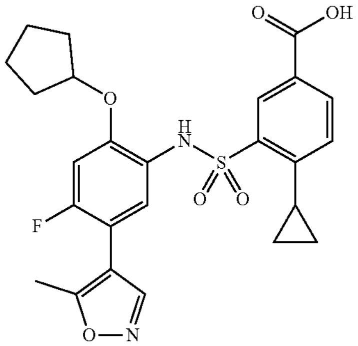
(25)
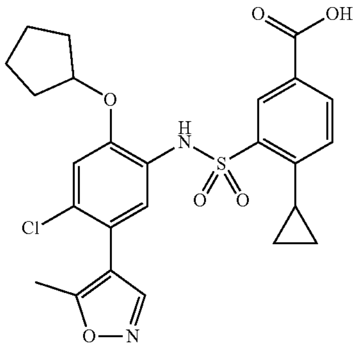
(26)
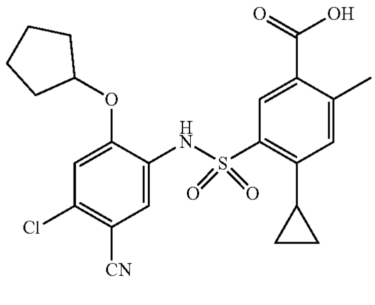
(27)
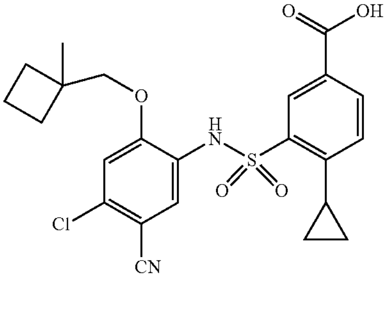
-continued
(28)
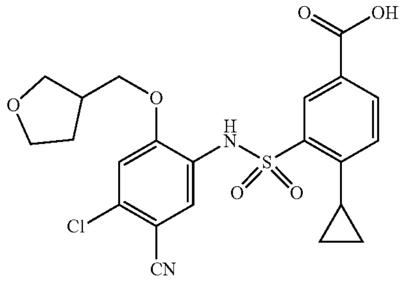
(29)
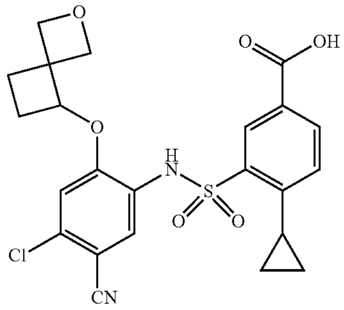
(30)
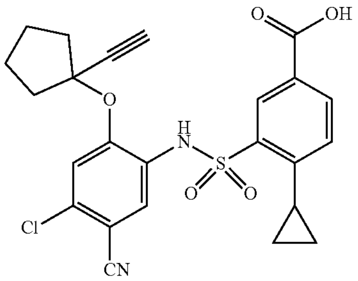
(31)
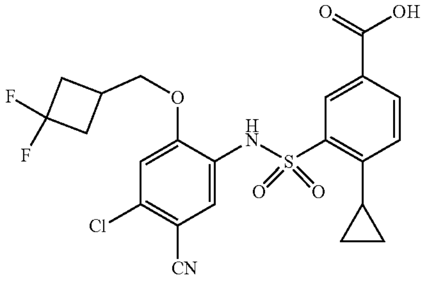
(32)
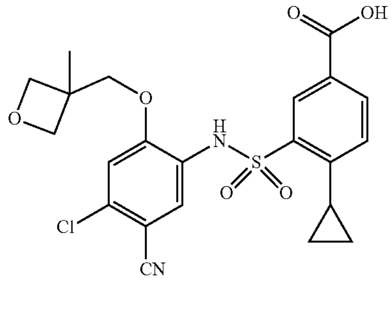

-continued
(33)
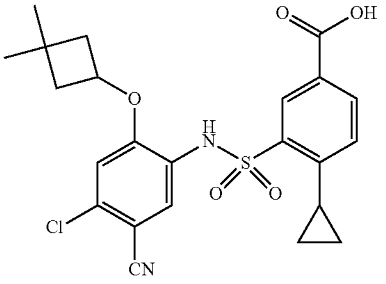
(34)
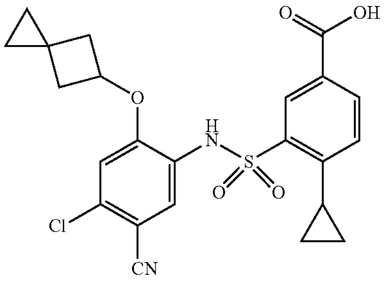
(35)
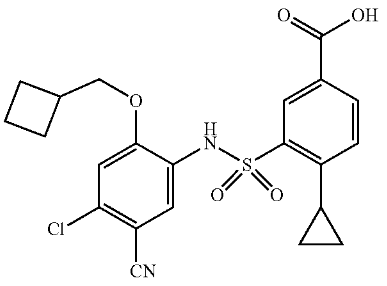
(36)
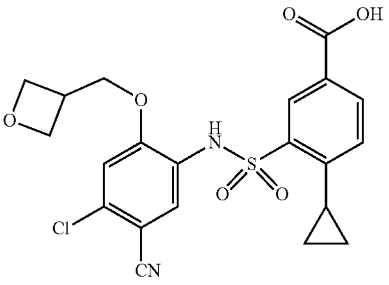
(37)
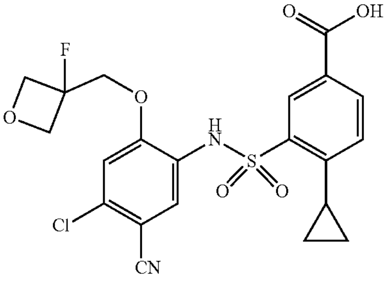
-continued
(38)
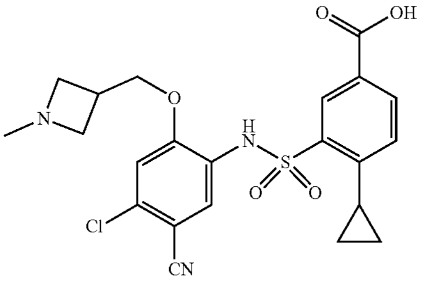
(39)
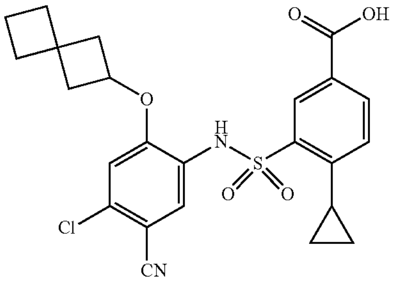
(40)
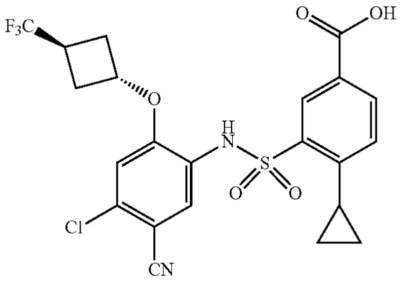
Trans relative
(41)
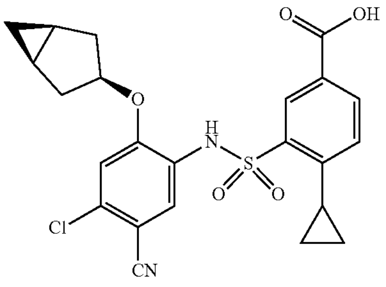
Cis relative
(42)
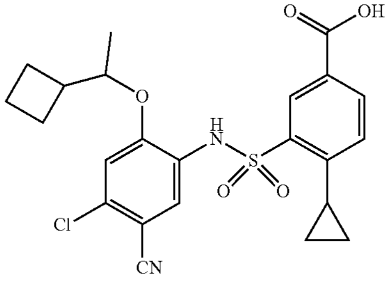

-continued
(43)
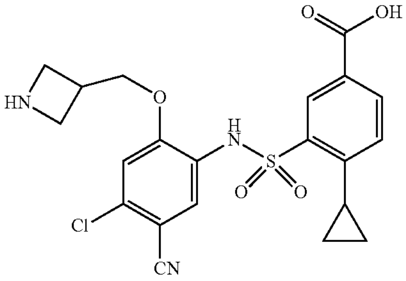
(44)
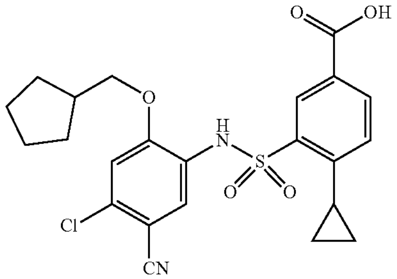
(45)
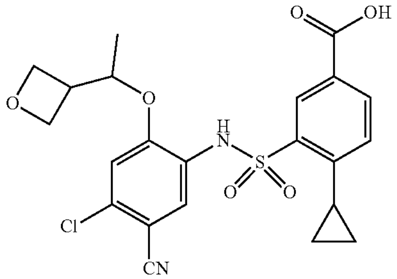
(46)
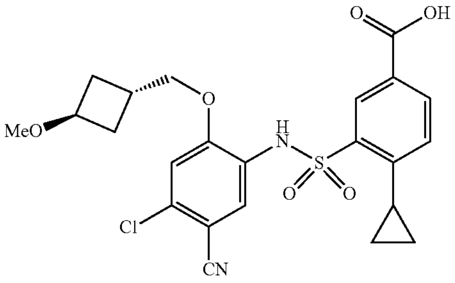
Trans relative
(47)
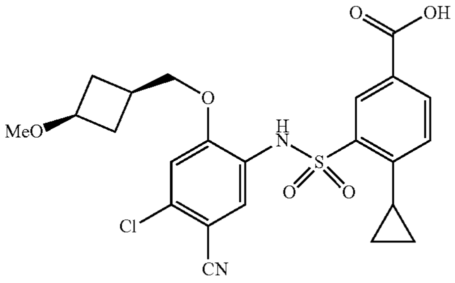
Cis relative
(48)
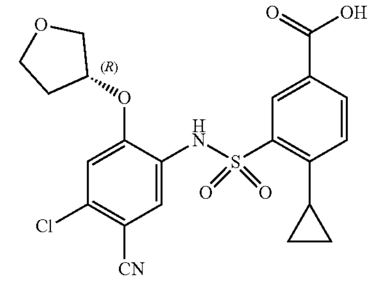
(49)
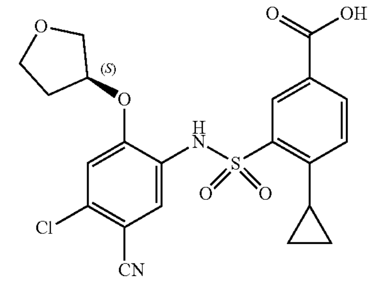
(50)
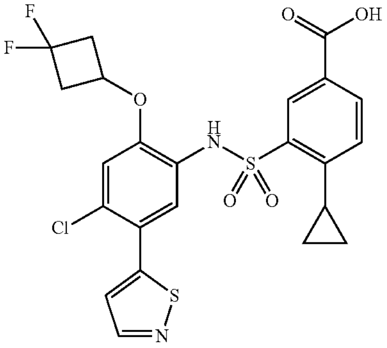
(51)
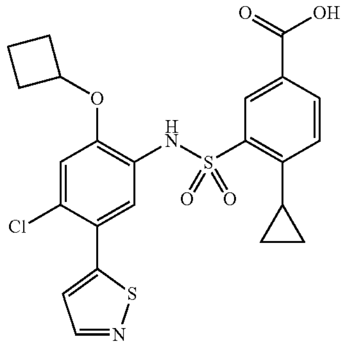
(52)
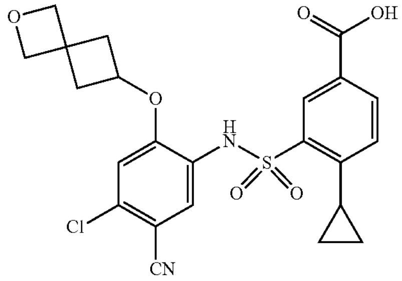

-continued
(53)
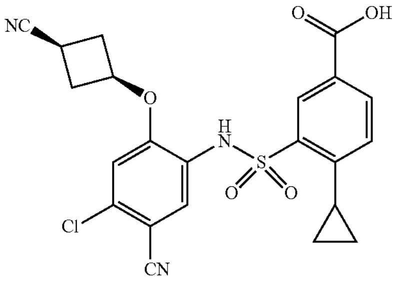
Cis relative
(54)
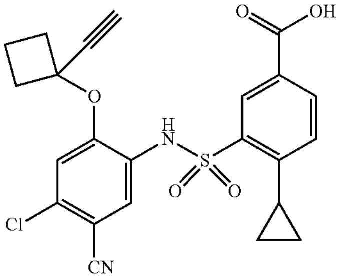
(55)
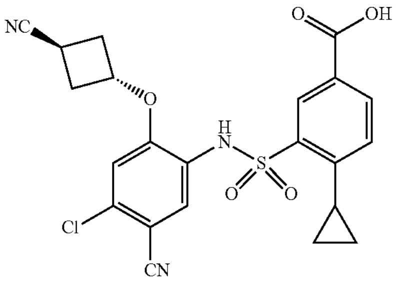
Trans relative
(56)
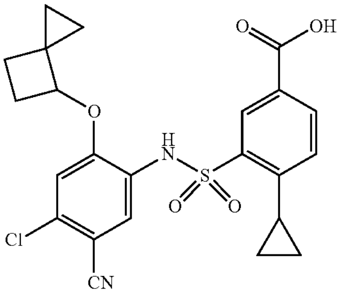
(57)
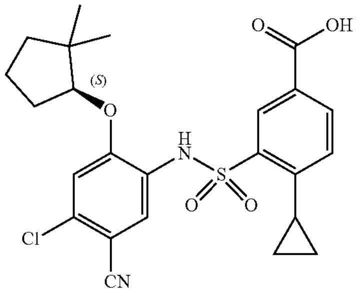
-continued
(58)
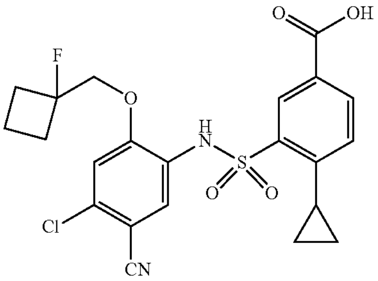
(59)
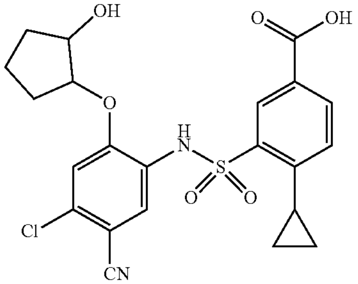
Trans racemate
(60)
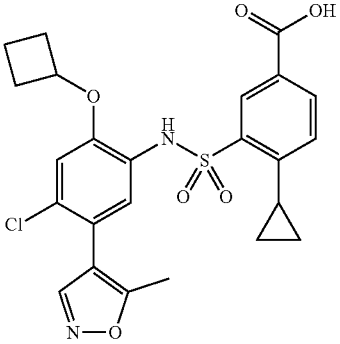
(61)
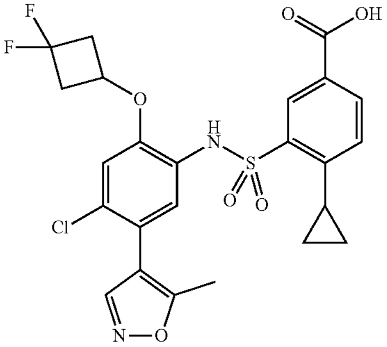
(62)
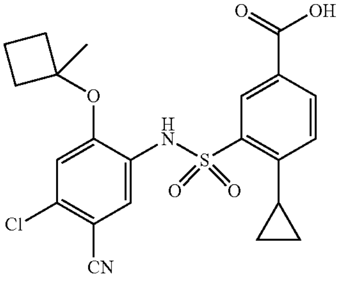

-continued
(63)
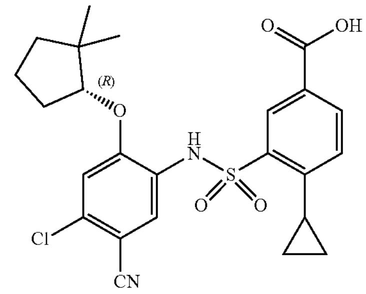
(64)
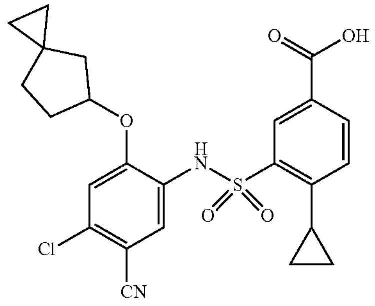
(65)
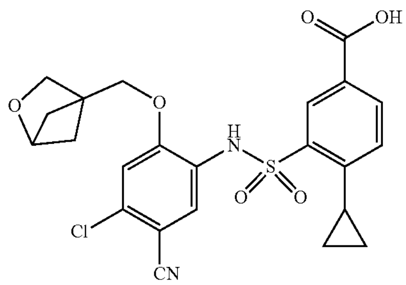
(66)
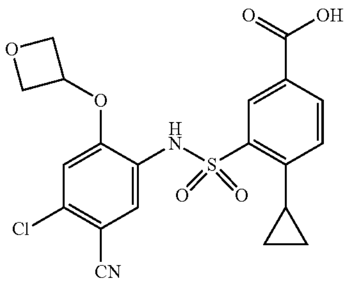
(67)
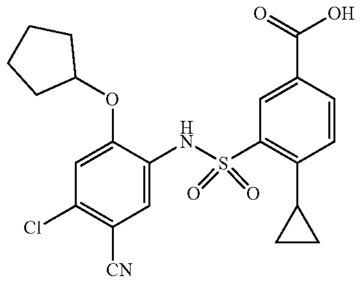
-continued
(68)
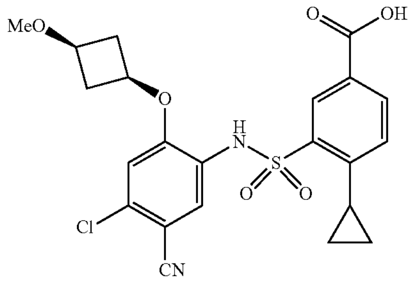
Cis relative
(69)
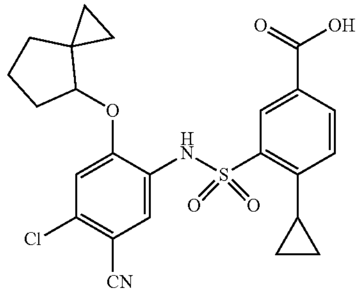
(70)
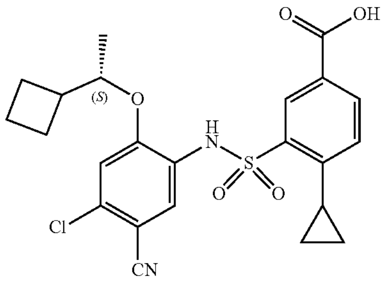
(71)
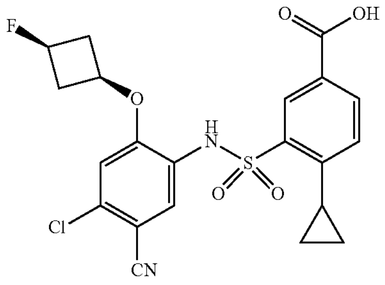
Cis relative
(72)
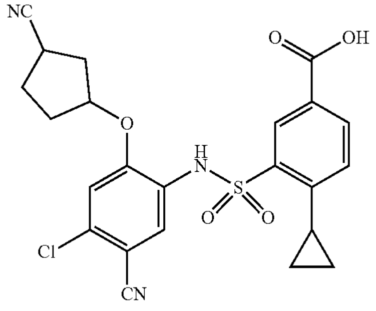
Trans racemate -continued
(73)
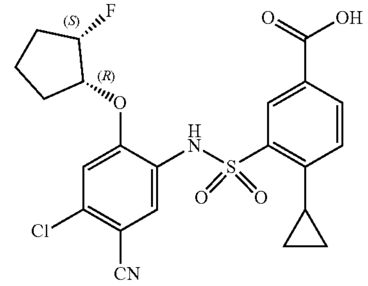
(74)
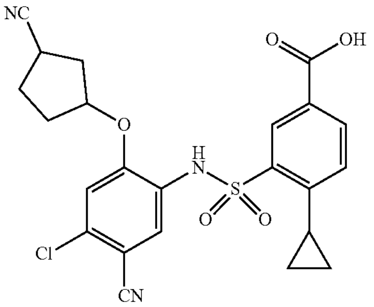
Cis racemate
(75)
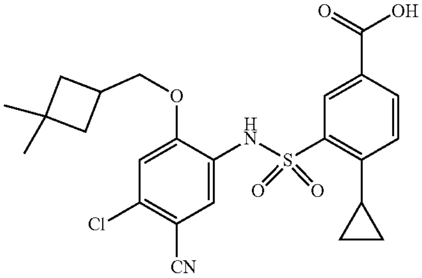
(76)
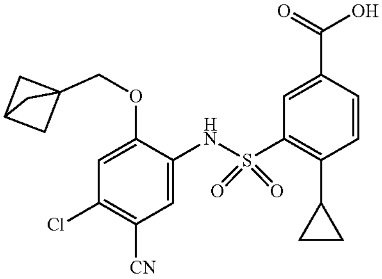
(77)
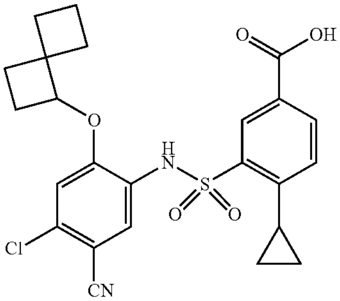
-continued
(78)
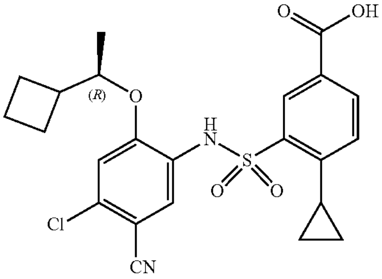
(79)
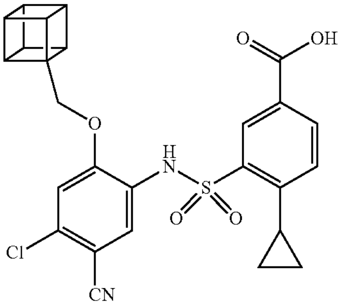
(80)
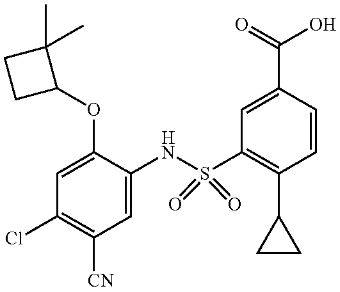
(81)
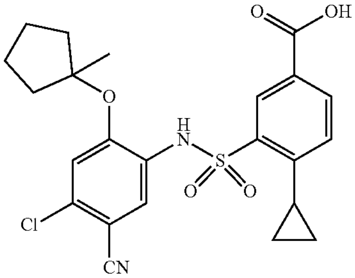
(82)
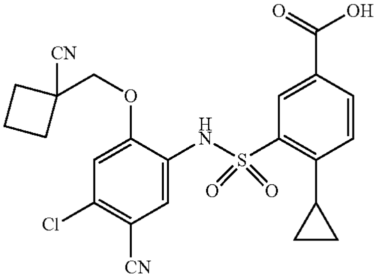

-continued
(83)
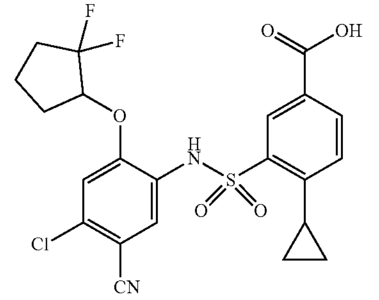
(84)
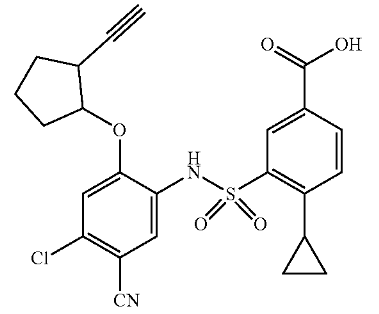
Trans racemate
(85)
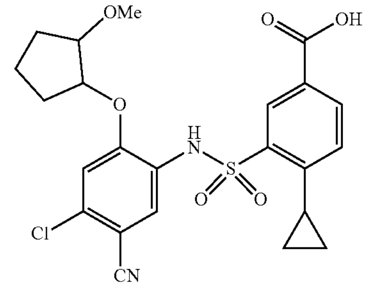
Trans racemate
(86)
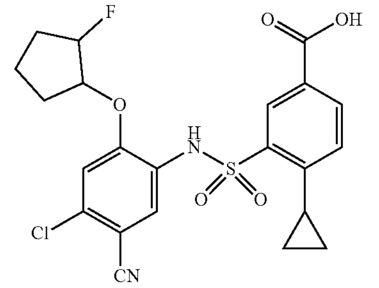
Trans racemate
(87)
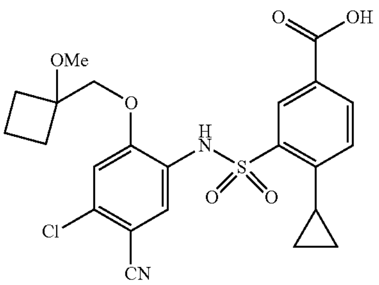
-continued
(88)
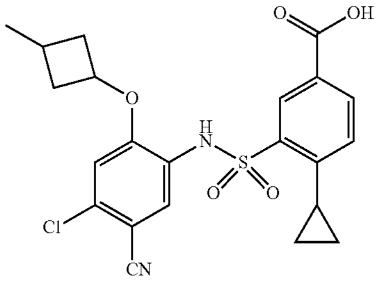
Cis/Trans
(89)
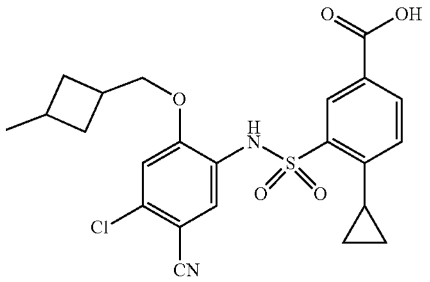
Cis/Trans
(90)
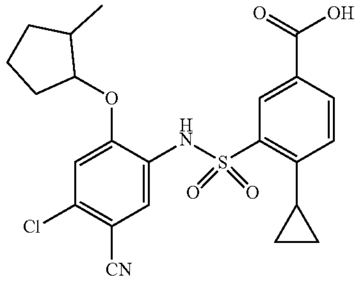
Trans racemate
(91)
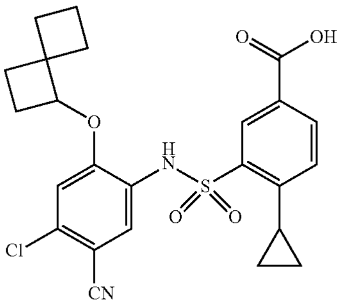
Enantiomer E1

-continued
(92)
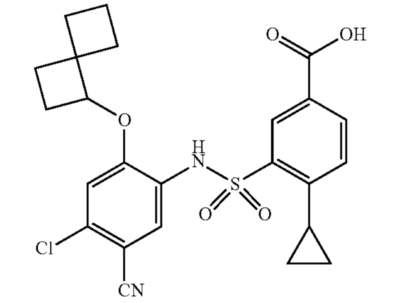
Enantiomer E2
(93)
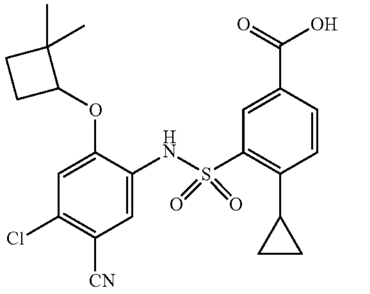
Enantiomer E1
(94)
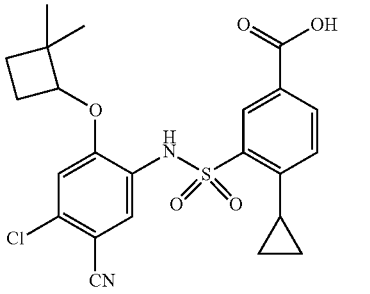
Enantiomer E2
(95)
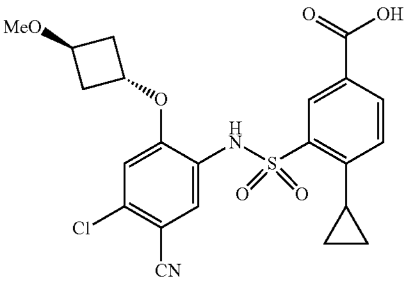
Trans relative
-continued
(96)
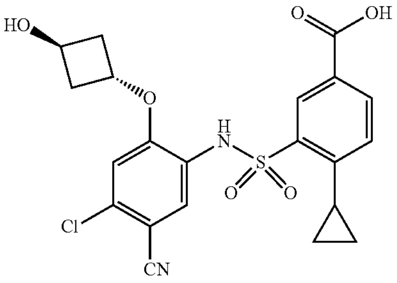
Trans relative
(97)
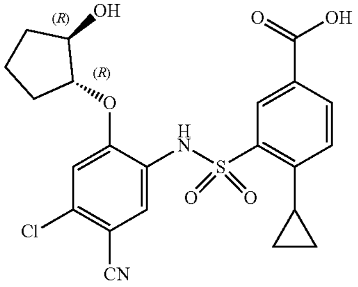
(98)
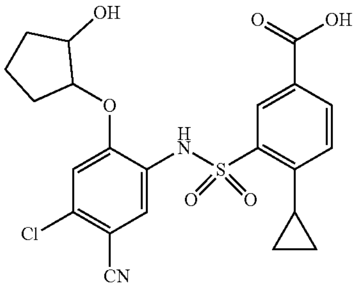
Cis racemate
(99)
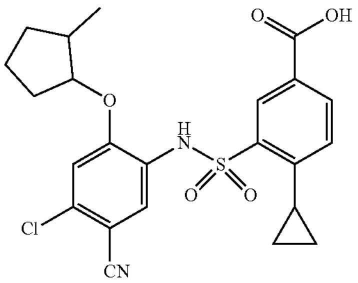
Trans diastereomer D1
(100)
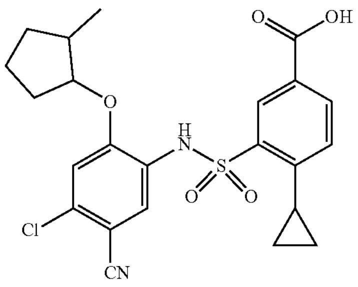
Trans diastereomer D2

-continued
(101)
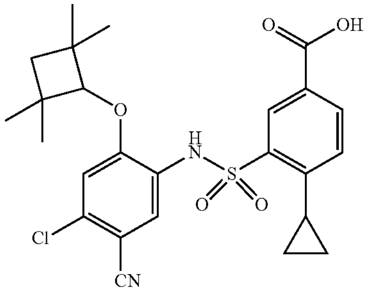
(102)
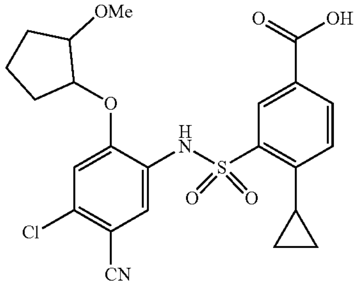
Cis racemate
(103)
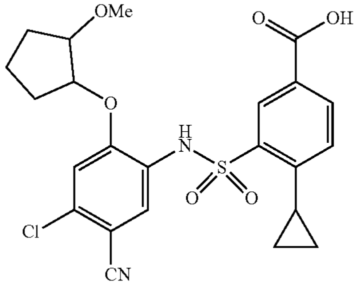
Trans diastereomer D1
(104)
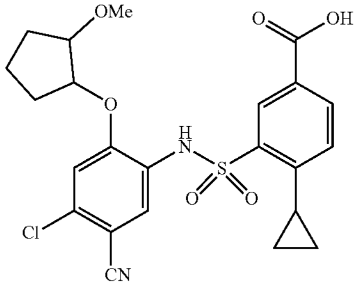
Trans diastereomer D2
(105)
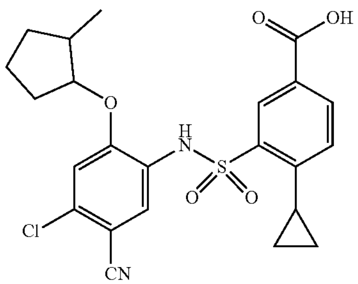
Cis racemate
-continued
(106)
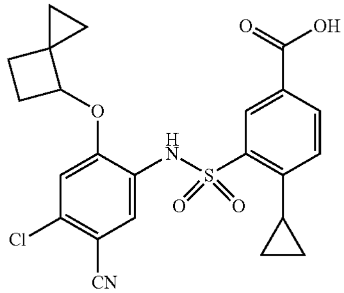
Enantiomer E1
(107)
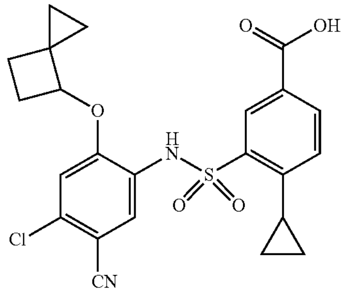
Enantiomer E2
(108)
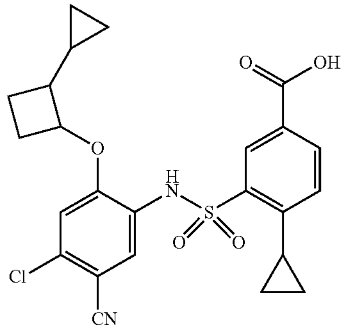
Cis/Trans
(109)
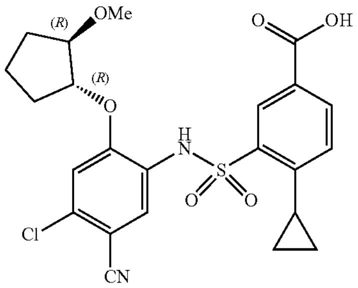

-continued
(110)
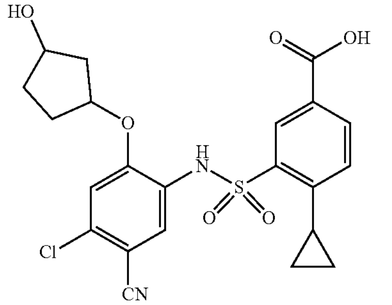
Cis racemate
(111)
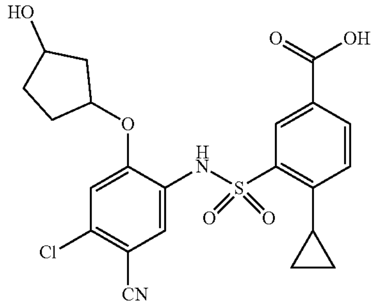
Trans racemate
(112)
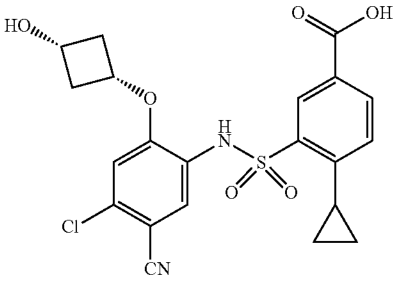
Cis relative
(113)
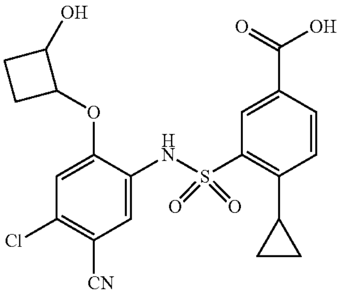
Cis racemate
-continued
(114)
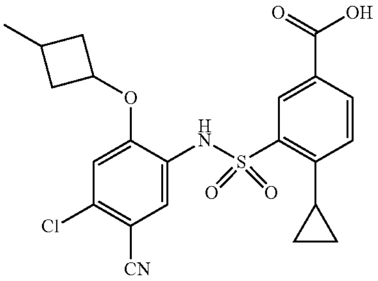
Diastereomer D1
(115)
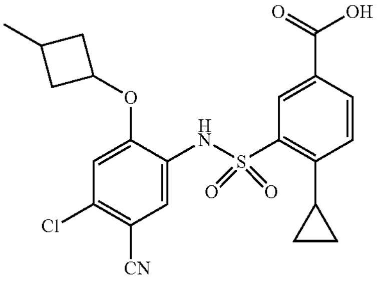
Diastereomer D2
(116)
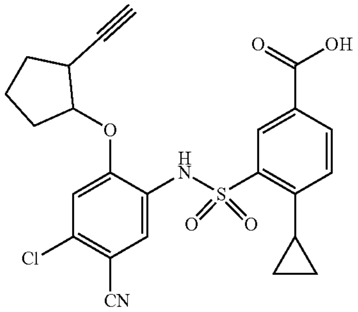
Trans diastereomer D1
(117)
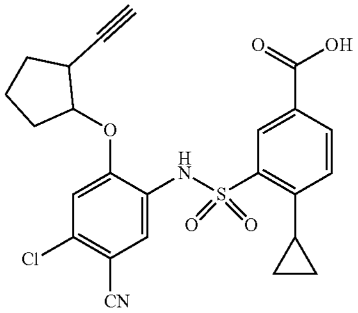
Trans diastereomer D2

-continued
(118)
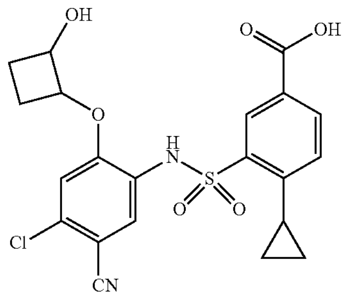
Trans racemate
(119)
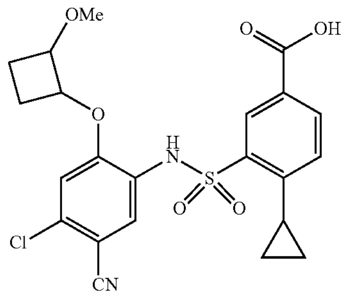
Trans racemate
(120)
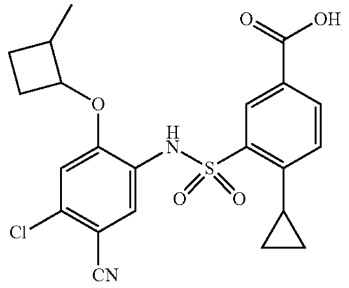
Diastereomer D1
(121)
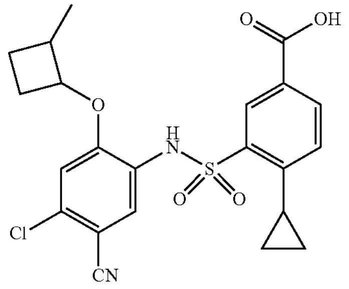
Diastereomer D2
-continued
(122)
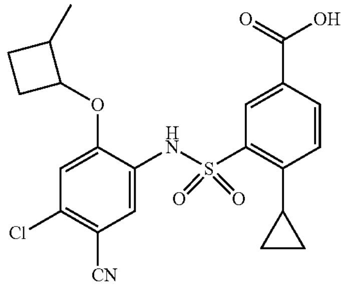
Diastereomer D3
(123)
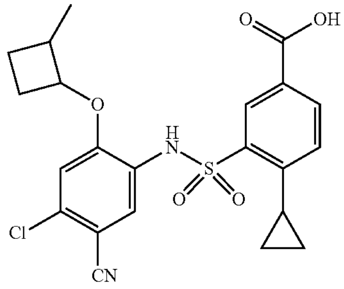
Diastereomer D4
(124)
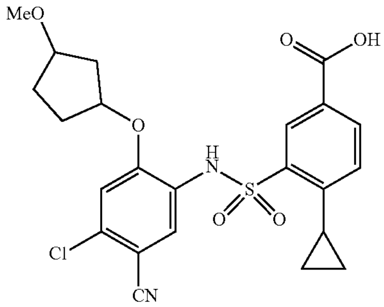
Cis/Trans
(125)
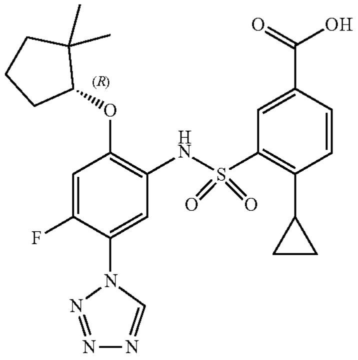

-continued
(126)
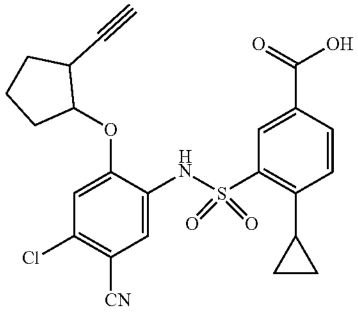
Cis diastereomer D1
(127)
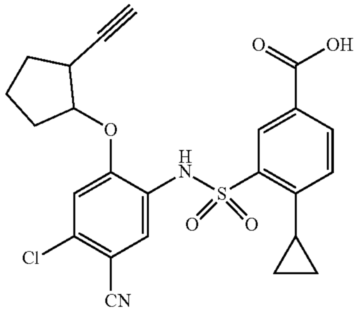
Cis diastereomer D2
(128)
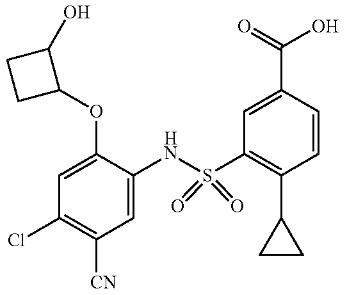
Trans diastereomer D1
(129)
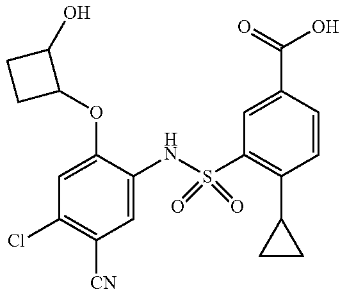
Trans diastereomer D2
-continued
(130)
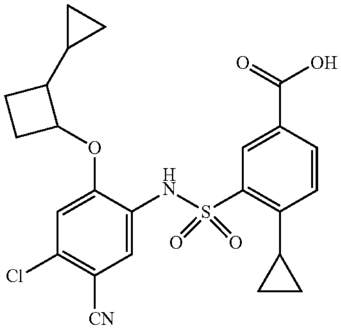
Diastereomer D1
(131)
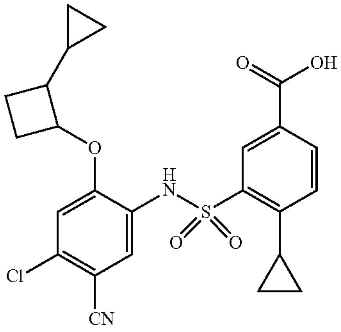
Diastereomer D2
(132)
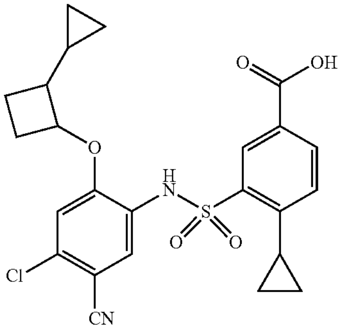
Diastereomer D3
(133)
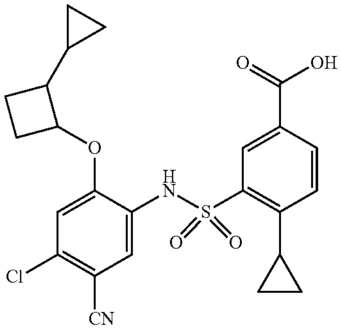
Diastereomer D4

-continued
(134)
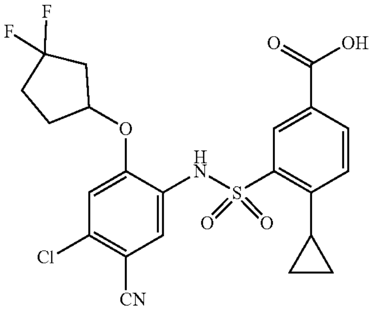
(135)
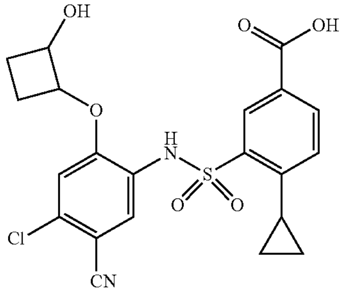
Cis diastereomer D1
(136)
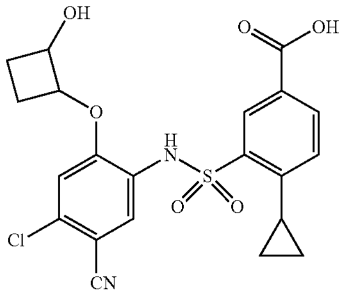
Cis diastereomer D2
(137)
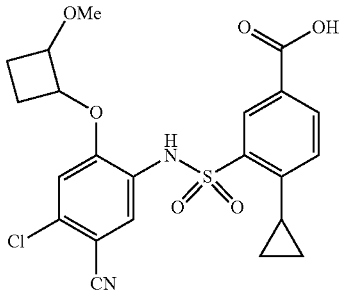
Cis racemate
-continued
(138)
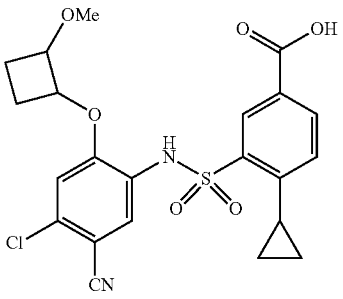
Trans diastereomer D1
(139)
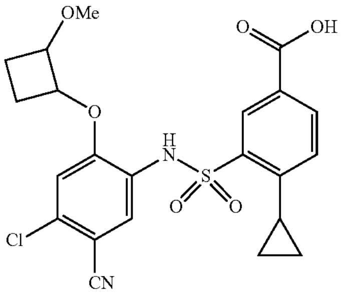
Trans diastereomer D2
(140)
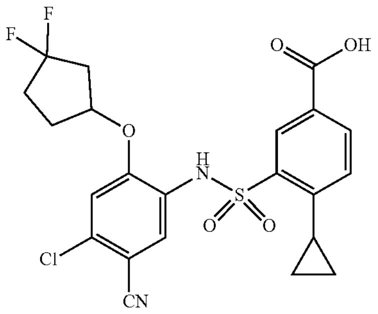
Enantiomer E1
(141)
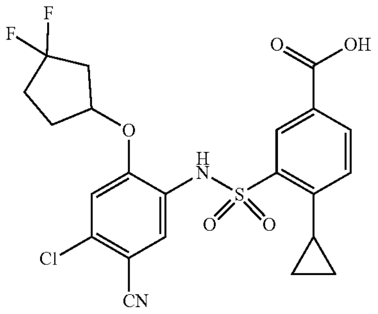
Enantiomer E2

-continued (142)

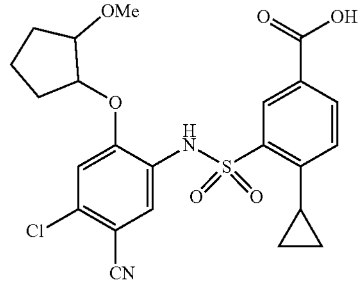

Cis diastereomer D1

(143)

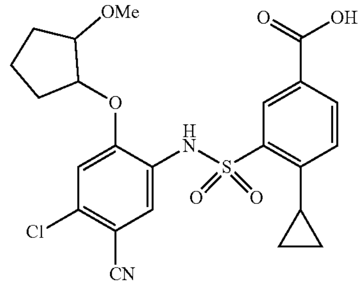

Cis diastereomer D2

(144)

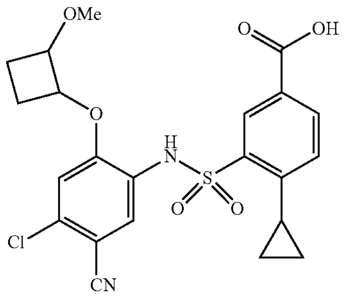

Cis diastereomer D1

(145)

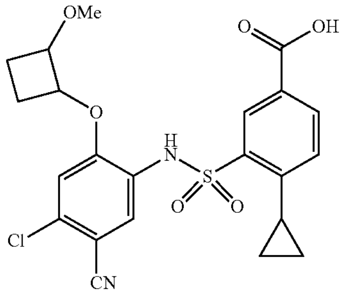

Cis diastereomer D2

(146)

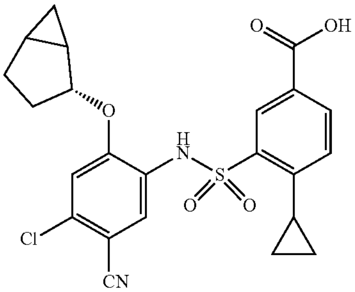

-continued (147)

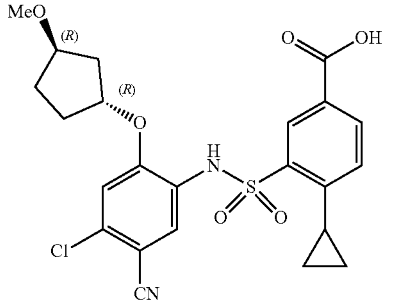

(148)

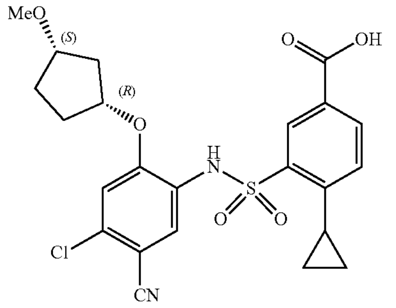

(149)

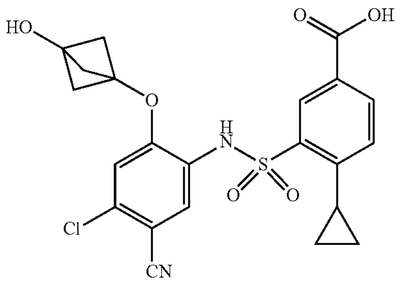

(150)

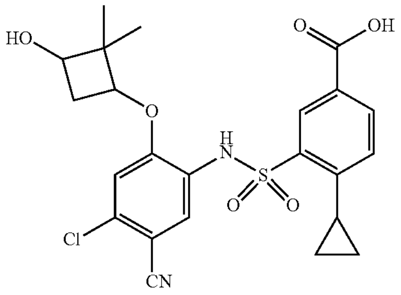

and pharmaceutically acceptable salts and hydrates thereof.

In one preferred embodiment, the compound of the invention exhibits an $IC_{50}$ against Decapeptide WRVYEKC(Dnp) ALK-acid (where Dnp is Dinitrophenyl maleimide) (10-mer) of 100 nM to 500 nM, more preferably, less than 100 nM. Further details of this assay are detailed in the accompanying examples.

In one preferred embodiment, the compound of the invention is selected from compounds 1, 4, 6, 8-13,16-37, 39-42, 44-51, 53-65, 68-94, 96-100, 102, 103, 105-111, 113-115, 117-126, 128, 130-134, 135-138 and 140-145.

In an even more preferred embodiment, the compound of the invention is selected from the following compounds 1, 8-12, 16-18, 20, 22-25, 27, 29, 33-35, 41, 42, 44, 47-48, 50, 51, 56-64, 69-74, 76-90, 92, 94, 96-100, 102, 103, 105-110, 113-115, 117-121, 123-126, 128, 131, 134, 136-138, 140-142 and 144.

Therapeutic Applications

A further aspect of the invention relates to compounds as described herein for use in medicine. The compounds have particular use in the field of oncology and immunoncology, as described in more detail below.

Yet another aspect of the invention relates to compounds as described herein for use in treating or preventing a disorder selected from a proliferative disorder, an immune disorder, an inflammatory disorder and a viral disorder.

In a preferred embodiment, the compound of the invention modulates ERAP1.

In one embodiment the compound inhibits the activity of ERAP1.

In an alternative embodiment the compound increases the activity of ERAP1.

In one embodiment the compound of the invention may change the repertoire of presented antigens.

One aspect of the invention relates to a compound as described herein for use in treating a proliferative disorder. Preferably, the proliferative disorder is a cancer or leukemia.

A cancer may be selected from: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

Without wishing to be bound by theory, it is understood that ERAP1 modulators are capable of changing at least 10% of the antigen and neoantigen repertoire of cancer cells, as measured using immunopeptidomics and mass spectrometry analysis. Approximately 50% of this change is an upregulation in the presentation of certain antigens and neoantigens, whilst the other 50% is the presentation of entirely novel antigens and neoantigens. Both changes lead to an increase in the visibility of the tumour to the immune system, leading to measurable changes in the $CD8^+$ T cell repertoire and $CD8^+$ T cell activation status. This change in $CD8^+$ T cell response leads to immune-mediated tumour clearance, and can be potentially enhanced by combining with cancer therapeutics such as antibody checkpoint inhibitors (e.g. anti-PD-1).

Without wishing to be bound by theory, it is understood that modulators of ERAP1 cause killing of cancer cells by natural killer (NK) cells due to disruption of the interaction between killer cell Ig-like receptors (KIR) or lectin-like receptor CD94-NKG2A on NK cells with classical or non-classical MHC-1-peptide (pMHC-I) complexes on cancer cells.

In one preferred embodiment, the disorder is cancer, and the compound increases the visibility of cancer cells to the immune system by altering the repertoire of antigens and neoantigens presented to the immune system.

A further aspect of the invention relates to a method of increasing the visibility of cancer cells to the immune system in a subject by altering the repertoire of antigens and neoantigens presented to the immune system, said method comprising administering to the subject a compound of formula (I).

In one preferred embodiment, the compound increases the CD8+ T cell response to the cancer cell.

In one preferred embodiment, the compound of the invention is for use in the treatment of a disease of uncontrolled cell growth, proliferation and/or survival, an inappropriate cellular immune response, or an inappropriate cellular inflammatory response, particularly in which the uncontrolled cell growth, proliferation and/or survival, inappropriate cellular immune response, or inappropriate cellular inflammatory response is modulated by the ERAP1 pathway.

In one preferred embodiment, the disease of uncontrolled cell growth, proliferation and/or survival, inappropriate cellular immune response, or inappropriate cellular inflammatory response is selected from a haematological tumour, a solid tumour and/or metastases thereof.

More preferably, the compound is for use in treating a disorder selected from leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The compound may kill cancer cells, reduce the number of proliferating cells in the cancer and/or reduce the volume or size of a tumour comprising the cancer cells. The compound may reduce the number of metastasising cancer cells.

In one embodiment the compound may be used (or is for use) in treating cancer in a subject who has previously had cancer. The compound may be used to reduce the likelihood of the cancer recurring, or the likelihood of further cancer developing. The compound may induce a neoantigen in the recurring or further cancer to which the subject already possesses an existing immune response. As such, the compound may increase or boost an immune response against the cancer.

In one embodiment the compound is for use in preventing cancer. The compound may be used for prophylaxis against the development of cancer. That is to say, the compound may stimulate an immune response, such as a vaccine response, against a future cancer. The compound may stimulate in a subject an immune response directed to a neoantigen. Once a cancer develops in the subject, they may be treated again with the compound (or a different compound) to stimulate development of the same neoantigen, thereby eliciting the subject's pre-exisiting immune response to said neoantigen to treat or prevent the cancer.

The same or a different compound may be used before and after the cancer develops in a subject.

In one embodiment the compound may be used for the prevention of cancer.

In one embodiment the subject may previously have had cancer, may have a familial history of cancer, may have a high risk for developing cancer, may have a genetic predisposition to developing cancer, or may have been exposed to a carcinogenic agent. In one embodiment the subject may be in remission from cancer.

One embodiment provides ex vivo generated antigen-presenting cells, such as dendritic cells (DCs). The antigen-presenting cells may be produced ex vivo to present neo-antigens, such as those generated by a compound according to the present invention. The compound may be used in a method for producing ex vivo an antigen-presenting cell which presents a neo-antigen, and wherein the cell may be used as a vaccine against cancer.

The antigen presenting cell such as a dendritic cell may be pulsed or loaded with the neo-antigen or genetically modified (via DNA or RNA transfer) to express one, two or more neo-antigens. Methods of preparing dendritic cell vaccines are known in the art. The neo-antigen may be generated from the subject's normal tissue in which ERAP1 is modulated with a compound according to the invention. Sources of normal tissue may be fibroblasts or B cells, for example, that can be readily expanded in vitro. Alternatively, RNA from the cancer, total or mRNA enriched poly A+ RNA may be used. Poly A+ RNA can be also amplified to generate sufficient antigen for DC loading and thereby limit the ex vivo culture step.

In one embodiment a dendritic cell which has been treated with the compound as described above may be used to treat a subject. The dendritic cell may be contacted with the compound ex vivo, and then the dendritic cell may be administered to the subject. The compound may therefore be used in vitro or in vivo, for example either for in situ treatment or for ex vivo treatment followed by the administration of the treated cells to the subject.

Another aspect of the invention relates to a compound as described above for use in treating an immune disorder. In one preferred embodiment, the immune disorder is an autoimmune disorder.

Examples of the autoimmune disorders include, but are not limited to: rheumatoid arthritis (RA), myasthenia gravis (MG), multiple sclerosis (MS), systemic lupus erythematosus (SLE), autoimmune thyroiditis (Hashimoto's thyroiditis), Graves' disease, inflammatory bowel disease, autoimmune uveoretinitis, polymyositis and certain types of diabetes, systemic vasculitis, polymyositis-dermatomyositis, systemic sclerosis (scleroderma), Sjogren's Syndrome, ankylosing spondylitis and related spondyloarthropathies, rheumatic fever, hypersensitivity pneumonitis, allergic bronchopulmonary aspergillosis, inorganic dust sarcoidosis, autoimmune anemia, immunological platelet disorders, cryopathies such as cryofibrinogenemia, psoriasis, Behçet's disease, birdshot chorioretinopathy and autoimmune polyendocrinopathies.

Polymorphisms in the ERAP1 gene that impact ERAP1 enzymatic activity are strongly associated with an increased risk of autoimmunity, including the diseases ankylosing spondylitis, psoriasis, Behçet's disease and birdshot chorioretinopathy[11]. Variants of ERAP1 that reduce ERAP1 enzymatic activity are protective against disease, whilst those that reportedly elevate activity are associated with increased disease risk[12]. This suggests that modulation of ERAP1 activity could be an effective treatment for autoimmune diseases.

Thus, in one preferred embodiment, the immune disorder is selected from ankylosing spondylitis, psoriasis, Behçet's disease and birdshot chorioretinopathy.

In one preferred embodiment, the immune disorder is ankylosing spondylitis. Ankylosing spondylitis (AS) is a type of arthritis in which there is long term inflammation of the joints of the spine. Typically, the joints where the spine joins the pelvis are also affected. Occasionally other joints such as the shoulders or hips are involved. Between 0.1% and 1.8% of people are affected and onset is typically in young adults. Although the cause of ankylosing spondylitis is unknown, it involves a combination of genetic and environmental factors. More than 90% of those affected have a specific human leukocyte antigen known as the HLA-B27 antigen.[13] In addition, certain variants of ERAP1, in conjunction with HLA-B27, are clearly associated with either an elevated or reduced risk of disease, providing evidence of a clear role for modulated antigen presentation in disease.[18] There is no cure for ankylosing spondylitis and current treatments serve only to improve symptoms and prevent worsening. Medications used to date include NSAIDs, steroids, DMARDs such as sulfasalazine, and biologic agents such as infliximab.

In one preferred embodiment, the immune disorder is Behçet's disease (BD). Behçet's disease (BD) is a type of inflammatory disorder which affects multiple parts of the body. The most common symptoms include painful mouth sores, genital sores, inflammation of parts of the eye, and arthritis. The cause is not well-defined, and whilst environmental factors play a role, genetic studies have shown an increased risk of disease in patients carrying HLA-B51 in conjunction with specific variants of ERAP1.[19] The disease is primarily characterized by auto-inflammation of the blood vessels, hence it is sometimes characterised as an auto-inflammatory disease. There is currently no cure for Behçet's disease, but the symptoms can be controlled with medicines that reduce inflammation in the affected parts of the body, for example, with corticosteroids, immunosuppressants or biological therapies that target the biological processes involved in the process of inflammation. In one preferred embodiment, the immune disorder is birdshot chorioretinopathy. Birdshot chorioretinopathy, also known as Birdshot Uveitis or HLA-A29 Uveitis, is a rare form of bilateral posterior uveitis affecting the eye. It causes severe, progressive inflammation of both the choroid and retina. Symptoms include floaters, blurred vision, photopsia (flashing lights in eyes), loss of color vision and nyctalopia. Birdshot chorioretinopathy is thought to be an autoimmune disease. The disease has strong association with the Human leukocyte antigen haplotype (HLA)-A29. This indicates a role for T-lymphocytes in the pathogenesis. Birdshot chorioretinopathy is associated with IL-17, a hallmark cytokine of TH17 cells that play an important role in autoimmunity.[15, 16] A genome-wide association study has ascertained HLA-A29:02 as the primary risk factor and identified that both ERAP1 and ERAP2 are associated with birdshot chorioretinopathy.[17, 20] Genetic variants within the ERAP1 and ERAP2 loci modulate enzyme activity and also mRNA and protein expression. ERAP2 is an aminopeptidase that, together with ERAP1, trims peptides in the endoplasmic reticulum and loads these peptides on HLA molecules for presentation to T cells of the immune system.

In one preferred embodiment, the immune disorder is psoriasis. Psoriasis is a chronic skin disease in which skin cells rapidly build up on the surface of the skin forming scales and red patches that are itchy and sometimes painful. The cause is not well-defined but includes both environmental and genetic factors. HLA-C06 strongly associates with risk of disease and variants in ERAP1, possibly in conjunction with HLA-C06, are also strongly associated with disease.[21] There is no cure for psoriasis and current treatments serve only to improve symptoms and prevent worsening. Medications used in therapy include steroids, methotrexate, sulfasalazine, and biologic agents such as etanercept.

Another aspect of the invention relates to a compound as described above for use in treating or preventing a viral disorder. Modulators of ERAP1 such as the compounds described herein are capable of changing the antigen repertoire of multiple viruses, which leads to the recognition and destruction of viral infected cells. Accordingly, ERAP1 modulators have potential therapeutic applications in the treatment of viral infection and diseases. ERAP1 modulates certain viral antigens, including those from human papilloma virus (HPV), human cytomegalovirus (CMV) hepatitis C (HCV) and human immunodeficiency virus (HIV)[8, 9, 10]. In addition, knockdown of ERAP1 in HPV infected cells changes the repertoire of presented HPV antigens leading to greater recognition by $CD8^+$ T cells[8].

In one preferred embodiment, the viral disorder is a viral disease or viral infection selected from HIV, HPV, CMV and HCV.

In one preferred embodiment, the viral disorder is HIV.

In one preferred embodiment, the viral disorder is HPV.

In one preferred embodiment, the viral disorder is CMV.

In one preferred embodiment, the viral disorder is HCV.

Another aspect relates to a compound as described herein for use in the prevention or treatment of a disorder caused by, associated with or accompanied by abnormal activity against ERAP1.

Another aspect relates to a compound as described herein for use in the prevention or treatment of an ERAP1-associated disease or disorder.

Yet another aspect relates to the use of a compound as described herein in the preparation of a medicament for the prevention or treatment of a disorder caused by, associated with or accompanied by any abnormal activity against ERAP1.

As used herein the phrase "preparation of a medicament" includes the use of the components of the invention directly as the medicament in addition to their use in any stage of the preparation of such a medicament.

Another aspect relates to the use of a compound as described above in the preparation of a medicament for treating or preventing a disorder selected from a proliferative disorder, an immune disorder, a viral disorder and an inflammatory disorder.

Yet another aspect relates to the use of a compound as described herein in the preparation of a medicament for the prevention or treatment of an ERAP1-associated disease or disorder.

Another aspect of the invention relates to a method of treating an ERAP1-associated disease or disorder in a subject. The method according to this aspect of the present invention is effected by administering to a subject in need thereof a therapeutically effective amount of a compound of the present invention, as described hereinabove, either per se, or, more preferably, as a part of a pharmaceutical composition, mixed with, for example, a pharmaceutically acceptable carrier, as is detailed hereinafter.

Yet another aspect of the invention relates to a method of treating a subject having a disease state alleviated by modulation of ERAP1 wherein the method comprises administering to the subject a therapeutically effective amount of a compound according to the invention.

Another aspect relates to a method of treating a disease state alleviated by modulation of ERAP1, wherein the method comprises administering to a subject a therapeutically effective amount of a compound according to the invention.

Preferably, the subject is a mammal, more preferably a human.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

The term "therapeutically effective amount" refers to that amount of the compound being administered which will relieve to some extent one or more of the symptoms of the disease or disorder being treated.

For any compound used in this invention, a therapeutically effective amount, also referred to herein as a therapeutically effective dose, can be estimated initially from cell culture assays. For example, a dose can be formulated in animal models to achieve a circulating concentration range that includes the $IC_{50}$ or the $IC_{100}$ as determined in cell culture. Such information can be used to more accurately determine useful doses in humans. Initial dosages can also be estimated from in vivo data. Using these initial guidelines one of ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{50}$ and the $ED_{50}$. The dose ratio between toxic and therapeutic effect is the therapeutic index and can be expressed as the ratio between $LD_{50}$ and $ED_{50}$. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (see, e.g., Fingl et al, 1975, The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day. Preferably, therapeutically effective serum levels will be achieved by administering multiple doses each day. In cases of local administration or selective uptake, the effective local concentration of the drug may not be related to plasma concentration. One skilled in the art will be able to optimize therapeutically effective local dosages without undue experimentation.

As used herein, "ERAP1-related disease or disorder" refers to a disease or disorder characterized by inappropriate ERAP1 activity. Inappropriate activity refers to either an increase or decrease in ERAP1 activity relative to wildtype ERAP1 (Uniprot ID Q9NZ08), caused by variation in the ERAP1 protein sequence, as measured by enzyme or cellular assays. Inappropriate activity could also be due to overexpression of ERAP1 in diseased tissue compared with healthy adjacent tissue.

Preferred diseases or disorders that the compounds described herein may be useful in preventing include proliferative disorders, viral disorders, immune disorders and inflammatory disorders as described hereinbefore.

Thus, the present invention further provides use of compounds as defined herein for the manufacture of medicaments for the treatment of diseases where it is desirable to modulate ERAP1. Such diseases include proliferative disorders, viral disorders, immune disorders and inflammatory disorders as described hereinbefore.

In one preferred embodiment, the compound activates ERAP1's conversion of (L)-leucine-7-amido-4-methylcoumarin (L-AMC) to (L)-leucine and the fluorescent molecule 7-amino-4-methylcoumarin. While the same assay can also identify inhibitors of ERAP1's cleavage of the amide bond in L-AMC, for the purposes of this application this assay is referred to as the "L-AMC activator assay". The potency of any activator is calculated and expressed as the concentration of the activator required to increase the enzyme activity of ERAP1 by 50% over its baseline level (i.e. an $EC_{50}$).

In one preferred embodiment, the compound exhibits an $EC_{50}$ value in an L-AMC activator assay of less than about 25 μM. More preferably, the compound exhibits an $EC_{50}$ value in the L-AMC activator assay of less than about 10 μM, more preferably, less than about 5 μM, even more preferably, less than about 1 μM, even more preferably, less than about 0.1 μM, even more preferably, less than about 0.01 μM. In one preferred embodiment, the compound inhibits ERAP1's ability to hydrolyse the decapeptide substrate WRVYEKCdnpALK. This peptide has minimal fluorescence as the N-terminal tryptophan residue's fluorescence is quenched by the dinitrophenol (DNP) residue within the peptide. However, as ERAP1 hydrolyses the N-terminal amide bond and tryptophan is released this internal quenching is lost and the reaction is monitored by the increase in tryptophan fluorescence over the course of the assay. For the purposes of this application this assay is referred to as the "10mer inhibition assay" and compound potencies are calculated and expressed as $IC_{50}$ as would be familiar to a person skilled in the art.

In one preferred embodiment, the compound exhibits an $IC_{50}$ value in the 10mer assay of less than about 25 μM. More preferably, the compound exhibits an $IC_{50}$ value in the 10mer assay of less than about 10 μM, more preferably, less than about 5 μM, even more preferably, less than about 1 μM, even more preferably, less than about 0.1 μM, even more preferably, less than about 0.01 μM. In one preferred embodiment, the compound exhibits an $IC_{50}$ value in the 10mer assay of from about 100 nM to about 500 nM, more preferably, less than 100 nM.

Pharmaceutical Compostions

For use according to the present invention, the compounds or physiologically acceptable salt, ester or other physiologically functional derivative thereof, described herein, may be presented as a pharmaceutical formulation, comprising the compounds or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller. The carrier, or, if more than one be present, each of the carriers, must be acceptable in the sense of being compatible with the other ingredients of the formulation and not deleterious to the recipient.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release—controlling matrix or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds. Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound as described herein into conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates. Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. More preferably, the salt is a hydrochloride salt.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', 3rd edition, ed. March, J., John Wiley and Sons, New York, 1985).

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those compounds, and mixtures thereof. The terms used in the claims encompass these forms, provided said forms retain the appropriate functional activity (though not necessarily to the same degree).

The present invention also includes all suitable isotopic variations of the compound or a pharmaceutically acceptable salt thereof. An isotopic variation of a compound of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$ $^{32}P$, $^{35}S$, $^{18}F$ and $^{36}Cl$, respectively. Certain isotopic variations of the agent and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Atropisomers

Some of the compounds of the invention may exist as atropisomers. Atropisomers are stereoisomers arising because of hindered rotation about a single bond, where energy differences due to steric strain or other contributors create a barrier to rotation that is high enough to allow for isolation of individual conformers. The invention encompasses all such atropisomers.

Prodrugs

The invention further includes the compounds of the present invention in prodrug form, i.e. covalently bonded compounds which release the active parent drug in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms. Preferably the solvate is a hydrate.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free-flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

The dosage amount will further be modified according to the mode of administration of the compound. For example, to achieve an "effective amount" for acute therapy, parenteral administration of a compound is typically preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to modulate ERAP1. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

A further aspect of the invention relates to a combination comprising a compound as described herein and one or more additional active agents. In a particularly preferred embodiment, the one or more compounds of the invention are administered in combination with one or more additional active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance.

Beneficial combinations may be suggested by studying the activity of the test compounds with agents known or suspected of being valuable in the treatment of a particular disorder. This procedure can also be used to determine the order of administration of the agents, i.e. before, simultaneously, or after delivery. Such scheduling may be a feature of all the active agents identified herein.

In one preferred embodiment, the additional active agent is an immunotherapy agent, more preferably a cancer immunotherapy agent. An "immunotherapy agent" refers to a treatment that uses the subject's own immune system to fight diseases such as cancer.

In one preferred embodiment the compound of the invention inhibits the activity of ERAP1, and the compound is administered in combination with an immunotherapy. The compound may increase the sensitivity of cancer cells to an immunotherapy. The immunotherapy may be mediated by T cells. In one embodiment the compound may increase the number of CD8+ T cells in a tumour.

In one embodiment the compound may be used to treat cancers which are weakly responsive or not responsive to immunotherapies.

In one preferred embodiment, the additional active agent is a molecule capable of immune checkpoint intervention, a co-stimulatory antibody, a chemotherapy agent, a radiotherapy agent, a targeted therapy agent or an antibody, particularly a monoclonal antibody.

In one preferred embodiment the additional active agent is a molecule capable of immune checkpoint intervention.

Immune checkpoint molecules include CTLA-4, PD-1, VISTA, B7-H2, B7-H3, PD-1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4, B7.1, B7.2, ILT-2, ILT-4, TIGIT, HHLA2, IDO, CD39, CD73, A2aR and butyrophilins.

Immune checkpoint molecules include both inhibitory and activatory molecules, and interventions may apply to either or both types of molecule.

Immune checkpoint inhibitors include, but are not limited to, PD-1 inhibitors, PD-L1 inhibitors, LAG-3 inhibitors, TIM-3 inhibitors, TIGIT inhibitors, BTLA inhibitors and CTLA-4 inhibitors, for example. Co-stimulatory antibodies deliver positive signals through immune-regulatory receptors including but not limited to ICOS, CD137, CD27 OX-40 and GITR.

In one highly preferred embodiment, the the additional active agent is an antibody checkpoint inhibitor. Suitable examples of antibody checkpoint inhibitors, include, but are not limited to, anti-PD-1 antibodies, anti-PD-L1 antibodies and anti-CTLA4 antibodies.

In one preferred embodiment, the antibody checkpoint inhibitor is an anti-PD-1 antibody, more preferably selected from pembrolizumab, cemiplimab and nivolumab.

In one preferred embodiment, the antibody checkpoint inhibitor is an anti-PD-L1 antibody, more preferably selected from atezolizumab, avelumab and durvalumab.

In one preferred embodiment, the antibody checkpoint inhibitor is an anti-CTLA4 antibody, more preferably selected from ipilimumab and tremelimumab.

In one preferred embodiment the immunotherapy is an anti-cancer vaccine or virus, such as an oncolytic virus.

In one preferred embodiment the immunotherapy is a cell-based therapy. In one embodiment the cell-based therapy may be a T cell therapy, such as adoptive T cell therapy, or therapy with CAR-T cells.

Adoptive cell-based immunotherapy may include the following: Irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies can be further modified to express one or more gene products to further modulate immune responses, for example expressing cytokines such as GM-CSF, and/or to express tumor-associated antigen (TAA) antigens, such as Mage-1, gp-100, patient-specific neoantigen vaccines, and the like.

In a further embodiment, the immunotherapy may comprise non-cell-based immunotherapies. In one embodiment, compositions comprising antigens with or without vaccine-enhancing adjuvants may be used. Such compositions exist in many well-known forms, such as peptide compositions, oncolytic viruses, and recombinant antigen comprising fusion proteins.

In an alternative embodiment, immunomodulatory interleukins, such as IL-2, IL-6, IL-7, IL-12, IL-17, IL-23, as well as modulators thereof (e.g., blocking antibodies or more potent or longer lasting forms) may be used. Immunomodulatory cytokines, such as interferons, G-CSF, imiquimod, T F alpha, and the like, as well as modulators thereof (e.g., blocking antibodies or more potent or longer lasting forms) may also be used. In another embodiment, immunomodulatory chemokines, such as CCL3, CCL26, and CXCL7, and the like, as well as modulators thereof (e.g., blocking antibodies or more potent or longer lasting forms) may be used. In a further embodiment, immunomodulatory molecules targeting immunosuppression, such as STAT3 signaling modulators, FkappaB modulators, and immune checkpoint modulators, may be used.

In another embodiment, immunomodulatory drugs, such as immunocytostatic drugs, glucocorticoids, cytostatics, immunophilins and modulators thereof (e.g., rapamycin, a calcineurin inhibitor, tacrolimus, ciclosporin pimecrolimus, abetimus, gusperimus, ridaforolimus, everolimus, temsirolimus, zotarolimus, etc.), hydrocortisone (Cortisol), cortisone acetate, prednisone, prednisolone, methylprednisolone, dexamethasone, betamethasone, triamcinolone, fludrocortisone acetate, deoxycorticosterone acetate (doca) aldosterone, a non-glucocorticoid steroid, a pyrimidine synthesis inhibitor, leflunomide, teriflunomide, a folic acid analog, methotrexate, anti-thymocyte globulin, anti-lymphocyte globulin, thalidomide, lenalidomide, pentoxifylline, bupropion, curcumin, catechin, an opioid, an EVIPDH inhibitor, mycophenolic acid, myriocin, fingolimod, an NF-xB inhibitor, raloxifene, drotrecogin alfa, denosumab, an F-xB cascade inhibitor, disulfiram, olmesartan, dithiocarbamate, a proteasome inhibitor, bortezomib, MG132, Prol, PI-0052, curcumin, genistein, resveratrol, parthenolide, thalidomide, lenalidomide, flavopiridol, non-steroidal anti-inflammatory drugs (NSAIDs), arsenic tri oxide, dehydroxymethylepoxyquinomycin (DHMEQ), I3C(indole-3-carbinol)/DIM(di-indolmethane) (13C/DIM), Bay 1 1-7082, luteolin, cell permeable peptide SN-50, IKBa—super repressor overexpression, FKB decoy oligodeoxynucleotide (ODN), or a derivative or analog of any thereto, may be used.

In yet another embodiment, immunomodulatory antibodies or protein may be used. For example, antibodies that bind to CD40, Toll-like receptor (TLR), OX40, GITR, CD27, or to 4-IBB, T-cell bispecific antibodies, an anti-IL-2 receptor antibody, an anti-CD3 antibody, OKT3 (muromonab), otelixizumab, teplizumab, visilizumab, an anti-CD4 antibody, clenoliximab, keliximab, zanolimumab, an anti-CDI I a antibody, efalizumab, an anti-CD 18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BlyS) inhibiting antibody, belimumab, an CTLA4-Ig fusion protein, abatacept, belatacept, an anti-CTLA4 antibody, ipilimumab, tremelimumab, an anti-eotaxin 1 antibody, bertilimumab, an anti-a4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an IL-1 receptor antagonist, anakinra, an anti-IL-5 antibody, mepolizumab, an IgE inhibitor, omalizumab, talizumab, an IL12 inhibitor, an IL23 inhibitor, ustekinumab.

In one embodiment, the subject may be undergoing or have previously undergone treatment with a chemotherapeutic agent. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"- trichlorotriethylamine; trichothecenes (e.g., T-2 toxin, verracurin A, roridin A and anguidine); vindesine; dacarbazine; mannomustine; mitobronitol; mitolactol; pipobroman; gacytosine; arabinoside ("Ara-C"); cyclophosphamide; thiotepa; e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincris- X is NH, Y is $SO_2$ and Z, L, $R_1$, $R_3$, $R_4$—$R_9$ are as defined hereinabove, said process comprising the steps of:

(i) converting a compound of formula (II) to a compound of formula (III) by treating said compound of formula (II) with $Cs_2CO_3$ and Z-L-OH in a solvent;

(ii) reducing said compound of formula (III) to form a compound of formula (IV);

(iii) treating the compound of formula (IV) with a compound of formula (V) to form a compound of formula (VI); and (iv) hydrolysing said compound of formula (VI) to form a compound of formula (I).

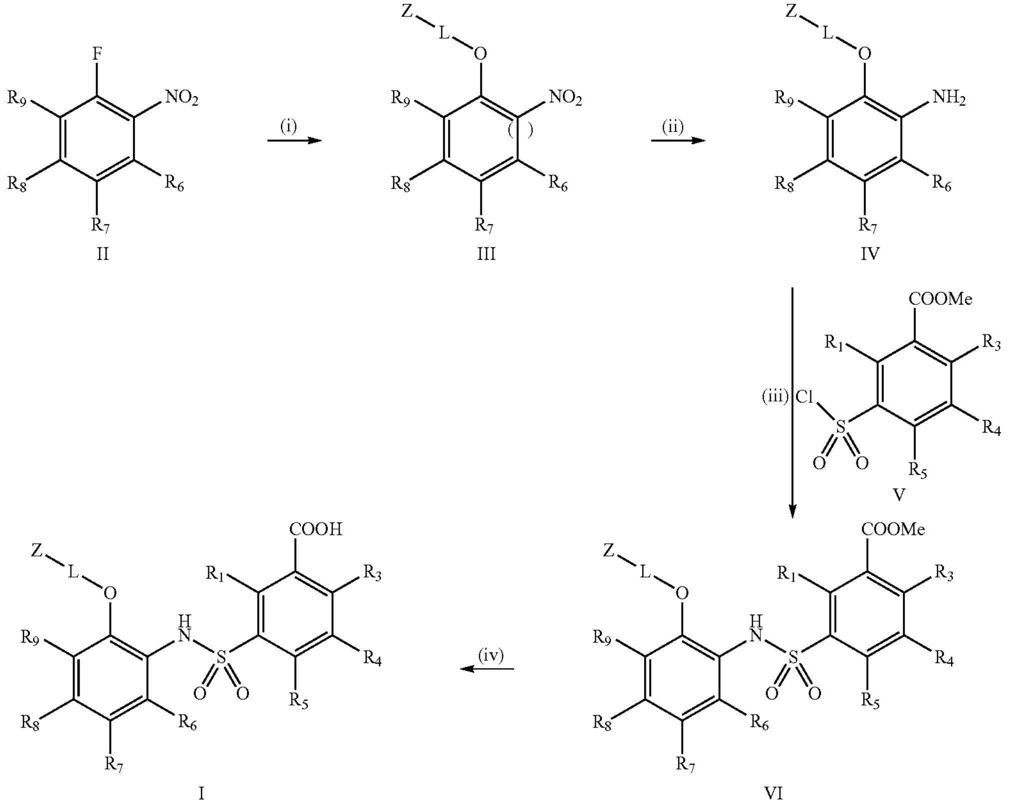

tine; NAVELBINE vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-a, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

Process

Another aspect of the invention relates to processes for preparing compounds of formula (I) as described herein.

In one aspect, the invention relates to a process for preparing a compound of formula (I), wherein $R_2$ is COOH, Preferably, step (i) is carried out in acetonitrile, more preferably at room temperature. The skilled person would understand that other organic solvents would also be suitable. Preferably, step (ii) comprises heating the compound of formula (III) with Fe, $NH_4Cl$ and $EtOH/H_2O$ (preferably v/v=4/1). Preferably, step (iii) is carried out in the presence of pyridine and dichloromethane at room temperature. Preferably, the hydrolysis step (iv) is carried in the presence of LiOH in THF at room temperature.

Preferred conditions for each step are set out hereinafter in Scheme 1 and in the accompanying examples.

In another aspect, the invention relates to a process for preparing a compound of formula (I), wherein $R_2$ is COOH, X is NH, Y is $SO_2$, $R_7$ is tetrazolyl and Z, L, $R_1$, $R_3$, $R_4$—$R_6$, $R_3$ and $R_9$ are as defined hereinabove, said process comprising the steps of:

(i) protecting the $NH_2$ group in a compound of formula (VII) with a suitable protecting group, PG, to give a compound of formula (VIII);

(ii) converting the compound of formula (VIII) to a compound of formula (IX) by treating said compound of formula (VIII) with $Cs_2CO_3$ and Z-L-OH in a solvent;

(iii) removing the protecting group PG from said compound of formula (IX) to give a compound of formula (X);

(iv) treating the compound of formula (X) with trimethoxymethane, $NaN_3$ and HOAc to form a compound of formula (XI);

(v) reducing said compound of formula (XI) to form a compound of formula (XII);

(vi) treating the compound of formula (XII) with a compound of formula (V) to form a compound of formula (XIII); and (vii) hydrolysing said compound of formula (XIII) to form a compound of formula (I).

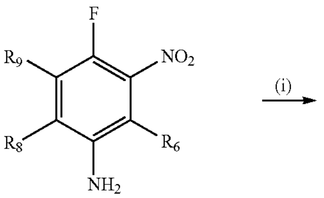

VII

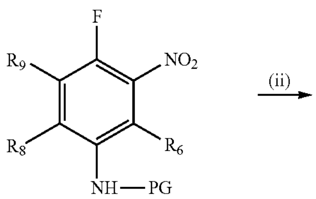

VIII

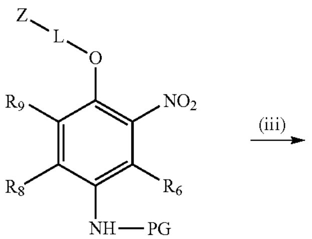

IX

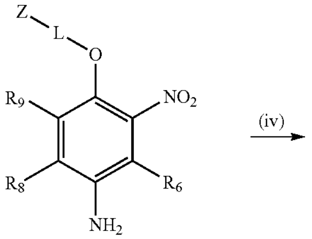

X

-continued

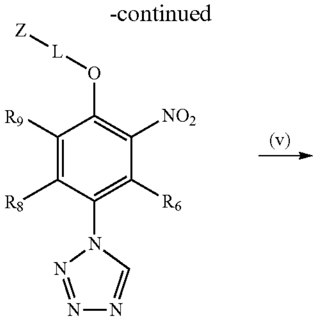

XI

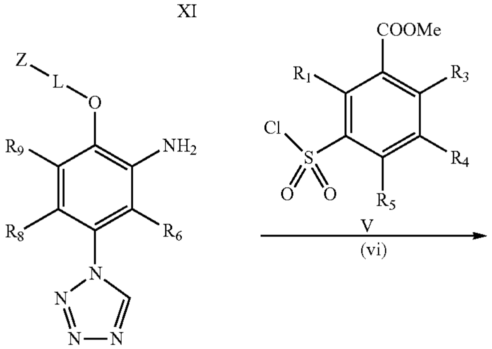

XII

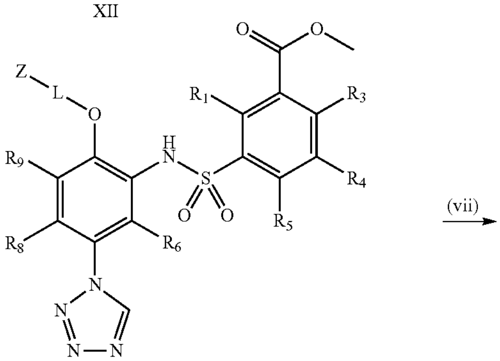

XIII

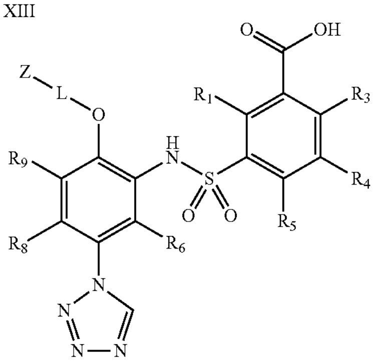
I

Preferably, the protecting group, PG, is Boc. The skilled person would understand that other amine protecting groups would also be suitable (see Green T., "Protective Groups in Organic Synthesis", Chapter 1, J. Wiley & Sons, Inc., 1991, 10-142). More preferably, step (i) comprises treating the compound of formula (VII) with $(Boc)_2O$, DMAP and TEA in DCM, at room temperature. Preferably, step (ii) comprises heating the compound of formula (VIII) with Fe, $NH_4Cl$ and $EtOH/H_2O$ (preferably v/v=4/1). Preferably, step (iii) comprises treating the compound of formula (IX) with an acid, more preferably, HCl in EtOAc. Preferably, step (iv) comprises heating the mixture of compound (X), trimethoxymethane, $NaN_3$ and HOAc to a temperature of at least 80° C. Preferably, step (v) comprises heating the compound of formula (XI) with Fe, $NH_4Cl$ and $EtOH/H_2O$ (preferably v/v=4/1). Preferably, step (vi) is carried out in the presence of pyridine and dichloromethane at room temperature. Preferably, the hydrolysis step (vii) is carried in the presence of LiOH in THF at room temperature.

Preferred conditions for each step are set out hereinafter in Scheme 2 and in the accompanying examples.

The present invention is further described by way of the following non-limiting examples.

EXAMPLES

Where the preparation of starting materials is not described, these are commercially available, known in the literature, or readily obtainable by those skilled in the art using standard procedures. Where it is indicated that compounds were prepared analogously to earlier examples or intermediates, it will be appreciated by the skilled person that the reaction time, number of equivalents of reagents, solvent, concentration and temperature can be modified for each specific reaction and that it may be necessary or desirable to employ different work-up or purification techniques.

Abbreviations

AcOH: acetic acid; Chloroform-d (deuterated chloroform); ca.: circa; DMSO-$d_6$ (deuterated dimethylsulfoxide); Methanol-$d_4$ (deuterated methanol); Boc (tert-butoxycarbonyl); $Boc_2O$ (di-tert-butyl dicarbonate); DMF (N,N-dimethylformamide); DCM (dichloromethane); PE (petroleum ether); ESI (electrospray atmospheric pressure ionization); IPA, isopropanol; TEA (triethylamine); TFA (trifluoroacetic acid); dioxane (1,4-dioxane); THF (tetrahydrofuran); EtOH (ethanol); $H_2O$ (water); MeCN (Acetonitrile); EtOAc (ethyl acetate); g (gram); h (hour); nm (nanometer); $^1H$ NMR (proton nuclear magnetic resonance); Hz (hertz); LC-MS (liquid chromatography-mass spectrometry); MS (mass spectrometry); mg (milligrams); MHz (megahertz); min (minutes); mL (millilitres), mmol (millimoles); ppm (parts per million); Rt (retention time); RT (room temperature); TLC (thin layer chromatography); v/v (volume/volume); m/z (mass charge ratio); HCl (hydrochloric acid); $K_3PO_4$ (potassium phosphate tribasic); HOAc (acetic acid); HCl (hydrochloric acid); CuCl (Copper(I) chloride); $SOCl_2$ (thionyl chloride); $Cs_2CO_3$ (cesium carbonate); $NH_4Cl$ (ammonium chloride); Fe (Iron); DIPEA (N,N-diisopropylethylamine); MW (microwave); $Pd(dppf)Cl_2$ ([1,1'Bis (diphenylphosphino)ferrocene]dichloropalladium); Xphos Pd G3: (2-Dicyclohexylphosphino-2,4,6-triisopropyl-1, 1-biphenyl)[2-(2-amino-1, 1-biphenyl)]palladium(II) methanesulfonate (CAS: 1445085-55-1); Pd-174: allyl(2-di-tert-butylphosphino-2,4,6-triisopropyl-1,1'-biphenyl)palladium (II) triflate (CAS: 1798782-25-8); $PdCl_2(AmPhos)_2$: bis(di-tert-butyl(4-dimethylaminophenyl)phosphine) dichloropalladium(II) (CAS: 887919-35-9); dppf: 1,1-ferrocenediyl-bis(diphenylphosphine); NaH (sodium hydride); DMAP (4-Dimethylaminopyridine); $NaN_3$ (Sodium azide); LiOH (Lithium hydroxide); $NH_2$—$NH_2$ (Hydrazinium hydroxide solution); DEA (diethylamine); DAST (diethylaminosulfur trifluoride); Pd/C (Palladium on carbon); NBS (N-Bromosuccinimide); PE (petroleum ether). Aq (aqueous); LC: liquid chromatography; HPLC: high performance liquid chromatography; M: molar, molecular ion; UV: ultraviolet; UPLC: ultra performance liquid chromatography. br: broad; d: doublet; ESI: electrospray ionisation; m: multiplet; MeOH: methanol; min: minutes; PDA: photodiode array; q: quartet; s: singlet, solid; t: triplet; TBME: tert-butyl methyl ether. Other abbreviations are intended to convey their generally accepted meaning.

General Schemes

Scheme 1

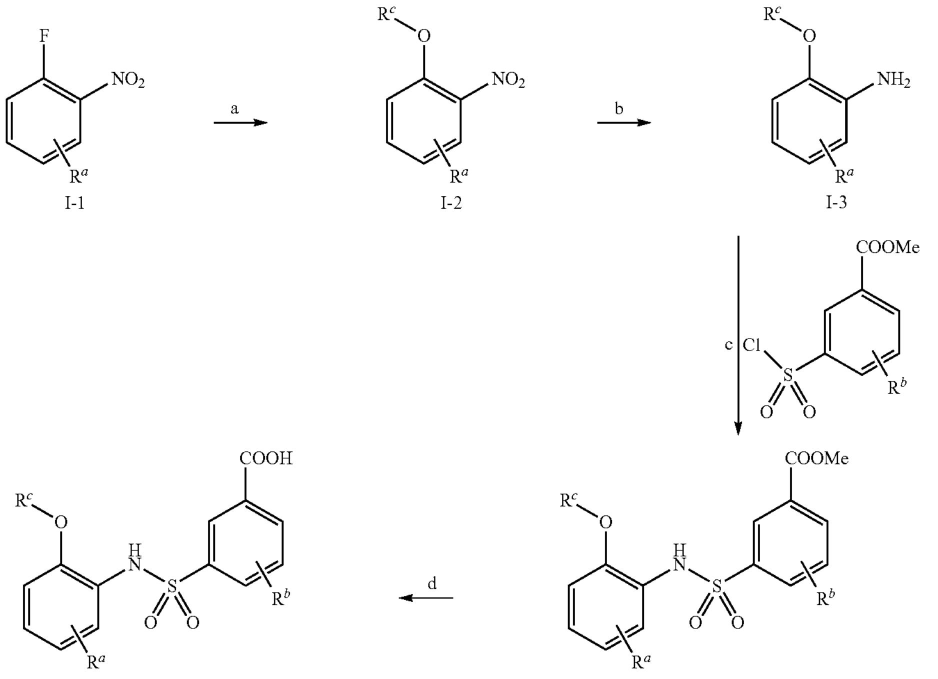

Reagents: (a) $Cs_2CO_3$, MeCN, RT; (b) Fe, $NH_4Cl$, $EtOH/H_2O$ (v/v = 4/1), 80° C.; (c) Pyridine, DCM, RT; (d) LiOH, THF, RT.

Scheme 2

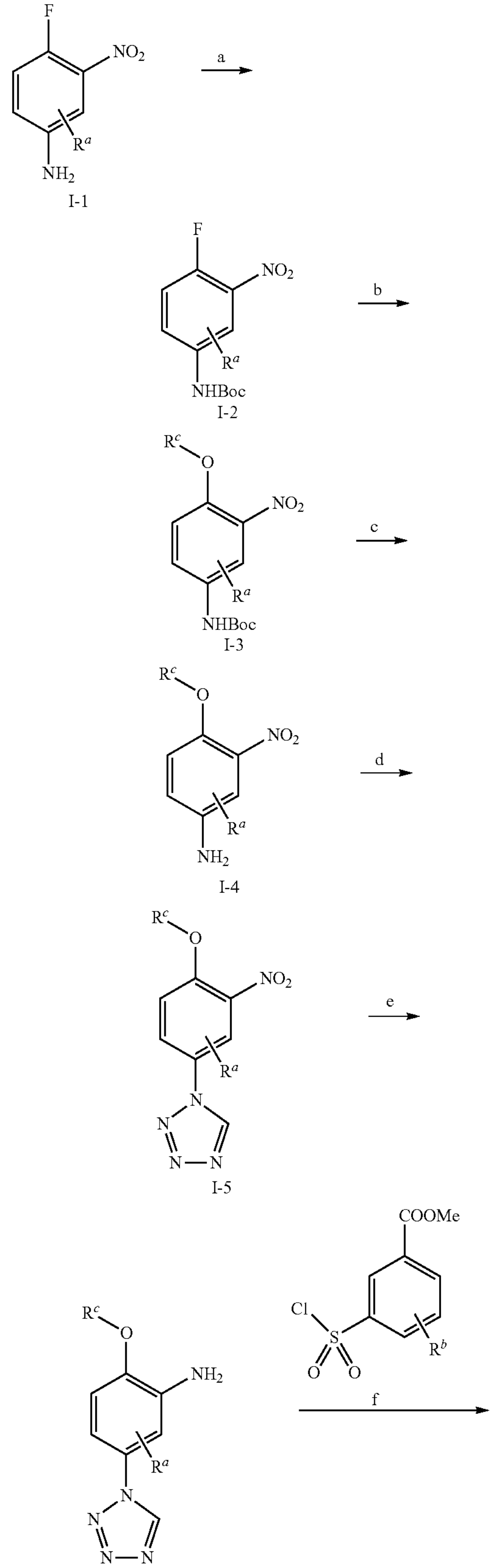

I-1
I-2
I-3
I-4
I-5
I-6

-continued

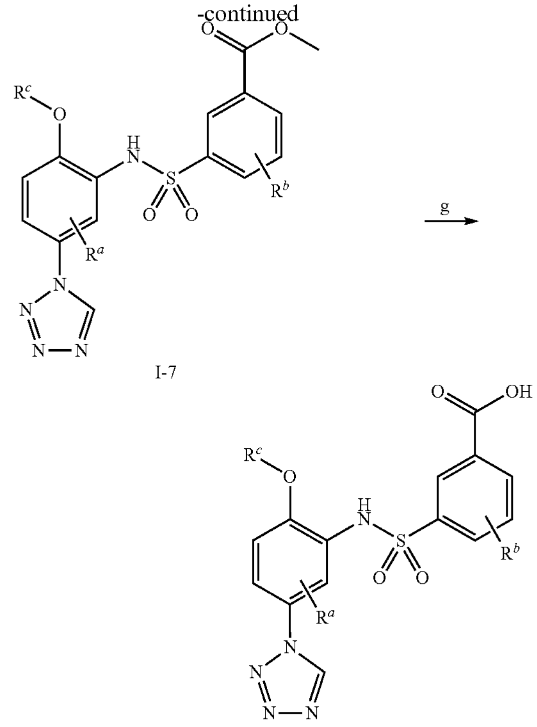

I-7

Reagents: (a) $(Boc)_2O$, DMAP, TEA, DCM, RT; (b) $Cs_2CO_3$, MeCN, RT; (c) HCl 4 mol/L in EtOAc, RT; (d) Trimethoxymethane, $NaN_3$, HOAc, 80° C.; (e) Fe, $NH_4Cl$, $EtOH/H_2O$ (v/v = 4/1), 80° C.; (f) Pyridine, DCM, RT; (g) LiOH (aq), THF, RT.

General Experimental Conditions

All starting materials and solvents were obtained either from commercial sources or prepared according to the literature citation. Reaction mixtures were magnetically stirred and reactions performed at room temperature (ca. 20° C.) unless otherwise indicated. Column chromatography was performed on an automated flash chromatography system, such as a Biotage Isolera Rf system, using pre-packed silica (40 μm) cartridges, unless otherwise indicated. $^1H$ NMR spectra were recorded using a Bruker AVANCE 400 MHz spectrometer. Data for $^1H$ are reported as chemical shift (ppm) and multiplicity (s=singlet, d=doublet, t=triplet, q=quartet, m=multiplet). Chemical shifts are expressed in parts per million using either the central peaks of the residual protic solvent or an internal standard of tetramethylsilane as references. The spectra were recorded at 298 K unless otherwise indicated.

Analytical UPLC-MS experiments to determine retention times and associated mass ions were performed using a Waters ACQUITY UPLC® H-Class system, equipped with ACQUITY PDA Detector and ACQUITY QDa Mass Detector, running one of the analytical methods described below. Analytical LC-MS experiments to determine retention times and associated mass ions were performed using an Agilent 1200 series HPLC system coupled to an Agilent 1956, 6100 or 6120 series single quadrupole mass spectrometer running one of the analytical methods described below.

Preparative HPLC Generic Methods:

HPLC Instruments: Shimadzu 20AP UV detector: SPD-20A. UV wavelength: 214 nm and 254 nm.

Conditions 1: Mobile phase A: water; Mobile phase B: acetonitrile.

Conditions 2: Mobile phase A: water with 0.1% trifluoroacetic acid; Mobile phase B: acetonitrile.

Conditions 3: Mobile phase A: water with 0.1% formic acid; Mobile phase B: acetonitrile.

Conditions 4: Mobile phase A: water with 0.1% ammonium hydroxide; Mobile phase B: acetonitrile.

Column: Agilent 10 Prep-C18 250×21.2 mm. Column temperature: Ambient LC gradient: 20% to 85% in 20 min; then 85% to 100% in 0.01 min; then hold 100% for 5 min; then 100% to 20% in 0.01 min; hold at 20% for 5 min.

LC Flow rate: 20 mL/min binary pump.

Nomenclature of structures was generated using 'Structure to Name' conversion from ChemDraw® Professional 17 (PerkinElmer).

Analytical Methods as Follows:

Method 1—Acidic Method (Shimadzu 3 Min)

Column: Shimadzu LC-20AD series, Binary Pump, Diode Array Detector. Agilent Poroshell 120 EC-C18, 2.7 μm, 4.6×50 mm column Detection: 2020, Quadrupole LC/MS, Ion Source: API-ESI, TIC: 100~900 m/z, Drying gas flow: 15 L/min, Nebulizer pressure: 1.5 L/min, Drying gas temperature: 250° C., Vcap: 4500V. Samples were dissolved in methanol at 1~10 μg/mL, then filtered through a 0.22 μm filter membrane. Injection volume: 1~10 μL. Detector: 214 nm, 254 nm. Detection wavelength: 214 nm, 254 nm.

Solvents: A: 0.05% v/v Formic acid in water, B: 0.05% v/v Formic acid in MeCN

Gradient:

| T (min) | A (%) | B (%) | Flow rate (mL/min) |
|---|---|---|---|
| 0.00 | 80 | 15 | 1.5 |
| 0.28 | 80 | 15 | 1.5 |
| 2.38 | 10 | 90 | 1.5 |
| 2.39 | 0 | 100 | 1.5 |
| 2.69 | 0 | 100 | 1.5 |
| 2.70 | 85 | 15 | 1.5 |
| 3.00 | 85 | 15 | 1.5 |

Method 2—Acidic 5 Min Method (Shimadzu 5 Min)

Column: Shimadzu LC-20AD series, Binary Pump, Diode Array Detector. Agilent Poroshell 120 EC-C18, 2.7 μm, 4.6×50 mm column.

Detection: 2020, Quadrupole LC/MS, Ion Source: API-ESI, TIC: 100~900 m/z, Drying gas flow: 15 L/min, Nebulizer pressure: 1.5 L/min, Drying gas temperature: 250° C., Vcap: 4500V. Samples were dissolved in methanol at 1~10 μg/mL, then filtered through a 0.22 μm filter membrane. Injection volume: 1~10 μL. Detection wavelength: 214 nm, 254 nm.

Solvents: A: 0.05% formic acid in water (v/v), B: 0.05% formic acid in MeCN (v/v).

Gradient:

| T (min) | A (%) | B (%) | Flow rate (mL/min) |
|---|---|---|---|
| 0.00 | 80 | 15 | 1.0 |
| 0.50 | 80 | 15 | 1.0 |
| 4.00 | 15 | 85 | 1.0 |
| 4.01 | 0 | 100 | 1.0 |
| 4.50 | 0 | 100 | 1.0 |
| 4.51 | 85 | 15 | 1.0 |
| 5.00 | 85 | 15 | 1.0 |

Method 3—Acidic Method (Waters QDa 3 Min)

Column: Waters QDa, Binary Pump, Diode Array Detector. Waters CORTECS UPLC, C18, 1.6 μm, 2.1×50 mm column.

Detection: QDa, Quadrupole LC/MS, Ion Source: API-ES, TIC: 70~900 m/z,

Fragmentor: 70, Drying gas flow: 12 L/min, Nebulizer pressure: 36 psi, Drying gas temperature: 350° C., Vcap: 3000V. Samples were dissolved in methanol at 1~10 μg/mL, then filtered through a 0.22 μm filter membrane. Injection volume: 1~10 μL.

Detector: 214 nm, 254 nm.

Solvents: A: 0.05% Formate in water (v/v), B: 0.05% Formate in MeCN (v/v).

Gradient:

| T (min) | A (%) | B (%) | Flow rate (mL/min) |
|---|---|---|---|
| 0.00 | 80 | 20 | 0.6 |
| 1.80 | 20 | 80 | 0.6 |
| 2.65 | 20 | 80 | 0.6 |
| 2.80 | 80 | 20 | 0.6 |
| 3.00 | 80 | 20 | 0.6 |

Method 4—Acidic 3 Min Method

Column: Waters ACQUITY UPLC® CSH C18, 1.7 μm, 2.1×30 mm at 40° C.

Detection: UV PDA 210-400 nm, purity at 254 nm, ACQUITY QDa® ESI

Solvents: A: 0.1% v/v Formic acid in water, B: MeCN

Gradient:

| Time | % A | % B | Flow rate (ml/min) |
|---|---|---|---|
| 0.00 | 98 | 2 | 0.77 |
| 2.50 | 0 | 100 | 0.77 |
| 3.00 | 0 | 100 | 0.77 |

Method 5—Acidic 4 Min Method

Column: YMC TRI ART C18, 1.6 μm, 2.1×50 mm

Detection: UV PDA 210-400 nm, purity at 254 nm, ACQUITY QDa® ESI

Solvents: A: 0.1% v/v Formic acid in water, B: MeCN

Gradient:

| Time | % A | % B | Flow rate (mL/min) |
|---|---|---|---|
| 0.00 | 97 | 3 | 0.8 |
| 0.2 | 97 | 3 | 0.8 |
| 2.70 | 2 | 98 | 0.8 |
| 3.00 | 0 | 100 | 1.0 |
| 3.50 | 0 | 100 | 1.0 |
| 3.51 | 97 | 3 | 0.80 |
| 4.00 | 97 | 3 | 0.80 |

Compound Synthesis: The compounds of the invention may be prepared by methods well known to those skilled in the art, as described in the general synthetic schemes and using the appropriate Intermediates.

Intermediate 1. Methyl 3-(chlorosulfonyl)-4-methoxybenzoate

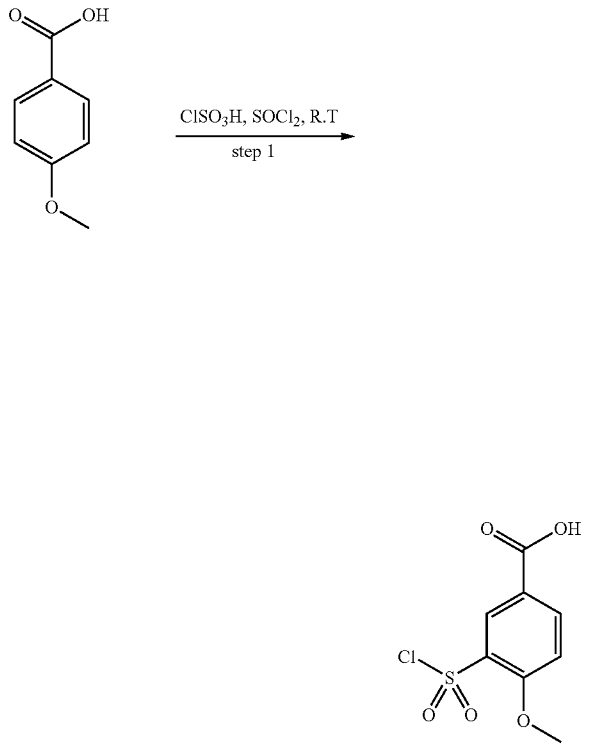

intermediate 1

Step 1: methyl 3-(chlorosulfonyl)-4-methoxybenzoate: A mixture of 4-methoxybenzoic acid (5.0 g, 32.9 mmol) and chlorosulfonic acid (9.5 g, 82.3 mmol) in $SOCl_2$ (30 mL) was stirred at R.T for 12 h. The reaction mixture was concentrated to give crude product. The crude product was purified by silica gel chromatography (eluting with 1/2 EtOAc/PE) to afford the title compound (5.34 g, 21.36 mmol, 65%) as a white solid. $^1H$ NMR (400 MHz, DMSO-$d_6$) δ 11.15 (s, 1H), 8.29 (d, J=2.3 Hz, 1H), 7.91 (dd, J=8.6, 2.3 Hz, 1H), 7.08 (d, J=8.7 Hz, 1H), 3.83 (s, 3H).

Intermediate 2. 3-(chlorosulfonyl)-4-ethylbenzoic acid

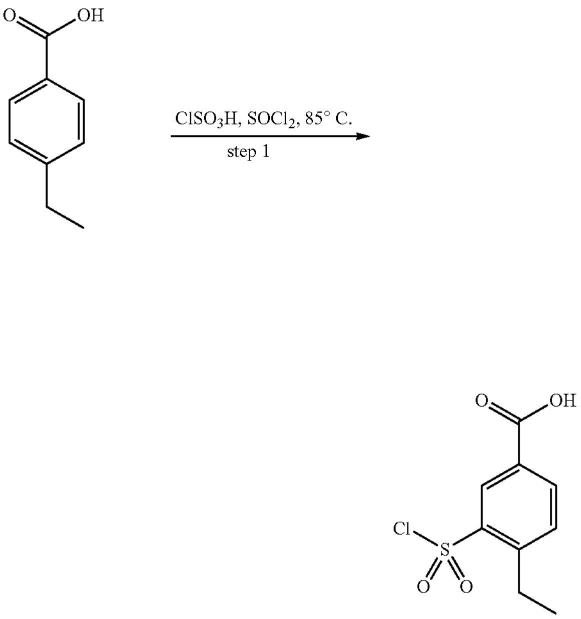

intermediate 2

Step 1: 3-(chlorosulfonyl)-4-ethylbenzoic acid: A mixture of 4-ethylbenzoic acid (4.5 g, 30.0 mmol) and chlorosulfonic acid (8.77 g, 75.0 mmol) in $SOCl_2$ (45 mL) was heated at 85° C. for 12 h. After cooling to room temperature, the reaction mixture was concentrated to give crude product. The crude product was purified by silica gel chromatography (eluting with 1/3 EtOAc/PE) to afford the title compound (2.2 g, 8.87 mmol, 30%) as a yellow solid. $^1H$ NMR (400 MHz, DMSO-$d_6$) δ 13.38 (s, 1H), 8.36 (d, J=1.9 Hz, 1H), 7.84 (dd, J=7.9, 2.0 Hz, 1H), 7.33 (d, J=7.9 Hz, 1H), 3.09 (q, J=7.5 Hz, 2H), 1.20 (t, J=7.5 Hz, 3H).

Intermediate 3. Methyl 3-(chlorosulfonyl)-4-cyclopropylbenzoate

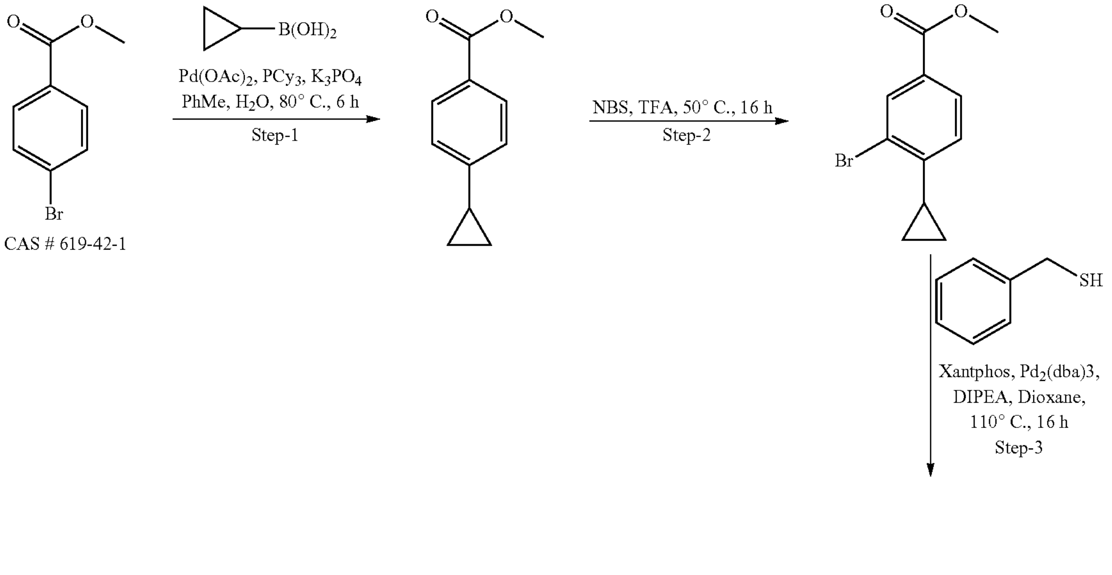

-continued

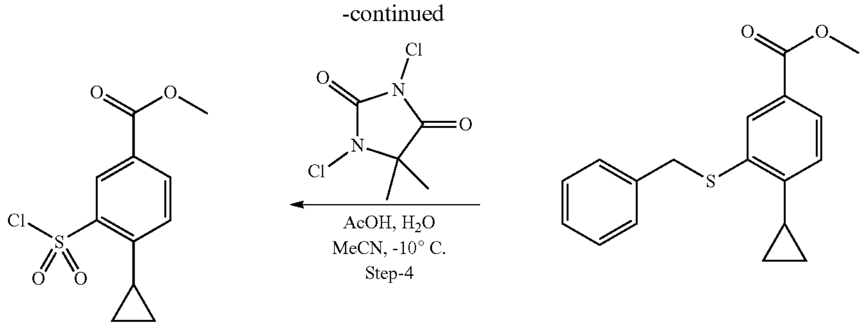

intermediate 3

Step 1: Methyl 4-cyclopropylbenzoate: To a solution of methyl 4-bromobenzoate (200 g, 934 mmol) in toluene (1800 ml) and water (400 ml) were added cyclopropylboronic acid (120.56 g, 1401 mmol), $K_3PO_4$ (396.2 g, 1869 mmol) and tricyclohexylphosphine (26.16 g, 93.4 mmol) at room temperature. The mixture was purged with $N_2$ for 45 min, then palladium (II) acetate (10.46 g, 46.7 mmol) was added. The mixture was heated at 80° C. for 6 h.* Reaction mixture was cooled to room temperature, filtered through a celite bed, washed with water (4.0 Lit.) and EtOAc (2x5.0 L). The combined organic layer was washed with water (5 L), dried over $Na_2SO_4$ and concentrated under reduce pressure to give 1201 g of crude material which was suspended in n-hexane (8 L) and stirred for 3 h at 0° C. The mixture was filtered through by celite and concentrated under reduce pressure to yielding title ester (800 g, 4545 mmol, quantitative, 98% purity) as a brown oil used directly in the next step.

* A total 5 parallel reactions (at 2x100 g and 3x200 g scale) were conducted and combined for work up. $^1H$ NMR (400 MHz, DMSO) δ 7.83-7.81 (d, J=8.0 Hz, 2H), 7.20-7.18 (d, J=8.4 Hz, 2H), 3.85 (s, 3H), 2.03-1.96 (m, 1H), 1.06-1.01 (m, 2H), 0.77-0.74 (m, 2H).

Step 2: Methyl 3-bromo-4-cyclopropylbenzoate: To a solution of step 1 ester (250 g, 1420 mmol) in TFA (3000 ml) was added portion wise NBS (252.8 g, 1420 mmol) at room temperature. Reaction mixture was heated at 50° C. for 16 h.* The mixture was cooled at room temperature and diluted with ice water (5.0 L) and extracted with n-hexane (2x5.0 L). The combined organic layer was washed with sat. $Na_2CO_3$ solution (2 L) followed by brine solution (2 L), dried over $Na_2SO_4$ and concentrated under reduce pressure. The crude material was purified by normal phase chromatography on silica gel (0-50% DCM in hexane) to give title ester (443 g, 1744 mmol, 39%, 95.7% purity) as an oil.

* A total 4 parallel reactions (at 1x100 g, 1x200 g and 2x250 g scale) were conducted and combined for work up. $^1H$ NMR (400 MHz, DMSO) δ 8.06 (s, 1H), 7.83 (d, J=8.0 Hz, 1H), 7.12 (d, J=8.4 Hz, 1H), 3.87 (s, 3H), 2.22 (m, 1H), 1.12-1.07 (m, 2H), 0.81-0.77 (m, 2H).

Step 3: Methyl 3-(benzylthio)-4-cyclopropylbenzoate: To a solution of step 2 ester (100 g, 393 mmol) in 1,4-dioxane (1400 ml) were added Xantphos (11.39 g, 19.6 mmol) and $Pd_2(dba)_3$ (9.01 g, 9.8 mmol) at room temperature. The reaction mixture was purged with $N_2$ for 30 min. DIPEA (145.1 ml, 787 mmol) and benzyl mercaptan (51.34 g, 413 mmol) were added and the reaction mixture was heated to 110° C. for 16 h.* The reaction mixture was cooled to room temperature, filtered through celite bed, the bed washed with hexane (3.0 L) and the combined organic filtrate was washed with distilled water (5.0 L). The combined organic layer was dried over $Na_2SO_4$, filtered and concentrated under reduce pressure. The crude product was purified by normal phase chromatography on silica gel (0-40% DCM in hexane) to yield title mercapto ether (425 g, 1429 mmol, 84%, 97% purity) as a yellow solid.

* A total 4 parallel reactions (at 1x100 g and 3x110 g scale) were conducted and combined for work up. LCMS: 3.11 min, MS: ES+ 299.53 (M+1); $^1H$ NMR (400 MHz, DMSO) δ 7.86 (s, 1H), 7.68 (d, J=8 Hz, 1H), 7.38 (m, 5H), 7.05 (d, J=8.0 Hz, 1H), 4.26 (s, 2H), 3.82 (s, 3H), 2.18 (m, 1H), 1.03 (m, 2H), 0.72 (m, 2H).

Step 4: Methyl 3-(chlorosulfonyl)-4-cyclopropylbenzoate: To a stirred solution of Step 3 mercapto ether (142 g, 184 mmol) in mixture of AcOH (114.3 ml), water (68.8 ml) and MeCN (3124 ml) was added 1,3-dichloro-5,5-dimethylhydantoin (187.6 g, 952 mmol) at 0° C. in one portion. The mixture was stirred at same temperature for 0.5 h. The reaction mixture was diluted with distilled water (10 L) and extracted with EtOAc (2x5.0 L). The combined organic layer was washed with distilled water (2x5.0), dried over $Na_2SO_4$, filtered and concentrated under reduce pressure. The crude product was purified by normal phase column chromatography on silica gel using 6-10% EtOAc in Hexane followed by trituration with n-hexane to yielding title sulfonylchloride (260 g, 970 mmol, 68%, 98% purity) as white crystalline solid.

* A total 3 parallel reactions (at 142 g scale) were conducted and combined for work up. LCMS: 2.480 min, MS: ES+ 275.1 (M+1); $^1H$ NMR (400 MHz, DMSO) δ 11.81 (br, 3H), 8.35 (s, 1H), 7.77 (d, J=8.0 Hz, 1H), 6.84 (d, J=8.4 Hz, 1H), 3.83 (s, 3H), 3.14 (m, 1H), 1.03 (d, J=6.8 Hz, 2H), 0.75 (d, J=4.4 Hz, 2H).

Intermediate 4. Methyl 5-(chlorosulfonyl)-4-cyclopropyl-2-fluorobenzoate

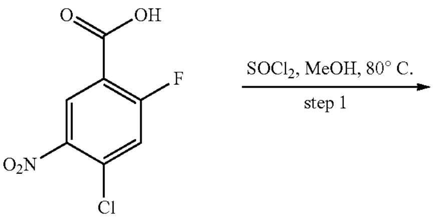

-continued

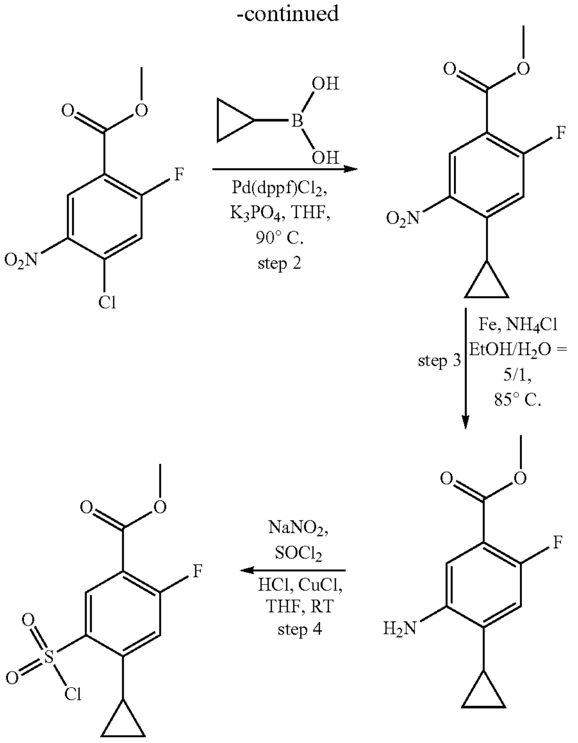

intermediate 4

Step 1: Methyl 4-chloro-2-fluoro-5-nitrobenzoate: To a solution of 4-chloro-2-fluoro-5-nitrobenzoic acid (10.0 g, 45.6 mmol) in MeOH (200 mL) at 0° C. was added $SOCl_2$ (30 mL). The resulting mixture was heated at reflux overnight. The solvent was removed under reduced pressure and the residue dissolved in EtOAc and washed with saturated $Na_2CO_3$, water and brine. The organic layer was dried over $Na_2SO_4$ and concentrated to give crude product. The crude product was purified by silica gel chromatography (eluting with 1/10 EtOAc/PE) to afford the title compound (9.82 g, 42.1 mmol, 92%) as an off-white solid. $^1H$ NMR (400 MHz, DMSO-$d_6$) δ 8.59 (d, J=6.9 Hz, 1H), 8.06 (d, J=10.2 Hz, 1H), 3.94 (s, 3H).

Step 2: Methyl 4-cyclopropyl-2-fluoro-5-nitrobenzoate: A mixture of Step 1 ester (6.0 g, 25.8 mmol), cyclopropylboronic acid (6.60 g, 77.4 mmol), $K_3PO_4$ (10.92 g, 51.6 mmol) and Pd(dppf)$Cl_2$ (1.92 g, 2.58 mmol) in THF (50 mL) was heated at 90° C. in a sealed tube for 16 h. The resulting mixture was filtered through celite, concentrated and purified by silica gel chromatography (eluting with 1/5 EtOAc/PE) to afford the title compound (5.4 g, 22.6 mmol, 88%) as an off-white solid. 1H NMR (400 MHz, DMSO-$d_6$) δ 8.42 (d, J=6.8 Hz, 1H), 7.27 (d, J=12.1 Hz, 1H), 3.93 (s, 3H), 2.46-2.34 (m, 1H), 1.25-1.12 (m, 2H), 1.08-0.94 (m, 2H).

Step 3: Methyl 5-amino-4-cyclopropyl-2-fluorobenzoate: A mixture of Step 2 ester (1.0 g, 4.2 mmol), iron powder (1.17 g, 21.0 mmol) and $NH_4Cl$ (0.45 g, 8.4 mmol) in a mixture of ethanol and water (5:1) was heated at 85° C. for 2 h. The resulting mixture was filtered through celite, concentrated to afford the title compound (0.85 g, 4.1 mmol, 98%) as a grey solid. UPLC-MS (Method 1) m/z 210.10 $(M+H)^+$ at 1.32 min.

Step 4: Methyl 5-(chlorosulfonyl)-4-cyclopropyl-2-fluorobenzoate: To a solution of methyl 5-amino-4-cyclopropyl-2-fluorobenzoate (0.85 g, 4.1 mmol) in a mixture of concentrated HCl (3 mL) and $H_2O$ (9.0 mL) at 0° C. was added $NaNO_2$ (0.56 g, 8.2 mmol) portionwise. The mixture was stirred at 0° C. for 30 min. To a solution of CuCl (40.8 mg, 0.41 mmol) in $H_2O$ (3 mL) at 0° C. was added dropwise $SOCl_2$ (1.75 mL). This solution was then added dropwise to the above reaction and the mixture stirred at 0° C. for 1 h. The reaction was diluted with EtOAc (50 mL) and $H_2O$ (50 mL), and the aqueous layer extracted with EtOAc (50 mL×2). The organic layer was dried over $Na_2SO_4$ and concentrated to afford the title compound (0.65 g, 2.2 mmol, 54%) as a yellow oil. $^1H$ NMR (400 MHz, DMSO-$d_6$) 8.29 (d, J=8.1 Hz, 2H), 6.64 (d, J=13.0 Hz, 2H), 3.92-3.82 (m, 1H), 3.82 (s, 3H), 1.14-0.98 (m, 2H), 0.90-0.71 (m, 2H).

Intermediate 5. Methyl 5-(chlorosulfonyl)-4-cyclopropyl-3-fluorobenzoate

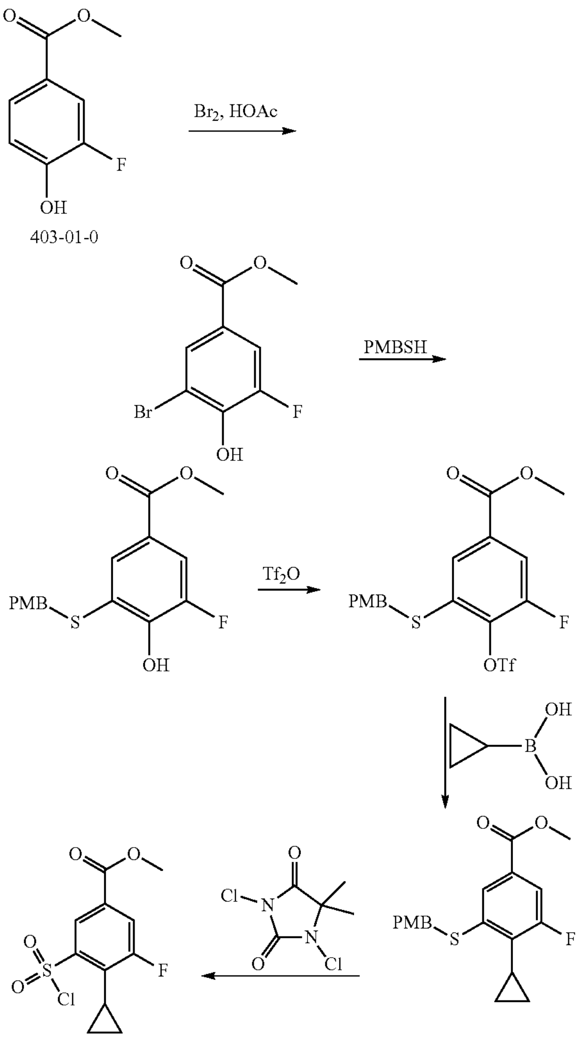

intermediate 5

Step 1: Methyl 3-bromo-5-fluoro-4-hydroxybenzoate: To a solution of methyl 3-fluoro-4-hydroxybenzoate (5.0 g, 29.4 mmol) in HOAc (50 mL) at 0° C. was added $Br_2$ (4.64 g, 29.4 mmol). The resulting mixture was stirred at room temperature for 4 h. The solvent was removed under reduced pressure and the residue dissolved in EtOAc and washed with saturated $Na_2CO_3$, water and brine. The organic layer was dried over $Na_2SO_4$ and concentrated to give crude product. The crude product was purified by silica gel chromatography (eluting with 1/3 EtOAc/PE) to afford the title compound (5.8 g, 23.4 mmol, 80%) as a yellow solid. UPLC-MS (Method 1) m/z 248.95 $(M-H)^-$ at 1.516 min. $^1H$ NMR (400 MHz, DMSO-$d_6$) δ 11.38 (s, 1H), 7.89 (t, J=1.7 Hz, 1H), 7.69 (dd, J=10.9, 2.0 Hz, 1H), 3.85 (s, 3H).

Step 2: Methyl 3-fluoro-4-hydroxy-5-((4-methoxybenzyl)thio)benzoate: A mixture of methyl 3-bromo-5-fluoro-4-hydroxybenzoate (5.8 g, 23.4 mmol), (4-methoxyphenyl)methanethiol (7.2 g, 46.8 mmol), DIPEA (6.0 g, 46.8 mmol), Xantphos (2.7 g, 4.68 mmol) and $Pd_2(dba)_3$ (2.14 g, 2.34 mmol) in dioxane (50 mL) was heated at 110° C. for 16 h. The resulting mixture was filtered through celite, concentrated and purified by silica gel chromatography (eluting with 1/10 EtOAc/PE) to afford the title compound (2.85 g, 8.85 mmol, 38%) as a white solid. UPLC-MS (Method 3) m/z 321.0 $(M-H)^-$ at 1.654 min.

Step 3: Methyl 3-fluoro-5-((4-methoxybenzyl)thio)-4-(((trifluoromethyl)sulfonyl)oxy) benzoate: To a solution of methyl 3-fluoro-4-hydroxy-5-((4-methoxybenzyl)thio)benzoate (2.85 g, 8.85 mmol) in DCM (50 mL) at 0° C. was added $Tf_2O$ (4.99 g, 17.7 mmol). Pyridine (1.39 g, 17.7 mmol) was added and the resulting mixture stirred at room temperature for 1 h. The solvent was removed under reduced pressure and the residue dissolved in EtOAc and washed with saturated $Na_2CO_3$, water and brine. The organic layer was dried over $Na_2SO_4$ and concentrated to give crude product. The crude product was purified by silica gel chromatography (eluting with 1/15 EtOAc/PE) to afford the title compound (1.43 g, 3.15 mmol, 36%) as a yellow oil. $^1H$ NMR (400 MHz, DMSO-$d_6$) δ 7.72-7.46 (m, 3H), 7.32-7.24 (m, 2H), 6.94-6.83 (m, 2H), 4.17 (s, 2H), 3.86 (s, 3H), 3.78 (s, 3H).

Step 4: Methyl 4-cyclopropyl-3-fluoro-5-((4-methoxybenzyl)thio)benzoate: A mixture of methyl 3-fluoro-5-((4-methoxybenzyl)thio)-4-(((trifluoromethyl)sulfonyl)-oxy) benzoate (1.2 g, 2.64 mmol), cyclopropylboronic acid (0.45 g, 5.28 mmol), $K_2CO_3$ (1.09 g, 7.92 mmol), and $Pd(PPh_3)_4$ (0.3 g, 0.26 mmol) in dioxane (30 mL) was heated at 100° C. for 16 h. The resulting mixture was filtered through celite, concentrated and purified by silica gel chromatography (eluting with 1/10 EtOAc/PE) to afford the title compound (0.52 g, 1.5 mmol, 57%) as a white solid. $^1H$ NMR (400 MHz, DMSO-$d_6$) δ 7.73-7.51 (m, 1H), 7.45-7.30 (m, 1H), 7.23 (s, 2H), 6.98-6.86 (m, 2H), 4.29 (s, 2H), 3.87 (s, 3H), 3.76 (s, 3H), 2.12-1.97 (m, 1H), 1.09-0.99 (m, 2H), 0.84-0.75 (m, 2H).

Step 5: Methyl 3-(chlorosulfonyl)-4-cyclopropyl-5-fluorobenzoate: To a mixture of methyl 4-cyclopropyl-3-fluoro-5-((4-methoxybenzyl)thio)benzoate (0.52 g, 1.5 mmol), HOAc (0.1 g, 1.65 mmol) and $H_2O$ (0.189 g, 10.5 mmol) in MeCN (10 mL) at −5° C. was added 1,3-dichloro-5,5-dimethylimidazolidine-2,4-dione (0.44 g, 2.25 mmol) and the solution stirred at the same temperature for 1 h. The mixture was extracted with EtOAc (100 mL), dried over $Na_2SO_4$ and concentrated to give crude the title compound (0.41 g, 1.4 mmol, 93%) as a yellow oil. The crude product was used in the next step directly without further purification.

Intermediate 6. Preparation of 2-(cyclopentyloxy)-5-(5-methylisoxazol-4-yl)aniline

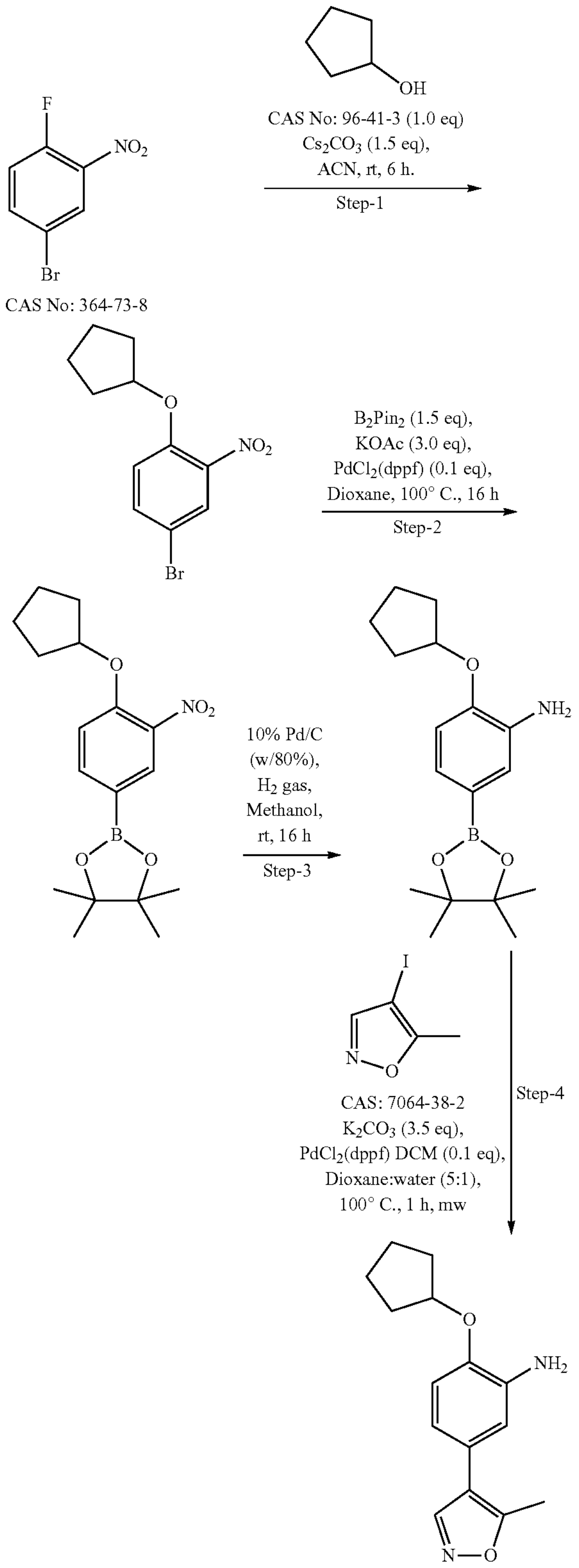

intermediate 6

Step 1: Synthesis of 4-bromo-1-(cyclopentyloxy)-2-nitrobenzene. Cyclopentanol (5.8 g, 68.18 mmol, 1.5 equiv) and $Cs_2CO_3$ (22.1 g, 68.68 mmol, 1.5 eq) were added to acetonitrile (100 mL) and stirred at room temperature. 4-bromo-1-fluoro-2-nitrobenzene (10.0 g, 45.45 mmol, 1.0 equiv) was added portion wise and the resulting reaction mixture was stirred at room temperature for 6 h. The reaction mixture was dilute with water (200 mL) and extracted with EtOAc (3×150 mL). The combined organic layer was dried over $Na_2SO_4$, filtered and concentrated under reduced pressure. The crude product was purified by column chromatography using 1% EtOAc in n-hexane to yield title compound (8.5 g, 65%) as a pale yellow liquid. $^1H$ NMR (400 MHz, DMSO-$d_6$): δ 1.58-1.62 (m, 3H), 1.63-1.72 (m, 3H), 1.87-1.98 (m, 2H), 5.02-5.05 (m, 1H), 7.33 (d, J=9.2 Hz, 1H), 7.77-7.79 (m, 1H), 8.07 (d, J=2.4 Hz, 1H).

Step 2: Synthesis of 2-(4-(cyclopentyloxy)-3-nitrophenyl)-4,4,5,5-tetramethyl-1,3,2-dioxaborolane. Step 1 bromide (4.0 g, 13.97 mmol, 1.0 equiv) and KOAc (4.1 g, 41.93 mmol, 3.0 equiv) were stirred in dioxane (40 mL) at room temperature. To this solution was portion wise added $B_2Pin_2$ (5.3 g, 20.95 mmol, 1.5 equiv) and resulting reaction mixture was purged under $N_2$ gas for 10 min. $PdCl_2$(dppf)DCM (1.1 g, 1.397 mmol, 0.1 equiv) was added and the reaction mixture was stirred at 90° C. for 16 h. The reaction mixture was filtered through a pad of celite and wash with EtOAc (100 mL). The filtrate was concentrated under reduced pressure and the crude material was purified by column chromatography using 5% EtOAc in n-hexane to give title dioxaborolane (3.0 g, 64%) as a light yellow liquid. $^1H$ NMR (400 MHz, DMSO-$d_6$): δ 1.31 (s, 12H), 1.57-1.59 (m, 2H), 1.59-1.73 (m, 4H), 1.90-1.95 (m, 2H), 5.07-5.09 (m, 1H), 7.36 (d, J=8.4 Hz, 1H), 7.83-7.86 (m, 1H), 7.98 (d, J=1.2 Hz, 1H).

Step 3: Synthesis of 2-(cyclopentyloxy)-5-(4,4,5,5-tetramethyl-1,3,2-dioxaborolan-2-yl)aniline. Step 2 dioxaborolane (3.0 g, 9.0 mmol, 1.0 equiv) was stirred in MeOH (40 mL) at room temperature. To this solution was added Pd/C (2.4 g, w/80%) and the resulting reaction mixture was purged under $H_2$ gas (hydrogen balloon) and stirred at room temperature for 16 h. The reaction mixture was filtered through a pad of celite and wash with EtOAc (100 mL). The filtrate was concentrated under reduced pressure yielding title aniline (2.6 g, 84%) as a light brown sticky liquid. LCMS [ESI, M+1]: 304.7. $^1H$ NMR (400 MHz, DMSO-$d_6$): δ 1.29 (s, 12H), 1.56-1.58 (m, 2H), 1.69-1.72 (m, 4H), 1.84-1.88 (m, 2H), 4.57 (s, 2H), 4.77-4.79 (t, J=5.6 Hz, 1H), 6.74 (d, J=8.0 Hz, 1H), 6.85-6.88 (m, 1H), 6.98 (d, J=1.2 Hz, 1H).

Step 4: Synthesis of 2-(cyclopentyloxy)-5-(5-methylisoxazol-4-yl)aniline. Step 3 aniline (0.2 g, 0.66 mmol, 1.0 equiv) and 4-iodo-5-methylisoxazole (0.17 g, 0.79 mmol, 1.2 equiv) were stirred in Dioxane:$H_2O$ (4:1) (12.5 mL) in a 30 mL microwave glass vial at room temperature. To this solution was added $K_2CO_3$ (0.3 g, 2.31 mmol, 3.5 equiv) and resulting reaction mixture was purged under $N_2$ gas for 10 min. $PdCl_2$(dppf)DCM (0.05 g, 0.06 mmol, 0.1 equiv) was added to the reaction mixture and sealed with cap. The resulting reaction mixture was heated under microwave at 100° C. for 1 h. Another 4 batches were prepared at an identical scale and the crude reaction mixtures combined for work up and purification. The reaction mixture was filtered through a pad of celite and washed with EtOAc (20 mL). The combined filtrate was dilute with water (25 mL) and extracted with EtOAc (3×25 mL). The combined organic layer was dried over $Na_2SO_4$, filtered and concentrated under reduced pressure. The crude product was purified by Flash chromatography using 15% EtOAc in n-hexane as mobile phase to give title aniline (0.25 g, 30%) as a light brown sticky liquid. LCMS [ESI, M+1]: 259.7. $^1H$ NMR (400 MHz, DMSO-$d_6$): δ 1.57 (s, 2H), 1.73 (s, 4H), 1.86-1.88 (d, 2H), 2.49 (s, 3H), 4.74 (s, 2H), 4.78 (s, 1H), 6.63 (d, J=2.0 Hz, 1H), 6.76 (d, J=1.6 Hz, 1H), 6.81 (d, J=8.0 Hz, 1H), 8.66 (s, 1H).

Intermediate 7. Preparation of 2-(cyclopentyloxy)-4-fluoro-5-(5-methylisoxazol-4-yl)aniline

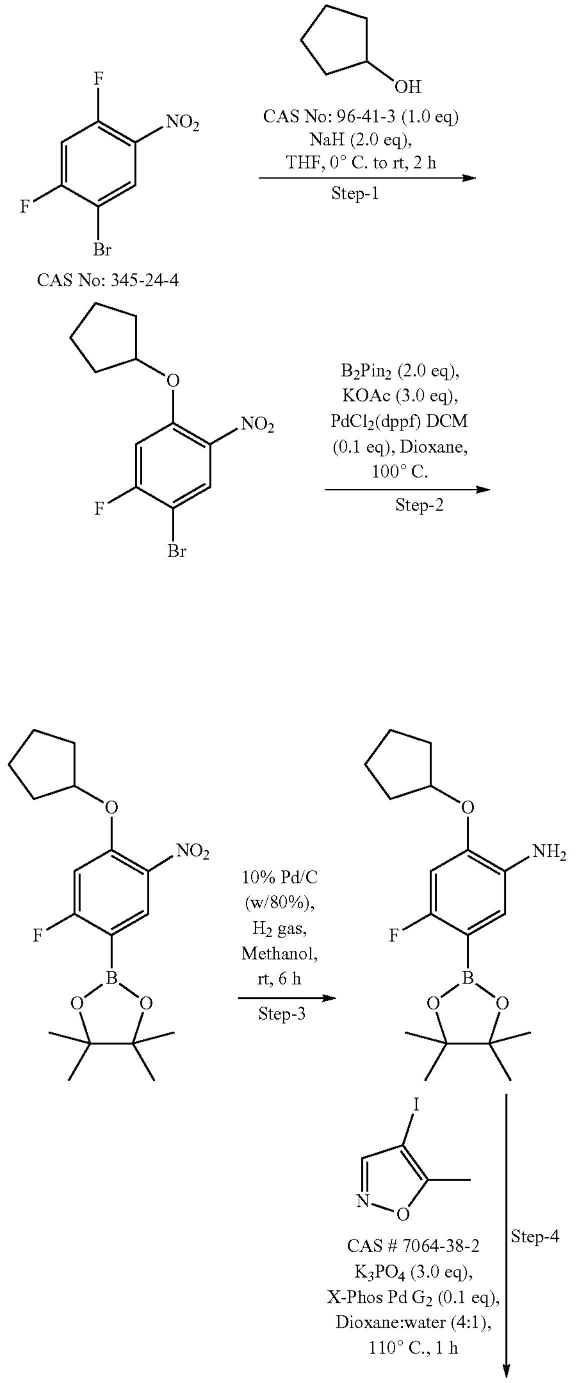

-continued

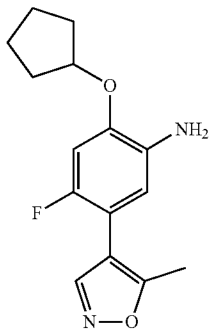

intermediate 7

Step 1: Synthesis of 1-bromo-4-(cyclopentyloxy)-2-fluoro-5-nitrobenzene. Cyclopentanol (4.3 g, 50.41 mmol, 1.0 equiv) and NaH (60%) (4.0 g, 100.82 mmol, 2.0 eq) were stirred in anhydrous THF (100 mL) at 0° C. To this solution was portion wise added 4-bromo-1-fluoro-2-nitrobenzene (10.0 g, 42.01 mmol, 1.0 equiv) at 0° C. and the resulting reaction mixture was slowly warmed and stirred at room temperature for 6 h. The reaction mixture was quenched with ice cold water (150 mL) and extracted with EtOAc (3x200 mL). The combined organic layer was dried over $Na_2SO_4$, filtered and concentrated under reduced pressure. The crude product was purified by column chromatography using 1% EtOAc in n-hexane to give title bromide (9.0 g, 70%) as a light yellow solid. LCMS [ESI, M+1]: 305.9. $^1$H NMR (400 MHz, DMSO-$d_6$): δ 1.56-1.75 (m, 6H), 1.89-1.93 (m, 2H), 5.06-5.09 (t, J=5.6 Hz, 1H), 7.54 (d, J=10.8 Hz, 1H), 8.31 (d, J=7.6 Hz, 1H).

Step 2: Synthesis of 2-(4-(cyclopentyloxy)-2-fluoro-5-nitrophenyl)-4,4,5,5-tetramethyl-1,3,2-dioxaborolane. Step 1 bromide (4.0 g, 13.15 mmol, 1.0 equiv) and KOAc (3.8 g, 39.45 mmol, 3.0 equiv) were stirred in dioxane (80 mL) at room temperature. To this solution was added $B_2Pin_2$ (6.0 g, 23.67 mmol, 1.8 equiv) and resulting reaction mixture was purged under $N_2$ gas for 10 min. $PdCl_2$(dppf)DCM (1.0 g, 1.315 mmol, 0.1 equiv) was the resulting reaction mixture was stirred at 100° C. for 5 h. The reaction mixture was filtered through a pad of celite and wash with EtOAc (100 mL) and the combined filtrate was concentrated under reduced pressure. The crude product was purified by column chromatography using 3% EtOAc in n-hexane to give title dioxaborolane (3.0 g, 65%) as a light brown sticky liquid. $^1$H NMR (400 MHz, DMSO-$d_6$): δ 1.29 (s, 12H), 1.59-1.61 (m, 2H), 1.64-1.75 (m, 4H), 1.91-1.96 (m, 2H), 5.10 (d, J=5.2 Hz, 1H), 7.23 (d, J=11.2 Hz, 1H), 8.07 (d, J=6.0 Hz, 1H).

Step 3: Synthesis of 2-(cyclopentyloxy)-4-fluoro-5-(4,4,5,5-tetramethyl-1,3,2-dioxaborolan-2-yl)aniline. Pd/C (2.4 g, w/80%) was added to a stirred solution of Step 2 dioxaborolane (3.0 g, 8.54 mmol, 1.0 equiv) in MeOH (60 mL) at room temperature. The resulting reaction mixture was purged under $H_2$ gas (balloon) and stirred for 6 h. The reaction mixture was filtered through a pad of celite and washed with MeOH (200 mL). The combined filtrate was concentrated under reduced pressure to give title aniline (2.5 g, 91%) as a light brown sticky liquid. LCMS [ESI, M+1]: 322.7. $^1$H NMR (400 MHz, DMSO-$d_6$): δ 1.25 (s, 12H), 1.56-1.58 (m, 2H), 1.71-1.72 (m, 4H), 1.89 (s, 2H), 4.66 (s, 2H), 4.80-4.82 (t, J=5.2 Hz, 1H), 6.60 (d, J=11.2 Hz, 1H), 6.88 (d, J=6.4 Hz, 1H).

Step 4: Synthesis of 2-(cyclopentyloxy)-4-fluoro-5-(5-methylisoxazol-4-yl)aniline. Step 3 aniline (1.0 g, 31.13 mmol, 1.0 equiv) and 4-iodo-5-methylisoxazole (0.97 g, 46.69 mmol, 1.5 equiv) were stirred in Dioxane:$H_2O$ (4:1) (30 mL) at room temperature. To this solution was added $K_3PO_4$ (0.86 g, 40.46 mmol, 1.5 equiv) and resulting reaction mixture was purged under $N_2$ gas for 15 min. X-phos Pd G2 (0.24 g, 0.3.11 mmol, 0.1 equiv) was added to the reaction mixture and sealed with cap. The reaction mixture was heated at 110° C. for 1 h under conventional heating, then diluted with water (200 mL) and extracted with EtOAc (3x100 mL). The combined organic layer was dried over $Na_2SO_4$, filtered and concentrated under reduced pressure. The crude product was purified by Flash chromatography using 7% EtOAc in n-hexane to give title aniline (0.290 g, 34%) as a light brown sticky liquid. LCMS [ESI, M+1]: 277.7. $^1$H NMR (400 MHz, DMSO-$d_6$): δ 1.57-1.61 (m, 2H), 1.73-1.75 (m, 4H), 1.89-1.92 (m, 2H), 2.49 (s, 3H), 4.61 (s, 2H), 4.80-4.83 (t, J=5.2 Hz, 1H), 6.64 (d, J=8.0 Hz, 1H), 6.80 (d, J=8.4 Hz, 1H), 8.58 (s, 1H).

Intermediate 8. Preparation of 4-chloro-2-(cyclopentyloxy)-5-(5-methylisoxazol-4-yl)aniline

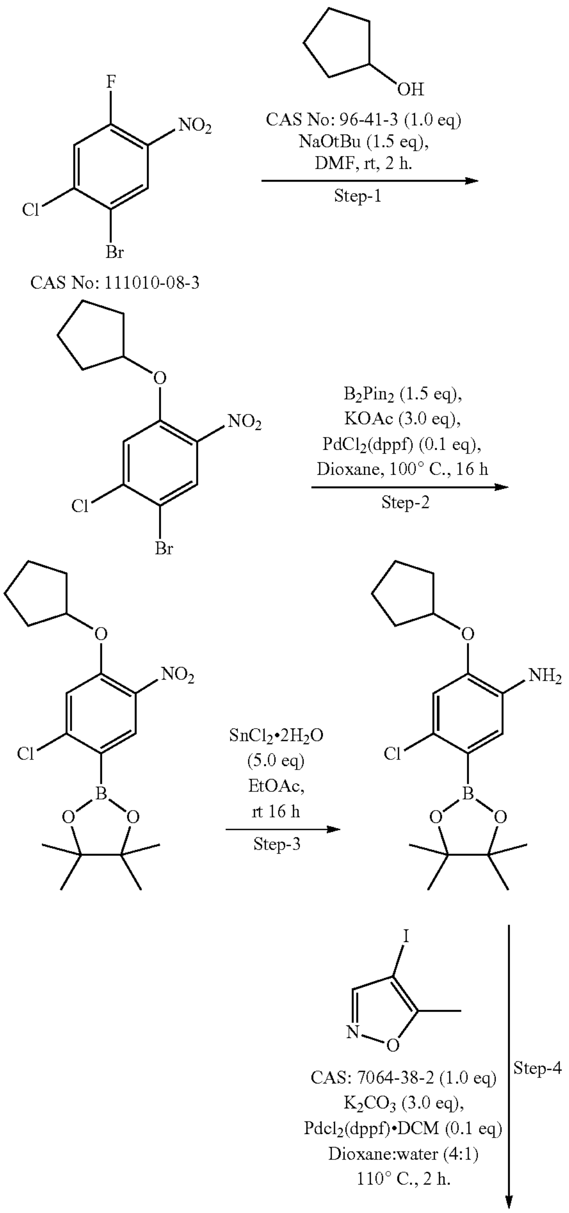

-continued

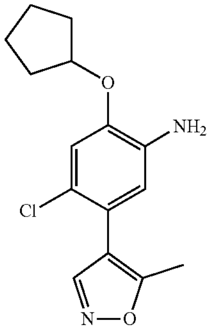

intermediate 8

Step 1: Synthesis of 1-bromo-2-chloro-4-(cyclopentyloxy)-5-nitrobenzene. A stirred solution of cyclopentanol (5.0 g, 58.95 mmol, 1.5 equiv) and NaOtBu (5.6 g, 58.95 mmol, 1.5 eq) in anhydrous DMF (100 mL) was prepared at room temperature. To this solution was added portion wise 1-bromo-2-chloro-4-fluoro-5-nitrobenzene (10.0 g, 39.30 mmol, 1.0 equiv) and resulting reaction mixture was stirred at room temperature for 2 h. The reaction mixture was diluted with water (100 mL) and extracted with ethyl acetate (3×150 mL). The combined organic layer was dried over $Na_2SO_4$, filtered and concentrated under reduced pressure. The crude product was purified by column chromatography using 1% ethyl acetate in n-hexane to give title bromide (7.8 g, 62%) as a light yellow solid. $^1$H NMR (400 MHz, DMSO-$d_6$): δ 1.56-1.60 (m, 2H), 1.62-1.74 (m, 4H), 1.87-1.92 (m, 2H), 5.12-5.14 (t, J=5.6 Hz, 1H), 7.70 (s, 1H), 8.31 (s, 1H).

Step 2: Synthesis of 2-(2-chloro-4-(cyclopentyloxy)-5-nitrophenyl)-4,4,5,5-tetramethyl-1,3,2-dioxaborolane. Step 1 bromide (3.0 g, 9.35 mmol, 1.0 equiv) and KOAc (2.7 g, 28.07 mmol, 3.0 equiv) were stirred in dioxane (40 mL) at room temperature. To this solution was added portion wise $B_2Pin_2$ (3.5 g, 14.02 mmol, 1.5 equiv) and resulting reaction mixture was purged under $N_2$ gas for 10 min. Then $PdCl_2$(dppf)DCM (0.76 g, 0.93 mmol, 0.1 equiv) and resulting reaction mixture was stirred at 90° C. for 16 h. The reaction mixture was filtered through a pad of celite, the bed washed with EtOAc (100 mL) and the combined filtrate was concentrated under reduced pressure. The crude product was purified by column chromatography using 5% ethyl acetate in n-hexane to give title dioxaborolane (1.6 g, 47%) as a yellow liquid. $^1$H NMR (400 MHz, DMSO-$d_6$): δ 1.30 (s, 12H), 1.57-1.61 (m, 2H), 1.64-1.75 (m, 4H), 1.90-1.96 (m, 2H), 5.15-5.18 (t, J=5.6 Hz, 1H), 7.44 (s, 1H), 8.06 (s, 1H).

Step 3: Synthesis of 4-chloro-2-(cyclopentyloxy)-5-(4,4,5,5-tetramethyl-1,3,2-dioxaborolan-2-yl)aniline. Step 2 dioxaborolane (1.2 g, 3.55 mmol, 1.0 equiv) was stirred in EtOAc (30 mL) at room temperature. To this solution was added $SnCl_2$·2H2O (3.6 g, 17.77 mmol, 5.0 eq) and resulting reaction mixture was stirred at room temperature for 16 h, then diluted with water (200 mL) and extracted with EtOAc (3×200 mL). The combined organic layer was dried over $Na_2SO_4$, filtered and concentrated under reduced pressure. The crude product was purified by flash chromatography using 10% ethyl acetate in n-hexane to give title aniline (1.0 g, 98%) as a light brown sticky solid. LCMS [ESI, M+1]: 338.8. $^1$H NMR (400 MHz, DMSO-$d_6$): δ 1.23-1.30 (m, 12H), 1.55 (s, 2H), 1.70-1.72 (d, 4H), 1.87-1.88 (d, 2H), 4.74 (s, 2H), 4.81 (s, 1H), 6.73 (s, 1H), 6.95 (s, 1H).

Step 4: Synthesis of 4-chloro-2-(cyclopentyoxy)-5-(5-methylisoxazol-4-yl)aniline. Step 3 aniline (1.0 g, 2.96 mmol, 1.0 equiv) and 4-iodo-5-methylisoxazole (0.17 g, 2.96 mmol, 1.0 equiv) were stirred in Dioxane:$H_2O$ (4:1) (12.5 mL) in a 30 mL glass vial at room temperature. To this solution was added $K_2CO_3$ (1.4 g, 10.36 mmol, 3.5 equiv) and resulting reaction mixture was purged under $N_2$ gas for 10 min, then $PdCl_2$(dpp)·DCM (0.24 g, 0.296 mmol, 0.1 equiv) added and sealed with cap. Then resulting reaction mixture was stirred in microwave at 100° C. for 1 h, then filtered through a pad of celite bed and the bed washed with EtOAc (25 mL). The combined filtrate was diluted with water (25 mL) and extracted with EtOAc (3×20 mL). The combined organic layer was dried over $Na_2SO_4$, filtered and concentrated under reduced pressure. The crude product was purified by Flash chromatography using 15% ethyl acetate in n-hexane to give title aniline (0.282 g, 33%) as an off white. LCMS [ESI, M+1]: 293.7. $^1$H NMR (400 MHz, DMSO-$d_6$): δ 1.57 (s, 2H), 1.73 (s, 4H), 1.88 (s, 2H), 2.32 (s, 3H), 4.83 (s, 2H), 4.91 (s, 1H), 6.60 (s, 1H), 6.90 (s, 1H), 8.57 (s, 1H).

Intermediate 9. Preparation of 2-((cyclopentyloxy)-5-(isothiazol-5-yl) aniline

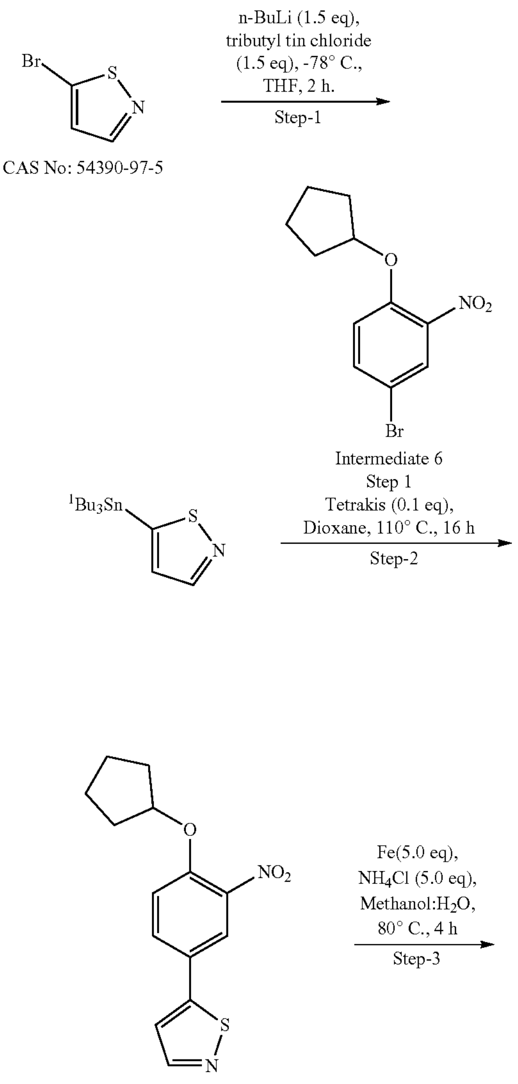

-continued

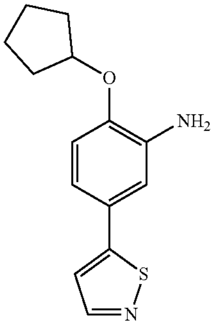

intermediate 9

Step 1: 5-(tributylstannyl)isothiazole. To a solution of 5-bromoisothiazole (4.0 g, 24.38 mmol) in THF (200 mL) was added n-BuLi (1.6 M in hexane (22.86 mL, 36.58 mmol) drop wise at −78° C. under nitrogen atmosphere. The reaction mixture was stirred at −78° C. for 30 min, then tri butyl tin chloride (11.90 g, 36.58 mmol) was added drop wise at −78° C. The reaction mixture was further stirred at −78° C. for 1 h then quenched into sat. ammonium chloride solution (500 mL) and extracted with diethyl ether (2×250 mL). The combined organic layer was dried over sodium sulfate and concentrated under reduced pressure.* Crude was purified by manual column chromatography using neutral alumina (eluted with hexane to 3% ethyl acetate in hexane as a mobile phase) to give title isothiazole as light yellow liquid (10.00 g, 54.8%)

* This reaction performed in two parallel batches (4.0 g×2=8.0 g) and combined for work up and purification. LCMS: 2.989 min, MS: ES+ 374.20, 376.10 (M, M+2): $^1$H NMR (400 MHz, DMSO) δ 8.72 (s, 1H), 7.45-7.44 (m, 1H), 1.54-1.48 (m, 6H), 1.31-1.23 (m, 6H), 1.17-1.13 (m, 6H), 0.847 (t, J=7.2 Hz, 9H).

Step 2: 5-(4-(cyclopentyloxy)-3-nitrophenyl) isothiazole. A solution of 4-bromo-1-(cyclopentyloxy)-2-nitrobenzene (intermediate 6 Step 1) (2.00 g, 6.98 mmol) in 1,4-dioxane (40 mL) was purged with $N_2$ gas for 10 min in 100 ml seal tube. Step 1 (5-(tributylstannyl) isothiazole) (3.92 g, 10.48 mmol) and tetrakis (0.808 g, 0.698 mmol) were added and further purged with $N_2$ gas for 5 min. The sealed tube was capped and heated at 110° C. for 16 h, then poured into water (100 mL) and extracted with ethyl acetate (2×100 mL). The combined organic layer was dried over sodium sulfate and concentrated under reduced pressure. Crude was purified by FCC using neutral alumina (eluted at 20% ethyl acetate in hexane as a mobile phase) to give title isothiazole as off white solid (1.4 g, 68.99%). LCMS: 2.785 min, MS: ES+ 291.2 (M+1); $^1$H NMR (400 MHz, DMSO) δ 8.60 (d, J=1.6 Hz, 1H), 8.26 (d, J=2.0 Hz, 1H), 7.97 (dd, J=8.8, 2.4 Hz, 1H), 7.84 (d, J=1.2 Hz, 1H), 7.47 (d, J=8.8 Hz, 1H), 5.13 (t, J=5.6 Hz, 1H), 1.95-1.92 (m, 2H), 1.77-1.60 (m, 6H).

Step 3: 2-(cyclopentyloxy)-5-(isothiazol-5-yl)aniline. To a solution of Step 2 isothiazole (0.700 g, 2.41 mmol) in methanol:water (9:1) (14 mL) were added iron powder (0.675 g, 12.05 mmol) and ammonium chloride (0.645 g, 12.05 mmol) at room temperature. The reaction mixture was stirred at 90° C. for 3 h, then filtered through celite, the bed washed with ethyl acetate (2×50 mL), filtrate diluted with Water (50 mL) and the organic layer separated. The combined organic layer was dried over anhydrous sodium sulfate and concentrated under reduced pressure. Crude was triturated in n-pentane:diethyl ether (7:3) (10 mL) to give title aniline as light brown solid (0.299 g, 47.6%). LCMS: 2.717 min, MS: ES+ 261.6 (M+1); $^1$H NMR (400 MHz, DMSO) δ 8.49 (s, 1H), 7.51 (s, 1H), 6.95-6.83 (m, 3H), 4.89 (s, 2H), 4.82 (s, 1H), 1.89 (s, 2H), 1.74 (s, 4H), 1.57 (s, 2H).

Intermediate 10. Preparation of 2-(cyclopentyloxy)-4-fluoro-5-(isothiazol-5-yl)aniline

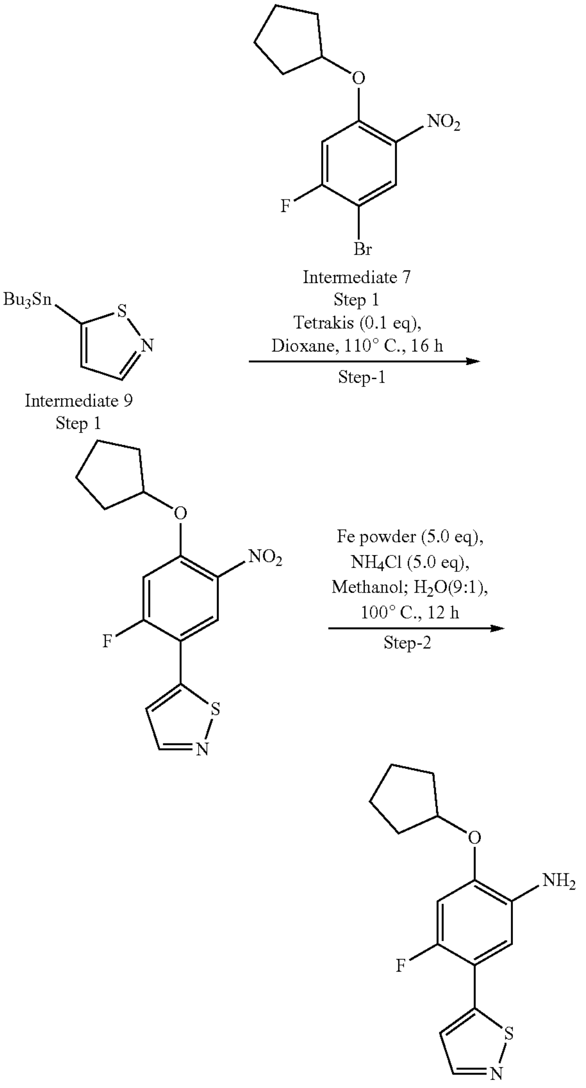

intermediate 10

Step 1: 5-(4-(cyclopentyloxy)-2-fluoro-5-nitrophenyl) isothiazole. A solution of 1-bromo-4-(cyclopentyloxy)-2-fluoro-5-nitrobenzene (Intermediate 7 Step 1) (2.00 g, 6.57 mmol) in 1, 4-dioxane (40 mL) was purged with $N_2$ gas for 10 min in a 100 mL seal tube. 5-(tributylstannyl) isothiazole (Intermediate 9 Step 1) (3.69 g, 9.86 mmol) and tetrakis (0.759 g, 0.657 mmol) were added and further purged with $N_2$ gas for 5 min. The reaction mixture was sealed with cap and heated at 110° C. for 16 h, then poured into water (100 mL) and extracted with ethyl acetate (2×75 mL). The combined organic layer was dried over anhydrous sodium sulfate and concentrated under reduced pressure. Crude was purified by FCC using neutral alumina (eluted at 12% ethyl acetate in hexane as a mobile phase) to give title isothiazole as white solid (0.9 g, 44.4%). LCMS: 2.968 min, MS: ES+

309.1 (M+1); $^{1}$H NMR (400 MHz, DMSO) δ 8.63 (t, J=2.0 Hz, 1H), 8.59 (d, J=8.0 Hz, 1H), 8.01 (d, J=2.0 Hz, 1H), 7.58 (d, J=12.8 Hz, 1H), 5.15 (t, J=5.6 Hz, 1H), 1.98-1.93 (m, 2H), 1.79-1.59 (m, 6H).

Step 2: 2-(cyclopentyloxy)-4-fluoro-5-(isothiazol-5-yl) aniline. To a solution of Step 1 isothiazole (0.700 g, 2.27 mmol) in methanol:water (9:1) (14 mL) were added iron powder (0.635 g, 11.35 mmol) and ammonium chloride (0.607 g, 11.35 mmol) at room temperature. The reaction mixture was stirred at 90° C. for 3 h, filtered through celite, the bed washed with ethyl acetate (2×50 mL), the filtrate diluted with water (75 mL) and the organic layer was separated. The combined organic layer was dried over anhydrous sodium sulfate and concentrated under reduced pressure. Crude was purified by FCC using neutral alumina (eluted at 10% ethyl acetate in hexane as a mobile phase) to give a brown solid. The solid diluted with DCM (2 mL) and precipitated out by n-pentane (10 mL), filtered and dried in vacuo to give title aniline as light brown solid (0.262 g, 41.5%). LCMS: 2.409 min, MS: ES+ 279.6 (M+1); $^{1}$H NMR (400 MHz, DMSO) δ 8.54 (d, J=1.6 Hz, 1H), 7.58 (d, J=1.6 Hz, 1H), 7.05 (d, J=7.6 Hz, 1H), 6.90 (d, J=12.8 Hz, 1H), 4.87 (t, J=5.6 Hz, 1H), 4.75 (s, 2H), 1.93-1.89 (m, 2H), 1.77-1.74 (m, 4H), 1.58-1.56 (m, 2H).

Intermediate 11. Preparation of 4-chloro-2-(cyclopentyloxy)-5-(isothiazol-5-yl)

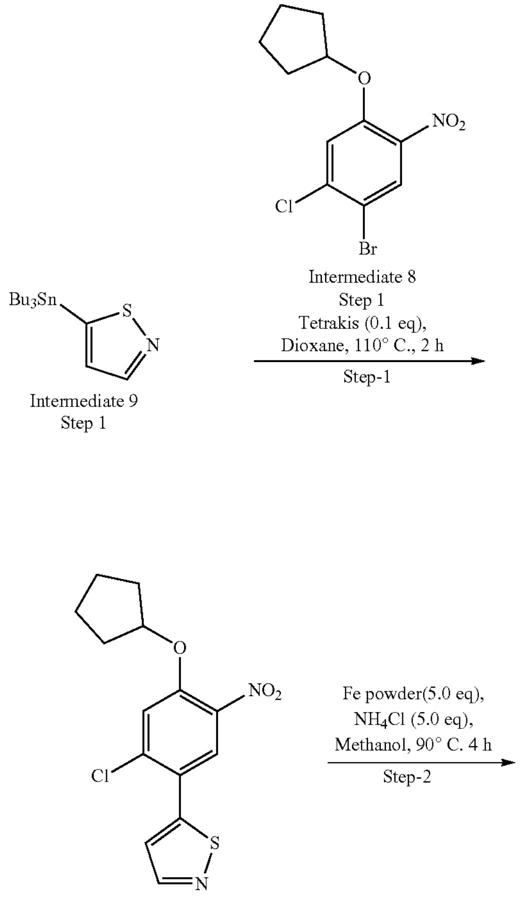

-continued

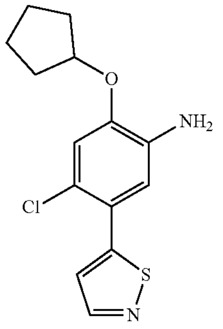

intermediate 11

Step 1: 5-(2-chloro-4-(cyclopentyloxy)-5-nitrophenyl) isothiazole. A solution of 1-bromo-2-chloro-4-(cyclopentyloxy)-5-nitrobenzene (Intermediate 8 Step 1) (2.00 g, 6.23 mmol) in 1, 4-dioxane (40 mL, 20V) was purged with $N_2$ gas for 10 min in a 100 mL seal tube. 5-(tributylstannyl) isothiazole (Intermediate 9 Step 1) (3.50 g, 9.35 mmol) and tetrakis (0.721 g, 0.623 mmol) were added and further purged with $N_2$ gas for 5 min. The reaction mixture was sealed with cap and heated at 110° C. for 16 h, then poured into water (100 mL) and extracted with ethyl acetate (2×100 mL). The combined organic layer was dried over anhydrous sodium sulfate and concentrated under reduced pressure. Crude was purified by FCC using neutral alumina (eluted at 8% ethyl acetate in hexane as a mobile phase) to give title isothiazole as white solid (1.1 g, 54.3%). LCMS: 2.936 min, MS: ES+ 325.1 (M+1); $^{1}$H NMR (400 MHz, DMSO) δ 8.64 (d, J=1.6 Hz, 1H), 8.42 (s, 1H), 7.92 (d, J=2.0 Hz, 1H), 7.71 (s, 1H), 5.21 (s, 1H), 1.97-1.92 (m, 2H), 1.78-1.59 (m, 6H).

Step 2: 4-chloro-2-(cyclopentyloxy)-5-(isothiazol-5-yl) aniline. To a solution of Step 1 isothiazole (0.700 g, 2.15 mmol) in methanol:water (9:1) (14 mL) were added iron powder (0.603 g, 10.77 mmol) and ammonium chloride (0.576 g, 10.77 mmol) at room temperature. The reaction mixture was stirred at 90° C. for 3 h, then cooled and filtered through celite bed, and the bed washed with ethyl acetate (2 a 50 mL). The combined filtrate was washed with water (100 mL) and the combined organic layer was dried over anhydrous sodium sulfate, filtered and concentrated under reduced pressure. Crude was triturated with n-pentane:diethyl ether (7:3) (10 mL) to give title aniline as a light brown solid (0.313 g, 49.4%). LCMS: 2.954 min, MS:ES+ 295.6 (M+1); $^{1}$H NMR (400 MHz, DMSO) δ 8.56 (s, 1H), 7.59 (s, 1H), 7.04 (s, 1H), 6.96 (s, 1H), 5.03 (s, 2H), 4.88 (s, 1H), 1.92-1.90 (m, 2H), 1.77-1.74 (m, 4H), 1.58 (s, 2H).

Intermediate 12. Preparation of 4-chloro-2-cyclobutoxy-5-(5-methylisoxazol-4-yl)aniline

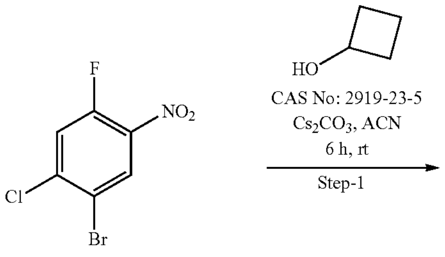

CAS No: 111010-08-3

-continued

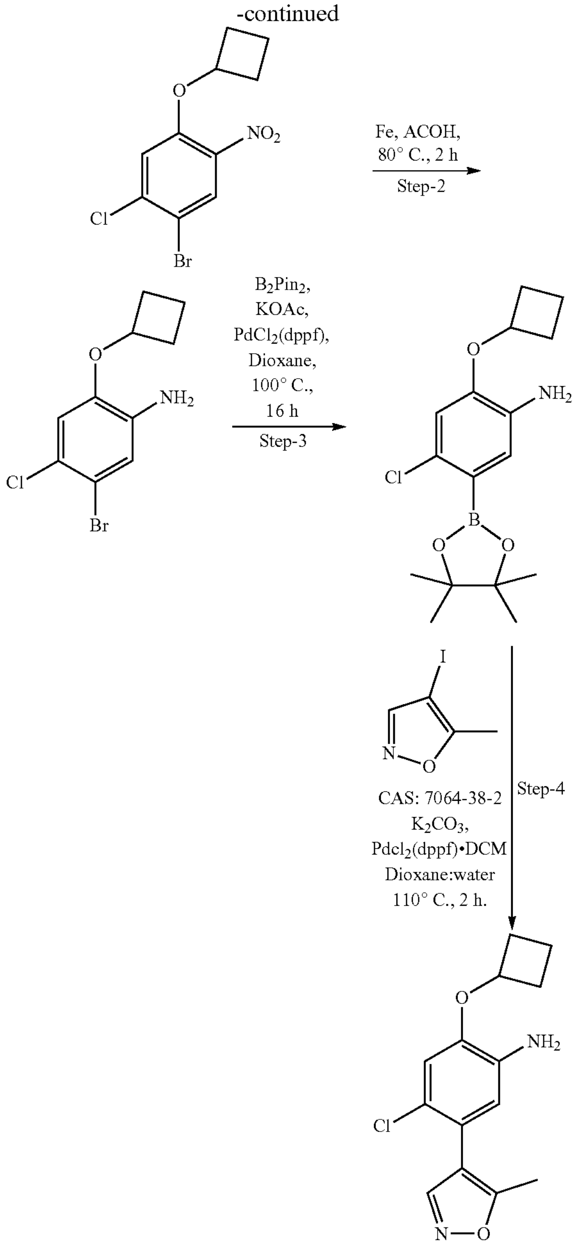

Intermediate 12

Step 1: Synthesis of 1-bromo-2-chloro-4-cyclobutoxy-5-nitrobenzene. To a stirred solution of cyclobutanol (CAS #2919-23-5, Angene) (1.71 g, 0.0237 mol, 1.0 eq.) and $Cs_2CO_3$ (15.45 g, 0.4745 mol, 2 eq.) in ACN (60 mL) was prepared at room temperature. 1-bromo-2-chloro-4-fluoro-5-nitrobenzene (CAS #111010-08-3, Combi block) (6 g, 0.0237 mol, 1.0 equiv) was added portion wise to the reaction mixture and stirred at room temperature for 6 h. The reaction mixture was poured in to ice cold water and the precipitate collected and dried to yielding title ether (5 g, 69.2%) as a light-yellow solid. $^1H$ NMR (400 MHz, DMSO-$d_6$): δ 8.34 (s, 1H), 7.48 (s, 1H), 4.99-4.85 (m, 1H), 2.53-2.43 (m, 2H), 2.08-2.00 (m, 2H), 1.84-1.79 (m, 1H), 1.66-1.59 (m, 1H)

Step 2: Synthesis of 5-bromo-4-chloro-2-cyclobutoxyaniline. A solution of Step 1 ether (4 g, 0.013 mol, 1 eq.) and iron powder (3.67 g, 0.0655 mol, 5 eq.) in acetic acid (40 ml) was stirred at room temperature, then heated to 80° C. for 2 h. The mixture was cooled, filtered through a pad of celite bed and washed with EtOAc (2×100 mL). The filtrate was concentrated under reduced pressure and the crude residue was purified by column chromatography using 2% EtOAc in n-Hexane as mobile phase yielding title aniline (3.1 g, 85.9%) as a light pink solid. $^1H$ NMR (400 MHz, DMSO-$d_6$): δ 6.90 (s, 1H), 6.76 (s, 1H), 5.13 (s, 1H), 4.71-4.64 (m, 1H), 2.44-2.36 (m, 2H), 2.09-2.00 (m, 2H), 1.81-1.79 (m, 1H) 1.76-1.74 (m, 1H)

Step 3: Synthesis of 4-chloro-2-cyclobutoxy-5-(4,4,5,5-tetramethyl-1,3,2-dioxaborolan-2-yl)aniline. A solution of Step 2 aniline (1.2 g, 0.0043 mol, 1.0 eq.) and KOAc (2.14 g, 0.0021 mol, 5.0 eq.) in dioxane (12 ml, 10V) was stirred at room temperature. To this solution was portion wise added $B_2Pin_2$ (2.21 g, 0.0087 mol, 2.0 eq.) and resulting reaction mixture was purged under Argon gas for 20 min. $PdCl_2$(dppf)DCM (0.63 g, 0.00077 mol, 0.2 eq.) was added and resulting reaction mixture was purged under Argon for 10 min, then stirred at 80° C. for 16 h. The reaction mixture was cooled, then filtered through a pad of celite bed and washed with EtOAc (2×100 mL). The filtrate was concentrated under reduced pressure And the crude residue was purified by column chromatography using 4% EtOAc in n-Hexane as mobile phase yielding title dioxaborolane (0.9 g, 2.78 mmol, 65%) as a light pink solid. UPLC-MS (Method 5) m/z 324.2 $(M+H)^+$ at 2.72 min.

Step 4: Synthesis of 4-chloro-2-cyclobutoxy-5-(5-methylisoxazol-4-yl)aniline. A solution of Step 3 dioxaborolane (0.7 g, 2.16 mol, 1.0 eq.) and 4-iodo-5-methylisoxazole (CAS #7064-38-2, Enamine) (0.0.45 g, 2.16 mol, 1.0 eq.) in Dioxane:$H_2O$ (8:2) was added to a 30 mL microwave glass vial at room temperature. $K_2CO_3$ (1.04 g, 7.58 mol, 3.5 eq.) was added and the resulting reaction mixture was purged under Argon gas for 20 min. $PdCl_2$(dpp)DCM (0.17 g, 0.216 mol, 0.1 eq.) was added to the reaction mixture and heated under microwave at 110° C. for 1 h. The resulting reaction mixture was filtered through a pad of celite and washed with EtOAc (2×100 mL). The filtrate was concentrated under reduced pressure and the crude material was purified by column chromatography using 5% EtOAc in n-Hexane as mobile phase giving title aniline (0.25 g, 41.5%) as a light pink solid. UPLC-MS (Method 5) m/z 279.1 $(M+H)^+$ at 2.46 min.; 1H NMR (400 MHz, DMSO-$d_6$): δ 8.57 (s, 1H), 6.75 (s, 1H), 6.63 (s, 1H), 4.97 (s, 2H), 4.75-4.71 (m, 1H), 2.28 (s, 1H), 2.10-2.05 (m, 2H), 1.81-1.78 (m, 1H), 1.66-1.63 (m, 1H), 1.31-1.18 (m, 2H)

Intermediate 13. Preparation of 4-chloro-2-(3,3-difluorocyclobutoxy)-5-(5-methylisoxazol-4-yl)aniline

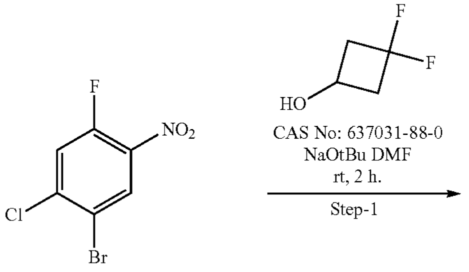

CAS No: 111010-08-3

-continued

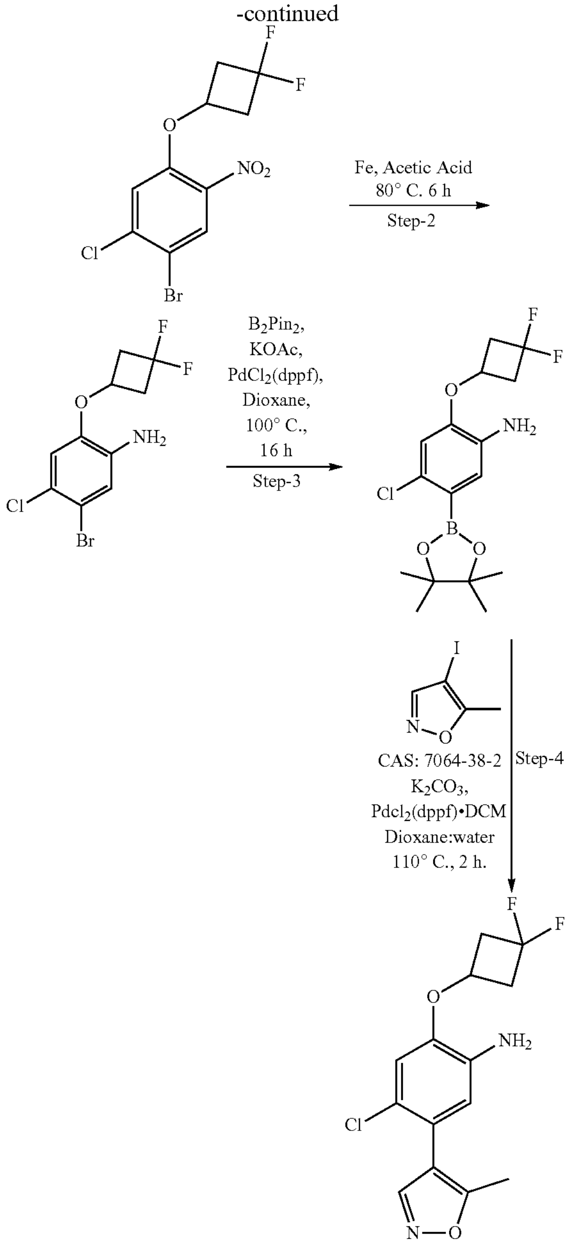

Intermediate 13

Step 1: Synthesis of 1-bromo-2-chloro-4-(3,3-difluorocyclobutoxy)-5-nitrobenzene. A solution of 3,3-difluorocyclobutan-1-ol (CAS #637031-88-0, Angene) (2.56 g, 0.0237 mol, 1.0 eq.) and $Cs_2CO_3$ (15.45 g, 0.4745 mol, 2 eq.) in MeCN (60 mL) was stirred at room temperature. 1-bromo-2-chloro-4-fluoro-5-nitrobenzene (CAS #111010-08-3, Combi block) (6 g, 0.0237 mol, 1.0 equiv) was added portion wise and resulting reaction mixture was stirred at room temperature for 6 h. The reaction mixture was poured in to ice cold water and the precipitate filtered and dried to give title ether as a light-yellow solid, (5 g, 14.6 mmol, 62%). $^1$H NMR (400 MHz, DMSO-$d_6$): δ 8.39 (s, 1H), 7.60 (s, 1H), 5.05-5.02 (m, 1H), 3.31-3.25 (m, 2H), 2.81-2.74 (m, 2H).

Step 2: Synthesis of 5-bromo-4-chloro-2-(3,3-difluorocyclobutoxy)aniline. A solution of Step 1 ether (4 g, 0.012 mol, 1 eq.) and iron powder (3.28 g, 0.058 mol, 5 eq.) in acetic acid (40 ml) was prepared at room temperature, then stirred at 80° C. for 2 h. The reaction mixture was filtered through a pad of celite bed and washed with EtOAc (2×100 mL). The combined filtrate was concentrated under reduced pressure and the crude residue was purified by column chromatography using 2% EtOAc in n-Hexane as mobile phase to give title aniline as a light pink solid, (3.1 g, 10 mmol, 76%). UPLC-MS (Method 5): m/z 311.8 (M+H)+, at 2.20 min.; $^1$H NMR (400 MHz, DMSO-$d_6$): δ 6.93 (S, 1H), 6.88 (S, 1H), 5.28 (s, 2H), 4.80-4.73 (m, 2H), 3.24-3.13 (m, 2H), 2.80-2.67 (m, 2H).

Step 3: Synthesis of 4-chloro-2-(3,3-difluorocyclobutoxy)-5-(4,4,5,5-tetramethyl-1,3,2-dioxaborolan-2-yl)aniline A solution of Step 2 aniline (1.2 g, 0.0038 mol, 1.0 eq) and KOAc (2.14 g, 0.0021 mol, 5.0 eq.) was stirred in dioxane (12 ml) at room temperature. $B_2Pin_2$ (2.21 g, 0.0087 mol, 2.3 eq.) was added portionwise and the resulting reaction mixture was purged under Argon gas for 20 min. $PdCl_2$(dppf)DCM (0.63 g, 0.00077 mol, 0.2 eq.) was added and the reaction mixture was purged under Argon for 10 min, then stirred at 80° C. for 16 h. The reaction mixture was filtered through a pad of celite bed and washed with EtOAc (2×100 mL). The combined filtrate was concentrated under reduced pressure and the crude residue was purified by column chromatography using 4% EtOAc in n-Hexane as mobile phase to give title dioxaborolane as a light pink solid, (0.7 g, 50.4%). UPLC-MS (Method 5): m/z 360.1 (M+H)+, at 2.63 min.

Step 4: Synthesis of 4-chloro-2-(3,3-difluorocyclobutoxy)-5-(5-methylisoxazol-4-yl)aniline A stirred solution of Step 3 dioxaborolane (0.7 g, 1.94 mol, 1.0 eq.) and 4-iodo-5-methylisoxazole (CAS #7064-38-2, Enamine) (0.400 g, 1.94 mol, 1.0 eq.) was stirred in dioxane:$H_2O$ (8:2) in a 30 mL microwave glass vial at room temperature. $K_2CO_3$ (0.94 g, 6.82 mol, 3.5 eq.) was added and the resulting reaction mixture was purged under Argon gas for 20 min. $PdCl_2$ (dppf)DCM (0.17 g, 0.216 mol, 0.1 eq.) and sealed with a cap. The resulting reaction mixture was heated under microwave at 110° C. for 1 h, cooled, filtered through a pad of celite and washed with EtOAc (2×100 mL). Then combined filtrate was concentrated under reduced pressure and the crude residue was purified by column chromatography using 5% EtOAc in n-Hexane as mobile phase to give title aniline as a light pink solid, (0.26 g, 0.72 mmol, 37%). UPLC-MS (Method 5): m/z 315.1 $(M+H)^+$, at 2.35 min.; $^1$H NMR (400 MHz, DMSO-$d_6$): δ 8.58 (S, 1H), 6.86 (s, 1H), 6.63 (s, 1H), 5.12 (m, 2H), 4.83-4.80 (m, 1H), 3.23-3.18 (m, 2H), 2.79-2.74 (m, 2H). 2.37 (S, 3H).

Intermediate 14. Preparation of 4-chloro-2-cyclobutoxy-5-(isothiazol-5-yl)aniline

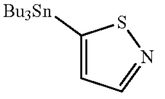

+

Intermediate 9
Step 1

-continued

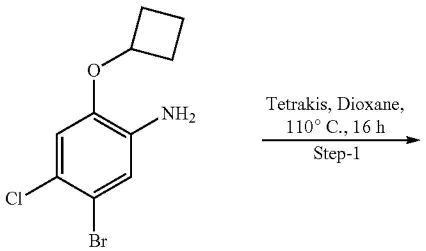

Intermediate 12
Step 2

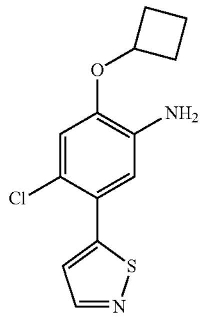

Intermediate 14

Step 1: Synthesis of 4-chloro-2-cyclobutoxy-5-(isothiazol-5-yl)aniline. A solution of Intermediate 12 Step 2 (1.20 g, 4.34 mmol) in 1, 4-dioxane (12 mL) was purged with $N_2$ gas for 10 min in 10 ml sealed tube. 5-(tributylstannyl) isothiazole (Intermediate 9 Step 1; 2.4 g, 6.52 mmol) and tetrakis (0.500 g, 0.43 mmol) were added and further purged with $N_2$ gas for 5 min, then heated at 110° C. for 16 h. The mixture was cooled, poured into water (100 mL) and extracted with ethyl acetate (2×100 mL). The combined organic layer was dried over anhydrous sodium sulfate and concentrated under reduced pressure. The crude was purified by FCC using neutral alumina (eluted at 5% Ethyl acetate in Hexane as a mobile phase) to give title aniline as an off-white solid (0.33 g, 27.5%). LCMS: 2.467 min, MS: ES+ 281.1 (M+1); $^1$H NMR (400 MHz, DMSO) δ 8.57 (d, J=1.6 Hz, 1H), 7.60 (d, J=1.6 Hz, 1H), 7.05 (s, 1H), 6.80 (s, 1H), 5.10 (s, 2H), 4.79-4.76 (m, 1H), 2.50-2.41 (m, 2H), 2.14-2.04 (m, 2H), 1.84-1.77 (m, 1H), 1.69-1.62 (m, 1H).

Intermediate 15. Preparation of 4-chloro-2-(3,3-difluorocyclobutoxy)-5-(isothiazol-5-yl)aniline

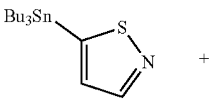

Intermediate 9
Step 1

-continued

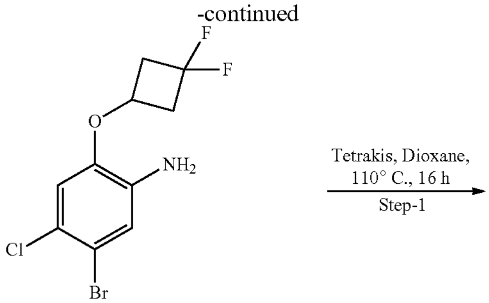

Intermediate 13
Step 2

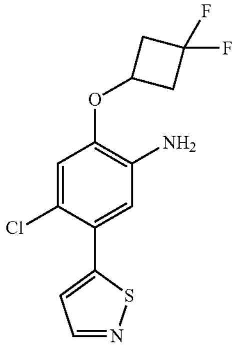

Intermediate 15

Step 1: Synthesis of 4-chloro-2-(3,3-difluorocyclobutoxy)-5-(isothiazol-5-yl)aniline. A solution of Intermediate 13 Step 2 (1.50 g, 4.84 mmol) in 1, 4-dioxane (12 mL) was purged with $N_2$ gas for 10 min in 10 ml seal tube. Intermediate 9 Step 1 (2.68 g, 7.22 mmol) and tetrakis (0.555 g, 0.48 mmol) were added and further purged with $N_2$ gas for 5 min, then heated at 110° C. for 16 h. After cooling, the reaction mixture was poured into water (100 mL) and extracted with ethyl acetate (2×100 mL). The combined organic layer was dried over anhydrous sodium sulfate and concentrated under reduced pressure. Crude was purified by FCC using neutral alumina (eluted at 5% ethyl acetate in hexane as a mobile phase) to give title aniline as off-white solid (0.33 g, 22%). UPLC-MS (Method 5): m/z 317.1 $(M+H)^+$ at 2.37 min; $^1$H NMR (400 MHz, DMSO) δ 8.57 (d, J=1.2 Hz, 1H), 7.61 (d, J=1.2 Hz, 1H), 7.06 (s, 1H), 6.92 (s, 1H), 5.25 (brs, 2H), 4.85 (brs, 1H), 3.29-3.18 (m, 2H), 2.84-2.72 (m, 2H).

Example 1: 3-(N-(4-chloro-5-cyano-2-(cyclopentyloxy)phenyl)sulfamoyl)-4-cyclopropylbenzoic acid

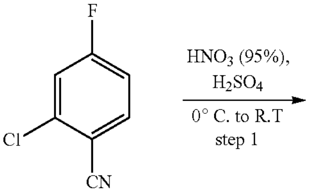

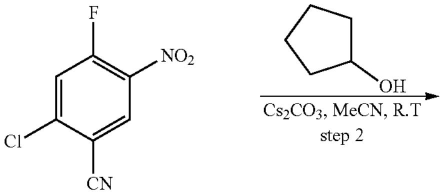

-continued

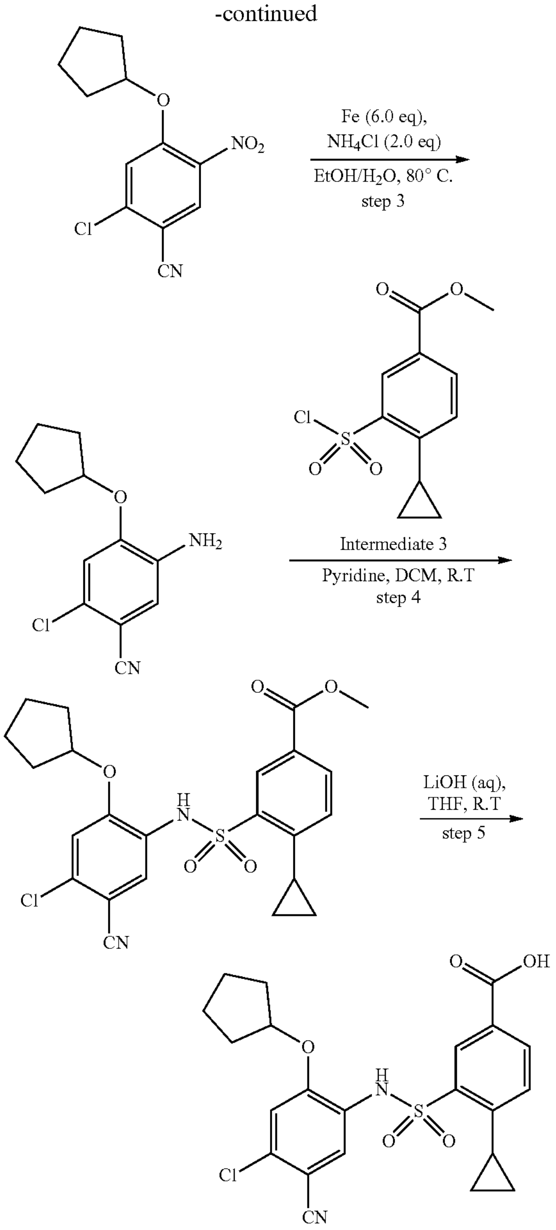

Step 1: 2-chloro-4-fluoro-5-nitrobenzonitrile: To a solution of 2-chloro-4-fluorobenzonitrile (20.0 g, 129.0 mmol) in $H_2SO_4$ (98%, 40 mL) at 0° C. was added dropwise fuming nitric acid (20 mL). The resulting mixture was stirred at 0° C. for 30 min. The solution was poured into ice water and the white precipitate that formed was collected by filtration and washed with water to afford the title compound (20.7 g, 103.5 mmol, 80% yield) as a white solid. $^1$H NMR (400 MHz, DMSO-$d_6$) δ 8.95 (d, J=7.7 Hz, 1H), 8.28 (d, J=10.9 Hz, 1H).

Step 2: 2-chloro-4-(cyclopentyloxy)-5-nitrobenzonitrile: A mixture of 2-chloro-4-fluoro-5-nitrobenzonitrile (8.6 g, 43.0 mmol), cyclopentanol (1.85 g, 215.0 mmol) and $Cs_2CO_3$ (28.0 g, 86.0 mmol) in MeCN (100 mL) was stirred at room temperature overnight. The reaction mixture was filtered through celite. The filtrate was concentrated and purified by Biotage Isolera One ($C_{18}$ column, eluting with 10% to 90% MeCN/$H_2O$) to afford the title compound (5.2 g, 19.5 mmol, 45% yield) as a white solid. $^1$H NMR (400 MHz, DMSO-$d_6$) δ 8.62 (s, 1H), 7.81 (s, 1H), 5.26 (td, J=5.6, 2.8 Hz, 1H), 2.04-1.90 (m, 2H), 1.88-1.69 (m, 2H), 1.73-1.56 (m, 4H).

Step 3: 5-amino-2-chloro-4-(cyclopentyloxy)benzonitrile: A mixture of 2-chloro-4-(cyclopentyloxy)-5-nitrobenzonitrile (3.9 g, 14.7 mmol) iron powder (4.9 g, 88.2 mmol) and $NH_4Cl$ (1.6 g, 29.4 mmol) in a mixture of EtOH and water (v/v=5/1, 120 mL) was heated at 85° C. for 2 h. The resulting mixture was filtered through celite and concentrated to afford the title compound (2.36 g, 10.0 mmol, 68% yield) as a yellow solid. UPLC-MS (Method 3) m/z 235, 237 $(M-H)^-$ at 2.03 min.

Step 4: Methyl 3-(N-(4-chloro-5-cyano-2-(cyclopentyloxy)phenyl)sulfamoyl)-4-cyclopropylbenzoate: To a solution of 5-amino-2-chloro-4-(cyclopentyloxy)benzonitrile (2.36 g, 10.0 mmol) and pyridine (1.7 g, 21.6 mmol) in DCM (100 mL) at room temperature was added methyl 3-(chlorosulfonyl)-4-cyclopropylbenzoate (Intermediate 3; 2.96 g, 10.8 mmol) and the solution stirred at RT overnight. The solvent was removed in vacuo and the crude product was purified by Biotage Isolera One ($Cl_8$ column, eluting with 10% to 90% MeCN/$H_2O$) to give the title compound (1.20 g, 2.5 mmol, 25% yield) as a white solid. UPLC-MS (Method 1) m/z 473.05 $(M-H)^-$ at 2.383 min.

Step 5: 3-(N-(4-chloro-5-cyano-2-(cyclopentyloxy)phenyl)sulfamoyl)-4-cyclopropylbenzoic acid: To solution of methyl 3-(N-(4-chloro-5-cyano-2-(cyclopentyloxy)phenyl)sulfamoyl)-4-cyclopropylbenzoate (1.2 g, 2.5 mmol) in mixture of THF and $H_2O$ (v/v=1:1, 40 mL) was added LiOH (360 mg, 15.0 mmol) and the reaction stirred at RT overnight. The solvent was removed in vacuo and the crude product purified by Biotage Isolera One ($C_{18}$ column, eluting with 10% to 90% MeCN/$H_2O$, contained 0.1% HCOOH) to give the title compound (1.06 g, 2.3 mmol, 92% yield) as a red solid. UPLC-MS (Method 1) m/z 459.05 $(M-H)^-$ at 2.150 min. $^1$H NMR (400 MHz, DMSO-$d_6$) δ 13.22 (s, 1H), 10.06 (s, 1H), 8.32 (t, J=1.4 Hz, 1H), 8.00 (dd, J=8.2, 1.9 Hz, 1H), 7.67 (s, 1H), 7.26 (s, 1H), 7.11 (d, J=8.3 Hz, 1H), 4.77-4.80 (m, 1H), 2.68-2.60 (td, J=8.4, 4.2 Hz, 1H), 1.76-1.73 (m, 2H), 1.47-1.45 (dt, J=7.9, 3.3 Hz, 1H), 1.44-1.38 (m, 5H), 0.99-0.96 (m, 2H), 0.79-0.78 (m, 2H).

The following examples were prepared by methods analogous to Example 1, substituting appropriate starting materials and intermediates where necessary. When using intermediates 1 & 2 and following general scheme 1, sulphonamide formation occurs in presence of free acid and therefore the target acid is prepared directly with no need for penultimate ester hydrolysis.

| Example | Structure | Name/Analytical Data |
|---|---|---|
| 2 | 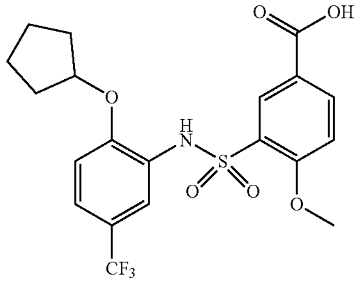 | 3-(N-(2-(cyclopentyloxy)-5-(trifluoromethyl)phenyl)sulfamoyl)-4-methoxybenzoic acid. UPLC-MS (Method 1) m/z 458.00 $(M-H)^-$ at 2.064 min. $^1H$ NMR (400 MHz, DMSO-$d_6$) δ 13.12 (s, 1H), 9.29 (s, 1H), 8.25 (d, J = 2.2 Hz, 1H), 8.12 (dd, J = 8.7, 2.2 Hz, 1H), 7.53 (d, J = 2.3 Hz, 1H), 7.44 (dd, J = 8.7, 2.3 Hz, 1H), 7.27 (d, J = 8.8 Hz, 1H), 7.10 (d, J = 8.7 Hz, 1H), 4.79 (t, J = 3.8 Hz, 1H), 3.75 (s, 3H), 1.82 (dt, J = 12.3, 4.4 Hz, 2H), 1.55-1.44 (m, 6H). |
| 3 | 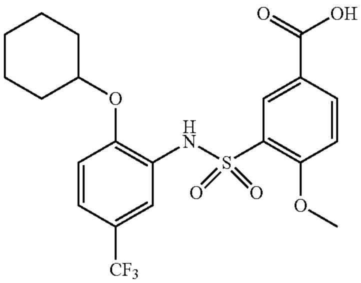 | 3-(N-(2-(cyclohexyloxy)-5-(trifluoromethyl)phenyl)sulfamoyl)-4-methoxybenzoic acid. UPLC-MS (Method 1) m/z 472.00 $(M-H)^-$ at 2.166 min. $^1H$ NMR (400 MHz, DMSO-$d_6$) δ 13.08 (s, 1H), 9.19 (s, 1H), 8.23 (d, J = 2.2 Hz, 1H), 8.14 (dd, J = 8.7, 2.3 Hz, 1H), 7.54 (d, J = 2.3 Hz, 1H), 7.42 (dd, J = 8.8, 2.3 Hz, 1H), 7.32 (d, J = 8.8 Hz, 1H), 7.17 (d, J = 8.7 Hz, 1H), 4.35 (tt, J = 8.2, 3.7 Hz, 1H), 3.83 (s, 3H), 1.75-1.74 (m, 2H), 1.73-1.71 (dd, J = 11.8, 5.3 Hz, 2H), 1.55-1.46 (m, 1H), 1.36-1.08 (m, 5H). |
| 4 | 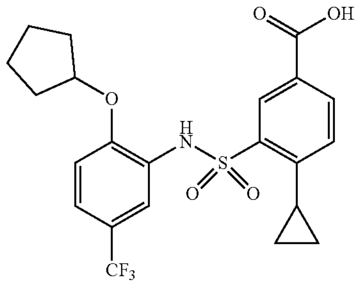 | 3-(N-(2-(cyclopentyloxy)-5-(trifluoromethyl)phenyl)sulfamoyl)-4-cyclopropylbenzoic acid. UPLC-MS (Method 1) m/z 468.00 $(M-H)^-$ at 2.251 min. $^1H$ NMR (400 MHz, DMSO-$d_6$) δ 13.20 (s, 1H), 9.93 (s, 1H), 8.34 (d, J = 1.9 Hz, 1H), 7.97 (dd, J = 8.2, 1.9 Hz, 1H), 7.48-7.41 (m, 2H), 7.11-7.06 (dd, J = 11.3, 8.4 Hz, 2H), 4.74 (td, J = 6.4, 3.0 Hz, 1H), 2.68 (dq, J = 8.5, 4.1, 3.1 Hz, 1H), 1.82-1.75 (m, 2H), 1.54-1.40 (ddp, J = 25.6, 9.1, 4.6 Hz, 6H), 1.00-0.95 (m, 2H), 0.79-0.75 (m, 2H). |
| 5 | 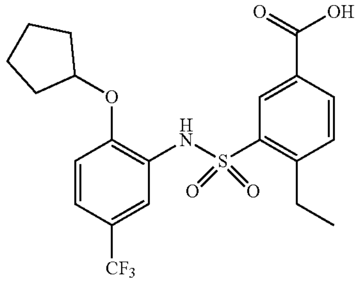 | 3-(N-(2-(cyclopentyloxy)-5-(trifluoromethyl)phenyl)sulfamoyl)-4-ethylbenzoic acid. UPLC-MS (Method 1) m/z 456.00 $(M-H)^-$ at 1.837 min. $^1H$ NMR (400 MHz, DMSO-$d_6$) δ 13.19 (s, 1H), 9.95 (s, 1H), 8.26 (d, J = 1.8 Hz, 1H), 8.04 (dd, J = 8.0, 1.8 Hz, 1H), 7.55-7.51 (m, 2H), 7.45-7.42 (dd, J = 8.6, 2.4 Hz, 1H), 7.05-7.03 (d, J = 8.7 Hz, 1H), 4.70 (dt, J = 6.5, 3.4 Hz, 1H), 3.02-2.96 (q, J = 7.4 Hz, 2H), 1.81-1.75 (td, J = 8.2, 3.6 Hz, 2H), 1.54-1.51 (m, 2H), 1.47-1.40 (m, 4H), 1.17-1.14 (t, J = 7.4 Hz, 3H). |
| 6 | 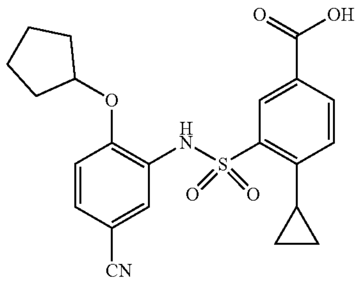 | 3-(N-(5-cyano-2-(cyclopentyloxy)phenyl)sulfamoyl)-4-cyclopropylbenzoic acid. UPLC-MS (Method 1) m/z 425.00 $(M-H)^-$ at 1.963 min. $^1H$ NMR (400 MHz, DMSO-$d_6$) δ 13.19 (s, 1H), 9.94 (s, 1H), 8.32 (d, J = 2.9 Hz, 1H), 7.98 (d, J = 8.2 Hz, 1H), 7.59-7.56 (t, J = 6.4 Hz, 2H), 7.11-7.06 (dd, J = 14.1, 8.4 Hz, 2H), 4.73 (s, 1H), 2.65 (s, 1H), 1.77-1.75 (m, 2H), 1.48-1.40 (d, J = 12.5 Hz, 6H), 1.00-0.95 (p, J = 4.6 Hz, 2H), 0.79-0.77 (d, J = 5.3 Hz, 2H). |

-continued

| Example | Structure | Name/Analytical Data |
|---|---|---|
| 7 | 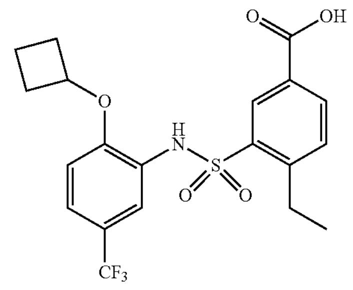 | 3-(N-(2-cyclobutoxy-5-(trifluoromethyl)phenyl)sulfamoyl)-4-ethylbenzoic acid. UPLC-MS (Method 2) m/z 442.15 (M − H)$^-$ at 3.078 min. $^1$H NMR (400 MHz, DMSO-$d_6$) δ 13.20 (s, 1H), 10.04 (s, 1H), 8.25 (d, J = 1.8 Hz, 1H), 8.07-8.05 (dd, J = 8.0, 1.8 Hz, 1H), 7.57- 7.53 (m, 2H), 7.44-7.42 (dd, J = 8.7, 2.3 Hz, 1H), 6.87-6.85 (d, J = 8.6 Hz, 1H), 4.54 (p, J = 7.0, 6.6 Hz, 1H), 3.07-3.04 (q, J = 7.4 Hz, 2H), 2.25-2.21 (m, 2H), 1.67-1.49 (m, 4H), 1.20-1.16 (t, J = 7.4 Hz, 3H). 3-(N-(5-cyano-2-(cyclopentyloxy)-4-fluorophenyl)sulfamoyl)-4-cyclopropylbenzoic acid. |
| 11 | 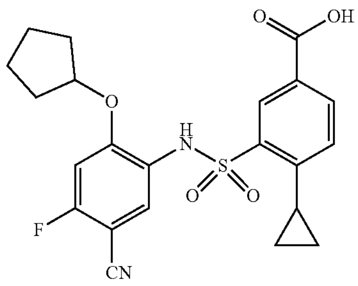 | UPLC-MS (Method 1) m/z 443.05 (M − H)$^-$ at 1.970 min. $^1$H NMR (400 MHz, DMSO-$d_6$) δ 13.20 (s, 1H), 9.94 (s, 1H), 8.28 (d, J = 1.9 Hz, 1H), 7.98-7.96 (dd, J = 8.2, 1.9 Hz, 1H), 7.64 (d, J = 7.2 Hz, 1H), 7.17-7.12 (dd, J = 18.4, 10.0 Hz, 2H), 4.71 (dd, J = 6.4, 3.5 Hz, 1H), 2.63 (td, J = 8.3, 4.2 Hz, 1H), 1.77-1.72 (m, 2H), 1.44-1.30 (q, J = 7.2, 6.0 Hz, 6H), 1.00-0.95 (m, 2H), 0.82-0.78 (m, 2H). |
| 12 | 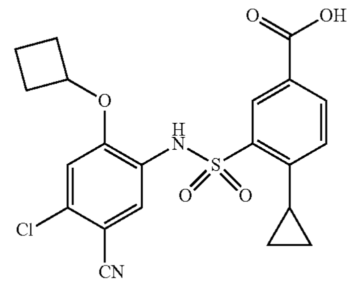 | 3-(N-(4-chloro-5-cyano-2-cyclobutoxyphenyl)sulfamoyl)-4-cyclopropylbenzoic acid. UPLC-MS (Method 1) m/z 445.00 (M − H)$^-$ at 2.017 min. $^1$H NMR (400 MHz, DMSO-$d_6$) δ 13.22 (s, 1H), 10.17 (s, 1H), 8.30 (d, J = 1.8 Hz, 1H), 8.01-7.99 (dd, J = 8.2, 1.9 Hz, 1H), 7.71 (s, 1H), 7.15 (d, J = 8.3 Hz, 1H), 7.07 (s, 1H), 4.65 (m, 1H), 2.74 (m, 1H), 2.26-2.18 (m, 2H), 1.67-1.46 (m, 4H), 1.05 −1.01 (m, 2H), 0.85-0.81 (m, 2H). |
| 13 | 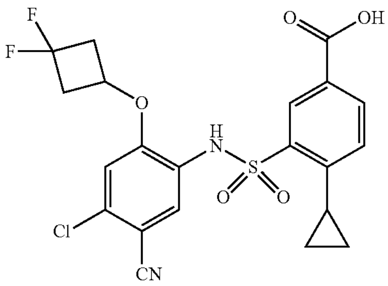 [SMILES: N#Cc1cc(NS(=O)(=O)c2cc(C(=O)O)ccc2C2CC2)c(OC2CC(F)(F)C2)cc1Cl] | 3-(N-(4-chloro-5-cyano-2-(3,3-difluorocyclobutoxy)phenyl)sulfamoyl)-4-cyclopropylbenzoic acid. UPLC-MS (Method 1) m/z 480.95 (M − H)$^-$ at 1.984 min. $^1$H NMR (400 MHz, DMSO-$d_6$) δ 13.22 (s, 1H), 10.33 (s, 1H), 8.33 (d, J = 1.8 Hz, 1H), 8.00 (dd, J = 8.2, 1.8 Hz, 1H), 7.72 (s, 1H), 7.26 (s, 1H), 7.12 (d, J = 8.3 Hz, 1H), 4.76 (m, 1H), 3.09 (m, 2H), 2.74 (tt, J = 8.4, 5.1 Hz, 1H), 2.56-2.55 (d, J = 5.1 Hz, 1H), 2.45-2.43 (d, J = 5.1 Hz, 1H), 1.04-1.02 (dt, J = 8.3, 3.3 Hz, 2H), 0.83-0.81 (m, 2H). |
| 14 | 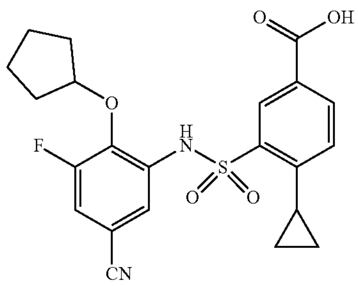 [SMILES: N#Cc1cc(F)c(OC2CCCC2)c(NS(=O)(=O)c2cc(C(=O)O)ccc2C2CC2)c1] | 3-(N-(5-cyano-2-(cyclopentyloxy)−3-fluorophenyl)sulfamoyl)-4-cyclopropylbenzoic acid. UPLC-MS (Method 1) m/z 443.05 (M − H)$^-$ at 2.096 min. $^1$H NMR (400 MHz, DMSO-$d_6$) δ 8.44 (d, J = 1.8 Hz, 1H), 7.83-7.80 (m, 1H), 7.21 (s, 1H), 6.86 (d, J = 8.3 Hz, 2H), 5.25 (s, 1H), 1.70-1.64 (m, 4H), 1.57-1.55 (t, J = 5.4 Hz, 1H), 1.54-1.46 (m, 4H), 1.00-0.97 (m, 2H), 0.75-0.74 (m, 2H). |

-continued

| Example | Structure | Name/Analytical Data |
|---|---|---|
| 15 | 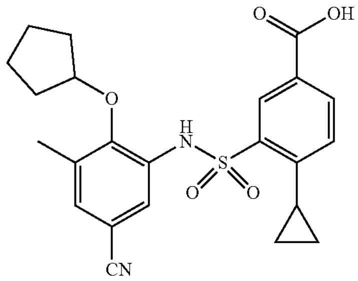 [SMILES: Cc1cc(C#N)cc(NS(=O)(=O)c2cc(C(=O)O)ccc2C2CC2)c1OC1CCCC1] | 3-(N-(5-cyano-2-(cyclopentyloxy)-3-methylphenyl)sulfamoyl)-4-cyclopropylbenzoic acid. UPLC-MS (Method 1) m/z 439.05 (M − H)$^-$ at 2.116 min. $^1$H NMR (400 MHz, DMSO-$d_6$) δ 13.27 (s, 1H), 10.02 (s, 1H), 8.35 (d, J = 1.7 Hz, 1H), 8.04 (dd, J = 8.2, 1.8 Hz, 1H), 7.53 (d, J = 1.9 Hz, 1H), 7.18 (d, J = 8.3 Hz, 1H), 7.06 (d, J = 1.9 Hz, 1H), 4.82 (tt, J = 5.5, 3.2 Hz, 1H), 2.75 (tt, J = 8.5, 5.1 Hz, 1H), 2.20 (s, 3H), 1.72-1.60 (dddd, J = 29.6, 19.4, 10.9, 6.1 Hz, 6H), 1.51-1.49 (m, 2H), 1.10-1.08 (m, 2H), 0.90-0.88 (m, 2H). |
| 16 | 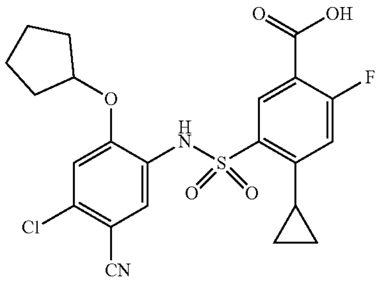 [SMILES: N#Cc1cc(NS(=O)(=O)c2cc(C(=O)O)c(F)cc2C2CC2)c(OC2CCCC2)cc1Cl] | 5-(N-(4-chloro-5-cyano-2-(cyclopentyloxy)phenyl)sulfamoyl)-4-cyclopropyl-2-fluorobenzoic acid. UPLC-MS (Method 1) m/z 477.00 (M − H)$^-$ at 2.109 min. $^1$H NMR (400 MHz, DMSO-$d_6$) δ 13.48 (s, 1H), 10.10 (s, 1H), 8.30 (d, J = 7.5 Hz, 1H), 7.68 (s, 1H), 7.29 (s, 1H), 6.97-6.94 (d, J = 12.5 Hz, 1H), 4.82 (t, J = 4.4 Hz, 1H), 2.60 (m, 1H), 1.83-1.74 (d, J = 6.0 Hz, 2H), 1.49-1.40 (m, 6H), 0.99-0.95 (m, 2H), 0.87-0.82 (m, 2H). |
| 17 | 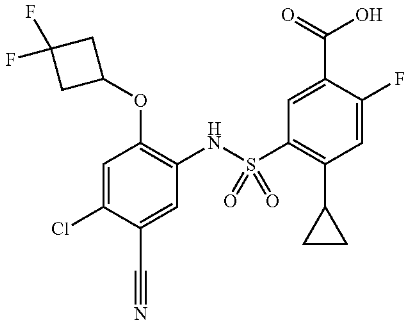 [SMILES: N#Cc1cc(NS(=O)(=O)c2cc(C(=O)O)c(F)cc2C2CC2)c(OC2CC(F)(F)C2)cc1Cl] | 5-(N-(4-chloro-5-cyano-2-(3,3-difluorocyclobutoxy)phenyl)sulfamoyl)-4-cyclopropyl-2-fluorobenzoic acid. UPLC-MS (Method 1) m/z 498.95 (M − H)$^-$ at 1.932 min. $^1$H NMR (400 MHz, DMSO-$d_6$) δ 13.49 (s, 1H), 10.33 (s, 1H), 8.30 (d, J = 7.4 Hz, 1H), 7.74 (s, 1H), 7.28 (s, 1H), 6.96 (d, J = 12.4 Hz, 1H), 4.78 (t, J = 4.6 Hz, 1H), 3.16-3.09 (m, 2H), 2.69 (t, J = 6.1 Hz, 1H), 2.56 −2.50 (m, 2H), 1.03-1.01 (m, 2H), 0.88 −0.85 (m, 2H). |
| 18 | 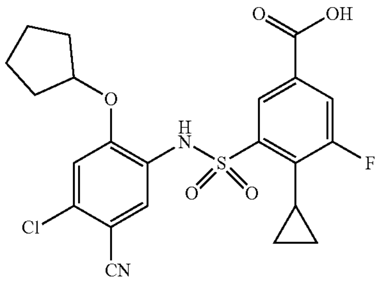 [SMILES: N#Cc1cc(NS(=O)(=O)c2cc(C(=O)O)cc(F)c2C2CC2)c(OC2CCCC2)cc1Cl] | 3-(N-(4-chloro-5-cyano-2-(cyclopentyloxy)phenyl)sulfamoyl)-4-cyclopropyl-5-fluorobenzoic acid UPLC-MS (Method 1) m/z 477.05 (M − H)$^-$ at 2.116 min. $^1$H NMR (400 MHz, DMSO-d6) δ 8.17 (s, 1H), 7.75-7.67 (m, 2H), 7.27 (s, 1H), 4.84 (d, J = 6.4 Hz, 1H), 2.50-2.46 (m, 1H), 1.80-1.79 (m, 2H), 1.44-1.32 (m, 6H), 1.13-1.12 (d, J = 5.7 Hz, 2H), 0.97-0.95 (d, J = 8.5 Hz, 2H). |
| 19 | 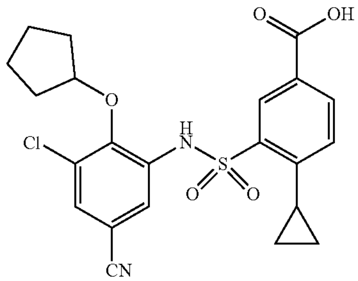 [SMILES: N#Cc1cc(Cl)c(OC2CCCC2)c(NS(=O)(=O)c2cc(C(=O)O)ccc2C2CC2)c1] | 3-(N-(3-chloro-5-cyano-2-(cyclopentyloxy)phenyl)sulfamoyl)-4-cyclopropylbenzoic acid. UPLC-MS (Method 1) m/z 459.05 (M − H)$^-$ at 2.189 min. $^1$H NMR (400 MHz, DMSO-$d_6$) δ 13.29 (s, 1H), 10.37 (s, 1H), 8.37 (d, J = 1.8 Hz, 1H), 8.06 (dd, J = 8.1, 1.9 Hz, 1H), 7.92 (s, 1H), 7.30 (d, J = 2.0 Hz, 1H), 7.19 (d, J = 8.3 Hz, 1H), 4.93 (s, 1H), 2.74 (t, 1H), 1.72-1.56 (m, 6H), 1.49-1.47 (m, 2H), 1.12-1.09 (m, 2H), 0.91-0.88 (m, 2H), |

Example 20: 3-(N-(2-(cyclopentyloxy)-5-(isothiazol-5-yl)phenyl)sulfamoyl)-4-cyclopropylbenzoic acid

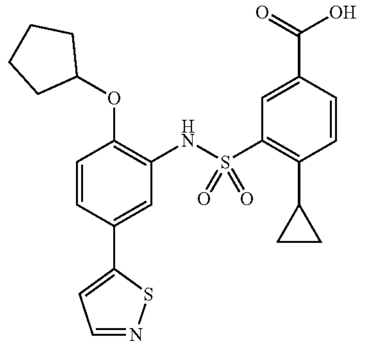 [SMILES: O=C(O)c1ccc(C2CC2)c(S(=O)(=O)Nc2cc(-c3ccns3)ccc2OC2CCCC2)c1]

Step 1: methyl 3-(N-(2-(cyclopentyloxy)-5-(isothiazol-5-yl)phenyl)sulfamoyl)-4-cyclopropylbenzoate: A mixture of 2-(cyclopentyloxy)-5-(isothiazol-5-yl)aniline (Intermediate 9) (100 mg, 380 μmol, 99% purity), methyl 3-(chlorosulfonyl)-4-cyclopropylbenzoate (157 mg, 570 μmol) and pyridine (92.0 μL, 1.14 mmol) in DCM (2 mL) was heated to 35° C. and stirred for 3 days. The mixture was concentrated onto silica and purified by chromatography on silica gel (12 g cartridge, 0-100% EtOAc/isohexane) to afford the title compound (171 mg, 340 μmol, 89%, 99% purity) as a light-yellow solid. UPLC-MS (Method 4): m/z 499.4 $(M+H)^+$, 497.2 $(M-H)^-$, at 2.01 min. $^1H$ NMR (500 MHz, DMSO-$d_6$) δ 9.81 (s, 1H), 8.53 (d, J=1.8 Hz, 1H), 8.41 (d, J=1.9 Hz, 1H), 8.00 (dd, J=8.2, 1.9 Hz, 1H), 7.58 (d, J=1.8 Hz, 1H), 7.51-7.45 (m, 2H), 7.15 (d, J=8.3 Hz, 1H), 7.01 (d, J=9.2 Hz, 1H), 4.76-4.70 (m, 1H), 3.84 (s, 3H), 2.80-2.73 (m, 1H), 1.82-1.75 (m, 2H), 1.56-1.40 (m, 6H), 1.06-0.98 (m, 2H), 0.84-0.77 (m, 2H).

Step 2: 3-(N-(2-(cyclopentyloxy)-5-(isothiazol-5-yl)phenyl)sulfamoyl)-4-cyclopropylbenzoic acid: A mixture of the product from Step 1 above (171 mg, 340 μmol, 99% purity) and $LiOH{\cdot}H_2O$ (58.0 mg, 1.38 mmol) in THF/MeOH/$H_2O$ (4:1:1, 2.1 mL) was stirred at 40° C. overnight. The mixture was diluted with $H_2O$ (5 mL), acidified to ~pH 4 using 1 M HCl(aq), and extracted with EtOAc (3×15 mL). The organic extracts were combined, washed with brine (15 mL), dried ($MgSO_4$) and the solvent was removed in vacuo. The residue was loaded onto silica and purified by chromatography on silica gel (12 g cartridge, 0-10% MeOH/DCM) and then triturated with TBME to afford the title compound (97.3 mg, 199 μmol, 59%, 99% purity) as a light-yellow solid. UPLC-MS (Method 4): m/z 485.3 $(M+H)^+$, 483.2 $(M-H)^-$, at 1.83 min. $^1H$ NMR (500 MHz, DMSO-$d_6$) δ 13.23 (s, 1H), 9.76 (s, 1H), 8.52 (d, J=1.8 Hz, 1H), 8.41 (d, J=1.9 Hz, 1H), 7.98 (dd, J=8.2, 1.9 Hz, 1H), 7.57 (d, J=1.8 Hz, 1H), 7.49-7.45 (m, 2H), 7.12 (d, J=8.2 Hz, 1H), 7.01 (d, J=8.8 Hz, 1H), 4.76-4.70 (m, 1H), 2.79-2.71 (m, 1H), 1.83-1.74 (m, 2H), 1.58-1.41 (m, 6H), 1.05-0.97 (m, 2H), 0.83-0.76 (m, 2H).

The following examples were prepared by methods analogous to Example 20, substituting appropriate starting materials and intermediates where necessary:

| Example | Structure | Name/Analytical Data |
|---|---|---|
| 21 | 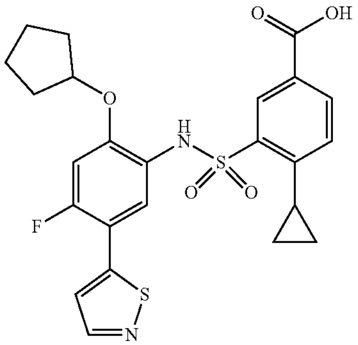 [SMILES: O=C(O)c1ccc(C2CC2)c(S(=O)(=O)Nc2cc(-c3ccns3)c(F)cc2OC2CCCC2)c1] | 3-(N-(2-(cyclopentyloxy)-4-fluoro-5-(isothiazol-5-yl)phenyl)sulfamoyl)-4-cyclopropylbenzoic acid<br>UPLC-MS (Method 4): m/z 503.3 $(M + H)^+$, 501.1 $(M - H)^-$, at 1.86 min. $^1H$ NMR (500 MHz, DMSO-$d_6$) δ 13.22 (s, 1H), 9.80 (s, 1H), 8.57 (t, J = 1.9 Hz, 1H), 8.34 (d, J = 1.8 Hz, 1H), 7.98 (dd, J = 8.2, 1.9 Hz, 1H), 7.70 (d, J = 1.8 Hz, 1H), 7.68 (d, J = 8.2 Hz, 1H), 7.12 (d, J = 8.3 Hz, 1H), 7.05 (d, J = 13.0 Hz, 1H), 4.73 - 4.66 (m, 1H), 2.75 - 2.66 (m, 1H), 1.82 - 1.71 (m, 2H), 1.52 - 1.32 (m, 6H), 1.02 - 0.94 (m, 2H), 0.84 - 0.77 (m, 2H). |
| 22 | 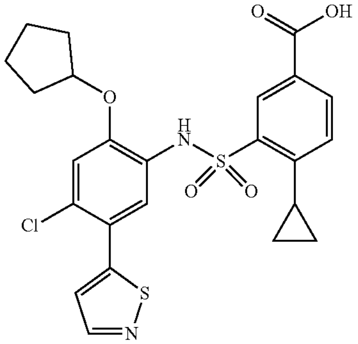 [SMILES: O=C(O)c1ccc(C2CC2)c(S(=O)(=O)Nc2cc(-c3ccns3)c(Cl)cc2OC2CCCC2)c1] | 3-(N-(4-chloro-2-(cyclopentyloxy)-5-(isothiazol-5-yl)phenyl)sulfamoyl)-4-cyclopropylbenzoic acid<br>UPLC-MS (Method 4): m/z 519.0 $(M + H)^+$, 517.1 $(M - H)^-$, at 1.98 min. $^1H$ NMR (500 MHz, DMSO-$d_6$) δ 13.26 (s, 1H), 9.95 (s, 1H), 8.57 (d, J = 1.8 Hz, 1H), 8.39 (d, J = 1.9 Hz, 1H), 7.99 (dd, J = 8.2, 1.8 Hz, 1H), 7.60 (d, J = 1.9 Hz, 1H), 7.59 (s, 1H), 7.17 (s, 1H), 7.12 (d, J = 8.2 Hz, 1H), 4.81 - 4.75 (m, 1H), 2.77 - 2.68 (m, 1H), 1.84 - 1.75 (m, 2H), 1.58 - 1.40 (m, 6H), 1.04 - 0.96 (m, 2H), 0.84 - 0.77 (m, 2H). |

Example 23: 3-(N-(2-(cyclopentyloxy)-5-(isothiazol-5-yl)phenyl)sulfamoyl)-4-cyclopropylbenzoic acid

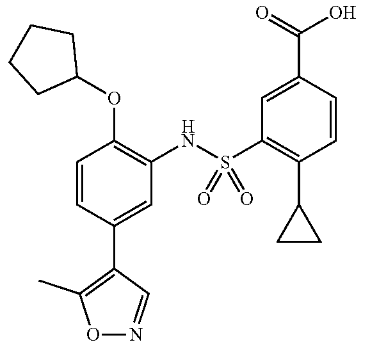 [SMILES: Cc1oncc1-c1ccc(OC2CCCC2)c(NS(=O)(=O)c2cc(C(=O)O)ccc2C2CC2)c1]

Step 1: methyl 3-(N-(2-(cyclopentyloxy)-5-(5-methylisoxazol-4-yl)phenyl)sulfamoyl)-4-cyclopropylbenzoate: A mixture of 2-(cyclopentyloxy)-5-(5-methylisoxazol-4-yl) aniline (intermediate 6) (100 mg, 383 μmol, 99% purity), methyl 3-(chlorosulfonyl)-4-cyclopropylbenzoate (160 mg, 582 μmol) and pyridine (100 μL, 1.24 mmol) in DCM (2 mL) was heated to 35° C. and stirred over the weekend. The mixture was concentrated onto silica and purified by chromatography on silica gel (12 g cartridge, 0-100% EtOAc/isohexane) to afford the title compound (178 mg, 0.35 mmol, 91%, 97% purity) as a pale orange foam. UPLC-MS (Method 4): m/z 497.3 $(M+H)^+$, 495.3 $(M-H)^-$, at 1.96 min.

Step 2: 3-(N-(2-(cyclopentyloxy)-5-(5-methylisoxazol-4-yl)phenyl)sulfamoyl)-4-cyclopropylbenzoic acid: A mixture of the product from Step 1 above (180 mg, 352 μmol, 97% purity) and HCl (4 M in dioxane) (500 μL, 2.00 mmol) in dioxane/$H_2O$ (2:1, 1.5 mL) was heated to 50° C. and stirred overnight. Conc. HCl (500 μL, 37% w/w) and THF (0.50 mL) were added and the mixture was heated to 70° C. and stirred for 24 h. Additional conc. HCl (500 μL, 37% w/w) was added and the reaction was stirred at 70° C. for 24 h. The mixture was diluted with $H_2O$ (10 mL) and extracted with EtOAc (3×20 mL). The organic extracts were combined, washed with brine (10 mL), dried ($MgSO_4$) and concentrated onto silica. The crude product was partially purified by chromatography on silica gel (12 g cartridge, 0-10% MeOH/DCM), then purified by preparative HPLC (Waters X-Select CSH $C_{18}$ ODB prep column, 130Å, 5 μm, 30 mm×100 mm, 40-70% (0.1% formic acid(aq))/MeCN) to afford the title compound (33 mg, 68 μmol, 19%, 99% purity) as a white fluffy solid. UPLC-MS (Method 4): m/z 483.4 $(M+H)^+$, 481.3 $(M-H)^-$, at 1.80 min. $^1H$ NMR (500 MHz, DMSO-$d_6$) δ 13.23 (br s, 1H), 9.61 (s, 1H), 8.70 (s, 1H), 8.37 (d, J=1.8 Hz, 1H), 7.96 (dd, J=8.2, 1.9 Hz, 1H), 7.30 (d, J=2.2 Hz, 1H), 7.23 (dd, J=8.5, 2.3 Hz, 1H), 7.11 (d, J=8.3 Hz, 1H), 6.97 (d, J=8.6 Hz, 1H), 4.78-4.57 (m, 1H), 2.83-2.67 (m, 1H), 2.44 (s, 3H), 1.84-1.71 (m, 2H), 1.59-1.38 (m, 6H), 1.06-0.95 (m, 2H), 0.86-0.76 (m, 2H).

The following examples were prepared by methods analogous to Example 23, substituting appropriate starting materials and intermediates where necessary:

| Example | Structure | Name/Analytical Data |
| --- | --- | --- |
| 24 | 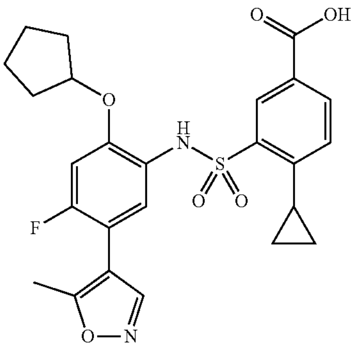 [SMILES: Cc1oncc1-c1cc(NS(=O)(=O)c2cc(C(=O)O)ccc2C2CC2)c(OC2CCCC2)cc1F] | 3-(N-(2-(cyclopentyloxy)-4-fluoro-5-(5-methylisoxazol-4-yl)phenyl)sulfamoyl)-4-cyclopropylbenzoic acid<br>UPLC-MS (Method 4): m/z 501.3 $(M + H)^+$, 499.2 $(M - H)^-$, at 1.81 min. $^1H$ NMR (500 MHz, DMSO-$d_6$) δ 13.23 (br s, 1H), 9.68 (s, 1H), 8.62 (d, J = 1.7 Hz, 1H), 8.31 (d, J = 1.8 Hz, 1H), 7.96 (dd, J = 8.2, 1.9 Hz, 1H), 7.25 (d, J = 8.2 Hz, 1H), 7.10 (d, J = 8.3 Hz, 1H), 6.95 (d, J = 12.3 Hz, 1H), 4.71 - 4.58 (m, 1H), 2.78 - 2.61 (m, 1H), 2.38 (s, 3H), 1.82 - 1.67 (m, 2H), 1.55 - 1.31 (m, 6H), 1.04 - 0.93 (m, 2H), 0.87 - 0.74 (m, 2H).<br>3-(N-(4-chloro-2-(cyclopentyloxy)-5-(5-methylisoxazol-4-yl)phenyl)sulfamoyl)-4-cyclopropylbenzoic acid |
| 25 | 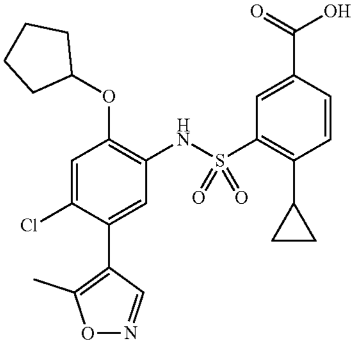 [SMILES: Cc1oncc1-c1cc(NS(=O)(=O)c2cc(C(=O)O)ccc2C2CC2)c(OC2CCCC2)cc1Cl] | UPLC-MS (Method 4): m/z 517.4 $(M + H)^+$, 515.2 $(M - H)^-$, at 1.89 min. $^1H$ NMR (500 MHz, DMSO-$d_6$) δ 13.25 (br s, 1H), 9.81 (s, 1H), 8.60 (s, 1H), 8.33 (d, J = 1.8 Hz, 1H), 7.97 (dd, J = 8.2, 1.9 Hz, 1H), 7.20 (s, 1H), 7.15 - 7.07 (m, 2H), 4.80 - 4.67 (m, 1H), 2.79 - 2.66 (m, 1H), 2.28 (s, 3H), 1.87 - 1.69 (m, 2H), 1.61 - 1.34 (m, 6H), 1.07 - 0.95 (m, 2H), 0.90 - 0.75 (m, 2H). |

Example 8: 3-(N-(2-(cyclopentyloxy)-5-(1H-tetrazol-1-yl)phenyl)sulfamoyl)-4-cyclopropylbenzoic acid

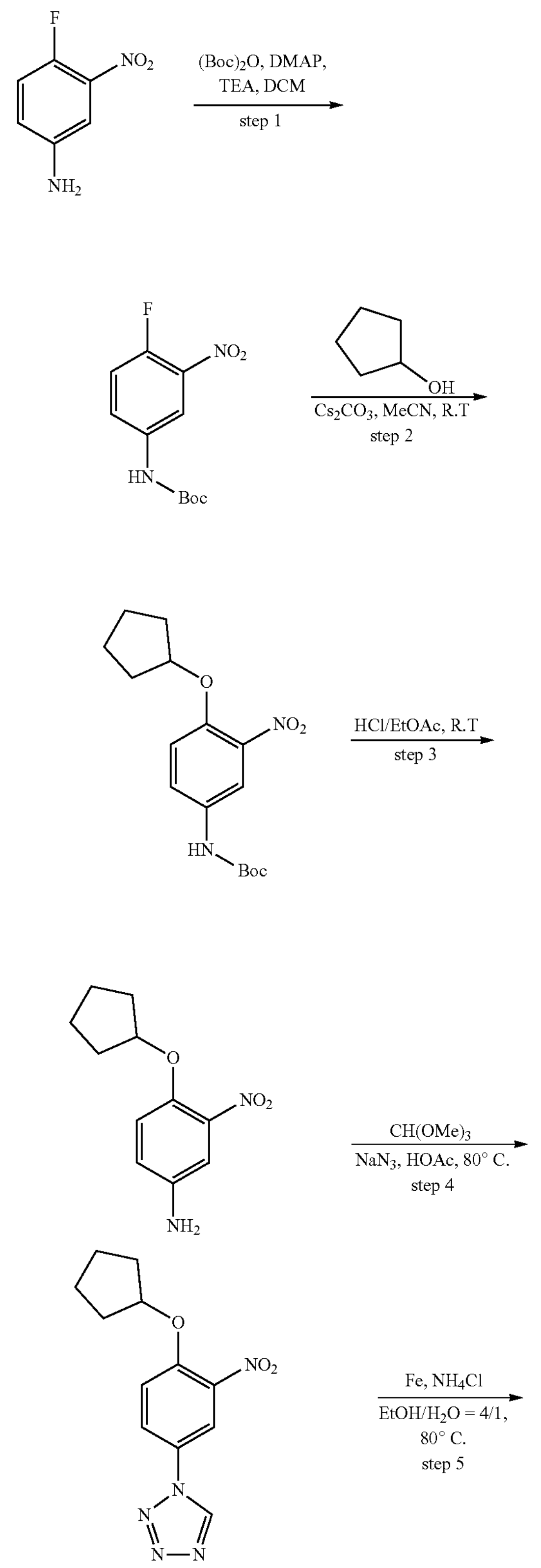

-continued

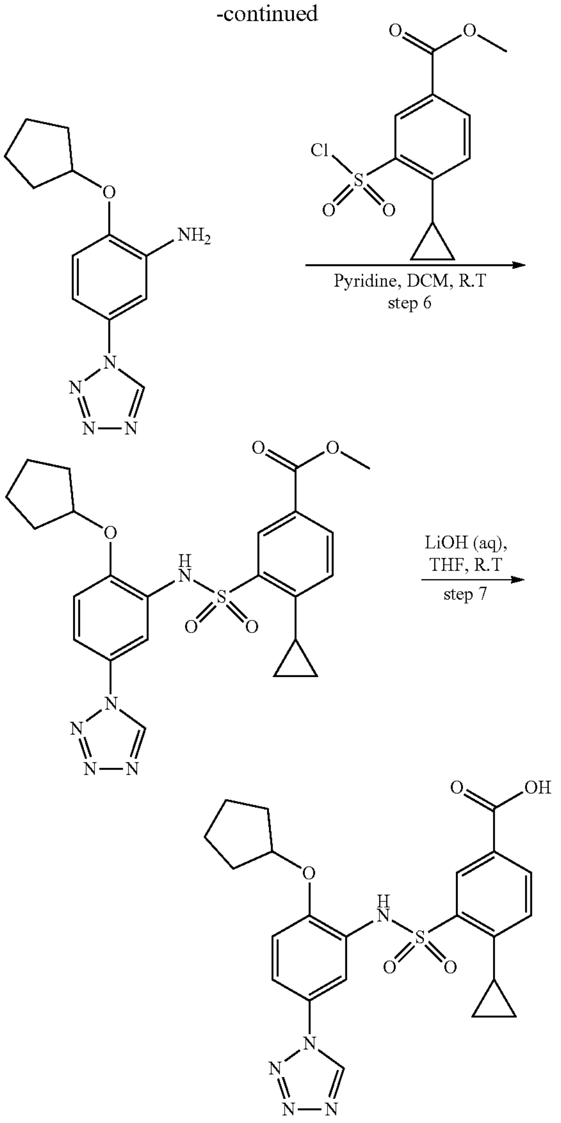

Step 1: tert-butyl (4-fluoro-3-nitrophenyl)carbamate: A mixture of 4-fluoro-3-nitroaniline (1.56 g, 10.0 mmol), di-tert-butyl dicarbonate (4.36 g, 20.0 mmol), TEA (4.04 g, 40.0 mmol) and DMAP (0.622 g, 5.0 mmol) in DCM (20 mL) was stirred at R.T for 12 h. The solvent was removed under reduced pressure and the residue dissolved in EtOAc and washed with saturated $Na_2CO_3$, water and brine. The organic layer was dried over $Na_2SO_4$ and concentrated to give crude product. The crude product was purified by silica gel chromatography (eluting with 1/10 EtOAc/PE) to afford the title compound (2.0 g, 7.81 mmol, 39%) as a yellow oil. 1H NMR (400 MHz, DMSO-$d_6$) δ 8.13 (dd, J=6.7, 2.7 Hz, 1H), 7.76 (ddd, J=8.9, 4.0, 2.7 Hz, 1H), 7.62 (dd, J=10.9, 8.9 Hz, 1H), 1.39 (s, 9H).

Step 2: tert-butyl (4-(cyclopentyloxy)-3-nitrophenyl)carbamate. A mixture of Step 1 carbamate (0.76 g, 3.0 mmol), cyclopentanol (0.52 g, 6.0 mmol) and $Cs_2CO_3$ (1.85 g, 6.0 mmol) in MeCN (20 mL) was stirred at R.T for 12 h. The reaction mixture was filtered through celite and the filtrate was concentrated and purified by Biotage Isolera One ($C_{18}$ column, eluting with 10% to 90% MeCN/$H_2O$) to give the title compound (0.61 g, 1.89 mmol, 63%).

Step 3: 4-cyclopentyloxy-3-nitroaniline: A solution of Step 2 carbamate (0.61 g, 1.89 mmol) in HCl EtOAc solution (4 M, 3 mL) was stirred at room temperature for 2 h. The resulting mixture was concentrated and dried under vacuum to afford the title compound (0.22 g, 0.97 mmol, 51%). UPLC-MS (Method 3) m/z 223.0 $(M+H)^+$ at 0.94 min.

Step 4: 1-(4-cyclopentyloxy-3-nitrophenyl)-1H-tetrazole: A mixture of Step 3 aniline (0.22 g, 1.0 mmol), trimethylorthoformate (0.63 g, 6.0 mmol), $NaN_3$ (0.13 g, 2.0 mmol) in HOAc (5 mL) was heated at 80° C. for 2 h. The solvent was removed under reduced pressure and the residue dissolved in EtOAc and washed with saturated $Na_2CO_3$, water and brine. The organic layer was dried over $Na_2SO_4$ and concentrated to give crude product. The crude product was purified by Biotage Isolera One ($C_{18}$ column, eluting with 10% to 90% $MeCN/H_2O$) to give the title compound (0.24 g, 0.88 mmol, 88%). UPLC-MS (Method 3) m/z 276.0 $(M+H)^+$ at 1.22 min.

Step 5: 2-cyclopentyloxy-5-(1H-tetrazol-1-yl)aniline: A mixture of Step 4 tetrazole (0.24 g, 0.88 mmol), iron powder (0.29 g, 5.28 mmol) and $NH_4Cl$ (0.09 g, 1.78 mmol) in a mixture of EtOH and water (24 mL, $EtOH/H_2O$ (v/v=5/1)) was heated at 85° C. for 2 h. The resulting mixture was filtered through celite and concentrated to afford the title compound (0.17 g, 0.69 mmol, 78%). UPLC-MS (Method 3) m/z 246.0 $(M+H)^+$ at 1.21 min.

Step 6: methyl 4-cyclopropyl-3-(N-(2-isopropoxy-5-(1H-tetrazol-1-yl)phenyl) sulfamoyl)benzoate: To a solution of Step 5 aniline (0.17 g, 0.69 mmol) and pyridine (0.11 g, 1.38 mmol) in dry DCM (5 mL) was added methyl 3-(chlorosulfonyl)-4-cyclopropylbenzoate (intermediate 3) (0.18 g, 0.68 mmol) and the solution stirred at RT for 4 h. The solvent was removed in vacuo and the crude product was purified by Biotage Isolera One ($C_{18}$ column, eluting with 10% to 90% $MeCN/H_2O$) to give the title compound (0.16 g, 0.33 mmol, 52%). UPLC-MS (Method 3) m/z 482.0 $(M-H)^-$ at 1.99 min.

Step 7: 3-(N-(2-(cyclopentyloxy)-5-(1H-tetrazol-1-yl) phenyl)sulfamoyl)-4-cyclopropylbenzoic acid. A mixture of Step 6 ester (0.16 g, 0.33 mmol) and LiOH (0.069 g, 1.67 mmol) in THF (5 mL) and water (5 mL) was stirred at R.T for 2 h. The THF was removed under reduced pressure and the pH of the aqueous solution was adjusted to 3 with 2M HCl. The mixture was extracted with EtOAc (20 mL×3), dried over $Na_2SO_4$ and concentrated under vacuum to afford the title compound (0.048 g, 0.108 mmol, 31%) as a white solid. UPLC-MS (Method 1) m/z 468.05 $(M-H)^-$ at 1.823 min. $^1H$ NMR (400 MHz, DMSO-$d_6$) δ 13.20 (s, 1H), 9.95 (s, 2H), 8.37 (d, J=1.9 Hz, 1H), 7.98-7.96 (dd, J=8.2, 1.9 Hz, 1H), 7.78 (d, J=2.7 Hz, 1H), 7.62-7.60 (dd, J=8.9, 2.7 Hz, 1H), 7.15-7.12 (dd, J=11.4, 8.7 Hz, 2H), 4.73 (m, 1H), 2.73 (td, J=8.5, 4.3 Hz, 1H), 1.79-1.78 (m, 2H), 1.50-1.43 (m, 6H), 1.01-0.97 (m, 2H), 0.80-0.77 (m, 2H).

The following examples were prepared by methods analogous to Example 8, substituting appropriate starting materials and intermediates where necessary:

| Example | Structure | Name/Analytical Data |
|---|---|---|
| 9 | 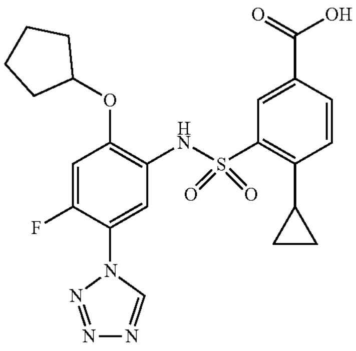 [SMILES: O=C(O)c1ccc(C2CC2)c(S(=O)(=O)Nc2cc(-n3cnnn3)c(F)cc2OC2CCCC2)c1] | 3-(N-(2-(cyclopentyloxy)-4-fluoro-5-(1H-tetrazol-1-yl)phenyl)sulfamoyl)-4-cyclopropylbenzoic acid. UPLC-MS (Method 1) m/z 486.05 $(M-H)^-$ at 1.761 min. $^1H$ NMR (400 MHz, DMSO-$d_6$) δ 13.18 (s, 1H), 9.95 (s, 1H), 9.83 (d, J = 1.4 Hz, 1H), 8.35 (d, J = 1.9 Hz, 1H), 7.99-7.97 (dd, J = 8.2, 1.9 Hz, 1H), 7.69 (d, J = 7.9 Hz, 1H), 7.26 (d, J = 12.5 Hz, 1H), 7.12 (d, J = 8.3 Hz, 1H), 4.74 (tt, J = 5.8, 2.7 Hz, 1H), 2.72 (td, J = 8.4, 4.1 Hz, 1H), 1.80-1.77 (h, J = 5.9, 5.1 Hz, 2H), 1.47-1.38 (m, 6H), 1.03-0.98 (m, 2H), 0.82-0.78 (m, 2H). |
| 10 | 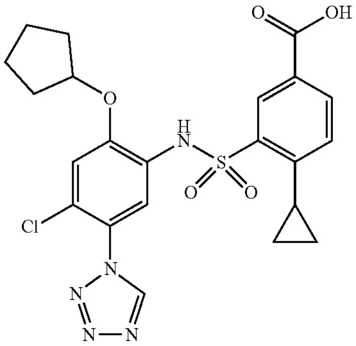 [SMILES: O=C(O)c1ccc(C2CC2)c(S(=O)(=O)Nc2cc(-n3cnnn3)c(Cl)cc2OC2CCCC2)c1] | 3-(N-(4-chloro-2-(cyclopentyloxy)-5-(1H-tetrazol-1-yl)phenyl)sulfamoyl)-4-cyclopropylbenzoic acid. UPLC-MS (Method 1) m/z 502.00 $(M-H)^-$ at 1.867 min. $^1H$ NMR (400 MHz, DMSO-$d_6$) δ 13.20 (s, 1H), 10.10 (s, 1H), 9.82 (s, 1H), 8.38 (d, J = 1.8 Hz, 1H), 8.00 (dd, J = 8.3, 1.9 Hz, 1H), 7.60 (s, 1H), 7.32 (s, 1H), 7.13 (d, J = 8.3 Hz, 1H), 4.82 (t, J = 6.5 Hz, 1H), 2.71 (td, J = 8.3, 4.3 Hz, 1H), 1.80-1.78 (m, 2H), 1.49-1.42 (m, 6H), 1.02-1.00 (m, 2H), 0.82-0.79 (m, 2H). |

Example 52: 3-(N-(2-((2-oxaspiro[3.3]heptan-6-yl)oxy)-4-chloro-5-cyanophenyl)sulfamoyl)-4-cyclopropylbenzoic acid

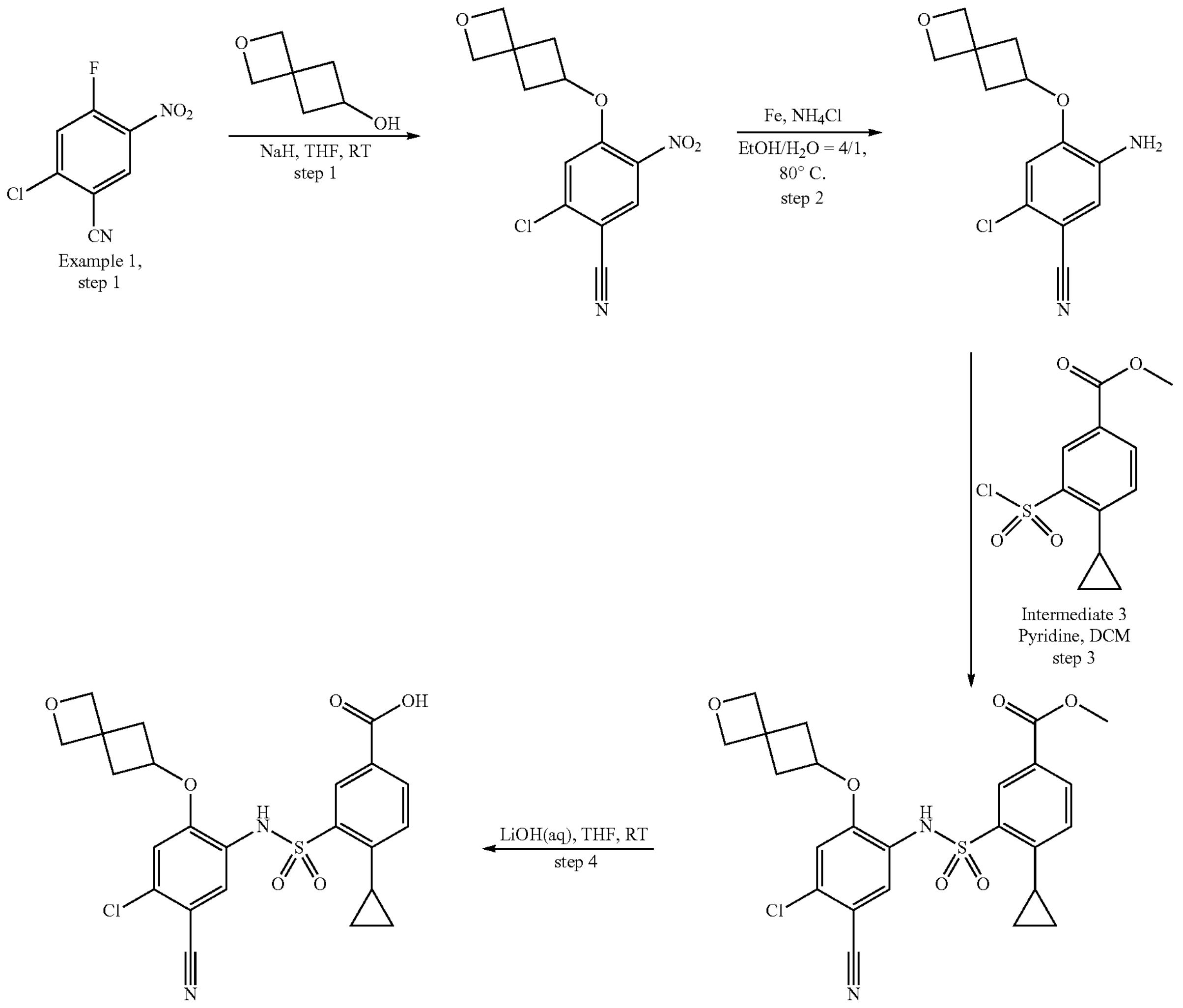

Step 1: 4-((2-oxaspiro[3.3]heptan-6-yl)oxy)-2-chloro-5-nitrobenzonitrile: A mixture of 2-chloro-4-fluoro-5-nitrobenzonitrile (Example 1, step 1) (0.150 g, 0.75 mmol), 2-oxaspiro[3.3]heptan-6-ol (0.085 g, 0.75 mmol) and NaH (0.022 g, 0.90 mmol, 60%) in THF (5 mL) was stirred at RT for 12 h. The reaction mixture was filtered through celite. The filtrate was concentrated and purified by silica gel chromatography (eluting with 50% EtOAc/PE) to afford the title compound (0.180 g, 0.40 mmol, 53% yield, 65% purity) as a yellow solid. $^1H$ NMR (400 MHz, DMSO-$d_6$) δ 8.67 (s, 1H), 7.61 (s, 1H), 4.97 (p, J=6.8 Hz, 1H), 4.64 (s, 2H), 4.55 (s, 2H), 2.87 (ddd, J=10.3, 6.8, 3.2 Hz, 2H), 2.34-2.23 (m, 2H).

Step 2: 4-((2-oxaspiro[3.3]heptan-6-yl)oxy)-5-amino-2-chlorobenzonitrile: A mixture of 4-((2-oxaspiro[3.3]heptan-6-yl)oxy)-2-chloro-5-nitrobenzonitrile (0.180 g, 0.41 mmol, 65%), iron powder (0.114 g, 2.04 mmol) and $NH_4Cl$ (0.044 g, 0.82 mmol) in a mixture of EtOH and water (3 mL, EtOH/$H_2O$ (v/v=5/1)) was heated at 85° C. for 2 h. The resulting mixture was filtered through celite and concentrated to afford the crude product, which was purified by Biotage Isolera One ($C_{18}$ column, eluting with 10% to 90% MeCN/$H_2O$) to afford the title compound (0.071 g, 0.27 mmol, 66% yield) as a yellow oil. UPLC-MS (Method 3) m/z 265.0 $(M+H)^+$ at 1.089 min.

Step 3: methyl 3-(N-(2-((2-oxaspiro[3.3]heptan-6-yl)oxy)-4-chloro-5-cyanophenyl)sulfamoyl)-4-cyclopropylbenzoate: To a solution of 4-((2-oxaspiro[3.3]heptan-6-yl)oxy)-5-amino-2-chlorobenzonitrile (0.071 g, 0.27 mmol) in pyridine (0.043 g, 0.54 mmol) was added methyl 3-(chlorosulfonyl)-4-cyclopropylbenzoate (0.074 g, 0.27 mmol) and the solution stirred at RT for 16 h. The solvent was removed in vacuo and the crude product purified by Biotage Isolera One ($C_{18}$ column, eluting with 10% to 90% MeCN/$H_2O$) to afford the title compound (0.073 g, 0.15 mmol, 55% yield) as a white solid. UPLC-MS (Method 3) m/z 501.00 $(M-H)^-$ at 1.570 min.

Step 4: 3-(N-(2-((2-oxaspiro[3.3]heptan-6-yl)oxy)-4-chloro-5-cyanophenyl)sulfamoyl)-4-cyclopropylbenzoic acid: A mixture of methyl 3-(N-(2-((2-oxaspiro[3.3]heptan-6-yl)oxy)-4-chloro-5-cyanophenyl)sulfamoyl)-4-cyclopropylbenzoate (0.055 g, 0.11 mmol) and LiOH (0.013 g, 0.55 mmol) in a mixture of THF (1 mL) and water (1 mL) was stirred at RT for 16 h. The THF was removed under reduced pressure and the pH of the aqueous solution was adjusted to 3 with 2M HCl. The mixture was extracted with EtOAc (20 mL×3), dried over $Na_2SO_4$ and concentrated under vacuum to afford the crude product, which was purified by Biotage Isolera One ($C_{18}$ column, eluting with 10% to 90% MeCN/$H_2O$) to afford the title compound (0.026 g, 0.053 mmol, 48% yield,) as a white solid. UPLC-MS (Method 1) m/z 487.00 $(M-H)^-$ at 1.750 mm. H NMR (400 MHz, DMSO-$d_6$) b 13.28 (s, 1H), 10.18 (s, 1H), 8.30 (d, J=1.8 Hz, 1H), 7.99 (dd, J=8.2, 1.8 Hz, 1H), 7.75 (s, 1H), 7.18-7.10 (m, 2H), 4.63-4.51 (m, 1H), 4.55 (2, 2H), 4.43 (s, 2H), 2.71 (td, J=8.3, 4.2 Hz, 1H), 2.62 (ddd, J=10.1, 6.9, 3.3 Hz, 2H), 1.73 (ddd, J=10.1, 7.0, 3.3 Hz, 2H), 1.02 (dt, J=8.2, 3.3 Hz, 2H), 0.91-0.78 (m, 2H).

The following examples were prepared by methods analogous to Example or 52, substituting appropriate starting materials and intermediates where necessary:

| Example | Structure | Name/Analytical Data |
|---|---|---|
| 26 | 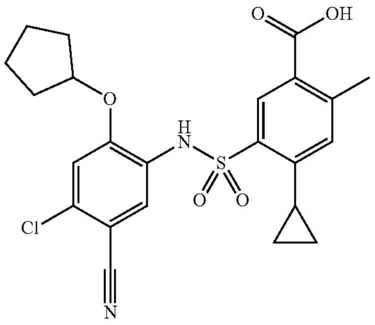 [SMILES: Cc1cc(C2CC2)c(S(=O)(=O)Nc2cc(C#N)c(Cl)cc2OC2CCCC2)cc1C(=O)O] | 5-(N-(4-chloro-5-cyano-2-(cyclopentyloxy)phenyl)sulfamoyl)-4-cyclopropyl-2-methylbenzoic acid<br>UPLC-MS (Method 1) m/z 473.05 $(M - H)^-$ at 2.150 min. $^1H$ NMR (400 MHz, DMSO-$d_6$) δ 8.25 (s, 1H), 7.61 (s, 1H), 7.22 (s, 1H), 6.86 (s, 1H), 4.90-4.80 (m, 1H), 2.75-2.63 (m, 1H), 1.90-1.77 (m, 2H), 1.60-1.42 (m, 6H), 1.01-0.93 (m, 2H), 0.87-0.77 (m, 2H). Three protons obscured by solvent. |
| 27 | 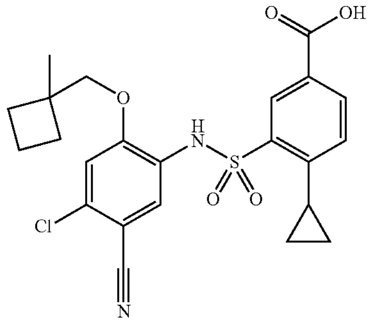 [SMILES: CC1(COc2cc(Cl)c(C#N)cc2NS(=O)(=O)c2cc(C(=O)O)ccc2C2CC2)CCC1] | 3-(N-(4-chloro-5-cyano-2-((1-methylcyclobutyl)methoxy)phenyl)sulfamoyl)-4-cyclopropylbenzoic acid<br>UPLC-MS (Method 3) m/z 473.00 $(M - H)^-$ at 1.67 min. $^1H$ NMR (400 MHz, DMSO-$d_6$) δ 10.07 (br s, 1H), 8.36 (d, J = 1.8 Hz, 1H), 7.96 (dd, J = 8.2, 1.8 Hz, 1H), 7.57 (s, 1H), 7.43 (s, 1H), 7.08 (d, J = 8.3 Hz, 1H), 3.82 (s, 2H), 2.60-2.50 (m, 1H), 1.82-1.68 (m, 4H), 1.57-1.47 (m, 2H), 0.99 (s, 3H), 0.95-0.89 (m, 2H), 0.82-0.76 (m, 2H). |
| 28 | 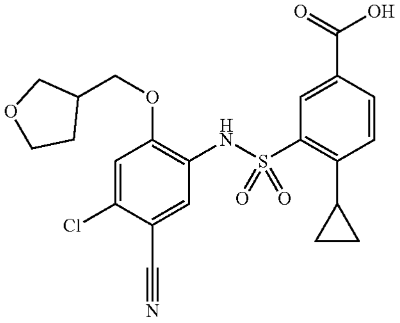 [SMILES: N#Cc1cc(NS(=O)(=O)c2cc(C(=O)O)ccc2C2CC2)c(OCC2CCOC2)cc1Cl] | 3-(N-(4-chloro-5-cyano-2-((tetrahydrofuran-3-yl)methoxy)phenyl)sulfamoyl)-4-cyclopropylbenzoic acid<br>UPLC-MS (Method 1) m/z 475.00 $(M - H)^-$ at 1.750 min. $^1H$ NMR (400 MHz, DMSO-$d_6$) δ 13.23 (s, 1H), 10.18 (s, 1H), 8.35 (d, J = 1.8 Hz, 1H), 7.99 (dd, J = 8.2, 1.9 Hz, 1H), 7.65 (s, 1H), 7.39 (s, 1H), 7.12-7.10 (d, J = 8.3 Hz, 1H), 3.87-3.80 (m, 2H), 3.68-3.62 (m, 1H), 3.58-3.52 (m, 2H), 3.33-3.31 (m, 1H), 2.64-2.61 (m, 1H), 2.39-2.32 (m, 1.88-1.82 (m, 1H), 1.47-1.40 (m 1H), 0.99-0.95 (m, 2H), 0.82 - 0.79 (m, 2H). |
| 29 | 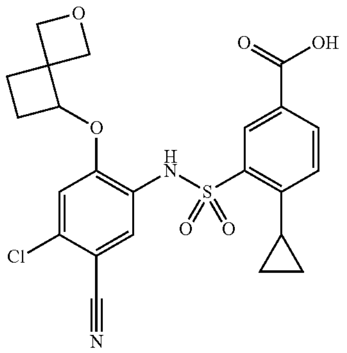 [SMILES: N#Cc1cc(NS(=O)(=O)c2cc(C(=O)O)ccc2C2CC2)c(OC2CCC23COC3)cc1Cl] | 3-(N-(2-((2-oxaspiro[3.3]heptan-5-yl)oxy)-4-chloro-5-cyanophenyl)sulfamoyl)-4-cyclopropylbenzoic acid<br>UPLC-MS (Method 1) m/z 487.05 $(M - H)^-$ at 1.750 min. $^1H$ NMR (400 MHz, DMSO-$d_6$) δ 10.34 (s, 1H), 8.39 (d, J = 1.8 Hz, 1H), 8.02-7.95 (m, 1H), 7.71 (s, 1H), 7.31 (s, 1H), 7.09 (d, J = 8.3 Hz, 1H), 4.82 (t, J = 7.2 Hz, 1H), 4.71 (d, J = 6.3 Hz, 1H), 4.51 (d, J = 6.9 Hz, 1H), 4.39 (d, J = 6.9 Hz, 1H), 4.19 (d, J = 6.3 Hz, 1H), 2.71-2.57 (m, 1H), 2.18-2.08 (m, 1H), 2.05-1.90 (m, 1H), 1.84-1.72 (m, 1H), 1.43-1.21 (m, 2H), 1.07-0.71 (m, 4H). |

-continued

| Example | Structure | Name/Analytical Data |
|---|---|---|
| 30 | 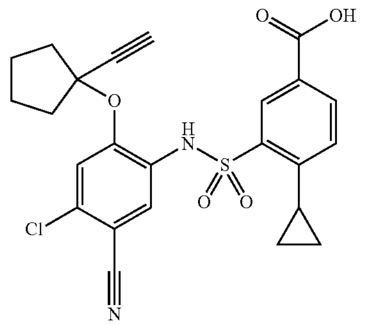 [SMILES: C#CC1(Oc2cc(Cl)c(C#N)cc2NS(=O)(=O)c2cc(C(=O)O)ccc2C2CC2)CCCC1] | 3-(N-(4-chloro-5-cyano-2-((1-ethynylcyclopentyl)oxy)phenyl)sulfamoyl)-4-cyclopropylbenzoic acid UPLC-MS (Method 1) m/z 483.00 $(M-H)^-$ at 2.016 min. $^1$H NMR (400 MHz, DMSO-$d_6$) δ 8.35 (d, J = 1.8 Hz, 1H), 7.97 (dd, J = 8.2, 1.9 Hz, 1H), 7.69 (s, 1H), 7.41 (s, 1H), 7.08-7.06 (d, J = 8.3 Hz, 1H), 3.83 (s, 1H), 2.76-2.62 (m, 1H), 2.06-1.93 (m, 4H), 1.60-1.50 (m, 4H), 0.98-0.93 (m, 2H), 0.79-0.76 (m, 2H). |
| 31 | 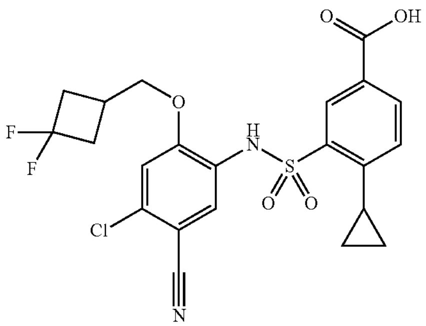 [SMILES: N#Cc1cc(NS(=O)(=O)c2cc(C(=O)O)ccc2C2CC2)c(OCC2CC(F)(F)C2)cc1Cl] | 3-(N-(4-chloro-5-cyano-2-((3,3-difluorocyclobutyl)methoxy)phenyl) sulfamoyl)-4-cyclopropylbenzoic acid UPLC-MS (Method 1) m/z 495.00 $(M-H)^-$ at 1.983 min. $^1$H NMR (400 MHz, DMSO-$d_6$) δ 8.37 (d, J = 1.7 Hz, 1H), 7.99 (d, J = 8.2 Hz, 1H), 7.65 (s, 1H), 7.38 (s, 1H), 7.12 (d, J = 8.3 Hz, 1H), 4.03 (d, J = 6.2 Hz, 2H), 2.68 (tt, J = 8.8, 5.2 Hz, 1H), 2.57 (d, J = 6.1 Hz, 1H), 2.463 (m, 1H), 2.32-2.26 (m, 3H), 0.98-0.96 (m, 2H), 0.80-0.79 (m, 2H). |
| 32 | 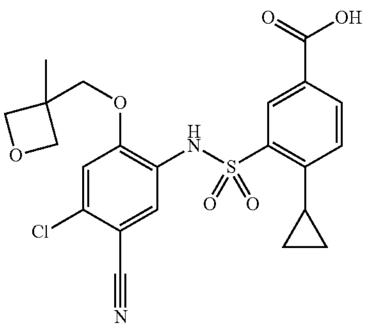 [SMILES: CC1(COc2cc(Cl)c(C#N)cc2NS(=O)(=O)c2cc(C(=O)O)ccc2C2CC2)COC1] | 3-(N-(4-chloro-5-cyano-2-((3-methyloxetan-3-yl)methoxy)phenyl)sulfamoyl)-4-cyclopropylbenzoic acid UPLC-MS (Method 1) m/z 475.00 $(M-H)^-$ at 1.716 min. $^1$H NMR (400 MHz, DMSO-$d_6$) δ 8.36 (s, 1H), 7.98-7.96 (dd, J = 8.3, 8.0 Hz, 1H), 7.60 (s, 1H), 7.45 (s, 1H), 7.10-7.08 (d, J = 8.0 Hz, 1H), 4.27-4.25 (d, J = 5.9 Hz, 2H), 4.17-4.12 (m, 4H), 2.59-2.50 (m, 1H), 1.16 (s, 3H), 0.97-0.93 (m, 2H), 0.81-0.78 (m, 2H). |
| 33 | 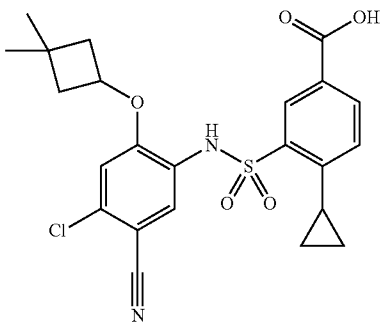 [SMILES: CC1(C)CC(Oc2cc(Cl)c(C#N)cc2NS(=O)(=O)c2cc(C(=O)O)ccc2C2CC2)C1] | 3-(N-(4-chloro-5-cyano-2-(3,3-dimethylcyclobutoxy)phenyl)sulfamoyl)-4-cyclopropylbenzoic acid UPLC-MS (Method 2) m/z 473.15 $(M-H)^-$ at 4.400 min. $^1$H NMR (400 MHz, DMSO-$d_6$) δ 8.32 (d, J = 1.8 Hz, 1H), 7.97-7.95 (m, 1H), 7.64 (s, 1H), 7.11-7.05 (m, 2H), 4.72-4.66 (p, J = 7.0 Hz, 1H), 2.77 (s, 1H), 2.18-2.08 (m, 2H), 1.55-1.50 (m, 2H), 1.09 (s, 3H), 1.02-0.99 (m, 5H), 0.80-0.79 (m, 2H). |

-continued

| Example | Structure | Name/Analytical Data |
| --- | --- | --- |
| 34 | 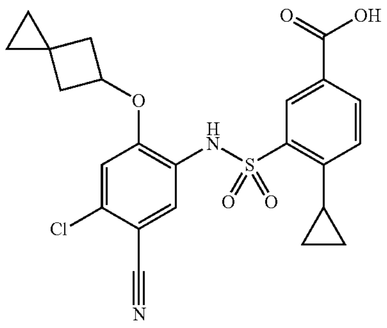 [SMILES: N#Cc1cc(NS(=O)(=O)c2cc(C(=O)O)ccc2C2CC2)c(OC2CC3(CC3)C2)cc1Cl] | 3-(N-(4-chloro-5-cyano-2-(spiro[2.3]hexan-5-yloxy)phenyl)sulfamoyl)-4-cyclopropylbenzoic acid UPLC-MS (Method 2) m/z 471.15 $(M - H)^-$ at 4.266 min. $^1H$ NMR (400 MHz, DMSO-$d_6$) δ 13.18 (s, 1H), 10.21 (s, 1H), 8.33 (d, J = 1.8 Hz, 1H), 8.02 (dd, J = 8.3, 1.8 Hz, 1H), 7.75 (s, 1H), 7.19-7.08 (m, 2H), 4.90 (p, J = 6.7 Hz, 1H), 2.76 (td, J = 8.4, 4.3 Hz, 1H), 2.30-2.20 (m, 2H), 1.97-1.87 (m, 2H), 1.07-0.98 (m, 2H), 0.92-0.79 (m, 2H), 0.48-0.38 (m, 2H), 0.38-0.29 (m, 2H). |
| 35 | 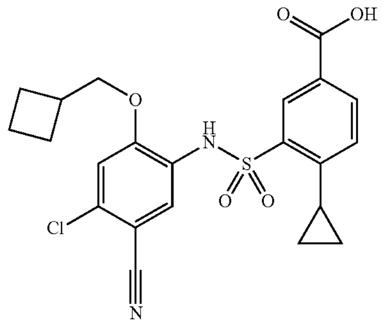 [SMILES: N#Cc1cc(NS(=O)(=O)c2cc(C(=O)O)ccc2C2CC2)c(OCC2CCC2)cc1Cl] | 3-(N-(4-chloro-5-cyano-2-(cyclobutylmethoxy)phenyl)sulfamoyl)-4-cyclopropylbenzoic acid UPLC-MS (Method 1) m/z 459.00 $(M - H)^-$ at 2.016 min. $^1H$ NMR (400 MHz, DMSO-$d_6$) δ 13.31 (s, 1H), 10.21 (s, 1H), 8.43 (d, J = 1.8 Hz, 1H), 8.08 (dd, J = 8.2, 1.9 Hz, 1H), 7.71 (s, 1H), 7.45 (s, 1H), 7.21 (d, J = 8.3 Hz, 1H), 3.99 (d, J = 6.7 Hz, 2H), 2.72 (s, 1H), 2.51 (p, J = 7.3 Hz, 1H), 1.94-1.79 (m, 4H), 1.76-1.64 (m, 2H), 1.13-1.03 (m, 2H), 0.97-0.86 (m, 2H). |
| 36 | 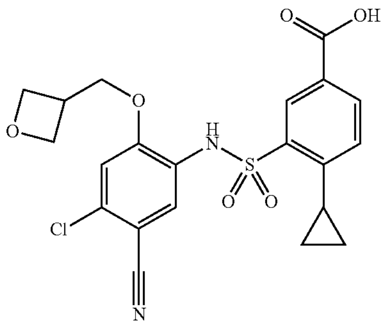 [SMILES: N#Cc1cc(NS(=O)(=O)c2cc(C(=O)O)ccc2C2CC2)c(OCC2COC2)cc1Cl] | 3-(N-(4-chloro-5-cyano-2-(oxetan-3-ylmethoxy)phenyl)sulfamoyl)-4-cyclopropylbenzoic acid UPLC-MS (Method 2) m/z 461.10 $(M - H)^-$ at 3.700 min. $^1H$ NMR (400 MHz, DMSO-$d_6$) δ 13.29 (s, 1H), 10.24 (s, 1H), 8.34 (d, J = 1.8 Hz, 1H), 8.01 (dd, J = 8.2, 1.8 Hz, 1H), 7.68 (s, 1H), 7.45 (s, 1H), 7.15 (d, J = 8.3 Hz, 1H), 4.57 (dd, J = 7.7, 6.2 Hz, 2H), 4.26-4.16 (m, 4H), 3.14 (dq, J = 7.8, 6.0 Hz, 1H), 2.64 (td, J = 8.5, 4.4 Hz, 1H), 1.02 (dt, J = 8.3, 3.3 Hz, 2H), 0.91-0.80 (m, 2H). |
| 37 | 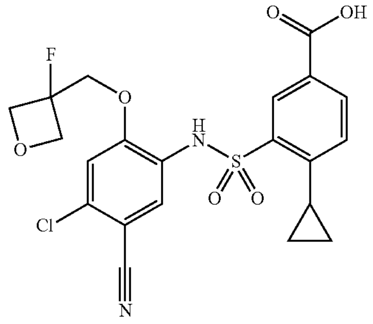 [SMILES: N#Cc1cc(NS(=O)(=O)c2cc(C(=O)O)ccc2C2CC2)c(OCC2(F)COC2)cc1Cl] | 3-(N-(4-chloro-5-cyano-2-((3-fluorooxetan-3-yl)methoxy)phenyl)sulfamoyl)-4-cyclopropylbenzoic acid UPLC-MS (Method 1) m/z 478.95 $(M - H)^-$ at 1.716 min. $^1H$ NMR (400 MHz, DMSO-$d_6$) δ 10.36 (s, 1H), 8.37 (d, J = 1.8 Hz, 1H), 7.99 (dd, J = 8.2, 1.8 Hz, 1H), 7.62 (s, 1H), 7.46 (s, 1H), 7.12 (d, J = 8.2 Hz, 1H), 4.65-4.46 (m, 6H), 2.69 (tt, J = 8.8, 5.3 Hz, 1H), 1.01 (dt, J = 8.4, 3.3 Hz, 2H), 0.91-0.78 (m, 2H). |

-continued

| Example | Structure | Name/Analytical Data |
|---|---|---|
| 38 | 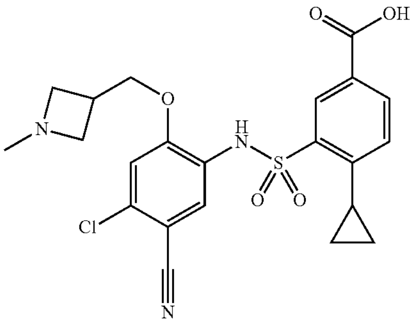 [SMILES: CN1CC(COc2cc(Cl)c(C#N)cc2NS(=O)(=O)c2cc(C(=O)O)ccc2C2CC2)C1] | 3-(N-(4-chloro-5-cyano-2-((1-methylazetidin-3-yl)methoxy)phenyl)sulfamoyl)-4-cyclopropylbenzoic acid<br>UPLC-MS (Method 1) m/z 474.05 $(M - H)^-$ at 2.000 min. $^1H$ NMR (400 MHz, DMSO-$d_6$) δ 10.80 (s, 1H), 10.44-10.36 (m, 1H), 8.35 (s, 1H), 8.02 (d, J = 8.2 Hz, 1H), 7.63 (s, 1H), 7.44 (s, 1H), 7.16 (d, J = 8.3 Hz, 1H), 4.17-4.07 (m, 4H), 3.76 (s, 2H), 3.07 (s, 1H), 2.77 (s, 3H), 2.69-2.60 (m, 1H), 1.04 (d, J = 8.2 Hz, 2H), 0.88 (d, J = 5.5 Hz, 2H). |
| 39 | 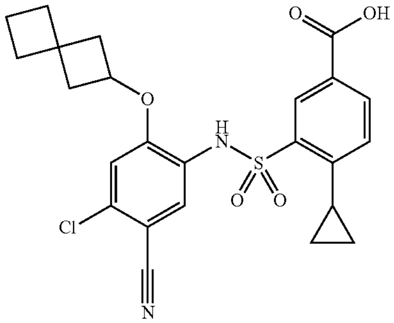 [SMILES: N#Cc1cc(NS(=O)(=O)c2cc(C(=O)O)ccc2C2CC2)c(OC2CC3(CCC3)C2)cc1Cl] | 3-(N-(4-chloro-5-cyano-2-(spiro[3.3]heptan-2-yloxy)phenyl)sulfamoyl)-4-cyclopropylbenzoic acid<br>UPLC-MS (Method 1) m/z 485.05 $(M - H)^-$ at 2.083 min. $^1H$ NMR (400 MHz, DMSO-$d_6$) δ 13.15 (s, 1H), 10.11 (s, 1H), 8.30 (d, J = 1.8 Hz, 1H), 7.99 (dd, J = 8.2, 1.8 Hz, 1H), 7.72 (s, 1H), 7.18-7.10 (m, 2H), 4.57 (p, J = 7.1 Hz, 1H), 2.73 (td, J = 8.4, 4.4 Hz, 1H), 2.37 (ddd, J = 9.8, 6.9, 3.2 Hz, 2H), 1.98 (t, J = 7.3 Hz, 2H), 1.86 (t, J = 6.9 Hz, 2H), 1.84-1.71 (m, 2H), 1.54 (ddd, J = 9.9, 7.3, 3.1 Hz, 2H), 1.07-0.98 (m, 2H), 0.91-0.77 (m, 2H). |
| 40<br>Trans<br>relative | 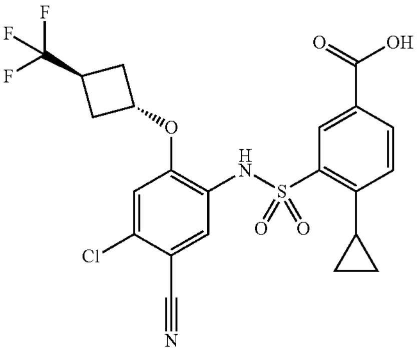 [SMILES: N#Cc1cc(NS(=O)(=O)c2cc(C(=O)O)ccc2C2CC2)c(O[C@H]2C[C@H](C(F)(F)F)C2)cc1Cl] | 3-(N-(4-chloro-5-cyano-2-((trans)-3-(trifluoromethyl)cyclobutoxy)phenyl)sulfamoyl)-4-cyclopropylbenzoic acid<br>UPLC-MS (Method 3) m/z 513.00 $(M - H)^-$ at 1.587 min. $^1H$ NMR (400 MHz, DMSO-$d_6$) δ 13.21 (s, 1H), 10.27 (s, 1H), 8.32 (d, J = 1.8 Hz, 1H), 7.99-7.97 (dd, J = 8.3, 1.8 Hz, 1H), 7.70 (s, 1H), 7.15-7.11 (m, 2H), 4.68-4.61 (m, J = 7.2 Hz, 1H), 2.78-2.71 (m, 2H), 2.58-2.54 (m, 2H), 1.94-1.87 (m, 2H), 1.04-1.00 (m, 2H), 0.85 (dt, J = 12.3, 9.3 Hz, 2H). |
| 41<br>Cis<br>relative | 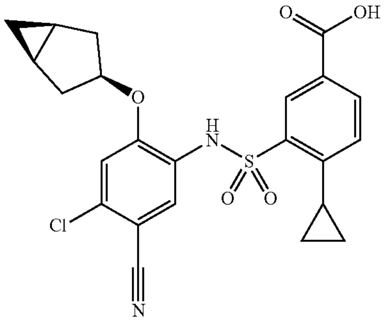 [SMILES: N#Cc1cc(NS(=O)(=O)c2cc(C(=O)O)ccc2C2CC2)c(O[C@@H]2C[C@@H]3C[C@@H]3C2)cc1Cl] | Cis-3-(N-(2-(bicyclo[3.1.0]hexan-3-yloxy)-4-chloro-5-cyanophenyl)sulfamoyl)-4-cyclopropylbenzoic acid<br>UPLC-MS (Method 1) m/z 471.05 $(M - H)^-$ at 2.016 min. $^1H$ NMR (400 MHz, DMSO-$d_6$) δ 13.15 (s, 1H), 10.13 (s, 1H), 8.30 (d, J = 1.8 Hz, 1H), 8.00 (dd, J = 8.2, 1.8 Hz, 1H), 7.69 (s, 1H), 7.34 (s, 1H), 7.14 (d, J = 8.3 Hz, 1H), 4.56 (p, J = 7.3 Hz, 1H), 2.74-2.69 (m, 1H), 2.08 (dd, J = 12.6, 7.3 Hz, 2H), 1.39 (s, 2H), 1.18-1.16 (m, 2H), 1.03-1.01 (m, 2H), 0.82-0.80 (dt, J = 8.3, 3.3 Hz, 2H), 0.31-0.29 (m, 1H), 0.06-0.04 (m, 1H). |

-continued

| Example | Structure | Name/Analytical Data |
|---|---|---|
| 42 | 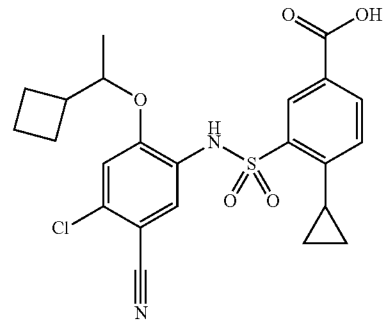 [SMILES: CC(Oc1cc(Cl)c(C#N)cc1NS(=O)(=O)c1cc(C(=O)O)ccc1C1CC1)C1CCC1] | 3-(N-(4-chloro-5-cyano-2-(1-cyclobutylethoxy)phenyl)sulfamoyl)-4-cyclopropylbenzoic acid UPLC-MS (Method 1) m/z 473.00 $(M-H)^-$ at 2.050 min. $^1H$ NMR (400 MHz, DMSO-$d_6$) δ 13.25 (s, 1H), 10.09 (s, 1H), 8.33 (d, J = 1.8 Hz, 1H), 8.01 (dd, J = 8.2, 1.9 Hz, 1H), 7.66 (s, 1H), 7.44 (s, 1H), 7.16 (d, J = 8.3 Hz, 1H), 4.62-4.51 (m, 1H), 2.71 (tt, J = 8.4, 5.2 Hz, 1H), 2.23-2.09 (m, 1H), 1.84-1.56 (m, 6H), 1.11-0.97 (m, 2H), 0.90-0.81 (m, 2H), 0.79 (d, J = 6.0 Hz, 3H). |
| 43 | 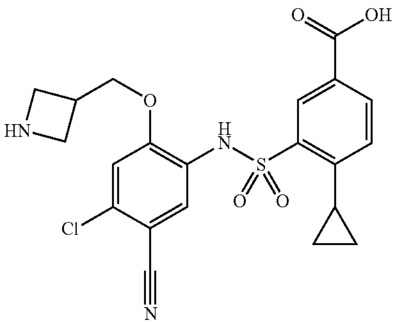 [SMILES: N#Cc1cc(NS(=O)(=O)c2cc(C(=O)O)ccc2C2CC2)c(OCC2CNC2)cc1Cl] | 3-(N-(2-(azetidin-3-ylmethoxy)-4-chloro-5-cyanophenyl)sulfamoyl)-4-cyclopropylbenzoic acid UPLC-MS (Method 1) m/z 460.00 $(M-H)^-$ at 0.983 min. $^1H$ NMR (400 MHz, DMSO-$d_6$) δ 8.45 (d, J = 1.8 Hz, 1H), 8.21 (s, 1H), 7.91 (d, J = 8.3 Hz, 1H), 7.43 (d, J = 6.1 Hz, 1H), 7.27 (s, 1H), 6.99 (d, J = 8.2 Hz, 1H), 4.32-4.27 (m, 2H), 4.19-4.12 (m, 2H), 3.76 (dd, J = 10.5, 5.0 Hz, 2H), 3.09-3.00 (m, 1H), 3.00-2.89 (m, 1H), 1.05-0.99 (m, 2H), 0.83-0.77 (m, 2H). |
| 44 | 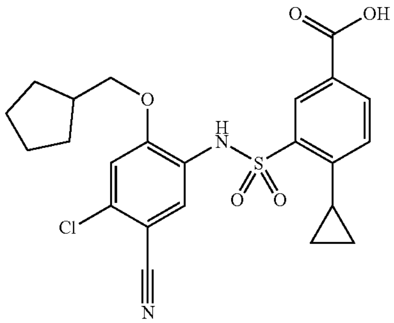 [SMILES: N#Cc1cc(NS(=O)(=O)c2cc(C(=O)O)ccc2C2CC2)c(OCC2CCCC2)cc1Cl] | 3-(N-(4-chloro-5-cyano-2-(cyclopentylmethoxy)phenyl)sulfamoyl)-4-cyclopropylbenzoic acid UPLC-MS (Method 1) m/z 473.10 $(M-H)^-$ at 2.150 min. $^1H$ NMR (400 MHz, DMSO-$d_6$) δ 10.14 (s, 1H), 8.37 (s, 1H), 8.00 (d, J = 8.0 Hz, 1H), 7.66 (s, 1H), 7.38 (s, 1H), 7.12 (d, J = 8.3 Hz, 1H), 3.78 (d, J = 7.1 Hz, 2H), 2.66-2.54 (m, 1H), 2.03-1.87 (m, 1H), 1.62-1.36 (m, 6H), 1.10-0.99 (m, 2H), 1.04-0.91 (m, 2H), 0.91-0.77 (m, 2H). |
| 45 | 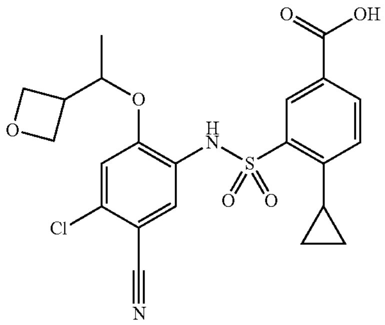 [SMILES: CC(Oc1cc(Cl)c(C#N)cc1NS(=O)(=O)c1cc(C(=O)O)ccc1C1CC1)C1COC1] | 3-(N-(4-chloro-5-cyano-2-(1-(oxetan-3-yl)ethoxy)phenyl)sulfamoyl)-4-cyclopropylbenzoic acid UPLC-MS (Method 1) m/z 475.00 $(M-H)^-$ at 1.683 min. $^1H$ NMR (400 MHz, DMSO-$d_6$) δ 10.14 (s, 1H), 8.33 (d, J = 1.8 Hz, 1H), 8.01 (dd, J = 8.3, 1.8 Hz, 1H), 7.69 (s, 1H), 7.51 (s, 1H), 7.16 (d, J = 8.3 Hz, 1H), 5.03-4.92 (m, 1H), 4.56 (dd, J = 8.1, 6.2 Hz, 1H), 4.47 (dd, J = 7.7, 6.3 Hz, 1H), 4.20 (t, J = 6.2 Hz, 1H), 4.16 (t, J = 6.1 Hz, 1H), 2.98-2.88 (m, 1H), 2.74-2.64 (m, 1H), 1.06-0.99 (m, 2H), 0.92-0.78 (m, 5H). |

-continued

| Example | Structure | Name/Analytical Data |
|---|---|---|
| 46<br>Trans<br>relative | 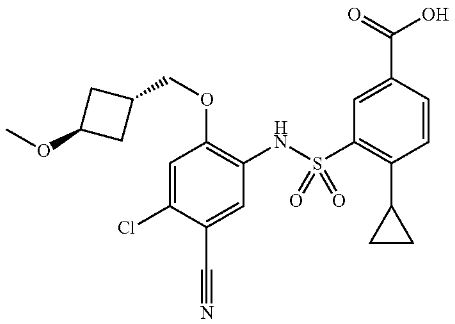 [SMILES: CO[C@H]1C[C@H](COc2cc(Cl)c(C#N)cc2NS(=O)(=O)c2cc(C(=O)O)ccc2C2CC2)C1] | 3-(N-(4-chloro-5-cyano-2-((trans-3-methoxycyclobutyl)methoxy)phenyl) sulfamoyl)-4-cyclopropylbenzoic acid<br>UPLC-MS (Method 1) m/z 489.00 $(M - H)^-$ at 1.850 min. $^1H$ NMR (400 MHz, DMSO-$d_6$) δ 13.23 (s, 1H), 10.16 (s, 1H), 8.36 (d, J = 1.8 Hz, 1H), 8.00 (dd, J = 8.2, 1.8 Hz, 1H), 7.64 (s, 1H), 7.39 (s, 1H), 7.14 (d, J = 8.3 Hz, 1H), 3.96 (d, J = 7.2 Hz, 2H), 3.86 (p, J = 6.6 Hz, 1H), 3.09 (s, 3H), 2.70-2.54 (m, 1H), 2.37-2.25 (m, 1H), 1.88-1.76 (m, 4H), 1.05-0.92 (m, 2H), 0.91-0.79 (m, 2H). |
| 47<br>Cis<br>relative | 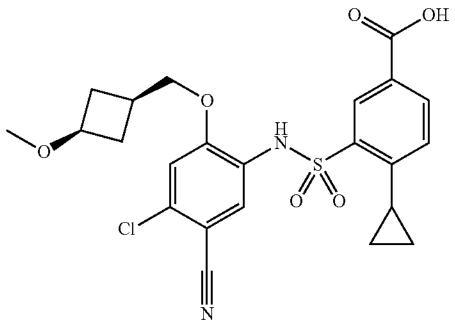 [SMILES: CO[C@H]1C[C@@H](COc2cc(Cl)c(C#N)cc2NS(=O)(=O)c2cc(C(=O)O)ccc2C2CC2)C1] | 3-(N-(4-chloro-5-cyano-2-((cis-3-methoxycyclobutyl)methoxy)phenyl) sulfamoyl)-4-cyclopropylbenzoic acid<br>UPLC-MS (Method 1) m/z 489.00 $(M - H)^-$ at 1.916 min. $^1H$ NMR (400 MHz, DMSO-$d_6$) δ 13.26 (s, 1H), 10.13 (s, 1H), 8.37 (d, J = 1.8 Hz, 1H), 8.01 (dd, J = 8.2, 1.8 Hz, 1H), 7.66 (s, 1H), 7.38 (s, 1H), 7.14 (d, J = 8.3 Hz, 1H), 3.92 (d, J = 6.4 Hz, 2H), 3.65 (p, J = 7.2 Hz, 1H), 3.10 (s, 3H), 2.66-2.55 (m, 1H), 2.19-2.07 (m, 2H), 2.04-1.87 (m, 1H), 1.50-1.37 (m, 2H), 1.05-0.95 (m, 2H), 0.91-0.78 (m, 2H). |
| 48 | 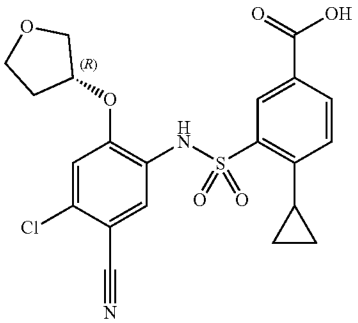 | (R)-3-(N-(4-chloro-5-cyano-2-((tetrahydrofuran-3-yl)oxy)phenyl)sulfamoyl)-4-cyclopropylbenzoic acid<br>UPLC-MS (Method 1) m/z 460.95 $(M - H)^-$ at 1.650 min. $^1H$ NMR (400 MHz, DMSO-$d_6$) δ 13.19 (s, 1H), 10.23 (s, 1H), 8.34 (d, J = 1.9 Hz, 1H), 7.99 (dd, J = 8.2, 1.9 Hz, 1H), 7.68 (s, 1H), 7.33 (s, 1H), 7.12 (d, J = 8.3 Hz, 1H), 5.05-4.98 (m, 1H), 3.81 (dd, J = 10.3, 5.1 Hz, 1H), 3.68-3.57 (m, 2H), 3.56-3.50 (m, 1H), 2.72-2.62 (m, 1H), 2.16-2.02 (m, 1H), 1.75-1.64 (m, 1H), 1.06-0.95 (m, 2H), 0.86-0.76 (m, 2H). |
| 49 | 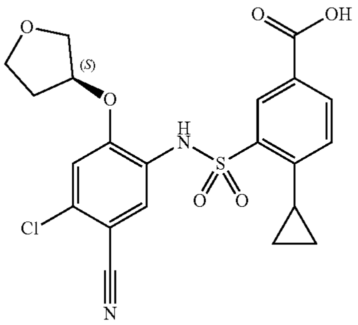 | (S)-3-(N-(4-chloro-5-cyano-2-((tetrahydrofuran-3-yl)oxy)phenyl)sulfamoyl)-4-cyclopropylbenzoic acid<br>Analytical data consistent with Example 48. |

-continued

| Example | Structure | Name/Analytical Data |
|---|---|---|
| 53 Cis relative | 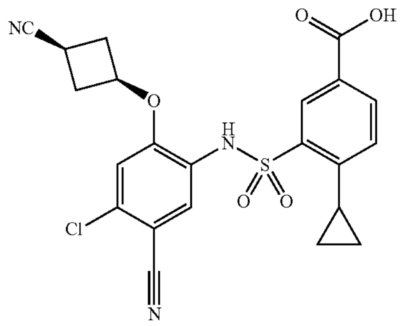 [SMILES: N#Cc1cc(NS(=O)(=O)c2cc(C(=O)O)ccc2C2CC2)c(O[C@H]2C[C@@H](C#N)C2)cc1Cl] | 3-(N-(4-chloro-5-cyano-2-(cis-3-cyanocyclobutoxy)phenyl)sulfamoyl)-4-cyclopropylbenzoic acid UPLC-MS (Method 1) m/z 470.00 $(M-H)^-$ at 1.716 min. $^1H$ NMR (400 MHz, DMSO-$d_6$) δ 10.33 (s, 1H), 8.31 (d, J = 1.8 Hz, 1H), 8.02 (dd, J = 8.3, 1.8 Hz, 1H), 7.74 (s, 1H), 7.20-7.12 (m, 2H), 4.73 (p, J = 7.1 Hz, 1H), 2.98 (p, J = 9.1 Hz, 1H), 2.78 (dtt, J = 9.6, 6.8, 3.4 Hz, 3H), 2.11 (tdd, J = 9.8, 7.4, 2.8 Hz, 2H), 1H), 1.14-1.02 (m, 2H), 0.95-0.83 (m, 2H). |
| 54 | 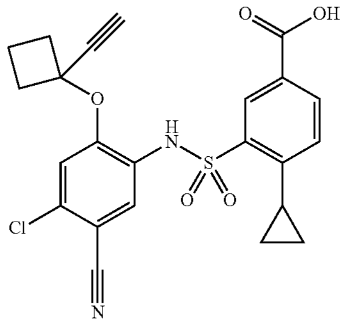 [SMILES: C#CC1(Oc2cc(Cl)c(C#N)cc2NS(=O)(=O)c2cc(C(=O)O)ccc2C2CC2)CCC1] | 3-(N-(4-chloro-5-cyano-2-(1-ethynylcyclobutoxy)phenyl)sulfamoyl)-4-cyclopropylbenzoic acid UPLC-MS (Method 1) m/z 468.95 $(M-H)^-$ at 1.950 min. $^1H$ NMR (400 MHz, DMSO-$d_6$) δ 13.23 (s, 1H), 10.29 (s, 1H), 8.33 (d, J = 1.8 Hz, 1H), 8.01 (dd, J = 8.3, 1.9 Hz, 1H), 7.79 (s, 1H), 7.14 (d, J = 8.3 Hz, 1H), 7.01 (s, 1H), 3.84 (s, 1H), 2.74 (td, J = 8.3, 4.3 Hz, 1H), 2.45 (td, J = 9.0, 8.5, 4.4 Hz, 2H), 2.15 (dt, J = 12.6, 9.7 Hz, 2H), 1.90-1.76 (m, 1H), 1.78-1.65 (m, 1H), 1.03 (dt, J = 8.3, 3.3 Hz, 2H), 0.90-0.76 (m, 2H). |
| 55 Trans relative | 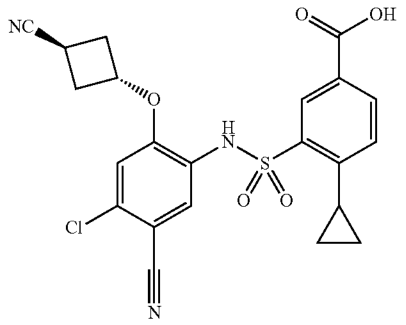 [SMILES: N#Cc1cc(NS(=O)(=O)c2cc(C(=O)O)ccc2C2CC2)c(O[C@H]2C[C@H](C#N)C2)cc1Cl] | 3-(N-(4-chloro-5-cyano-2-(trans-3-cyanocyclobutoxy)phenyl)sulfamoyl)-4-cyclopropylbenzoic acid UPLC-MS (Method 1) m/z 469.95 $(M-H)^-$ at 1.750 min. $^1H$ NMR (400 MHz, DMSO-$d_6$) δ 13.22 (s, 1H), 10.28 (s, 1H), 8.26 (d, J = 1.8 Hz, 1H), 7.99-7.92 (m, 1H), 7.66 (s, 1H), 7.17 (s, 1H), 7.10 (d, J = 8.3 Hz, 1H), 4.99-4.91 (m, 1H), 3.26-3.19 (m, 1H), 2.66 (s, 3H), 2.25-2.12 (m, 2H), 1.00 (d, J = 8.1 Hz, 2H), 0.80 (d, J = 5.7 Hz, 2H). |
| 56 | 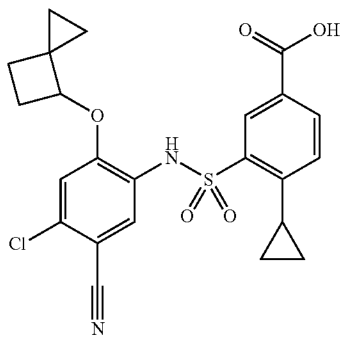 [SMILES: N#Cc1cc(NS(=O)(=O)c2cc(C(=O)O)ccc2C2CC2)c(OC2CCC23CC3)cc1Cl] | 3-(N-(4-chloro-5-cyano-2-(spiro[2.3]hexan-4-yloxy)phenyl)sulfamoyl)-4-cyclopropylbenzoic acid UPLC-MS (Method 1) m/z 471.00 $(M-H)^-$ at 2.083 min. $^1H$ NMR (400 MHz, DMSO-$d_6$) δ 10.08 (s, 1H), 8.39 (d, J = 1.8 Hz, 1H), 8.02 (dd, J = 8.2, 1.8 Hz, 1H), 7.72 (s, 1H), 7.12 (d, J = 8.3 Hz, 1H), 7.04 (s, 1H), 4.83 (t, J = 6.2 Hz, 1H), 2.65-2.54 (m, 1H), 2.43-2.37 (m, 1H), 1.89-1.82 (m, 1H), 1.71-1.66 (td, J = 10.7, 3.8 Hz, 1H), 1.56-1.53 (m, 1H), 1.03-0.95 (m, 1H), 0.92-0.70 (m, 4H), 0.48-0.35 (m, 2H), 0.19-0.09 (m, 1H). |

-continued

| Example | Structure | Name/Analytical Data |
|---|---|---|
| 57 | 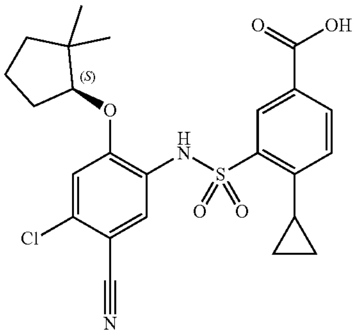 | (S)-3-(N-(4-chloro-5-cyano-2-((2,2-dimethylcyclopentyl)oxy)phenyl)sulfamoyl)-4-cyclopropylbenzoic acid<br>Analytical data consistent with Example 63. |
| 58 | 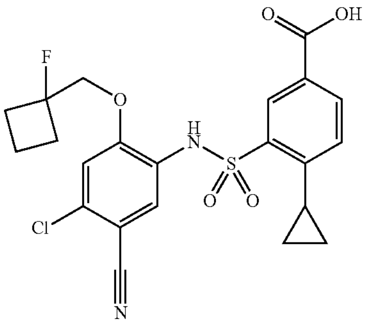 [SMILES: N#Cc1cc(NS(=O)(=O)c2cc(C(=O)O)ccc2C2CC2)c(OCC2(F)CCC2)cc1Cl] | 3-(N-(4-chloro-5-cyano-2-((1-fluorocyclobutyl)methoxy)phenyl)sulfamoyl)-4-cyclopropylbenzoic acid<br>UPLC-MS (Method 1) m/z 477.00 $(M-H)^-$ at 2.016 min. $^1H$ NMR (400 MHz, DMSO-$d_6$) δ 13.23 (s, 1H), 10.20 (s, 1H), 8.40-8.34 (m, 1H), 8.02 (dd, J = 8.3, 2.2 Hz, 1H), 7.59 (d, J = 2.3 Hz, 1H), 7.51 (d, J = 2.3 Hz, 1H), 7.16 (dd, J = 8.3, 2.3 Hz, 1H), 4.30 (d, J = 2.2 Hz, 1H), 4.24 (d, J = 2.2 Hz, 1H), 2.67 (s, 1H), 2.22-2.08 (m, 4H), 1.72 (s, 1H), 1.52-1.43 (m, 1H), 1.03 (d, J = 7.9 Hz, 2H), 0.86 (dd, J = 5.0, 2.4 Hz, 2H). |
| 59<br>Trans<br>racemate | 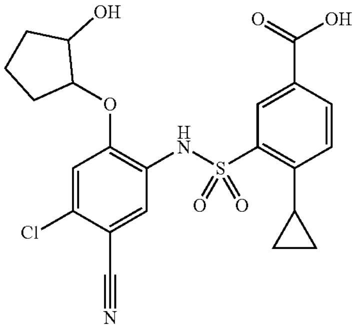 [SMILES: N#Cc1cc(NS(=O)(=O)c2cc(C(=O)O)ccc2C2CC2)c(OC2CCCC2O)cc1Cl] | 3-(N-(4-chloro-5-cyano-2-((trans-2-hydroxycyclopentyl)oxy)phenyl)sulfamoyl)-4-cyclopropylbenzoic acid<br>UPLC-MS (Method 1) m/z 474.95 $(M-H)^-$ at 1.716 min. $^1H$ NMR (400 MHz, DMSO-$d_6$) δ 13.26 (s, 1H), 10.11 (s, 1H), 8.37 (d, J = 1.8 Hz, 1H), 8.03 (dd, J = 8.2, 1.9 Hz, 1H), 7.72 (s, 1H), 7.43 (s, 1H), 7.16 (d, J = 8.2 Hz, 1H), 5.00-4.94 (m, 1H), 4.41-4.37 (m, 1H), 3.77-3.73 (m, 1H), 2.69-2.60 (m, 1H), 2.03-1.93 (m, 1H), 1.71-1.56 (m, 2H), 1.54-1.38 (m, 2H), 1.32-1.22 (m, 1H), 1.03-0.89 (s, 2H), 0.89-0.80 (m, 2H). |
| 62 | 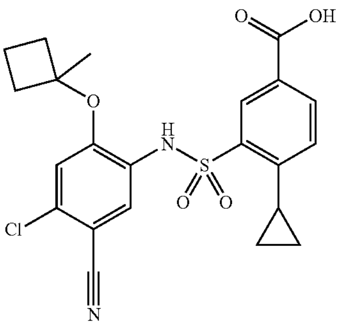 [SMILES: CC1(Oc2cc(Cl)c(C#N)cc2NS(=O)(=O)c2cc(C(=O)O)ccc2C2CC2)CCC1] | 3-(N-(4-chloro-5-cyano-2-(1-methylcyclobutoxy)phenyl)sulfamoyl)-4-cyclopropylbenzoic acid<br>UPLC-MS (Method 1) m/z 459.00 $(M-H)^-$ at 2.050 min. $^1H$ NMR (400 MHz, DMSO-$d_6$) δ 13.22 (s, 1H), 10.08 (s, 1H), 8.27 (s, 1H), 7.99 (d, J = 7.4 Hz, 1H), 7.72 (s, 1H), 7.13 (d, J = 8.3 Hz, 1H), 6.79 (s, 1H), 2.72 (s, 1H), 2.03 (t, J = 7.6 Hz, 4H), 1.65-1.53 (m, 2H), 1.22 (s, 3H), 1.02 (d, J = 8.1 Hz, 2H), 0.82 (d, J = 5.2 Hz, 2H). |

-continued

| Example | Structure | Name/Analytical Data |
|---|---|---|
| 63 | 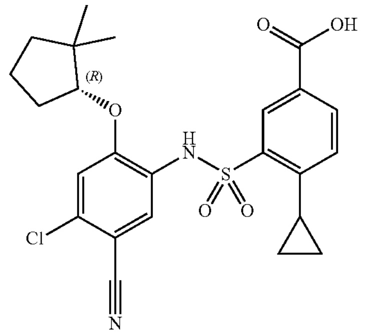 | (R)-3-(N-(4-chloro-5-cyano-2-((2,2-dimethylcyclopentyl)oxy)phenyl)sulfamoyl)-4-cyclopropylbenzoic acid UPLC-MS (Method 1) m/z 487.05 $(M-H)^-$ at 2.250 min. $^1H$ NMR (400 MHz, DMSO-$d_6$) δ 13.20 (s, 1H), 9.93 (s, 1H), 8.35 (d, J = 1.6 Hz, 1H), 8.01-7.94 (m, 1H), 7.58 (s, 1H), 7.37 (s, 1H), 7.08 (d, J = 8.3 Hz, 1H), 4.41-4.34 (m, 1H), 2.59-2.52 (m, 1H), 2.12-1.96 (m, 1H), 1.55-1.46 (m, 3H), 1.26-1.13 (m, 2H), 0.97-0.86 (m, 2H), 0.87 (s, 3H), 0.81-0.75 (m 2H), 0.72 (s, 3H). |
| 64 | 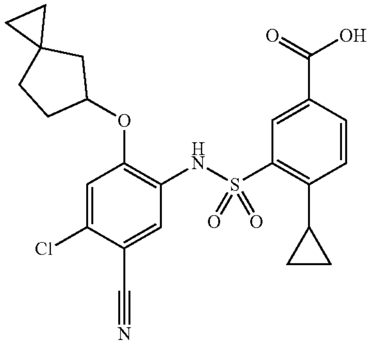 [SMILES: N#Cc1cc(NS(=O)(=O)c2cc(C(=O)O)ccc2C2CC2)c(OC2CCC3(CC3)C2)cc1Cl] | 3-(N-(4-chloro-5-cyano-2-(spiro[2.4]heptan-5-yloxy)phenyl)sulfamoyl)-4-cyclopropylbenzoic acid UPLC-MS (Method 1) m/z 485.00 $(M-H)^-$ at 2.183 min.$^1H$ NMR (400 MHz, DMSO-$d_6$) δ 13.20 (s, 1H), 10.10 (s, 1H), 8.33 (s, 1H), 7.98 (d, J = 8.3 Hz, 1H), 7.66 (s, 1H), 7.27 (s, 1H), 7.11 (d, J = 8.3 Hz, 1H), 4.93-4.85 (m, 1H), 2.71-2.62 (m, 1H), 2.03-1.89 (m, 1H), 1.84-1.73 (m, 1H), 1.60-0.56 (m, 2H), 1.46-1.38 (m, 1H), 1.28-1.21 (m, 1H), 1.02-0.95 (m, 2H), 0.87-0.77 (m, 2H), 0.44-0.28 (m, 4H). |
| 65 | 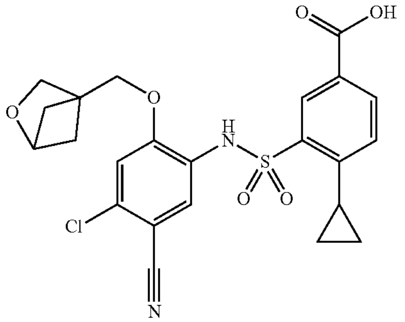 [SMILES: N#Cc1cc(NS(=O)(=O)c2cc(C(=O)O)ccc2C2CC2)c(OCC23COC(C2)C3)cc1Cl] | 3-(N-(2-((2-oxabicyclo[2.1.1]hexan-4-yl)methoxy)-4-chloro-5-cyanophenyl)sulfamoyl)-4-cyclopropylbenzoic acid UPLC-MS (Method 1) m/z 487.00 $(M-H)^-$ at 1.750 min. $^1H$ NMR (400 MHz, DMSO-$d_6$) δ 13.25 (s, 1H), 10.20 (s, 1H), 8.37 (d, J = 1.6 Hz, 1H), 8.03-7.93 (m, 1H), 7.64 (s, 1H), 7.44 (s, 1H), 7.08 (d, J = 8.3 Hz, 1H), 4.40 (s, 1H), 4.28 (s, 2H), 3.44 (s, 2H), 2.54 (s, 1H), 1.71 (d, J = 4.4 Hz, 2H), 1.33-1.26 (m, 2H), 0.98-0.90 (m, 2H), 0.80 (t, J = 5.4 Hz, 2H). |
| 66 | 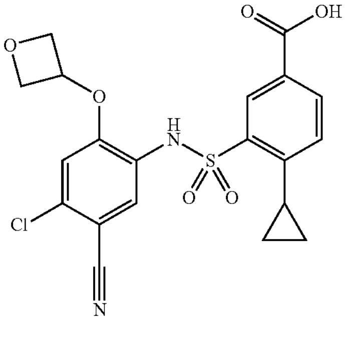 [SMILES: N#Cc1cc(NS(=O)(=O)c2cc(C(=O)O)ccc2C2CC2)c(OC2COC2)cc1Cl] | 3-(N-(4-chloro-5-cyano-2-(oxetan-3-yloxy)phenyl)sulfamoyl)-4-cyclopropylbenzoic acid UPLC-MS (Method 1) m/z 446.95 $(M-H)^-$ at 1.716 min.$^1H$ NMR (400 MHz, DMSO-$d_6$) δ 8.33 (s, 1H), 7.98 (d, J = 9.1 Hz, 1H), 7.73 (s, 1H), 7.11 (d, J = 8.3 Hz, 1H), 6.96 (s, 1H), 5.21 (p, J = 5.5 Hz, 1H), 4.77 (t, J = 6.7 Hz, 2H), 4.26 (dd, J = 7.0, 5.1 Hz, 2H), 2.78 (ddd, J = 13.4, 8.4, 5.4 Hz, 1H), 1.08-1.00 (m, 2H), 0.83 (q, J = 4.9 Hz, 2H). |

-continued

| Example | Structure | Name/Analytical Data |
|---|---|---|
| 68<br>Cis<br>relative | 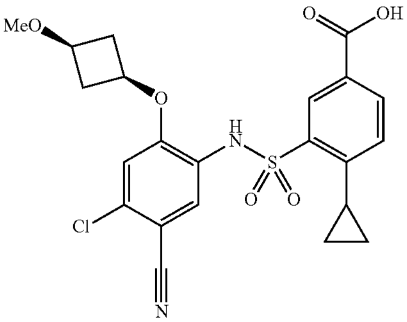 [SMILES: CO[C@H]1C[C@@H](Oc2cc(Cl)c(C#N)cc2NS(=O)(=O)c2cc(C(=O)O)ccc2C2CC2)C1] | 3-(N-(4-chloro-5-cyano-2-(cis-3-methoxycyclobutoxy)phenyl)sulfamoyl)-4-cyclopropylbenzoic acid<br>UPLC-MS (Method 1) m/z 474.95 $(M-H)^-$ at 1.783 min. $^1$H NMR (400 MHz, DMSO-$d_6$) δ 13.17 (s, 1H), 10.19 (s, 1H), 8.29 (d, J = 1.4 Hz, 1H), 7.98 (d, J = 8.1 Hz, 1H), 7.70 (s, 1H), 7.12 (d, J = 6.0 Hz, 2H), 4.35 (q, J = 6.9 Hz, 1H), 3.46 (p, J = 6.8 Hz, 1H), 3.09 (s, 3H), 2.73 (s, 1H), 2.64 (dt, J = 6.1, 2.8 Hz, 2H), 1.66-1.52 (m, 2H), 1.04 (d, J = 6.6 Hz, 2H), 0.82 (d, J = 4.0 Hz, 2H). |
| 69 | 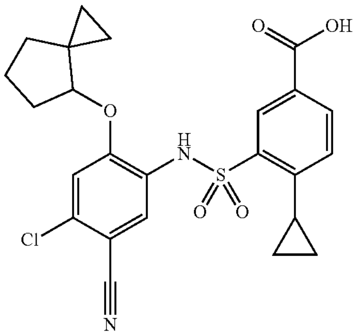 [SMILES: N#Cc1cc(NS(=O)(=O)c2cc(C(=O)O)ccc2C2CC2)c(OC2CCCC23CC3)cc1Cl] | 3-(N-(4-chloro-5-cyano-2-(spiro[2.4]heptan-4-yloxy)phenyl)sulfamoyl)-4-cyclopropylbenzoic acid<br>UPLC-MS (Method 3) m/z 485.00 $(M-H)^-$ at 1.987 min. $^1$H NMR (400 MHz, DMSO-$d_6$) δ 10.07 (br s, 1H), 8.36-8.31 (br m, 1H), 8.00-7.95 (br m, 1H), 7.68-7.64 (br m, 1H), 7.29-7.25 (br m, 1H), 7.13-7.09 (br m, 1H), 4.91-4.87 (br m, 1H), 2.68-2.64 (br m, 1H), 1.98-1.84 (br m, 1H), 1.82-1.77 (br m, 1H), 1.61-1.56 (br m, 2H), 1.46-1.41 (br m, 1H), 1.26-1.22 (br m, 1H), 1.01-0.97 (br m, 2H), 0.82-0.78 (br m, 2H), 0.51-0.24 (br m, 4H). |
| 71<br>Cis<br>relative | 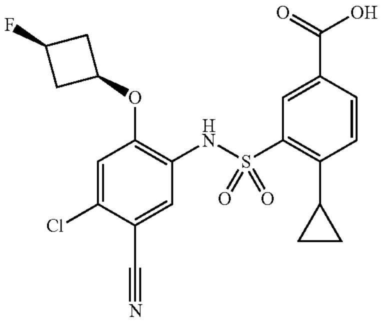 [SMILES: N#Cc1cc(NS(=O)(=O)c2cc(C(=O)O)ccc2C2CC2)c(O[C@H]2C[C@@H](F)C2)cc1Cl] | 3-(N-(4-chloro-5-cyano-2-(cis-3-fluorocyclobutoxy)phenyl)sulfamoyl)-4-cyclopropylbenzoic acid<br>UPLC-MS (Method 1) m/z 463.00 $(M-H)^-$ at 1.816 min. $^1$H NMR (400 MHz, DMSO-$d_6$) δ 13.21 (s, 1H), 10.26 (s, 1H), 8.30 (d, J = 1.7 Hz, 1H), 7.98 (dd, J = 8.2, 1.5 Hz, 1H), 7.73 (s, 1H), 7.13 (d, J = 7.8 Hz, 2H), 4.72 (dp, J = 56.4, 6.6 Hz, 1H), 4.31 (h, J = 6.6 Hz, 1H), 2.84 (ddd, J = 10.0, 6.7, 3.2 Hz, 2H), 2.80-2.71 (m, 1H), 2.08-1.82 (m, 2H), 1.14-0.98 (m, 2H), 0.92-0.76 (m, 2H). |
| 72<br>Trans<br>racemate | 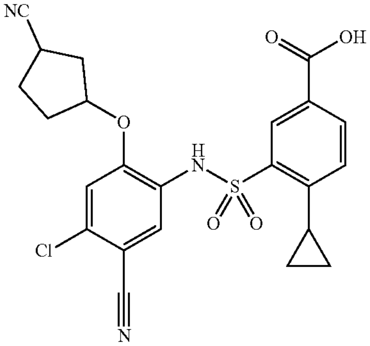 [SMILES: N#Cc1cc(NS(=O)(=O)c2cc(C(=O)O)ccc2C2CC2)c(OC2CCC(C#N)C2)cc1Cl] | 3-(N-(4-chloro-5-cyano-2-((trans-3-cyanocyclopentyl)oxy)phenyl)sulfamoyl)-4-cyclopropylbenzoic acid<br>UPLC-MS (Method 1) m/z 484.00 $(M-H)^-$ at 1.816 min. $^1$H NMR (400 MHz, DMSO-$d_6$) δ 13.26 (s, 1H), 10.13 (s, 1H), 8.32 (d, J = 1.7 Hz, 1H), 7.99 (dd, J = 8.2, 1.4 Hz, 1H), 7.70 (s, 1H), 7.33 (s, 1H), 7.11 (d, J = 8.3 Hz, 1H), 5.00-4.89 (m, 1H), 3.01 (p, J = 8.4 Hz, 1H), 2.71-2.57 (m, 1H), 2.00 (tt, J = 14.0, 8.1 Hz, 4H), 1.71 (dt, J = 12.8, 7.6 Hz, 1H), 1.46 (dt, J = 12.9, 6.4 Hz, 1H), 0.96 (q, J = 9.2, 8.7 Hz, 2H), 0.80 (d, J = 4.7 Hz, 2H). |

-continued

| Example | Structure | Name/Analytical Data |
|---|---|---|
| 74 Cis racemate | 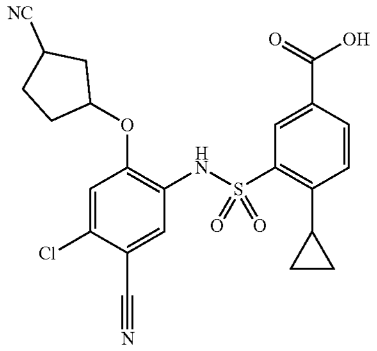 [SMILES: N#Cc1cc(NS(=O)(=O)c2cc(C(=O)O)ccc2C2CC2)c(OC2CCC(C#N)C2)cc1Cl] | 3-(N-(4-chloro-5-cyano-2-((cis-3-cyanocyclopentyl)oxy)phenyl)sulfamoyl)-4-cyclopropylbenzoic acid UPLC-MS (Method 1) m/z 484.00 (M − H)$^-$ at 1.783 min. $^1$H NMR (400 MHz, DMSO-$d_6$) δ 13.23 (s, 1H), 10.17 (s, 1H), 8.32 (d, J = 1.6 Hz, 1H), 8.04-7.94 (m, 1H), 7.69 (s, 1H), 7.30 (s, 1H), 7.12 (d, J = 8.3 Hz, 1H), 4.84 (s, 1H), 2.90 (q, J = 9.3, 8.2 Hz, 1H), 2.67 (d, J = 4.6 Hz, 1H), 2.49-2.40 (m, 1H), 1.96 (d, J = 11.5 Hz, 1H), 1.78 (ddt, J = 23.8, 18.1, 9.5 Hz, 3H), 1.61 (s, 1H), 1.07-0.95 (m, 2H), 0.83 (s, 2H). |
| 75 | 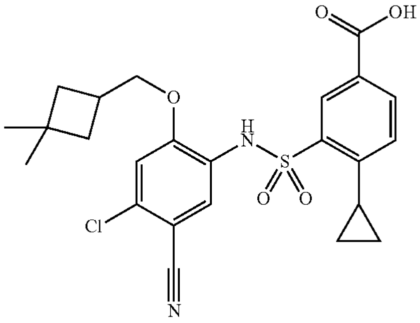 [SMILES: CC1(C)CC(COc2cc(Cl)c(C#N)cc2NS(=O)(=O)c2cc(C(=O)O)ccc2C2CC2)C1] | 3-(N-(4-chloro-5-cyano-2-((3,3-dimethylcyclobutyl)methoxy)phenyl) sulfamoyl)-4-cyclopropylbenzoic acid UPLC-MS (Method 1) m/z 487.05 (M − H)$^-$ at 2.283 min. $^1$H NMR (400 MHz, DMSO-$d_6$) δ 13.12 (s, 1H), 10.05 (s, 1H), 8.35 (d, J = 1.5 Hz, 1H), 7.97 (d, J = 8.3 Hz, 1H), 7.59 (s, 1H), 7.31 (s, 1H), 7.09 (d, J = 8.3 Hz, 1H), 3.86 (d, J = 6.7 Hz, 2H), 2.65 (s, 1H), 2.31 (d, J = 8.4 Hz, 1H), 1.62 (t, J = 10.0 Hz, 2H), 1.41 (t, J = 10.2 Hz, 2H), 1.07 (s, 3H), 0.97 (d, J = 8.5 Hz, 5H), 0.79 (d, J = 3.7 Hz, 2H). |
| 76 | 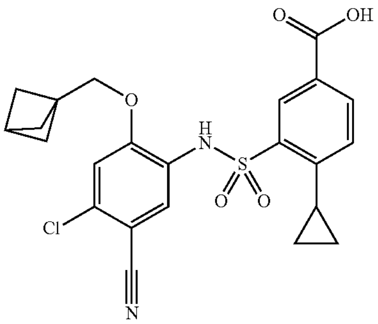 [SMILES: N#Cc1cc(NS(=O)(=O)c2cc(C(=O)O)ccc2C2CC2)c(OCC23CC(C2)C3)cc1Cl] | 3-(N-(2-(bicyclo[1.1.1]pentan-1-ylmethoxy)-4-chloro-5-cyanophenyl)sulfamoyl)-4-cyclopropylbenzoic acid UPLC-MS (Method 1) m/z 471.00 (M − H)$^-$ at 2.150 min. $^1$H NMR (400 MHz, DMSO-$d_6$) δ 13.21 (s, 1H), 10.11 (s, 1H), 8.36 (d, J = 1.6 Hz, 1H), 8.03-7.96 (m, 1H), 7.61 (s, 1H), 7.35 (s, 1H), 7.11 (d, J = 8.3 Hz, 1H), 3.95 (s, 2H), 2.58 (dd, J = 9.0, 3.9 Hz, 1H), 2.41 (s, 1H), 1.62 (s, 6H), 0.98 (q, J = 5.4, 4.1 Hz, 2H), 0.82 (t, J = 5.4 Hz, 2H). |
| 81 | 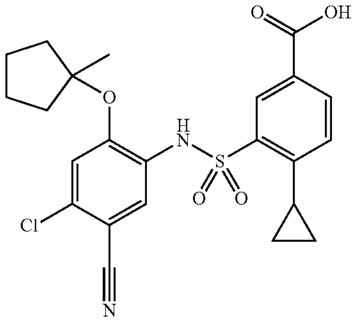 [SMILES: CC1(Oc2cc(Cl)c(C#N)cc2NS(=O)(=O)c2cc(C(=O)O)ccc2C2CC2)CCCC1] | 3-(N-(4-chloro-5-cyano-2-((1-methylcyclopentyl)oxy)phenyl)sulfamoyl)-4-cyclopropylbenzoic acid UPLC-MS (Method 1) m/z 473.00 (M − H)$^-$ at 2.116 min. $^1$H NMR (400 MHz, DMSO-$d_6$) δ 9.94 (s, 1H), 8.31 (d, J = 1.5 Hz, 1H), 8.02-7.94 (m, 1H), 7.69 (s, 1H), 7.14 (s, 1H), 7.10 (d, J = 8.3 Hz, 1H), 2.70-2.58 (m, 1H), 1.92-1.82 (m, 2H), 1.70-1.58 (m, 2H), 1.51-1.42 (m, 4H), 1.20 (s, 3H), 0.99-0.91 (m, 2H), 0.82-0.73 (m, 2H). |

-continued

| Example | Structure | Name/Analytical Data |
|---|---|---|
| 82 | 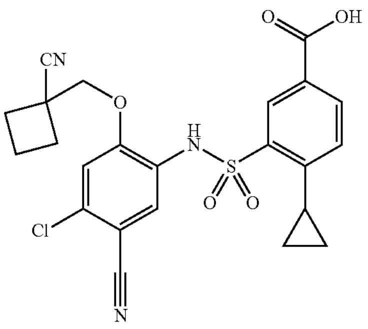 [SMILES: N#Cc1cc(NS(=O)(=O)c2cc(C(=O)O)ccc2C2CC2)c(OCC2(C#N)CCC2)cc1Cl] | 3-(N-(4-chloro-5-cyano-2-((1-cyanocyclobutyl)methoxy)phenyl) sulfamoyl)-4-cyclopropylbenzoic acid UPLC-MS (Method 1) m/z 483.95 $(M - H)^-$ at 1.816 min.$^1$H NMR (400 MHz, DMSO-$d_6$) δ 13.22 (s, 1H), 10.34 (s, 1H), 8.38 (d, J = 1.6 Hz, 1H), 7.99 (d, J = 8.2 Hz, 1H), 7.55 (d, J = 3.4 Hz, 2H), 7.13 (d, J = 8.3 Hz, 1H), 4.34 (s, 2H), 2.61 (s, 1H), 2.42-2.28 (m, 2H), 2.14 (dt, J = 12.1, 7.1 Hz, 2H), 1.99 (q, J = 7.7 Hz, 2H), 1.01 (d, J = 6.2 Hz, 2H), 0.83 (d, J = 3.7 Hz, 2H). |
| 83 | 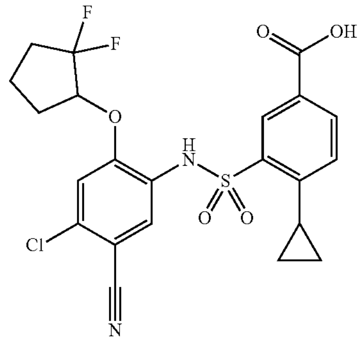 [SMILES: N#Cc1cc(NS(=O)(=O)c2cc(C(=O)O)ccc2C2CC2)c(OC2CCCC2(F)F)cc1Cl] | 3-(N-(4-chloro-5-cyano-2-((2,2-difluorocyclopentyl)oxy)phenyl)sulfamoyl)-4-cyclopropylbenzoic acid UPLC-MS (Method 1) m/z 494.95 $(M - H)^-$ at 1.916 min.$^1$H NMR (400 MHz, DMSO-$d_6$) δ 13.22 (s, 1H), 10.23 (s, 1H), 8.34 (d, J = 1.5 Hz, 1H), 7.99 (d, J = 8.2 Hz, 1H), 7.68 (s, 1H), 7.41 (s, 1H), 7.12 (d, J = 8.3 Hz, 1H), 5.04-4.99 (br m, 1H), 2.71-2.61 (m, 1H), 2.09-1.96 (m, 3H), 1.77-1.68 (m, 1H), 1.65-1.49 (m, 2H), 1.03-0.93 (m, 2H), 0.87-0.76 (br m, 2H). |
| 84 Trans racemate | 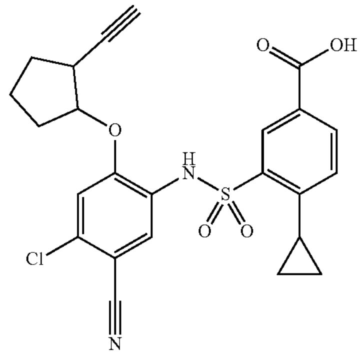 [SMILES: C#CC1CCCC1Oc1cc(Cl)c(C#N)cc1NS(=O)(=O)c1cc(C(=O)O)ccc1C1CC1] | 3-(N-(4-chloro-5-cyano-2-((trans-2-ethynylcyclopentyl)oxy)phenyl)sulfamoyl)-4-cyclopropylbenzoic acid UPLC-MS (Method 1) m/z 483.00 $(M - H)^-$ at 2.382 min.$^1$H NMR (400 MHz, DMSO-$d_6$) δ 13.25 (s, 1H), 10.19 (s, 1H), 8.33 (d, J = 1.7 Hz, 1H), 7.99 (dd, J = 8.3, 1.5 Hz, 1H), 7.68 (s, 1H), 7.36 (s, 1H), 7.12 (d, J = 8.3 Hz, 1H), 4.89-4.74 (m, 1H), 3.05 (d, J = 2.5 Hz, 1H), 2.71-2.56 (m, 2H), 2.05-1.80 (m, 2H), 1.65-1.54 (m, 1H), 1.57-1.41 (m, 2H), 1.40-1.27 (m, 1H), 1.06-0.93 (m, 2H), 0.85-0.77 (m, 2H). |
| 85 Trans racemate | 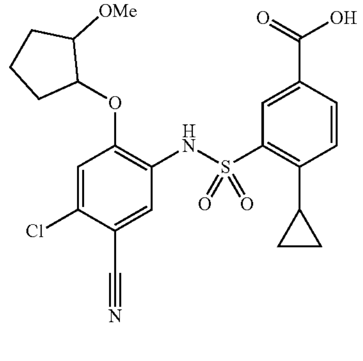 [SMILES: COC1CCCC1Oc1cc(Cl)c(C#N)cc1NS(=O)(=O)c1cc(C(=O)O)ccc1C1CC1] | 3-(N-(4-chloro-5-cyano-2-((trans-2-methoxycyclopentyl)oxy)phenyl)sulfamoyl)-4-cyclopropylbenzoic acid UPLC-MS (Method 1) m/z 489.05 $(M - H)^-$ at 1.983 min. $^1$H NMR (400 MHz, DMSO-$d_6$) δ 13.25 (s, 1H), 10.14 (s, 1H), 8.32 (d, J = 1.7 Hz, 1H), 7.99 (dd, J = 8.2, 1.5 Hz, 1H), 7.69 (s, 1H), 7.36 (s, 1H), 7.13 (d, J = 8.3 Hz, 1H), 4.71-4.60 (m, 1H), 3.46-3.39 (m, 1H), 3.13 (s, 3H), 2.65 (td, J = 8.4, 4.3 Hz, 1H), 1.98-1.84 (m, 1H), 1.77-1.64 (m, 1H), 1.55-1.37 (m, 3H), 1.25-1.21 (m, 1H), 1.04-0.94 (m, 2H), 0.88-0.70 (m, 2H). |

-continued

| Example | Structure | Name/Analytical Data |
|---|---|---|
| 86 Trans racemate | 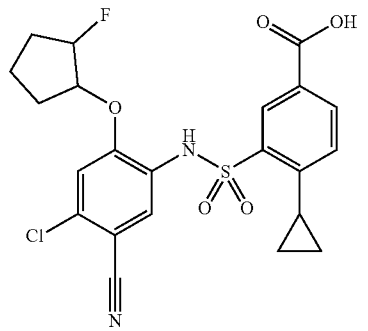 [SMILES: N#Cc1cc(NS(=O)(=O)c2cc(C(=O)O)ccc2C2CC2)c(OC2CCCC2F)cc1Cl] | 3-(N-(4-chloro-5-cyano-2-((trans-2-fluorocyclopentyl)oxy)phenyl)sulfamoyl)-4-cyclopropylbenzoic acid UPLC-MS (Method 1) m/z 476.95 $(M-H)^-$ at 2.250 min. $^1H$ NMR (400 MHz, DMSO-$d_6$) δ 13.28 (s, 1H), 10.23 (s, 1H), 8.35 (d, J = 1.8 Hz, 1H), 8.01 (dd, J = 8.2, 1.8 Hz, 1H), 7.73 (s, 1H), 7.39 (s, 1H), 7.14 (d, J = 8.3 Hz, 1H), 4.98-4.87 (m, 1H), 4.84-4.77 (m, 1H), 2.68 (hept, J = 5.1 Hz, 1H), 2.15-2.01 (m, 1H), 1.96-1.75 (m, 2H), 1.75-1.65 (m, 2H), 1.28 (ddd, J = 12.7, 7.5, 4.4 Hz, 1H), 1.08-0.93 (m, 2H), 0.83 (qd, J = 10.1, 4.5 Hz, 2H). |
| 87 | 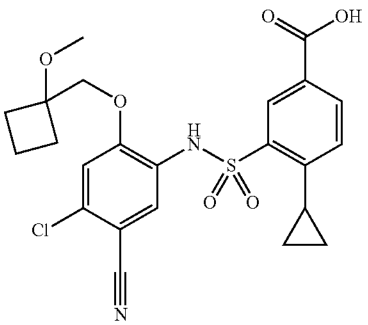 [SMILES: COC1(COc2cc(Cl)c(C#N)cc2NS(=O)(=O)c2cc(C(=O)O)ccc2C2CC2)CCC1] | 3-(N-(4-chloro-5-cyano-2-((1-methoxycyclobutyl)methoxy)phenyl)sulfamoyl)-4-cyclopropylbenzoic acid UPLC-MS (Method 1) m/z 489.05 $(M-H)^-$ at 1.916 min. $^1H$ NMR (400 MHz, DMSO-$d_6$) δ 10.01 (s, 1H), 8.35 (d, J = 1.7 Hz, 1H), 7.99 (dd, J = 8.2, 1.6 Hz, 1H), 7.51 (d, J = 8.8 Hz, 2H), 7.14 (d, J = 8.3 Hz, 1H), 4.10 (s, 2H), 3.02 (s, 3H), 2.60 (ddd, J = 13.5, 8.4, 5.2 Hz, 1H), 2.05-1.91 (m, 2H), 1.84 (dd, J = 12.7, 6.0 Hz, 2H), 1.54 (dq, J = 45.9, 9.8, 9.0 Hz, 2H), 1.06-0.91 (m, 2H), 0.88-0.78 (m, 2H). |
| 88 Cis/Trans mixture | 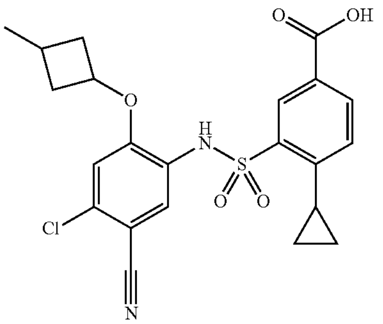 [SMILES: CC1CC(Oc2cc(Cl)c(C#N)cc2NS(=O)(=O)c2cc(C(=O)O)ccc2C2CC2)C1] | 3-(N-(4-chloro-5-cyano-2-(3-methylcyclobutoxy)phenyl)sulfamoyl)-4-cyclopropylbenzoic acid UPLC-MS (Method 1) m/z 459.00 $(M-H)^-$ at 2.116 min. $^1H$ NMR (400 MHz, DMSO-$d_6$) δ 13.23 (s, 1H), 10.15 (s, 1H), 8.30 (d, J = 1.7 Hz, 1H), 8.00 (dd, J = 8.2, 1.5 Hz, 1H), 7.71 (s, 1H), 7.15 (d, J = 8.3 Hz, 1H major), 7.14 (d, J = 8.3 Hz, 1H minor), 7.09 (s. 1H major), 7.05 (s, 1H minor), 4.90-4.68 (m, 1H minor), 4.46 (p, J = 7.2 Hz, 1H major), 2.76-2.65 (m, 1H), 2.45-2.34 (m, 2H), 1.95-1.86 (m, 1H minor), 1.86-1.73 (m, 1H major), 1.27-1.13 (m, 2H), 1.07 (d, J = 7.1 Hz, 3H minor), 1.04-0.99 (m, 2H), 0.97 (d, J = 6.6 Hz, 3H major), 0.87-0.77 (m, 2H). |
| 89 Cis/Trans mixture | 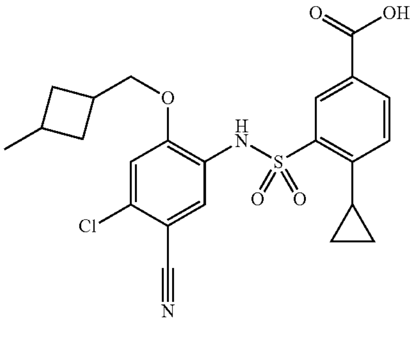 [SMILES: CC1CC(COc2cc(Cl)c(C#N)cc2NS(=O)(=O)c2cc(C(=O)O)ccc2C2CC2)C1] | 3-(N-(4-chloro-5-cyano-2-((3-methylcyclobutyl)methoxy)phenyl)sulfamoyl)-4-cyclopropylbenzoic acid UPLC-MS (Method 3) m/z 473.00 $(M-H)^-$ at 1.905 min. $^1H$ NMR (400 MHz, DMSO-$d_6$) δ 13.23 (s, 1H), 10.09 (s, 1H), 8.34 (dd, J = 5.6, 1.5 Hz, 1H), 8.03-7.95 (m, 1H), 7.62 (d, J = 6.7 Hz, 1H), 7.36 (d, J = 14.8 Hz, 1H), 7.12 (d, J = 7.6 Hz, 1H), 3.88 (dd, J = 35.8, 6.8 Hz, 2H), 2.66-2.55 (m, 1H), 2.43-2.09 (m, 2H), 2.03-1.91 (m, 1H), 1.78-1.67 (m, 1H), 1.56-1.44 (m, 1H), 1.27-1.14 (m, 1H), 1.06-0.96 (m, 3H), 0.93 (d, J = 6.6 Hz, 2H), 0.81 (d, J = 3.7 Hz, 2H). |

-continued

| Example | Structure | Name/Analytical Data |
| --- | --- | --- |
| 95 Trans relative | 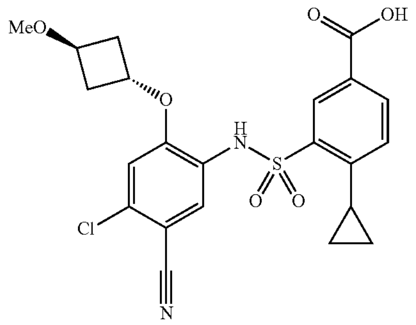 [SMILES: CO[C@H]1C[C@H](Oc2cc(Cl)c(C#N)cc2NS(=O)(=O)c2cc(C(=O)O)ccc2C2CC2)C1] | 3-(N-(4-chloro-5-cyano-2-(trans-3-methoxycyclobutoxy)phenyl)sulfamoyl)-4-cyclopropylbenzoic acid UPLC-MS (Method 2) m/z 475.10 $(M-H)^-$ at 3.933 min. $^1H$ NMR (400 MHz, DMSO-$d_6$) 13.23 (s, 1H), 10.21 (s, 1H), 8.32 (s, 1H), 8.00 (d, J = 7.3 Hz, 1H), 7.71 (s, 1H), 7.14 (d, J = 8.3 Hz, 1H), 7.06 (s, 1H), 4.88-4.71 (m, 1H), 3.86-3.73 (m, 1H), 3.10 (s, 3H), 2.75-2.66 (m, 1H), 2.31-2.19 (m, 2H), 2.01-1.90 (m, 2H), 1.02 (d, J = 6.7 Hz, 2H), 0.82 (d, J = 4.1 Hz, 2H). |
| 96 Trans relative | 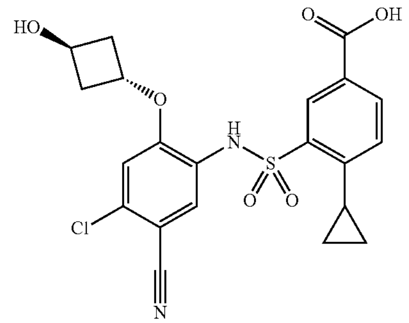 | 3-(N-(4-chloro-5-cyano-2-(trans-3-hydroxycyclobutoxy)phenyl)sulfamoyl)-4-cyclopropylbenzoic acid UPLC-MS (Method 2) m/z 461.15 $(M-H)^-$ at 3.633 min. $^1H$ NMR (400 MHz, DMSO-$d_6$) δ 13.23 (s, 1H), 10.20 (s, 1H), 8.31 (s, 1H), 7.99 (d, J = 8.1 Hz, 1H), 7.69 (s, 1H), 7.13 (d, J = 8.2 Hz, 1H), 7.00 (s, 1H), 5.11 (d, J = 5.3 Hz, 1H), 4.76 (s, 1H), 4.14 (d, J = 5.2 Hz, 1H), 2.71 (s, 1H), 2.19-2.07 (m, 2H), 2.03-1.92 (m, 2H), 1.02 (d, J = 6.5 Hz, 2H), 0.82 (d, J = 3.8 Hz, 2H). |
| 97 | 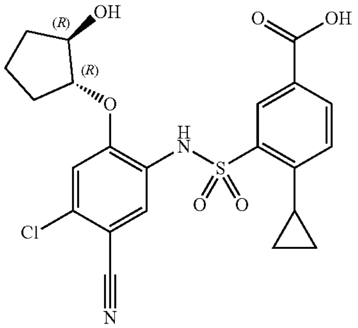 | 3-(N-(4-chloro-5-cyano-2-(((1R,2R)-2-hydroxycyclopentyl)oxy)phenyl)sulfamoyl)-4-cyclopropylbenzoic acid UPLC-MS (Method 2) m/z 475.10 $(M-H)^-$ at 3.700 min. $^1H$ NMR (400 MHz, DMSO-$d_6$) δ 13.19 (s, 1H), 10.07 (s, 1H), 8.32 (d, J = 1.7 Hz, 1H), 7.98 (dd, J = 8.2, 1.6 Hz, 1H), 7.67 (s, 1H), 7.38 (s, 1H), 7.11 (d, J = 8.3 Hz, 1H), 4.98 (s, 1H), 4.48-4.30 (m, 1H), 3.75 (s, 1H), 2.63 (ddd, J = 13.3, 8.3, 5.2 Hz, 1H), 1.94 (dt, J = 14.2, 7.3 Hz, 1H), 1.59 (ddq, J = 21.1, 14.4, 7.3 Hz, 2H), 1.47-1.34 (m, 2H), 1.31-1.24 (m, 1H), 0.97 (dt, J = 7.7, 4.0 Hz, 2H), 0.87-0.72 (m, 2H). |
| 98 Cis racemate | 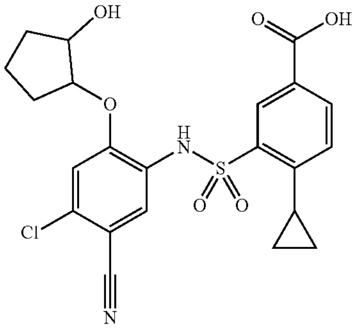 [SMILES: N#Cc1cc(NS(=O)(=O)c2cc(C(=O)O)ccc2C2CC2)c(OC2CCCC2O)cc1Cl] | 3-(N-(4-chloro-5-cyano-2-((cis-2-hydroxycyclopentyl)oxy)phenyl)sulfamoyl)-4-cyclopropylbenzoic acid UPLC-MS (Method 2) m/z 475.05 $(M-H)^-$ at 3.800 min. $^1H$ NMR (400 MHz, DMSO-$d_6$) δ 13.28 (s, 1H), 10.14 (s, 1H), 7.98 (dd, J = 8.2, 1.4 Hz, 1H), 7.69 (s, 1H), 7.34 (s, 1H), 7.07 (d, J = 8.3 Hz, 1H), 4.86 (s, 1H), 4.57 (d, J = 5.5 Hz, 1H), 3.92 (d, J = 4.1 Hz, 1H), 2.64-2.55 (m, 1H), 1.90 (d, J = 5.1 Hz, 1H), 1.68-1.56 (m, 1H), 1.41 (d, J = 3.8 Hz, 3H), 1.23 (s, 1H), 1.08 (t, J = 6.5 Hz, 1H), 0.89-0.78 (m, 2H), 0.65 (d, J = 5.8 Hz, 1H). |

Example 50: 3-(N-(4-chloro-2-(3,3-difluorocyclobutoxy)-5-(isothiazol-5-yl)phenyl)sulfamoyl)-4-cyclopropylbenzoic acid

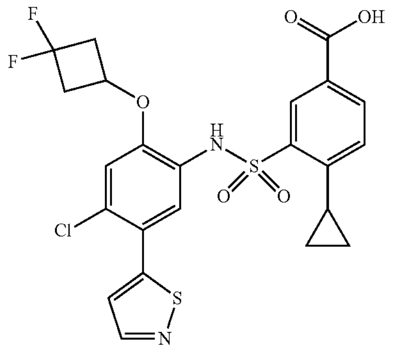 [SMILES: O=C(O)c1ccc(C2CC2)c(S(=O)(=O)Nc2cc(-c3ccns3)c(Cl)cc2OC2CC(F)(F)C2)c1]

Step 1: methyl 3-(N-(4-chloro-2-(3,3-difluorocyclobutoxy)-5-(isothiazol-5-yl)phenyl)sulfamoyl)-4-cyclopropylbenzoate: A solution of Intermediate 15 (165 mg, 521 μmol), methyl 3-(chlorosulfonyl)-4-cyclopropylbenzoate (215 mg, 781 μmol; Intermediate-3) and pyridine (126 μL, 1.56 mmol) in DCM (2 mL) was stirred at RT for 4 h. The reaction mixture was diluted with DCM (7 mL) and water (7 mL), and the phases separated. The aqueous phase was extracted with DCM (2×7 mL) and the combined organic phases were concentrated in vacuo. The residue was purified by chromatography on silica gel (12 g cartridge, 0-100% EtOAc/isohexane) to afford the title compound (236 mg, 0.41 mmol, 78% yield, 96% purity) as a white solid. UPLC (Method 4): m/z 556.3 $(M+H)^+$, 554.9 $(M-H)^-$, at 1.94 min. $^1$H NMR (500 MHz, DMSO) b 10.24 (s, 1H), 8.61 (d, J=1.9 Hz, 1H), 8.41 (s, 1H), 8.00 (d, J=8.2 Hz, 1H), 7.65 (s, 1H) 7.61 (s, 1H), 7.15 (m, 2H), 4.83-4.67 (m, 1H), 3.85 (s, 3H), 3.16-3.02 (m, 2H), 2.88-2.77 (m, 1H), 2.54-2.49 (m, 2H), 1.10-1.01 (m, 2H), 0.88-0.78 (m, 2H). Two protons obscured by solvent.

Step 2: 3-(N-(4-chloro-2-(3,3-difluorocyclobutoxy)-5-(isothiazol-5-yl)phenyl)sulfamoyl)-4-cyclopropylbenzoic acid: A solution of the product from Step 1 above (236 mg, 0.41 mmol, 96% purity) and $LiOH{\cdot}H_2O$ (71.4 mg, 1.70 mmol) in a mixture of THF (2 mL), water (0.5 mL) and MeOH (0.5 mL) was stirred at RT for 18 h. The reaction mixture was diluted with EtOAc (5 mL) and water (5 mL) after which it was acidified to pH~4. The layers were separated, and the aqueous layer extracted with EtOAc (2×5 mL). The organic phases were combined and concentrated in vacuo. The residue was purified by chromatography on silica gel (12 g cartridge, 0-5% (5% AcOH in MeOH)/DCM) to afford the title compound (169 mg, 0.29 mmol, 68% yield, 92% purity) as a white solid. UPLC-MS (Method 4): m/z 541.7 $(M+H)^+$, 539.3 $(M-H)^-$, at 1.80 min. $^1$H NMR (500 MHz, DMSO) δ 13.27 (s, 1H), 10.20 (s, 1H), 8.58 (d, J=1.8 Hz, 1H), 8.41 (d, J=1.9 Hz, 1H), 7.98 (dd, J=8.1, 1.9 Hz, 1H), 7.64 (s, 1H), 7.61 (d, J=1.9 Hz, 1H), 7.17-7.10 (m, 2H), 4.82-4.69 (m, 1H), 3.15-3.04 (m, 2H), 2.85-2.75 (m, 1H), 2.62-2.52 (m, 2H), 1.09-1.01 (m, 2H), 0.86-0.79 (m, 2H).

Example 51: 3-(N-(4-chloro-2-cyclobutoxy-5-(isothiazol-5-yl)phenyl)sulfamoyl)-4-cyclopropylbenzoic acid

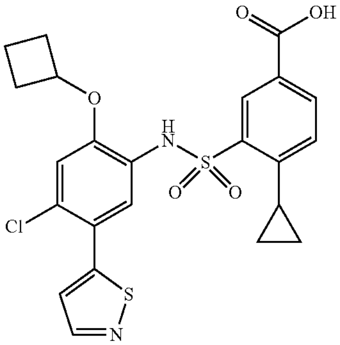 [SMILES: O=C(O)c1ccc(C2CC2)c(S(=O)(=O)Nc2cc(-c3ccns3)c(Cl)cc2OC2CCC2)c1]

The title compound (2.6 mg, 4.0 μmol, 78% purity) was prepared by methods analogous to Example 50, using Intermediate 14 in place of Intermediate 15. UPLC-MS (Method 4): m/z 506.4 $(M+H)^+$, 504.2 $(M-H)^-$, at 1.91 min. $^1$H NMR (500 MHz, DMSO) δ 13.26 (s, 1H), 10.05 (s, 1H), 8.58 (d, J=1.8 Hz, 1H), 8.37 (d, J=1.9 Hz, 1H), 8.03-7.97 (m, 1H), 7.65-7.61 (m, 2H), 7.15 (d, J=8.3 Hz, 1H), 6.97 (s, 1H), 4.65 (app. p, J=7.3 Hz, 1H), 2.85-2.76 (m, 1H), 2.29-2.21 (m, 2H), 1.77-1.47 (m, 4H), 1.08-1.01 (m, 2H), 0.85-0.80 (m, 2H).

Example 60: 3-(N-(4-chloro-2-cyclobutoxy-5-(5-methylisoxazol-4-yl)phenyl)sulfamoyl)-4-cyclopropylbenzoic acid

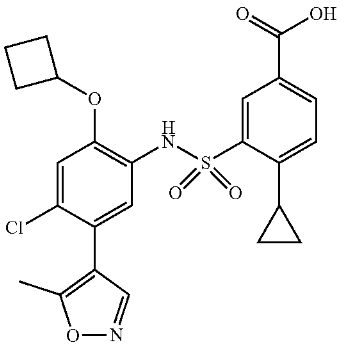 [SMILES: Cc1oncc1-c1cc(NS(=O)(=O)c2cc(C(=O)O)ccc2C2CC2)c(OC2CCC2)cc1Cl]

Step 1: methyl 3-(N-(4-chloro-2-cyclobutoxy-5-(5-methylisoxazol-4-yl)phenyl)sulfamoyl)-4-cyclopropylbenzoate: A solution of Intermediate 12 (120 mg, 431 μmol), methyl 3-(chlorosulfonyl)-4-cyclopropylbenzoate (215 mg, 781 μmol) and pyridine (126 μL, 1.56 mmol) in DCM (2 mL) was stirred at RT for 4 h. The reaction mixture was diluted with DCM (7 mL) and water (7 mL), and the phases separated. The aqueous phase was extracted with DCM (2×7 mL) and the combined organic phases were concentrated in vacuo. The residue was purified by chromatography on silica gel (12 g cartridge, 0-100% EtOAc/isohexane) to afford the title compound (193 mg, 0.366 mmol, 86% yield, 98% purity) as a pale red solid. UPLC-MS (Method 4): m/z 517.4 $(M+H)^+$, 515.2 $(M-H)^-$, at 1.97 min. $^1$H NMR (500 MHz, DMSO-$d_6$) δ 9.97 (s, 1H), 8.60 (s, 1H), 8.32 (d, J=1.9 Hz, 1H), 8.01 (d, J=8.2 Hz, 1H), 7.25 (s, 1H), 7.17 (d, J=8.3 Hz, 1H), 6.91 (s, 1H), 4.59 (p, J=6.9 Hz, 1H), 3.84 (s, 3H), 2.81 (s, 1H), 2.31 (s, 3H), 2.26-2.19 (m, 2H), 1.72-1.65 (m, 2H), 1.65-1.48 (m, 2H), 1.10-1.02 (m, 2H), 0.89-0.82 (m, 2H).

Step 2: 3-(N-(4-chloro-2-cyclobutoxy-5-(5-methylisoxazol-4-yl)phenyl)sulfamoyl)-4-cyclopropylbenzoic acid: To a solution of the product from Step 1 above (193 mg, 366 μmol, 98% purity) in dioxane (800 μL) and water (400 μL) was added conc. HCl(aq) (400 μL, 6.05 mmol) and the mixture was heated to 70° C. and stirred overnight. Additional conc. HCl(aq) (400 μL, 6.05 mmol) was added and stirring at 70° C. was continued for 7 h. Upon cooling to RT, the mixture was diluted with water (20 mL) and extracted with EtOAc (3x30 mL). The combined organic extracts were washed with brine (20 mL), dried ($MgSO_4$) and the solvent was removed in vacuo. The residue was loaded onto silica and purified by chromatography on silica gel (24 g cartridge, 0-10% MeOH/DCM), then triturated with TBME to afford the title compound (48.8 mg, 92.2 μmol, 25% yield, 95% purity) as a light-tan solid. UPLC-MS (Method 4): m/z 503.0 $(M+H)^+$, 501.2 $(M-H)^-$, at 1.84 min. $^1H$ NMR (500 MHz, DMSO-$d_6$) δ 13.22 (s, 1H), 9.93 (s, 1H), 8.60 (s, 1H), 8.31 (d, J=1.9 Hz, 1H), 7.99 (dd, J=8.2, 1.9 Hz, 1H), 7.24 (s, 1H), 7.15 (d, J=8.2 Hz, 1H), 6.91 (s, 1H), 4.64-4.55 (m, 1H), 2.84-2.75 (m, 1H), 2.30 (s, 3H), 2.28-2.19 (m, 2H), 1.75-1.66 (m, 2H), 1.66-1.57 (m, 1H), 1.57-1.48 (m, 1H), 1.09-1.01 (m, 2H), 0.88-0.81 (m, 2H).

Example 61: 3-(N-(4-chloro-2-(3,3-difluorocyclobutoxy)-5-(5-methylisoxazol-4-yl)phenyl)sulfamoyl)-4-cyclopropylbenzoic acid

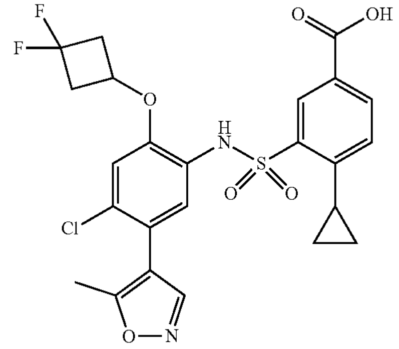 [SMILES: Cc1oncc1-c1cc(NS(=O)(=O)c2cc(C(=O)O)ccc2C2CC2)c(OC2CC(F)(F)C2)cc1Cl]

The title compound (57.3 mg, 102 μmol, 96% purity) was prepared by methods analogous to Example 60, using Intermediate 13 in place of Intermediate 12. UPLC-MS (Method 4): m/z 539.0 $(M+H)^+$, 537.2 $(M-H)^-$, at 1.74 min. $^1H$ NMR (500 MHz, DMSO-$d_6$) δ 13.23 (s, 1H), 10.08 (s, 1H), 8.59 (s, 1H), 8.33 (d, J=1.9 Hz, 1H), 7.97 (dd, J=8.2, 1.9 Hz, 1H), 7.28 (s, 1H), 7.12 (d, J=8.2 Hz, 1H), 7.10 (s, 1H), 4.78-4.67 (m, 1H), 3.14-3.02 (m, 2H), 2.84-2.75 (m, 1H), 2.59-2.44 (m, 2H), 2.28 (s, 3H), 1.08-1.01 (m, 2H), 0.87-0.80 (m, 2H).

Example 67: 3-(N-(4-chloro-5-cyano-2-(cyclopentyloxy)phenyl)sulfamoyl)-4-cyclopropyl-2-fluorobenzoic acid

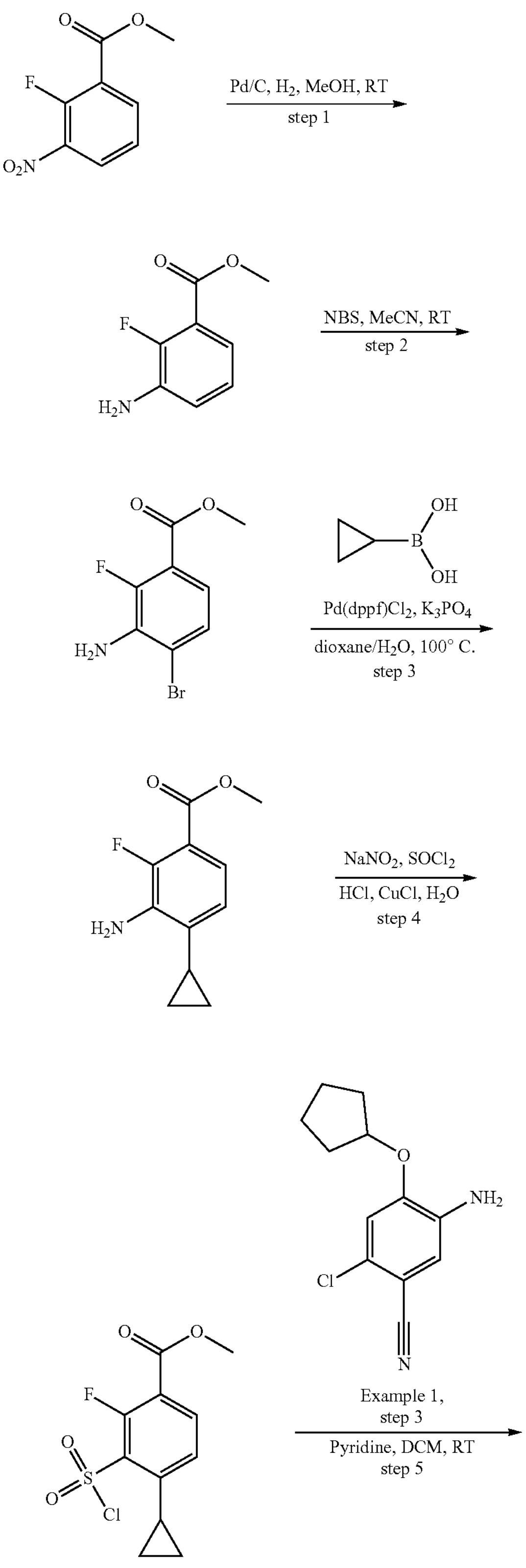

-continued

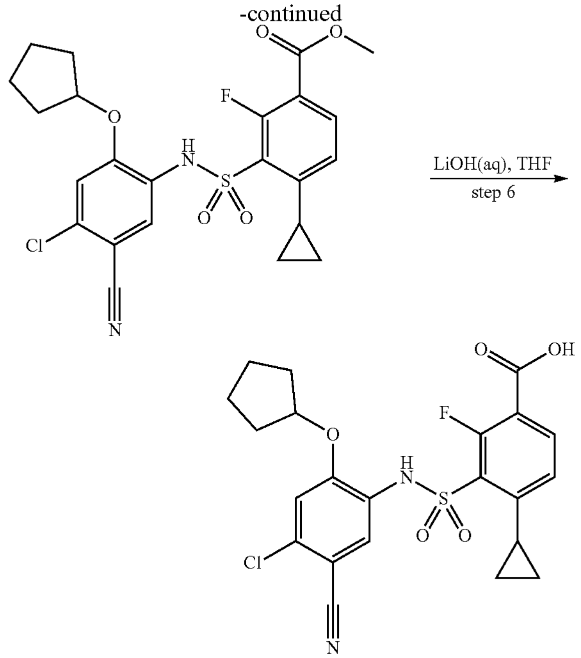

Reagents: (a) Pd/C, $H_2$, MeOH, RT; (b) NBS, MeCN, RT; (c) $Pd_2(dppf)Cl_2$, $K_3PO_4$, dioxane/$H_2O$(v/v = 10:1), 100° C.; (d) $NaNO_2$, CuCl, $SOCl_2$, HCl(cn), THF/$H_2O$(v/v = 10/1), RT; (e) Pyridine, DCM, RT; (f) LiOH (aq), THF, RT.

Step 1: methyl 3-amino-2-fluorobenzoate: A mixture of methyl 2-fluoro-3-nitrobenzoate (4.0 g, 4.2 mmol) and Pd/C (0.5 g, 10%) in Methanol was stirred at 25° C. for 2 h under a hydrogen atmosphere. The catalyst was removed by filtration through celite and the filtrate concentrated to afford the title compound (3.38 g, 2.0 mmol, 47% yield) as a yellow solid. UPLC-MS (Method 1) m/z 170.10 $(M+H)^+$ at 1.32 min.

Step 2: methyl 3-amino-4-bromo-2-fluorobenzoate: To a solution of Step 1 aniline (3.38 g, 20.0 mmol) in MeCN (20 mL) at 0° C. was added NBS (3.2 g, 18.0 mmol). The resulting mixture was stirred at room temperature for 16 h. The solvent was removed under reduced pressure and the residue dissolved in EtOAc and washed with saturated $Na_2CO_3$, water and brine. The organic layer was dried over $Na_2SO_4$ and concentrated to give crude product. The crude product was purified by silica gel chromatography (eluting with 1/10 EtOAc/PE) to afford the title compound (4.69 g, 18.9 mmol, 94% yield) as a yellow solid. UPLC-MS (Method 1) m/z 248.0, 250.0 $(M-H)^-$ at 1.516 min. 1H NMR (400 MHz, DMSO-$d_6$) δ 7.17 (dd, J=8.7, 1.3 Hz, 1H), 6.81 (dd, J=9.4, 8.7 Hz, 1H), 5.62 (s, 2H).

Step 3: methyl 3-amino-4-cyclopropyl-2-fluorobenzoate: A mixture of Step 2 bromide (4.69 g, 18.9 mmol), cyclopropylboronic acid (4.47 g, 56.7 mmol), $K_3PO_4$ (12.03 g, 56.7 mmol) and $Pd(dppf)Cl_2$ (1.39 g, 1.90 mmol) in a mixture of dioxane and $H_2O$ (v/v=10:1, 50 mL) was heated at 110° C. in a sealed tube for 16 h. The resulting mixture was filtered through celite, concentrated and purified by silica gel chromatography (eluting with 1/10 EtOAc/PE) to afford the title compound (2.84 g, 13.6 mmol, 24% yield) as a yellow solid. 1H NMR (400 MHz, DMSO-d6) δ 6.80 (dt, J=22.2, 9.0 Hz, 1H), 6.60 (d, J=8.4 Hz, 1H), 5.17 (s, 2H), 2.32-2.21 (m, 1H), 0.87-0.74 (m, 2H), 0.59-0.45 (m, 2H).

Step 4: methyl 3-(chlorosulfonyl)-4-cyclopropyl-2-fluorobenzoate: To a solution of Step 3 aniline (0.627 g, 3.0 mmol) in a mixture of concentrated HCl (2 mL) and $H_2O$ (4.0 mL) at 0° C. was added $NaNO_2$ (0.414 g, 6.0 mmol) portionwise. The mixture was stirred at 0° C. for 30 min. To a solution of CuCl (30.0 mg, 0.03 mmol) in $H_2O$ (1 mL) at 0° C. was added dropwise $SOCl_2$ (2.0 mL). This solution was then added dropwise to the above reaction and the mixture stirred at 0° C. for 1 h. The reaction was diluted with EtOAc (50 mL) and $H_2O$ (50 mL), and the aqueous layer extracted with EtOAc (50 mL×2). The combined organic layers were dried over $Na_2SO_4$ and concentrated to afford the title compound (0.153 g, 1.17 mmol, 78% yield) as an yellow oil. The crude product was used in the next step without purification.

Step 5: methyl 3-(N-(4-chloro-5-cyano-2-(cyclopentyloxy)phenyl)sulfamoyl)-4-cyclopropyl-2-fluorobenzoate: To a solution of Step 4 sulphonyl chloride (0.083 g, 0.35 mmol) in pyridine (1 mL) was added 5-amino-2-chloro-4-(cyclopentyloxy)benzonitrile (Example 1, Step 3; 0.354 g, 1.5 mmol) and the solution stirred at RT overnight. The solvent was removed in vacuo and the crude product purified by Biotage Isolera One ($C_{18}$ column, eluting with 10% to 90% MeCN/$H_2O$) to give the title compound (0.73 g, 0.15 mmol, 43% yield) as a white solid. UPLC-MS (Method 3) m/z 491.05 $(M-H)^-$ at 1.883 min.

Step 6: 3-(N-(4-chloro-5-cyano-2-(cyclopentyloxy)phenyl)sulfamoyl)-4-cyclopropyl-2-fluorobenzoic acid: To solution of Step 5 ester (0.073 g, 0.15 mmol) in mixture of THF and $H_2O$ (v/v=1:1, 4 mL) was added LiOH (35.5 mg, 1.5 mmol) and the reaction stirred at RT overnight. The solvent was removed in vacuo and the crude product purified by Biotage Isolera One ($C_{18}$ column, eluting with 10% to 90% MeCN/$H_2O$, contained 0.1% HCOOH) to give the title compound (22.6 mg, 0.047 mmol, 31% yield) as a red solid. UPLC-MS (Method 1) m/z 477.00 $(M-H)^-$ at 2.083 min. $^1H$ NMR (400 MHz, DMSO-$d_6$) δ 10.13 (s, 1H), 7.74 (s, 1H), 7.60 (t, J=7.9 Hz, 1H), 7.29 (s, 1H), 6.87 (d, J=8.4 Hz, 1H), 4.81 (dq, J=6.5, 3.0 Hz, 1H), 2.02 (td, J=8.3, 4.2 Hz, 1H), 1.80 (dt, J=11.8, 6.7 Hz, 2H), 1.60-1.46 (m, 2H), 1.49-1.40 (m, 4H), 1.13-1.04 (m, 2H), 0.84-0.75 (m, 2H).

Example 70: (S)-3-(N-(4-chloro-5-cyano-2-(1-cyclobutylethoxy)phenyl)sulfamoyl)-4-cyclopropylbenzoic acid

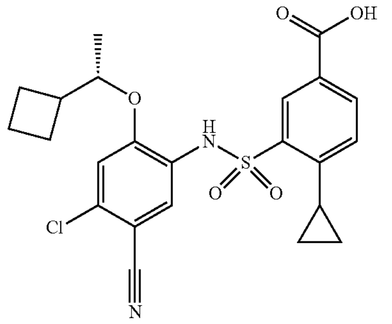 [SMILES: C[C@H](Oc1cc(Cl)c(C#N)cc1NS(=O)(=O)c1cc(C(=O)O)ccc1C1CC1)C1CCC1]

Step 1: (S)-2-chloro-4-(1-cyclobutylethoxy)-5-nitrobenzonitrile: To a suspension of NaH (60% in mineral oil) (257 mg, 6.42 mmol) in THF (15 mL) at 0° C. was added (S)-1-cyclobutylethan-1-ol (400 μL, 3.62 mmol) dropwise. The mixture was warmed to RT and stirred for 30 min. The product from Example 1 Step 1 (650 mg, 3.21 mmol, 99% purity) in THF (5 mL) was added and the mixture was heated to 60° C. and stirred overnight. The reaction was carefully quenched with water (20 mL) and extracted with EtOAc (3x50 mL). The combined organic extracts were washed with brine (20 mL), dried ($MgSO_4$) and the solvent was removed in vacuo. The residue was loaded onto silica and purified by chromatography on silica gel (24 g cartridge, 0-50% EtOAc/isohexane) to afford the title compound (196 mg, 649 μmol, 20% yield, 93% purity) as a yellow oil. UPLC (Method 4): $t_R$: 1.88 min. $^1$H NMR (500 MHz, DMSO-$d_6$) δ 8.62 (s, 1H), 7.90 (s, 1H), 4.94-4.85 (m, 1H), 2.61-2.51 (m, 1H), 1.98-1.70 (m, 6H), 1.17 (d, J=6.0 Hz, 3H).

Step 2: (S)-5-amino-2-chloro-4-(1-cyclobutylethoxy)benzonitrile: A mixture of the product from Step 1 above (198 mg, 656 μmol, 93% purity), ammonium chloride (211 mg, 3.94 mmol) and zinc (257 mg, 3.94 mmol) in THF (6 mL) and Water (2 mL) was stirred at RT overnight. The mixture was filtered through Celite®, washing with EtOAc, and the filtrate was extracted with EtOAc (3x15 mL). The combined organic extracts were washed with brine (15 mL), dried ($MgSO_4$) and the solvent was removed in vacuo to afford the title compound (160 mg, 625 μmol, 95% yield, 98% purity) as a sticky brown gum. UPLC-MS (Method 4): m/z 251.2 $(M+H)^+$ at 1.80 min. $^1$H NMR (500 MHz, DMSO-$d_6$) δ 7.14 (s, 1H), 6.96 (s, 1H), 5.23 (s, 2H), 4.60-4.51 (m, 1H), 2.61-2.51 (m, 1H), 2.02-1.72 (m, 6H), 1.12 (d, J=6.0 Hz, 3H).

Step 3: methyl (S)-3-(N-(4-chloro-5-cyano-2-(1-cyclobutylethoxy)phenyl)sulfamoyl)-4-cyclopropylbenzoate: A mixture of the product from Step 2 above (160 mg, 625 μmol, 98% purity), methyl 3-(chlorosulfonyl)-4-cyclopropylbenzoate (258 mg, 938 μmol) and pyridine (160 μL, 1.99 mmol) in DCM (5 mL) was heated to 35° C. and stirred for 2 days. The mixture was concentrated onto silica and purified by chromatography on silica gel (12 g cartridge, 0-50% EtOAc/isohexane) to afford the title compound (267 mg, 535 μmol, 86% yield, 98% purity) as a white solid. UPLC-MS (Method 4): m/z 487.2 $(M-H)^-$ at 2.04 min. $^1$H NMR (500 MHz, DMSO-$d_6$) δ 10.09 (s, 1H), 8.31 (d, J=1.9 Hz, 1H), 8.02 (dd, J=8.2, 1.9 Hz, 1H), 7.66 (s, 1H), 7.43 (s, 1H), 7.18 (d, J=8.2 Hz, 1H), 4.60-4.51 (m, 1H), 3.85 (s, 3H), 2.75-2.66 (m, 1H), 2.21-2.12 (m, 1H), 1.81-1.74 (m, 1H), 1.72-1.55 (m, 5H), 1.06-0.99 (m, 2H), 0.91-0.82 (m, 2H), 0.78 (d, J=6.0 Hz, 3H).

Step 4: (S)-3-(N-(4-chloro-5-cyano-2-(1-cyclobutylethoxy)phenyl)sulfamoyl)-4-cyclopropylbenzoic acid: A mixture of the product from Step 3 above (267 mg, 535 μmol, 98% purity) and LiOH·$H_2O$ (92.0 mg, 2.19 mmol) in THF/MeOH/water (4:1:1, 3 mL) was stirred at 40° C. overnight. The mixture was diluted with water (10 mL), acidified to ~pH 4 using 1 M HCl(aq) and extracted with EtOAc (3x15 mL). The combined organic extracts were washed with brine (10 mL), dried ($MgSO_4$) and the solvent was removed in vacuo. The residue was loaded onto silica and purified by chromatography on silica gel (24 g cartridge, 0-100% EtOAc/isohexane), then triturated with TBME/isohexane, to afford the title compound (127 mg, 262 μmol, 49% yield, 98% purity) as a white solid. UPLC-MS (Method 4): m/z 473.3 $(M-H)^-$ at 1.88 mx. H NMR (500 MHz, DMSO-$d_6$) δ 13.23 (s, 1H), 10.05 (s, 1H), 8.31 (d, J=1.9 Hz, 1H), 7.99 (dd, J=8.3, 1.9 Hz, 1H), 7.64 (s, 1H), 7.42 (s, 1H), 7.15 (d, J=8.3 Hz, 1H), 4.60-4.51 (m, 1H), 2.76-2.66 (n, 1H), 2.21-2.12 (m, 1H), 1.82-1.74 (s, 1H), 1.73-1.65 (m, 2H), 1.65-1.56 (m, 3H), 1.06-1.00 (s, 2H), 0.87-0.81 (m, 2H), 0.80 (d, J=6.0 Hz, 3H).

The following examples were prepared by methods analogous to Example 70, substituting appropriate starting materials and intermediates where necessary:

| Example | Structure | Name/Analytical Data |
| --- | --- | --- |
| 77 | 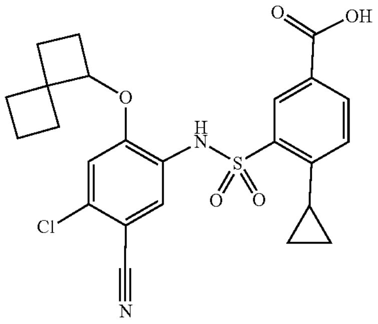 [SMILES: N#Cc1cc(NS(=O)(=O)c2cc(C(=O)O)ccc2C2CC2)c(OC2CCC23CCC3)cc1Cl] | 3-(N-(4-chloro-5-cyano-2-(spiro[3.3]heptan-1-yloxy)phenyl)sulfamoyl)-4-cyclopropylbenzoic acid<br>UPLC-MS (Method 4): m/z 487.4 $(M+H)^+$, 485.2 $(M-H)^-$, at 1.90 min. $^1$H NMR (500 MHz, DMSO-$d_6$) δ 13.23 (s, 1H), 10.14 (s, 1H), 8.38 (d, J = 1.9 Hz, 1H), 7.98 (dd, J = 8.2, 1.9 Hz, 1H), 7.67 (s, 1H), 7.24 (s, 1H), 7.08 (d, J = 8.3 Hz, 1H), 4.50 (t, J = 7.2 Hz, 1H), 2.60-2.51 (m, 1H), 2.21-2.07 (m, 2H), 1.94-1.85 (m, 1H), 1.81-1.61 (m, 3H), 1.57-1.31 (m, 4H), 0.98-0.91 (m, 1H), 0.91-0.83 (m, 1H), 0.82-0.73 (m, 2H). |
| 78 | 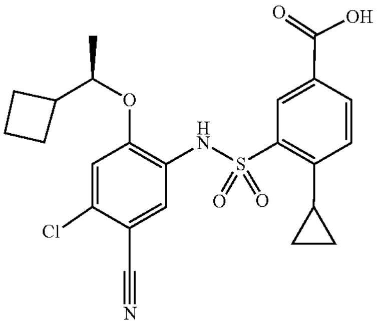 [SMILES: C[C@@H](Oc1cc(Cl)c(C#N)cc1NS(=O)(=O)c1cc(C(=O)O)ccc1C1CC1)C1CCC1] | (R)-3-(N-(4-chloro-5-cyano-2-(1-cyclobutylethoxy)phenyl)sulfamoyl)-4-cyclopropylbenzoic acid<br>UPLC-MS (Method 4): m/z 473.3 $(M-H)^-$ at 1.88 min. $^1$H NMR (500 MHz, DMSO-$d_6$) δ 13.23 (s, 1H), 10.05 (s, 1H), 8.31 (d, J = 1.9 Hz, 1H), 7.99 (dd, J = 8.3, 1.9 Hz, 1H), 7.64 (s, 1H), 7.42 (s, 1H), 7.15 (d, J = 8.3 Hz, 1H), 4.60-4.51 (m, 1H), 2.76-2.66 (m, 1H), 2.21-2.12 (m, 1H), 1.82-1.74 (m, 1H), 1.73-1.65 (m, 2H), 1.65-1.56 (m, 3H), 1.06-1.00 (m, 2H), 0.87-0.81 (m, 2H), 0.80 (d, J = 6.0 Hz, 3H). |

-continued

| Example | Structure | Name/Analytical Data |
|---|---|---|
| 79 | 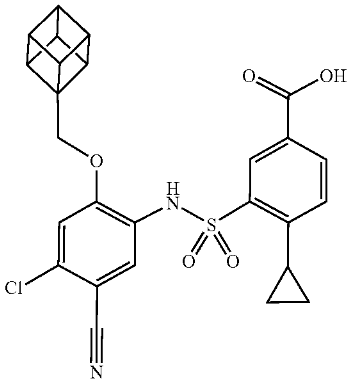 [SMILES: N#Cc1cc(NS(=O)(=O)c2cc(C(=O)O)ccc2C2CC2)c(OCC23C4C5C6C4C2C6C53)cc1Cl] | 3-(N-(4-chloro-2-(cuban-1-ylmethoxy)-5-cyanophenyl)sulfamoyl)-4-cyclopropylbenzoic acid UPLC-MS (Method 4): m/z 507.2 $(M-H)^-$ at 2.01 min. $^1H$ NMR (500 MHz, DMSO-$d_6$) δ 13.24 (s, 1H), 10.11 (s, 1H), 8.36 (d, J = 1.9 Hz, 1H), 7.99 (dd, J = 8.2, 1.9 Hz, 1H), 7.61 (s, 1H), 7.45 (s, 1H), 7.12 (d, J = 8.3 Hz, 1H), 4.15 (s, 2H), 3.98-3.90 (m, 1H), 3.84-3.77 (m, 3H), 3.77-3.71 (m, 3H), 2.61-2.52 (m, 1H), 0.99-0.91 (m, 2H), 0.83-0.76 (m, 2H). |
| 80 | 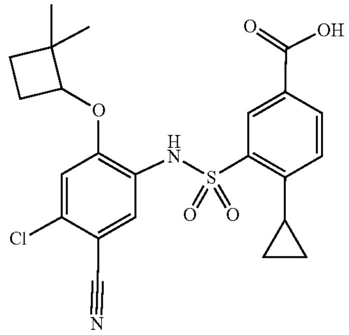 [SMILES: CC1(C)CCC1Oc1cc(Cl)c(C#N)cc1NS(=O)(=O)c1cc(C(=O)O)ccc1C1CC1] | 3-(N-(4-chloro-5-cyano-2-(2,2-dimethylcyclobutoxy)phenyl)sulfamoyl)-4-cyclopropylbenzoic acid UPLC-MS (Method 4): m/z 473.4 $(M-H)^-$ at 1.87 min. $^1H$ NMR (500 MHz, DMSO-$d_6$) δ 13.22 (s, 1H), 10.07 (s, 1H), 8.36 (d, J = 1.9 Hz, 1H), 7.98 (dd, J = 8.2, 1.9 Hz, 1H), 7.66 (s, 1H), 7.12-7.08 (m, 2H), 4.46 (t, J = 7.4 Hz, 1H), 2.61-2.54 (m, 1H), 2.23 - 2.13 (m, 1H), 1.75-1.64 (m, 1H), 1.46-1.30 (m, 2H), 1.04 (s, 3H), 1.01-0.95 (m, 1H), 0.93-0.85 (m, 1H), 0.81-0.77 (m, 2H), 0.76 (s, 3H). |
| 90 | 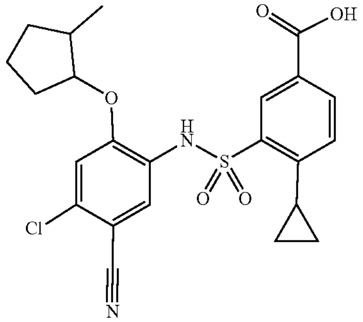 [SMILES: CC1CCCC1Oc1cc(Cl)c(C#N)cc1NS(=O)(=O)c1cc(C(=O)O)ccc1C1CC1] Trans racemate | 3-(N-(4-chloro-5-cyano-2-((trans-2-methylcyclopentyl)oxy)phenyl)sulfamoyl)-4-cyclopropylbenzoic acid UPLC-MS (Method 4): m/z 473.3 $(M-H)^-$ at 1.87 min. 1H NMR (500 MHZ, DMSO-$d_6$) δ 13.23 (s, 1H), 10.12 (s, 1H), 8.31 (d, J = 1.9 Hz, 1H), 7.98 (dd, J = 8.2, 1.9 Hz, 1H), 7.68 (s, 1H), 7.23 (s, 1H), 7.12 (d, J = 8.2 Hz, 1H), 4.37-4.30 (m, 1H), 2.73-2.66 (m, 1H), 1.97-1.86 (m, 1H), 1.85-1.76 (m, 1H), 1.73-1.63 (m, 1H), 1.54-1.40 (m, 2H), 1.07-0.97 (m, 3H), 0.86-0.79 (m, 6H). |

Example 73: 3-(N-(4-chloro-5-cyano-2-(((1R,2S)-2-fluorocyclopentyl)oxy)phenyl)sulfamoyl)-4-cyclopropylbenzoic acid

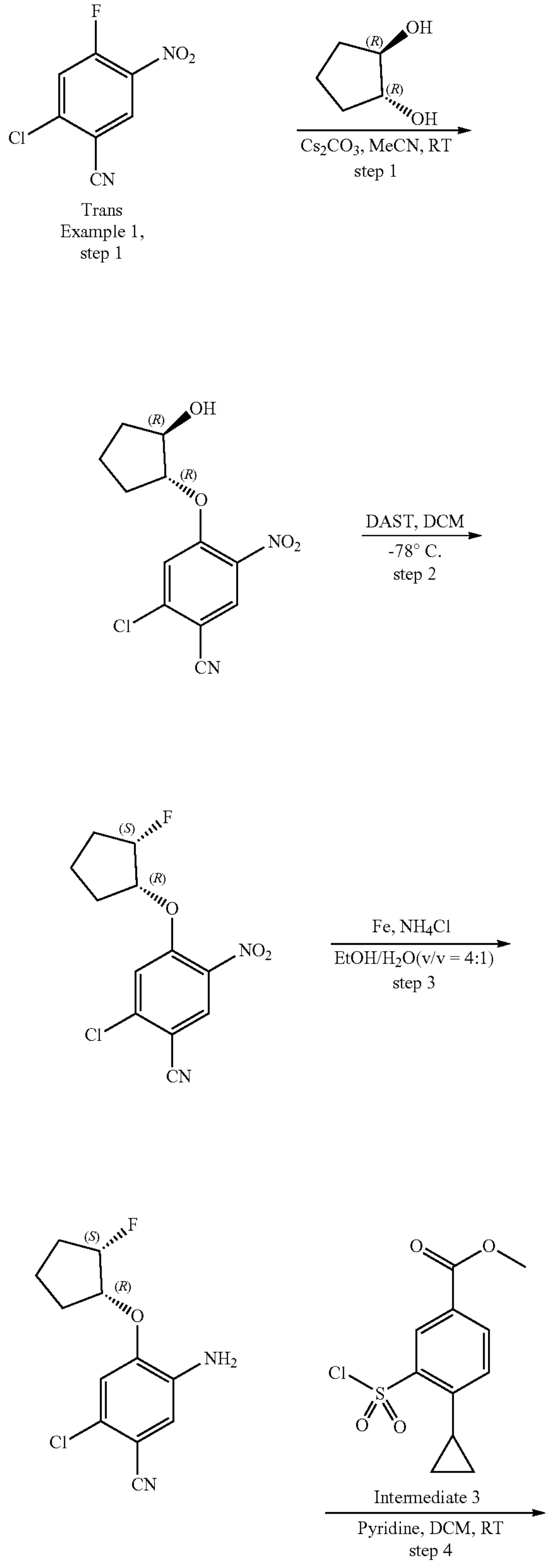

-continued

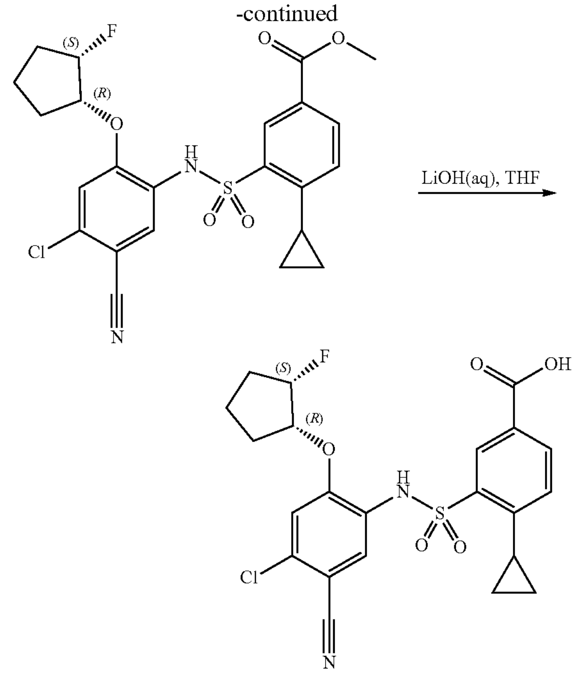

Reagents: (a) $Cs_2CO_3$, MeCN, RT; (b) DAST, DCM, -78° C.; (c) Fe, $NH_4Cl$, $EtOH/H_2O$ (v/v = 4/1), 80° C.; (d) Pyridine, DCM, RT; (e) LiOH (aq), THF, RT.

Step 1: 2-chloro-4-(((1R,2R)-2-hydroxycyclopentyl)oxy)-5-nitrobenzonitrile: Prepared from 2-chloro-4-fluoro-5-nitrobenzonitrile (Example 1, step 1) according to step 2 of Example 1.

Step 2: 2-chloro-4-(((1R,2S)-2-fluorocyclopentyl)oxy)-5-nitrobenzonitrile: To a solution of step 1 alcohol (0.200 g, 0.71 mmol) in DCM (5 mL) at −78° C. was added diethylaminosulfur trifluoride (0.686 g, 4.26 mmol) and the solution stirred at RT for 16 h. The solvent was removed in vacuo and the crude product purified by silica gel chromatography (eluting with 1/5 EtOAc/PE) to afford the title compound (0.070 g, 0.25 mmol, 35% yield) as a white solid. 1H NMR (400 MHz, Chloroform-d) δ 8.22 (s, 1H), 7.32 (s, 1H), 5.25-5.12 (t, J=5.1 Hz, 1H), 4.89 (dt, J=9.1, 4.3 Hz, 1H), 2.14 (dt, J=13.1, 7.8 Hz, 6H).

Step 3: 5-amino-2-chloro-4-(((1R,2S)-2-fluorocyclopentyl)oxy)benzonitrile: Prepared from 2-chloro-4-(((1R,2S)-2-fluorocyclopentyl)oxy)-5-nitrobenzonitrile according to step 3 of Example 1. UPLC-MS (Method 1) m/z 255.10 $(M+H)^+$ at 1.800 min.

Step 4: methyl 3-(N-(4-chloro-5-cyano-2-(((1R,2S)-2-fluorocyclopentyl)oxy)phenyl)sulfamoyl)-4-cyclopropylbenzoate: Prepared from Step 3 aniline and Intermediate 3 according to step 4 of Example 1. UPLC-MS (Method 1) m/z 491.00 $(M-H)^-$ at 2.183 min.

Step 5: 3-(N-(4-chloro-5-cyano-2-(((1R,2S)-2-fluorocyclopentyl)oxy)phenyl)sulfamoyl)-4-cyclopropylbenzoic acid: Prepared from Step 4 ester according to step 5 of Example 1. UPLC-MS (Method 1) m/z 477.00 $(M-H)^-$ at 1.950 min. $^1H$ NMR (400 MHz, DMSO-d) δ 13.19 (s, 1H), 10.22-10.01 (m, 1H), 8.34 (s, 1H), 7.98 (d, J=8.2 Hz, 1H), 7.63 (s, 1H), 7.49 (s, 1H), 7.12 (d, J=8.3 Hz, 1H), 5.03 (dd, J=53.7, 4.0 Hz, 1H), 4.82-4.72 (m, 1H), 2.67 (s, 1H), 1.90-1.69 (m, 4H), 1.64-1.42 (m, 2H), 1.05-0.96 (m, 2H), 0.81 (d, J=3.9 Hz, 2H).

Example 91: 3-(N-(4-chloro-5-cyano-2-(spiro[3.3]heptan-1-yloxy)phenyl)sulfamoyl)-4-cyclopropylbenzoic acid Enantiomer E1

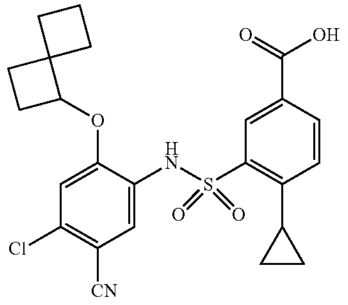

Enantiomer E1

Example 77 (85 mg, 173 μmol, 99% purity) was dissolved in 2.5 mL in DCM/MeOH mixture with sonication, filtered and was then separated by chiral SFC (Waters prep 100 with UV detection across all wavelengths with PDA as well as a QDA, 40° C., 120 bar on a ChiralPak IH 250×21 mm, 5 μM column, flow rate 65 mL/min, eluting with 25% MeOH/$CO_2$). The clean fractions were pooled, rinsed with methanol/DCM and concentrated in vacuo to afford the title compound (55 mg, 90 μmol, 52% yield, 80% purity) as a sticky white solid containing 20% w/w DMSO. SFC (Waters UPC$^2$, ChiralPak IH 4.6×250 mm, 5 μm column, flow rate 4 mL/min, eluting with 25% (0.1% ammonia in MeOH)/$CO_2$) $t_R$ 2.02 min. Other analytical data consistent with Example 77.

Example 92: 3-(N-(4-chloro-5-cyano-2-(spiro[3.3]heptan-1-yloxy)phenyl)sulfamoyl)-4-cyclopropylbenzoic acid Enantiomer E2

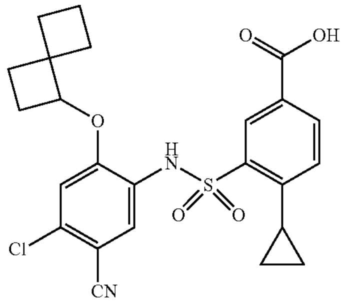

Enantiomer E2

The title compound (37 mg, 75 μmol, 43% yield, 99% purity) was obtained as a white solid from the chiral separation performed in Example 91. SFC (Waters UPC$^2$, ChiralPak IH 4.6×250 mm, 5 μm column, flow rate 4 mL/min, eluting with 25% (0.1% ammonia in MeOH)/$CO_2$) $t_R$ 2.40 min. Other analytical data consistent with Example 77.

Example 93: 3-(N-(4-chloro-5-cyano-2-(2,2-dimethylcyclobutoxy)phenyl)-sulfamoyl)-4-cyclopropylbenzoic acid Enantiomer E1

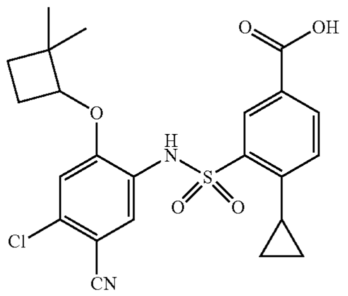

Enantiomer E1

Example 80 (108 mg, 225 μmol, 99% purity) was dissolved in 3.5 mL in DCM/MeOH mixture with sonication, filtered and was then separated by chiral SFC (Waters prep 100 with UV detection across all wavelengths with PDA as well as a QDA, 40° C., 120 bar on a ChiralPak IH 250×21 mm, 5 μM column, flow rate 65 mL/min, eluting with 20% MeOH/$CO_2$). The clean fractions were pooled, rinsed with methanol/DCM and concentrated in vacuo to afford the title compound (47 mg, 99 μmol, 44% yield, 99% purity) as a white solid. SFC (Waters UPC$^2$, ChiralPak IH 4.6×250 mm, 5 μm column, flow rate 4 mL/min, eluting with 20% (0.1% ammonia in MeOH)/$CO_2$) $t_R$ 2.42 min. Other analytical data consistent with Example 80.

Example 94: 3-(N-(4-chloro-5-cyano-2-(2,2-dimethylcyclobutoxy)phenyl)-sulfamoyl)-4-cyclopropylbenzoic acid Enantiomer E2

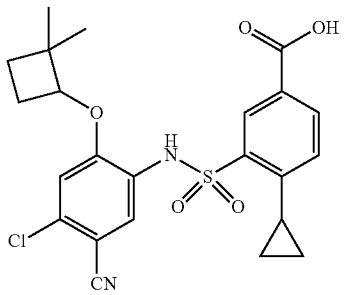

Enantiomer E2

The title compound (47 mg, 99 μmol, 44% yield, 99% purity) was obtained as a white solid from the chiral separation performed in Example 93. SFC (Waters UPC$^2$, ChiralPak IH 4.6×250 mm, 5 μm column, flow rate 4 mL/min, eluting with 20% (0.1% ammonia in MeOH)/$CO_2$) $t_R$ 2.80 min. Other analytical data consistent with Example 80.

Example 99: 3-(N-(4-chloro-5-cyano-2-((trans-2-methylcyclopentyl)oxy)-phenyl)sulfamoyl)-4-cyclopropylbenzoic acid Diastereomer D1

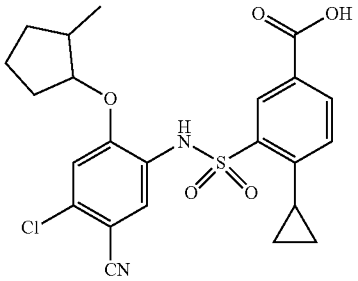

Trans diastereomer D1

Example 90 (477 mg, 934 μmol, 93% purity) was dissolved in DMSO (2.8 mL), filtered and purified by reverse phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters X-Select CSH C18 ODB prep column, 130Å, 5 μm, 30 mm×100 mm, flow rate 40 mL/min, eluting with a 0.1% Formic acid in water-MeCN gradient over 12.5 min using UV across all wavelengths with PDA as well as a QDA and ELS detector. At-column dilution pump gives 2 mL/min MeOH over the entire method, which is included in the following MeCN percentages. Gradient information: 0.0-0.5 min, 50% MeCN; 0.5-10.5 min, ramped from 50% MeCN to 80% MeCN; 10.5-10.6 min, ramped from 80% MeCN to 100% MeCN; 10.6-12.5 min, held at 100% MeCN. The clean fractions were concentrated in vacuo in a Genevac. The residue was dissolved in MeOH (30 mg/mL) with sonication, filtered and was then separated by chiral SFC (Waters prep 100 with a PDA and a QDA detectors, 40° C., 120 bar, Chiralpak IH 5 μM, 21 mm×250 mm column; flow rate 65 mL/min, 18% MeOH (0.1% TFA), 82% $CO_2$). The clean fractions were pooled, rinsed with MeOH and concentrated to dryness using a rocket evaporator. The residues were re-dissolved in methanol transferred into final vials and concentrated in vacuo on a Biotage V10 and dried in vacuo to afford the title compound (117 mg, 246 μmol, 26% yield, 99% purity) as a white solid. SFC (Waters UPC$^2$, ChiralPak IH 4.6×250 mm, 5 μm column, flow rate 4 mL/min, eluting with 25% (0.1% ammonia in EtOH)/$CO_2$) $t_R$ 2.66 min. Other analytical data consistent with Example 90.

Example 100: 3-(N-(4-chloro-5-cyano-2-((trans-2-methylcyclopentyl)oxy)-phenyl)sulfamoyl)-4-cyclopropylbenzoic acid Diastereomer D2

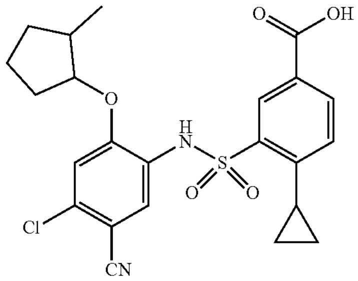

Trans diastereomer D2

The title compound (137 mg, 288 μmol, 30% yield, 99% purity) was obtained as a white solid from the chiral separation performed in Example 93. SFC (Waters UPC$^2$, ChiralPak IH 4.6×250 mm, 5 μm column, flow rate 4 mL/min, eluting with 25% (0.1% ammonia in EtOH)/$CO_2$) $t_R$ 2.90 min. Other analytical data consistent with Example 90.

Example 101: 3-(N-(4-chloro-5-cyano-2-(2,2,4,4-tetramethylcyclo-butoxy)phenyl)sulfamoyl)-4-cyclopropylbenzoic acid The title compound was prepared by methods analogous to Example 70, substituting appropriate starting materials and intermediates where necessary. UPLC (Method 4): m/z 501.2 $(M-H)^-$ at 2.03 min. $^1H$ NMR (500 MHz, DMSO) δ 13.20 (s, 1H), 9.94 (s, 1H), 8.37 (d, J=1.9 Hz, 1H), 7.98 (dd, J=8.2, 1.9 Hz, 1H), 7.63 (s, 1H), 7.08 (d, J=8.3 Hz, 1H), 7.02 (s, 1H), 4.29 (s, 1H), 1.42 (d, J=11.5 Hz, 1H), 1.35 (d, J=11.4 Hz, 1H), 1.11 (s, 6H), 0.95-0.85 (m, 2H), 0.81-0.75 (m, 8H) (1 proton obscured by DMSO signal)

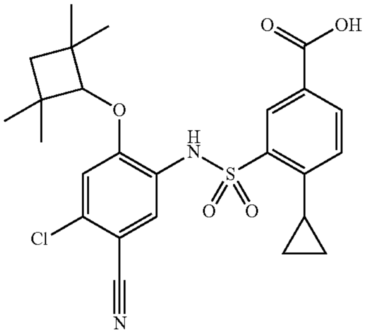 [SMILES: CC1(C)CC(C)(C)C1Oc1cc(Cl)c(C#N)cc1NS(=O)(=O)c1cc(C(=O)O)ccc1C1CC1]

Example 103: 3-(N-(4-chloro-5-cyano-2-((trans-2-methoxycyclopentyl)-oxy)phenyl)sulfamoyl)-4-cyclopropylbenzoic acid Diastereomer D1

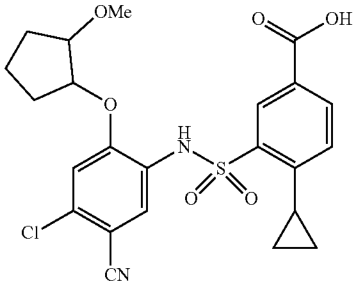

Trans diastereomer D1

Step 1: methyl 3-(N-(4-chloro-5-cyano-2-((trans-2-methoxycyclopentyl)-oxy)phenyl)sulfamoyl)-4-cyclopropylbenzoate Diastereomer D1: AcCl (100 μL, 1.41 mmol) was added dropwise to anhydrous MeOH (3.0 mL) and the resultant solution allowed to stand at RT for 10 min to form a dry solution of HCl/MeOH. Example 85 (71.5 mg, 146 μmol) was suspended in the HCl/MeOH solution, and the resultant mixture stirred at RT for 4 days. The mixture was concentrated in vacuo and the residue dissolved in MeOH (6.7 mg/mL), sonicated, filtered and was then separated by chiral SFC (Waters prep 15 with UV detection by DAD at 210-400 nm, 40° C., 120 bar, C4, 10×250 mm, 5 μm column, flow rate 15 mL/min, 30% MeOH/$CO_2$). The clean fractions were pooled and concentrated in vacuo to afford the title compound (24.3 mg, 48.1 μmol, 33% yield) as an off-white solid. UPLC-MS (Method 4): m/z 503.2 $(M-H)^-$ at 1.73 min. SFC (Waters $UPC^2$, C4, 4.6×250 mm, 5 μm column, flow rate 4 mL/min, 30% (0.1% ammonia in MeOH)/$CO_2$) $t_R$ 2.45 min.

Step 2: 3-(N-(4-chloro-5-cyano-2-((trans-2-methoxycyclopentyl)oxy)phenyl)sulfamoyl)-4-cyclopropylbenzoic acid Diastereomer D1: The product from Step 1 above (24.3 mg, 48.1 μmol) was combined with 1 M LiOH(aq) (238 μL, 238 μmol) in THF (1 mL) and the resultant solution was stirred at RT for 20 h. The mixture was diluted with water (1 mL) and concentrated in vacuo to remove THF. The resultant aqueous solution was acidified with 1 M HCl (0.3 mL) and the resultant white precipitate collected by filtration, washing with water. The solid was dissolved in MeCN and concentrated in vacuo to afford the title compound (22 mg, 44 μmol, 91% yield, 98% Purity) as a white powder. UPLC-MS (Method 4): m/z 490.9 $(M+H)^+$, 489.2 $(M-H)^-$, at 1.70 min. $^1H$ NMR (500 MHz, DMSO) δ 13.26 (s, 1H), 10.15 (s, 1H), 8.32 (d, J=1.9 Hz, 1H), 7.99 (dd, J=8.2, 1.9 Hz, 1H), 7.69 (s, 1H), 7.35 (s, 1H), 7.13 (d, J=8.3 Hz, 1H), 4.65 (dt, J=6.5, 3.3 Hz, 1H), 3.43 (dd, J=6.9, 4.4 Hz, 1H), 3.13 (s, 3H), 2.73-2.60 (m, 1H), 1.96-1.86 (m, 1H), 1.76-1.66 (m, 1H), 1.56-1.37 (m, 3H), 1.27-1.16 (m, 1H), 1.03-0.95 (m, 2H), 0.84-0.78 (m, 2H).

Example 104: 3-(N-(4-chloro-5-cyano-2-((trans-2-methoxycyclopentyl)-oxy)phenyl)sulfamoyl)-4-cyclopropylbenzoic acid Diastereomer D2

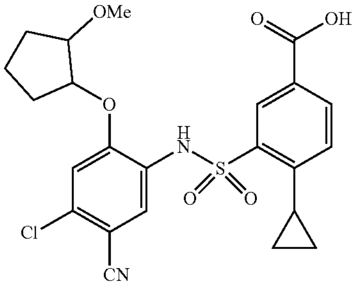

Trans diastereomer D2

Step 1: methyl 3-(N-(4-chloro-5-cyano-2-((trans-2-methoxycyclopentyl)-oxy)phenyl)sulfamoyl)-4-cyclopropylbenzoate Diastereomer D2: The title compound (24.6 mg, 48.7 μmol, 34% yield) was obtained as an off-white solid from the chiral separation performed in Example 103. SFC (Waters $UPC^2$, C4, 4.6×250 mm, 5 μm column, flow rate 4 mL/min, 30% (0.1% ammonia in MeOH)/$CO_2$) $t_R$ 2.78 min. Other analytical data consistent with Example 103 Step 1.

Step 2: 3-(N-(4-chloro-5-cyano-2-((trans-2-methoxycyclopentyl)oxy)phenyl)sulfamoyl)-4-cyclopropylbenzoic acid Diastereomer D2: The title compound (22 mg, 43 μmol, 87% yield) was obtained as a white powder using a method analogous to Example 103 Step 2. Analytical data consistent with Example 103 Step 2.

Example 105: 3-(N-(4-chloro-5-cyano-2-((cis-2-methylcyclopentyl)oxy)-phenyl)sulfamoyl)-4-cyclopropylbenzoic acid

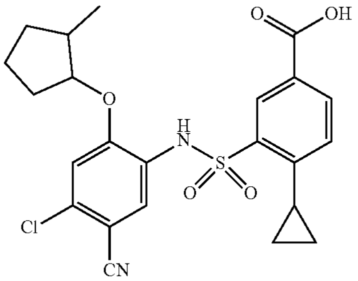

Cis racemate

The title compound was prepared by methods analogous to Example 70, substituting appropriate starting materials and intermediates where necessary. UPLC-MS (Method 4): m/z 473.2 $(M-H)^-$ at 1.87 min. $^1H$ NMR (500 MHz, DMSO-$d_6$) δ 13.19 (br s, 1H), 9.99 (br s, 1H), 8.35 (d, J=1.8 Hz, 1H), 7.96 (d, J=8.2 Hz, 1H), 7.58 (s, 1H), 7.41-7.25 (m, 1H), 7.09 (d, J=8.3 Hz, 1H), 4.82-4.69 (m, 1H), 2.05-1.91 (m, 1H), 1.91-1.82 (m, 1H), 1.64-1.56 (m, 1H), 1.56-1.47 (m, 1H), 1.46-1.20 (m, 4H), 1.00-0.90 (m, 2H), 0.84-0.75 (m, 2H), 0.69 (d, J=6.8 Hz, 3H).

Example 106: 3-(N-(4-chloro-5-cyano-2-(spiro[2.3]hexan-4-yloxy)phenyl)-sulfamoyl)-4-cyclopropylbenzoic acid. 1.50 diethylamine salt Enantiomer E1

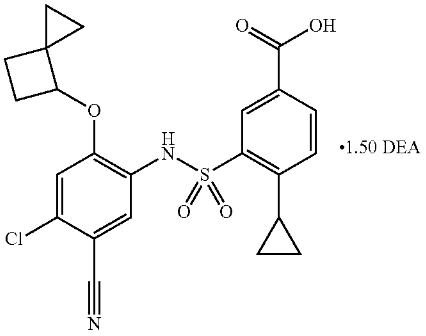

Enantiomer E1

Example 56 (22 mg, 46.5 μmol) was dissolved to 50 mg/mL in DCM/MeOH, sonicated, filtered and was then separated by chiral SFC (Waters prep 100 with a PDA and a QDA detectors, 40° C., 120 bar, Chiralpak IH, 21×250 mm, 5 μm column, flow rate 65 mL/min, (25% (0.1% diethylamine/MeOH)/$CO_2$). The clean fractions were pooled, rinsed with MeOH, and concentrated in vacuo to afford the title compound (5.3 mg, 8.9 μmol, 19% yield, 98% purity) as a clear colourless glass. UPLC-MS (Method 4): m/z 473.0 $(M+H)^+$, 471.2 $(M-H)^-$, at 1.82 min. $^1H$ NMR (500 MHz, DMSO) δ 8.38 (d, J=1.8 Hz, 1H), 7.75 (dd, J=8.1, 1.9 Hz, 1H), 7.32 (s, 1H), 6.76 (d, J=8.1 Hz, 1H), 6.63 (s, 1H), 4.82 (t, J=6.5 Hz, 1H), 3.30-3.23 (m, 1H), 2.85 (q, J=7.2 Hz, 6H), 2.47 (td, J=5.7, 3.1 Hz, 1H), 2.06-1.91 (m, 2H), 1.91-1.80 (m, 1H), 1.14 (t, J=7.2 Hz, 9H), 1.02-0.81 (m, 3H), 0.72-0.60 (m, 2H), 0.60-0.43 (m, 2H), 0.42-0.30 (m, 1H). SFC (Waters $UPC^2$, ChiralPak IH 4.6×250 mm, 5 μm column, flow rate 4 mL/min, 25% (0.1% ammonia·MeOH)/$CO_2$) $t_R$ 2.12 min.

Example 107: 3-(N-(4-chloro-5-cyano-2-(spiro[2.3]hexan-4-yloxy)phenyl)-sulfamoyl)-4-cyclopropylbenzoic acid, 1.65 diethylamine salt Enantiomer E2

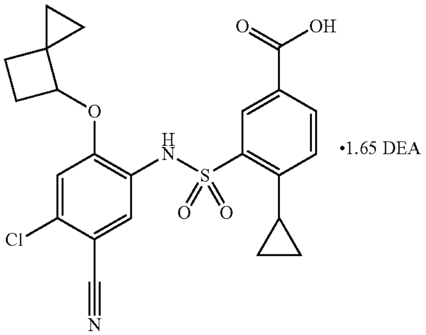

Enantiomer E2

The title compound (8.4 mg, 14 μmol, 30% yield, 98% purity) was obtained as a clear colourless glass from the chiral separation performed in Example 106. SFC (Waters $UPC^2$, ChiralPak IH 4.6×250 mm, 5 μm column, flow rate 4 mL/min, 25% (0.1% ammonia·MeOH)/$CO_2$) $t_R$ 2.48 min. Other analytical data consistent with Example 106.

Example 108: 3-(N-(4-chloro-5-cyano-2-(2-cyclopropylcyclobutoxy)-phenyl)sulfamoyl)-4-cyclopropylbenzoic acid

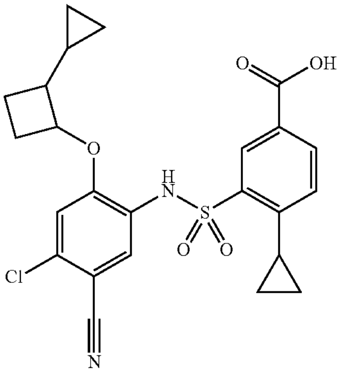

(racemic cis/trans)

The title compound was prepared by methods analogous to Example 70, substituting appropriate starting materials and intermediates where necessary. UPLC-MS (Method 4): m/z 485.2 $(M-H)^-$ at 1.88 min. $^1H$ NMR (500 MHz, DMSO-$d_6$) (10:1 mixture of diastereomers) δ 13.23 (br s, 1H), 10.18 (br s, 1H), 8.28 (d, J=1.9 Hz, 1H minor), 8.27 (d, J=1.8 Hz, 1H major), 7.99 (dd, J=8.2, 1.9 Hz, 1H major), 7.96 (dd, J=8.1, 1.8 Hz, 1H minor), 7.72 (s, 1H), 7.22 (s, 1H), 7.15 (d, J=8.4 Hz, 1H major), 7.14 (d, J=8.4 Hz, 1H minor), 4.77 (q, J=7.0 Hz, 1H minor), 4.49 (q, J=7.2 Hz, 1H major), 2.84-2.79 (m, 1H minor), 2.79-2.69 (m, 1H major), 2.20-2.12 (m, 1H minor), 2.12-2.03 (m, 1H major), 1.80-1.70 (m, 1H minor), 1.67-1.57 (m, 1H, major), 1.54-1.44 (m, 1H minor), 1.44-1.34 (m, 1H major), 1.30-0.91 (m, 4H), 0.91-0.71 (m, 2H), 0.39-0.30 (m, 1H major), 0.30-0.22 (m, 1H major), 0.15-0.04 (m, 1H minor), 0.00--0.08 (m, 1H major), −0.11--0.21 (m, 1H), −0.31--0.42 (m, 1H minor), −0.50--0.61 (m, 1H minor).

Example 114: 3-(N-(4-chloro-5-cyano-2-(3-methylcyclobutoxy)phenyl)sulfamoyl)-4-cyclopropylbenzoic acid Diastereomer D1

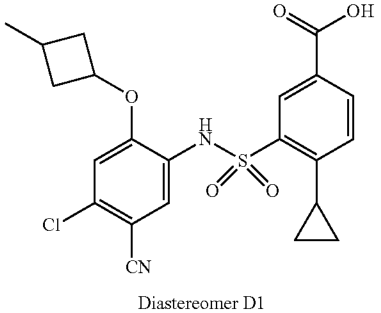 [SMILES: CC1CC(Oc2cc(Cl)c(C#N)cc2NS(=O)(=O)c2cc(C(=O)O)ccc2C2CC2)C1]

Diastereomer D1

Step 1: Methyl 3-(N-(4-chloro-5-cyano-2-(3-methylcyclobutoxy)phenyl)sulfamoyl)-4-cyclopropylbenzoate Diastereomer D1: Methyl 3-(N-(4-chloro-5-cyano-2-(3- methylcyclobutoxy)phenyl)sulfamoyl)-4-cyclopropylbenzoate (Example 88, 219 mg, 461 μmol) was dissolved in 5:1 EtOH:DCM (17.6 mg/mL) and was then purified by SFC (Lux iC5, 21.2×250 mm, 5 um column, 40° C., 125 bar, flow rate 50 mL/min, 20% EtOH/$CO_2$) to afford the title compound (147 mg, 309 μmol, 67% yield) as a colourless glass. UPLC-MS (Method 4): m/z 475.2 $(M+H)^+$, 473.2 $(M-H)^-$, at 1.98 min. SFC (Lux iC5, 4.6×250 mm, 5 μm column, 40° C., 125 bar, flow rate 4 mL/min, 20% (0.1% ammonia/EtOH)/$CO_2$) $t_R$ 10.1 min.

Step 2: 3-(N-(4-chloro-5-cyano-2-(3-methylcyclobutoxy)phenyl)sulfamoyl)-4-cyclopropylbenzoic acid Diastereomer D1: The product from Step 1 above (147 mg, 309 μmol) was dissolved in THF (5 mL) and treated with 1 M LiOH(aq) (1.55 mL, 1.55 mmol). The resultant mixture was stirred at RT for 24 h. The mixture was diluted with water (2 mL) and concentrated in vacuo to remove THF. The resultant solution was acidified using 1 M HCl(aq) and the white precipitate collected by filtration, washing with water, then dried in vacuo to afford the title compound (130 mg, 279 μmol, 90% yield, 99% purity) as a white solid. UPLC-MS (Method 4): m/z 461.3 $(M+H)^+$, 459.2 $(M-H)^-$, at 1.80 min. $^1H$ NMR (500 MHz, DMSO) δ 13.26 (br s, 1H), 10.16 (br s, 1H), 8.31 (d, J=1.8 Hz, 1H), 7.99 (dd, J=8.2, 1.9 Hz, 1H), 7.70 (s, 1H), 7.14 (d, J=8.2 Hz, 1H), 7.08 (s, 1H), 4.47 (p, J=7.3 Hz, 1H), 2.76-2.68 (m, 1H), 2.44-2.36 (m, 2H), 1.88-1.75 (m, 1H), 1.25-1.15 (m, 2H), 1.05-0.99 (m, 2H), 0.97 (d, J=6.6 Hz, 3H), 0.84-0.77 (m, 2H).

Example 115: 3-(N-(4-chloro-5-cyano-2-(3-methylcyclobutoxy)phenyl)sulfamoyl)-4-cyclopropylbenzoic acid Diastereomer D2

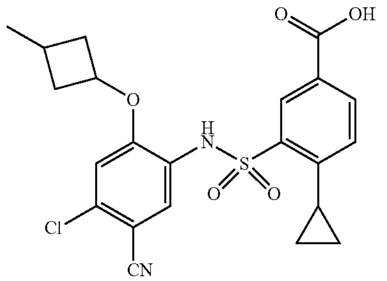

Diastereomer D2

Step 1: Methyl 3-(N-(4-chloro-5-cyano-2-(3-methylcyclobutoxy)phenyl)sulfamoyl)-4-cyclopropylbenzoate Diastereomer D2: The title compound (19 mg, 40.4 μmol, 9% yield) was obtained as a colourless glass from the separation performed in Example 114 Step 1. SFC (Lux iC5, 4.6×250 mm, 5 μm column, 40° C., 125 bar, flow rate 4 mL/min, 20% (0.1% ammonia/EtOH)/$CO_2$) $t_R$ 9.17 min. Other analytical data consistent with Example 114 Step 1.

Step 2: 3-(N-(4-chloro-5-cyano-2-(3-methylcyclobutoxy)phenyl)sulfamoyl)-4-cyclopropylbenzoic acid Diastereomer D2: The title compound (18.0 mg, 37.1 μmol, 92% yield, 95% purity) was prepared by a method analogous to Example 114 Step 2, substituting appropriate starting materials and intermediates where necessary. UPLC-MS (Method 4) m/z 461.6 $(M+H)^+$, 459.2 $(M-H)^-$, at 1.81 min. $^1H$ NMR (500 MHz, DMSO) δ 13.22 (s, 1H), 10.18 (s, 1H), 8.30 (d, J=1.9 Hz, 1H), 7.99 (dd, J=8.2, 1.9 Hz, 1H), 7.70 (s, 1H), 7.13 (d, J=8.3 Hz, 1H), 7.04 (s, 1H), 4.82 (p, J=6.5 Hz, 1H), 2.80-2.69 (m, 1H), 2.21-2.09 (m, 1H), 1.95-1.87 (m, 2H), 1.84-1.74 (m, 2H), 1.07 (d, J=7.1 Hz, 3H), 1.04-0.98 (m, 2H), 0.84-0.78 (m, 2H).

Example 120: 3-(N-(4-chloro-5-cyano-2-(2-methylcyclobutoxy)phenyl)sulfamoyl)-4-cyclopropylbenzoic acid Stereoisomer D1

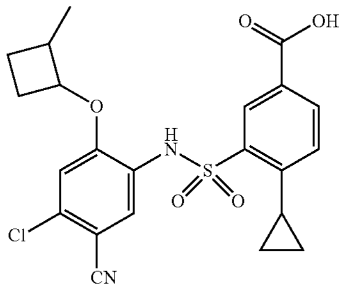

Diastereomer D1

Step 1: Methyl 3-(N-(4-chloro-5-cyano-2-(2-methylcyclobutoxy)phenyl)sulfamoyl)-4-cyclopropylbenzoate: The title compound (1.2 g, 2.53 mmol) was prepared by methods analogous to Example 70 Steps 1-3, substituting appropriate starting materials and intermediates where necessary.

Step 2: Methyl 3-(N-(4-chloro-5-cyano-2-(2-methylcyclobutoxy)phenyl)sulfamoyl)-4-cyclopropylbenzoate Stereoisomer D1: The product from Step 1 above (1.2 g, 2.53 mmol) was dissolved in a mixture of MeOH (11 mL) and THF (5 mL) and was then sonicated, filtered and separated by chiral SFC (Waters prep 100 with a PDA and a QDA detectors, 40° C., 120 bar, Chiralpak IH, 21×250 mm, 5 μm column, flow rate 65 mL/min, 25% MeOH/$CO_2$) to afford three fractions. The first eluting fraction was concentrated in vacuo to afford the title compound (379 mg, 0.774 mmol, 31% yield, 97% purity (3 wt % MeOH)) as a colourless glass. UPLC-MS (Method 4): m/z 475.3 $(M+H)^+$, 473.3 $(M-H)^-$, at 1.99 min. $^1H$ NMR (500 MHz, DMSO) δ 10.23 (s, 1H), 8.31 (d, J=1.9 Hz, 1H), 8.02 (dd, J=8.3, 1.9 Hz, 1H), 7.71 (s, 1H), 7.17 (d, J=8.3 Hz, 1H), 7.11 (s, 1H), 4.31 (q, J=7.1 Hz, 1H), 3.84 (s, 3H), 2.80-2.71 (m, 1H), 2.23-2.05 (m, 2H), 1.80-1.70 (m, 1H), 1.26-1.14 (m, 1H), 1.13-1.00 (m, 3H), 0.96 (d, J=6.7 Hz, 3H), 0.90-0.84 (m, 1H), 0.84-0.76 (m, 1H). SFC (Waters $UPC^2$, ChiralPak IH 4.6×250 mm, 5 μm column, flow rate 4 mL/min, 25% (0.1% ammonia/MeOH)/$CO_2$) $t_R$ 1.76 min.

Step 3: 3-(N-(4-chloro-5-cyano-2-(2-methylcyclobutoxy)phenyl)sulfamoyl)-4-cyclopropylbenzoic acid Stereoisomer D1: A solution of the product from Step 2 above (379 mg, 774 μmol, 97% purity) and $LiOH \cdot H_2O$ (134 mg, 3.19 mmol) in THF (4 mL), Water (1 mL) and MeOH (1 mL) was stirred at RT for 24 h. The resultant mixture was concentrated in vacuo and the resultant aqueous solution diluted with water (10 mL). The solution was acidified with 1M HCl(aq) and the resultant white precipitate collected by filtration, washing with water (5 mL). The solid was dried in vacuo to afford the title compound (275 mg, 591 μmol, 76% yield, 99% purity) as a white solid. UPLC-MS (Method 4): m/z 461.1 $(M+H)^+$, 459.2 $(M-H)^-$, at 1.82 min. $^1H$ NMR (500 MHz, DMSO) δ 13.24 (s, 1H), 10.19 (s, 1H), 8.31 (d, J=1.9 Hz, 1H), 7.99 (dd, J=8.2, 1.9 Hz, 1H), 7.69 (s, 1H), 7.14 (d, J=8.3 Hz, 1H), 7.09 (s, 1H), 4.32 (q, J=7.1 Hz, 1H), 2.80-2.72 (m, 1H), 2.24-2.07 (m, 2H), 1.76 (q, J=9.4 Hz, 1H), 1.28-1.19 (m, 1H), 1.14-1.01 (m, 3H), 0.97 (d, J=6.7 Hz, 3H), 0.89-0.82 (m, 1H), 0.81-0.75 (m, 1H)

Example 121: 3-(N-(4-chloro-5-cyano-2-(2-methylcyclobutoxy)phenyl)sulfamoyl)-4-cyclopropylbenzoic acid Stereoisomer D2

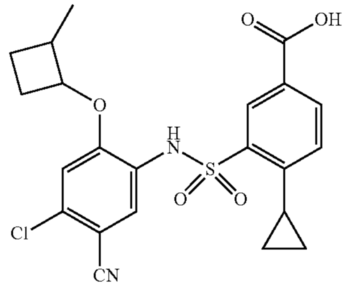

Diastereomer D2

Step 1: Methyl 3-(N-(4-chloro-5-cyano-2-(2-methylcyclobutoxy)phenyl)sulfamoyl)-4-cyclopropylbenzoate Stereoisomer D2: The second eluting fraction from Example 120 Step 2 was further purified by chiral SFC (Waters prep 100 with a PDA and a QDA detectors, 40° C., 120 bar, Lux C4, 21×250 mm, 5 μm column, flow rate 65 mL/min, 30% $MeOH/CO_2$) to obtain two fractions. The first eluting fraction was further purified by chiral SFC (Waters prep 100 with a PDA and a QDA detectors, 40° C., 120 bar, Chiralpak IH, 21×250 mm, 5 μm column, flow rate 65 mL/min, 25% $MeOH/CO_2$) to afford the title compound (275 mg, 0.538 mmol, 21% yield, 93% purity (7 wt % MeOH)) as a colourless glass. SFC (Waters $UPC^2$, ChiralPak IH 4.6×250 mm, 5 μm column, flow rate 4 mL/min, 25% (0.1% ammonia/MeOH)/$CO_2$) $t_R$ 1.96 min. Other analytical data consistent with Example 120 Step 2.

Step 2: 3-(N-(4-chloro-5-cyano-2-(2-methylcyclobutoxy)phenyl)sulfamoyl)-4-cyclopropylbenzoic acid Stereoisomer D2: The title compound (173 mg, 375 μmol, 70% yield) was prepared by a method analogous to Example 120 Step 3, substituting appropriate starting materials and intermediates where necessary. Analytical data consistent with Example 120.

Example 122: 3-(N-(4-chloro-5-cyano-2-(2-methylcyclobutoxy)phenyl)sulfamoyl)-4-cyclopropylbenzoic acid Stereoisomer D3

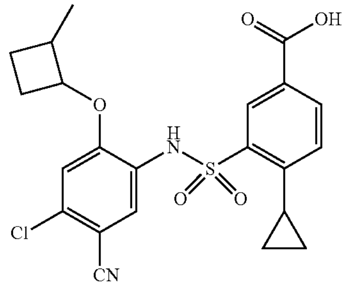

Diastereomer D3

Step 1: Methyl 3-(N-(4-chloro-5-cyano-2-(2-methylcyclobutoxy)phenyl)sulfamoyl)-4-cyclopropylbenzoate Stereoisomer D3: The second eluting fraction from Example 121 Step 1 was further purified by chiral SFC (Waters prep 100 with a PDA and a QDA detectors, 40° C., 120 bar, Lux C4, 21×250 mm, 5 μm column, flow rate 65 mL/min, 30% $MeOH/CO_2$) to afford the title compound (51 mg, 106 mmol, 4% yield, 99% purity) as a white solid. UPLC (Method 4): m/z 475.3 $(M+H)^+$, 473.3 $(M-H)^-$, at 1.97 min. $^1H$ NMR (500 MHz, DMSO) δ 10.20 (s, 1H), 8.33 (d, J=1.9 Hz, 1H), 8.00 (dd, J=8.2, 1.9 Hz, 1H), 7.68 (s, 1H), 7.14 (d, J=8.3 Hz, 1H), 7.07 (s, 1H), 4.65 (q, J=7.3 Hz, 1H), 3.84 (s, 3H), 2.73-2.65 (m, 2H), 2.18-2.09 (m, 1H), 2.01 (p, J=10.0 Hz, 1H), 1.74 (p, J=8.9 Hz, 1H), 1.27-1.23 (m, 1H), 1.08-0.95 (m, 2H), 0.90-0.78 (m, 2H), 0.64 (d, J=7.2 Hz, 3H). SFC (Waters $UPC^2$, ChiralPak IH 4.6×250 mm, 5 μm column, flow rate 4 mL/min, 25% (0.1% ammonia/MeOH)/$CO_2$) $t_R$ 2.00 min.

Step 2: 3-(N-(4-chloro-5-cyano-2-(2-methylcyclobutoxy)phenyl)sulfamoyl)-4-cyclopropylbenzoic acid Stereoisomer D3: The title compound (12 mg, 26 μmol, 24% yield, 97% purity) was prepared by a method analogous to Example 120 Step 3, substituting appropriate starting materials and intermediates where necessary. UPLC-MS (Method 4): m/z 461.4 $(M+H)^+$, 459.2 $(M-H)^-$, at 1.81 min. $^1H$ NMR (500 MHz, DMSO) δ 13.22 (s, 1H), 10.17 (s, 1H), 8.33 (d, J=1.9 Hz, 1H), 7.98 (dd, J=8.2, 1.9 Hz, 1H), 7.68 (s, 1H), 7.12 (d, J=8.3 Hz, 1H), 7.08 (s, 1H), 4.66 (q, J=7.2 Hz, 1H), 2.74-2.65 (m, 2H), 2.18-2.10 (m, 1H), 2.06-1.97 (m, 1H), 1.79-1.69 (m, 1H), 1.30-1.22 (m, 1H), 1.09-0.94 (m, 2H), 0.89-0.77 (m, 2H), 0.65 (d, J=7.2 Hz, 3H).

Example 123: 3-(N-(4-chloro-5-cyano-2-(2-methylcyclobutoxy)phenyl)sulfamoyl)-4-cyclopropylbenzoic acid Stereoisomer D4

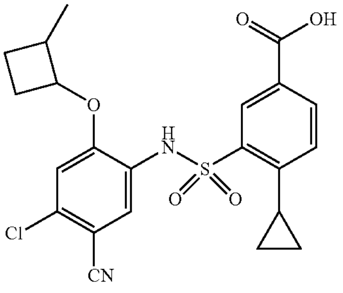

Diastereomer D4

Step 1: Methyl 3-(N-(4-chloro-5-cyano-2-(2-methylcyclobutoxy)phenyl)sulfamoyl)-4-cyclopropylbenzoate Stereoisomer D4: The third eluting fraction from Example 120 Step 2 was further purified by chiral SFC (Waters prep 100 with a PDA and a QDA detectors, 40° C., 120 bar, Chiralpak IH, 21×250 mm, 5 μm column, flow rate 65 mL/min, 25% $MeOH/CO_2$) to afford the title compound (85 mg, 177 mmol, 7% yield, 99% purity) as a white solid. SFC (Waters $UPC^2$, ChiralPak IH 4.6×250 mm, 5 μm column, flow rate 4 mL/min, 25% (0.1% ammonia/MeOH)/$CO_2$) $t_R$ 2.27 min. Other analytical data consistent with Example 122 Step 1.

Step 2: 3-(N-(4-chloro-5-cyano-2-(2-methylcyclobutoxy)phenyl)sulfamoyl)-4-cyclopropylbenzoic acid Stereoisomer D4: The title compound (67 mg, 135 μmol, 76% yield, 93% purity (6 wt % MeCN)) was prepared by a method analogous to Example 120 Step 3, substituting appropriate starting materials and intermediates where necessary. Analytical data consistent with Example 122.

Example 125: (R)-4-cyclopropyl-3-(N-(2-((2,2-dimethylcyclopentyl)oxy)-4-fluoro-5-(1H-tetrazol-1-yl)phenyl)sulfamoyl)benzoic acid

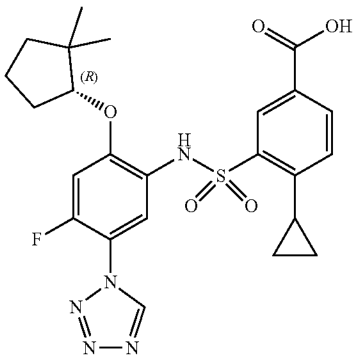

Step 1: tert-butyl (tert-butoxycarbonyl)(2,4-difluoro-5-nitrophenyl)carbamate: DMAP (0.18 g, 1.4 mmol) was added into a stirring solution of 2,4-difluoro-5-nitroaniline (2.5 g, 14 mmol) and di-tert-butyl dicarbonate (7.8 g, 36 mmol) in DCM (25 mL) and the resultant mixture was stirred at RT for 18 h. The reaction mixture was concentrated onto Celite® and purified by chromatography on silica gel (80 g cartridge, 0-50% EtOAc/isohexane) to afford the title compound (2.62 g, 6.6 mmol, 46% yield, 94% purity) as a clear colourless oil. $^1$H NMR (500 MHz, $CDCl_3$) δ 8.05 (t, J=7.6 Hz, 1H), 7.10 (dd, J=10.2, 8.9 Hz, 1H), 1.45 (s, 18H).

Step 2: tert-butyl (R)-(tert-butoxycarbonyl)(4-((2,2-dimethylcyclopentyl)oxy)-2-fluoro-5-nitrophenyl)carbamate: A mixture of the product from Step 1 above (1.39 g, 3.50 mmol, 94% purity) and (R)-2,2-dimethylcyclopentan-1-ol (400 mg, 3.50 mmol) in DMF (8 mL) was treated portionwise with $Cs_2CO_3$ (1.71 g, 5.25 mmol). The resultant mixture was stirred at RT for 4 days. Additional (R)-2,2-dimethylcyclopentan-1-ol (350 mg, 3.07 mmol) was added and stirring continued for a further 3 days. The mixture was partitioned between TBME (40 mL) and water (40 mL) and the phases separated. The organic phase was sequentially washed with water (40 mL), saturated $NaHCO_3$(aq) (40 mL) and brine (2×40 mL), then dried over $MgSO_4$, filtered, and concentrated in vacuo to afford a pale-yellow oil (1.51 g). The crude product was purified by chromatography on silica gel (24 g cartridge, 25-75% DCM/heptane) to afford the title compound (1.14 g, 1.92 mmol, 55% yield, 79% purity) as a pale-yellow oil. UPLC-MS (Method 4) m/z 491.4 $(M+Na)^+$ at 2.31 min. $^1$H NMR (500 MHz, $CDCl_3$) δ 7.85 (d, J=8.0 Hz, 1H), 6.77 (d, J=11.3 Hz, 1H), 4.24-4.19 (m, 1H), 2.26-2.13 (m, 1H), 1.90-1.66 (m, 3H), 1.45 (s, 18H), 1.54-1.41 (m, 2H), 1.16 (s, 3H), 1.03 (s, 3H).

Step 3: (R)-1-(4-((2,2-dimethylcyclopentyl)oxy)-2-fluoro-5-nitrophenyl)tetrazole: The product from Step 2 above (1.14 g, 1.92 mmol, 79% purity) was dissolved in DCM (12 mL) and treated with TFA (2 mL, 26.0 mmol). The resultant mixture was stirred at RT for 18 h, then concentrated in vacuo, azeotroping with DCM (30 mL) to afford a pale orange solid (891 mg). The solid was dissolved in triethyl orthoformate (22.0 mL, 132 mmol) and treated with AcOH (1 mL, 17.5 mmol). The resultant mixture was heated at 80° C. for 1 h, then trimethylsilyl azide (600 μL, 4.52 mmol) was added dropwise. Heating was continued for 2 h. Sodium acetate (300 mg, 3.66 mmol) was added, and heating was continued for 10 min. The mixture was concentrated in vacuo and the residue partitioned between TBME (25 mL) and saturated $NaHCO_3$(aq) (15 mL). The phases were separated, and the organic phase sequentially washed with saturated $NaHCO_3$(aq) (15 mL) and brine (15 mL), then dried over $MgSO_4$, filtered and concentrated in vacuo to afford a pale-yellow oil (750 mg). The oil was dissolved in AcOH (12 mL, 210 mmol) and treated with trimethyl orthoformate (1.53 mL, 14.0 mmol). Sodium azide (300 mg, 4.61 mmol) was added, and the resultant mixture heated at 80° C. for 2 h. The mixture was concentrated in vacuo and the residue partitioned between TBME (25 mL) and saturated $NaHCO_3$(aq) (15 mL). The phases were separated, and the organic phase sequentially washed with saturated $NaHCO_3$(aq) (15 mL) and brine (15 mL), then dried over $MgSO_4$, filtered and concentrated in vacuo to afford the title compound (662 mg, 1.67 mmol, 87% yield, 81% purity) as a pale-yellow oil. UPLC-MS (Method 4): m/z 322.0 $(M+H)^+$, 318.6 $(M+OH—HF)^-$, at 1.77 min. $^1$H NMR (500 MHz, $CDCl_3$) δ 9.03 (d, J=2.4 Hz, 1H), 8.50 (d, J=7.7 Hz, 1H), 7.03 (d, J=12.3 Hz, 1H), 4.32 (dd, J=6.0, 2.8 Hz, 1H), 2.32-2.21 (m, 1H), 1.91-1.73 (m, 3H), 1.57-1.47 (m, 1H), 1.19 (s, 3H), 1.17 (s, 3H).

Step 4: (R)-2-((2,2-dimethylcyclopentyl)oxy)-4-fluoro-5-(tetrazol-1-yl)aniline: The product from Step 3 above (662 mg, 1.67 mmol, 81% purity) was combined with $NH_4Cl$ (893 mg, 16.7 mmol) in THF (6 mL) and Water (2 mL). The resultant rapidly stirred suspension was cooled in an ice bath and treated portionwise with zinc (1.09 g, 16.7 mmol). The resultant mixture was allowed to warm to RT and stir for 4 h. The mixture was diluted with EtOAc (20 mL), and the phases separated. The aqueous phase was extracted with EtOAc (2×20 mL), and the extracts were filtered through Celite®, combined and concentrated in vacuo to afford a dark brown oil (574 mg). The oil was partitioned between DCM (8 mL) and water (4 mL), and the phases separated. The aqueous phase was extracted with DCM (2×2 mL) and the organic phases were combined, concentrated in vacuo and the residue purified by chromatography on silica gel (12 g cartridge, 0-10% EtOAc/DCM) to afford the title compound (416 mg, 1.36 mmol, 81% yield, 95% purity) as an off-white solid. UPLC-MS (Method 4): m/z 292.3 $(M+H)^+$ at 1.64 min. $^1$H NMR (500 MHz, $CDCl_3$) δ 8.98 (d, J=2.3 Hz, 1H), 7.37 (d, J=7.3 Hz, 1H), 6.76 (d, J=12.3 Hz, 1H), 5.66 (br s, 2H), 4.21 (dd, J=6.1, 3.4 Hz, 1H), 2.28-2.17 (m, 1H), 1.90-1.68 (m, 4H), 1.55-1.46 (m, 1H), 1.15 (s, 3H), 1.06 (s, 3H).

Step 5: Methyl (R)-4-cyclopropyl-3-(N-(2-((2,2-dimethylcyclopentyl)oxy)-4-fluoro-5-(tetrazol-1-yl)phenyl)sulfamoyl)benzoate: The product from Step 4 above (206 mg, 672 μmol, 95% purity) was combined with methyl 3-(chlorosulfonyl)-4-cyclopropylbenzoate (233 mg, 848 μmol) in DCM (4 mL) and treated with pyridine (172 μL, 2.13 mmol). The resultant solution was allowed to stand at RT for 18 h. The solution was sequentially washed with 1 M HCl(aq) (2×5 mL) and water (5 mL), dried ($MgSO_4$) and directly purified by chromatography on silica gel (12 g cartridge, 0-100% EtOAc/isohexane) to afford the title compound (340 mg, 623 μmol, 93% yield, 97% purity) as a pale pink solid. UPLC-MS (Method 4): m/z 530.4 $(M+H)^+$, 528.3 $(M-H)^-$, at 1.90 min. $^1$H NMR (500 MHz, DMSO) δ 9.88 (s, 1H), 9.83 (d, J=1.4 Hz, 1H), 8.39 (d, J=1.9 Hz, 1H), 7.99 (dd, J=8.3, 1.9 Hz, 1H), 7.58 (d, J=8.0 Hz, 1H), 7.34 (d, J=12.7 Hz, 1H), 7.11 (d, J=8.3 Hz, 1H), 4.31 (dd, J=6.3, 4.2 Hz, 1H), 3.84 (s, 3H), 2.67-2.58 (m, 1H), 2.07 (dq, J=13.8, 6.6 Hz, 1H), 1.57-1.45 (m, 3H), 1.31-1.14 (m, 2H), 1.01-0.91 (m, 2H), 0.89 (s, 3H), 0.84-0.77 (m, 2H), 0.76 (s, 3H).

Step 6: (R)-4-cyclopropyl-3-(N-(2-((2,2-dimethylcyclopentyl)oxy)-4-fluoro-5-(tetrazol-1-yl)phenyl)sulfamoyl) benzoic acid: The product from Step 5 above (337 mg, 617 μmol, 97% purity) was dissolved in THF (6 mL) and treated with 1 M LiOH(aq) (3.09 mL, 3.09 mmol). The resultant mixture was stirred at RT for 3 days. The mixture was diluted with water (2 mL) to afford a clear solution, which was concentrated in vacuo to remove THF. The resultant solution was acidified using 1 M HCl(aq) and the pale pink precipitate collected by filtration, washing with water, and dried in vacuo to afford the title compound (306 mg, 582 μmol, 94% yield, 98% purity) as an off-white powder. UPLC-MS (Method 4): m/z 516.1 $(M+H)^+$, 514.2 $(M-H)^-$, at 1.73 min. $^1H$ NMR (500 MHz, DMSO) δ 13.22 (br s, 1H), 9.90 (br s, 1H), 9.82 (d, J=1.4 Hz, 1H), 8.38 (d, J=1.9 Hz, 1H), 7.96 (dd, J=8.2, 1.9 Hz, 1H), 7.58 (d, J=8.1 Hz, 1H), 7.32 (d, J=12.6 Hz, 1H), 7.07 (d, J=8.3 Hz, 1H), 4.31 (dd, J=6.4, 4.2 Hz, 1H), 2.64 (s, 1H), 2.12-2.02 (m, 1H), 1.57-1.45 (m, 3H), 1.33-1.15 (m, 2H), 0.99-0.86 (m, 2H), 0.89 (s, 3H), 0.82-0.74 (m, 2H), 0.78 (s, 3H).

Example 130: 3-(N-(4-chloro-5-cyano-2-(2-cyclopropylcyclobutoxy)phenyl) sulfamoyl)-4-cyclopropylbenzoic acid Stereoisomer D1

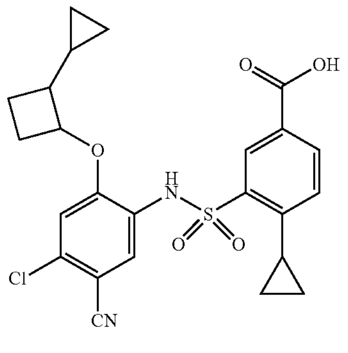

Diastereomer D1

Step 1: 3-(N-(4-chloro-5-cyano-2-(2-cyclopropylcyclobutoxy)phenyl)sulfamoyl)-4-cyclopropylbenzoic acid: The title compound (162 mg, 333 μmol) was prepared by methods analogous to Example 70, substituting appropriate starting materials and intermediates where necessary.

Step 2: Methyl 3-(N-(4-chloro-5-cyano-2-(2-cyclopropylcyclobutoxy)phenyl)sulfamoyl)-4-cyclopropylbenzoate Stereoisomer D1: Separation 1: The product from Step 1 above was dissolved in MeOH (25 mg/mL) with sonication, filtered and was then separated by chiral SFC (Waters prep 15 with UV detection by DAD at 210-400 nm, 40° C., 120 bar, Chiralpak IH 10×150 mm, 5 μm column, flow rate 15 mL/min, 20% (0.1% DEA/MeOH)/$CO_2$). The clean fractions were pooled, rinsed with MeOH and concentrated in vacuo to afford three fractions, each contaminated with DEA. Separation 2: The first eluting fraction was dissolved in MeOH (40 mg/mL) with sonication, filtered and was then separated by chiral SFC (Waters prep 100 with PDA and QDA detectors, 40° C., 120 bar, Chiralpak IH, 21 mm×250 mm, 5 μm column, flow rate 65 mL/min, 20% (0.1% TFA/MeOH)/$CO_2$). The clean fractions were pooled, rinsed with MeOH and concentrated in vacuo to afford two fractions, each of which had undergone esterification during solvent evaporation.

Step 3: 3-(N-(4-chloro-5-cyano-2-(2-cyclopropylcyclobutoxy)phenyl)sulfamoyl)-4-cyclopropylbenzoic acid stereoisomer D1: The first eluting fraction from Separation 2 in Step 2 above was subjected to a procedure analogous to Example 70 Step 4 to afford the title compound (47 mg, 96 μmol, 29% yield, 99% purity). UPLC-MS (Method 4): m/z 487.2 $(M+H)^+$, 485.2 $(M-H)^-$, at 1.89 min. $^1H$ NMR (500 MHz, DMSO) δ 13.24 (br s, 1H), 10.17 (br s, 1H), 8.26 (d, J=1.9 Hz, 1H), 7.99 (dd, J=8.2, 1.9 Hz, 1H), 7.72 (s, 1H), 7.22 (s, 1H), 7.15 (d, J=8.3 Hz, 1H), 4.49 (q, J=7.1 Hz, 1H), 2.80-2.71 (m, 1H), 2.09 (q, J=8.6 Hz, 1H), 1.62 (q, J=9.8 Hz, 1H), 1.44-1.34 (m, 1H), 1.27-1.19 (m, 1H), 1.17-1.09 (m, 1H), 1.09-1.00 (m, 2H), 0.88-0.79 (m, 2H), 0.79-0.71 (m, 1H), 0.39-0.30 (m, 1H), 0.30-0.23 (m, 1H), −0.00-−0.09 (m, 1H), −0.13-−0.21 (m, 1H). SFC (Waters UPC$^2$, ChiralPak IH 4.6×250 mm, 5 μm column, flow rate 4 mL/min, 20% (0.1% ammonia/MeOH)/$CO_2$) $t_R$ 3.17 min, 76% enantiomeric excess.

Example 131: 3-(N-(4-chloro-5-cyano-2-(2-cyclopropylcyclobutoxy)phenyl) sulfamoyl)-4-cyclopropylbenzoic acid Stereoisomer D2

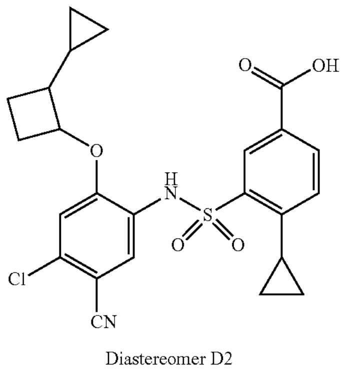 [SMILES: N#Cc1cc(NS(=O)(=O)c2cc(C(=O)O)ccc2C2CC2)c(OC2CCC2C2CC2)cc1Cl]

Diastereomer D2

The second eluting fraction from Separation 2 in Example 130 Step 2 was subjected to a procedure analogous to Example 120 Step 3 to afford the title compound (61 mg, 124 μmol, 37% yield, 99% purity). SFC (Waters UPC$^2$, ChiralPak IH 4.6×250 mm, 5 μm column, flow rate 4 mL/min, 20% (0.1% ammonia/MeOH)/$CO_2$) $t_R$ 3.41 min, 98% enantiomeric excess. Other analytical data consistent with Example 130.

Example 132 3-(N-(4-chloro-5-cyano-2-(2-cyclopropylcyclobutoxy)phenyl) sulfamoyl)-4-cyclopropylbenzoic acid Stereoisomer D3

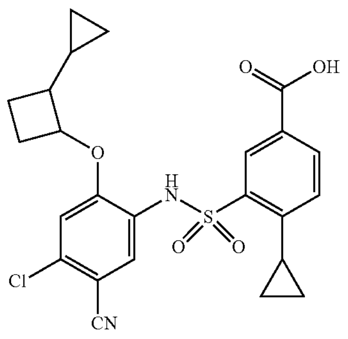

Diastereomer D3

The second eluting fraction from Separation 1 in Example 130 Step 2 was subjected to a procedure analogous to Example 120 Step 3 to afford the title compound (3.8 mg, 7.3 μmol, 2% yield, 94% purity). UPLC-MS (Method 4): m/z 485.2 $(M-H)^-$ at 1.88 min. $^1H$ NMR (500 MHz, DMSO) δ 13.22 (br s, 1H), 10.19 (br s, 1H), 8.28 (d, J=1.9 Hz, 1H), 7.96 (dd, J=8.2, 1.9 Hz, 1H), 7.72 (s, 1H), 7.14 (d, J=8.3 Hz, 1H), 7.10 (s, 1H), 4.77 (q, J=7.0 Hz, 1H), 2.86-2.77 (m, 1H), 2.21-2.09 (m, 2H), 1.97-1.88 (m, 1H), 1.80-1.68 (m, 1H), 1.54-1.42 (m, 1H), 1.16-1.09 (m, 1H), 1.09-1.01 (m, 1H), 0.99-0.92 (m, 1H), 0.83-0.75 (m, 1H), 0.37-0.21 (m, 1H), 0.15-0.01 (m, 1H), −0.13-−0.22 (m, 1H), −0.33-−0.43 (m, 1H), −0.51-−0.61 (m, 1H). SFC (Waters $UPC^2$, ChiralPak IH 4.6×250 mm, 5 μm column, flow rate 4 mL/min, 20% (0.1% ammonia/MeOH)/$CO_2$) $t_R$ 4.31 min, 98% enantiomeric excess.

Example 133: 3-(N-(4-chloro-5-cyano-2-(2-cyclopropylcyclobutoxy)phenyl) sulfamoyl)-4-cyclopropylbenzoic acid Stereoisomer D4

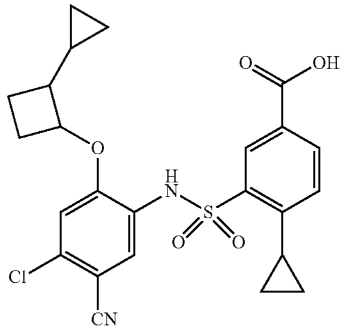

Diastereomer D4

The third eluting fraction from Separation 1 in Example 130 Step 2 was subjected to a procedure analogous to Example 120 Step 3 to afford the title compound (3.3 mg, 6.6 μmol, 1% yield, 98% purity). SFC (Waters $UPC^2$, ChiralPak IH 4.6×250 mm, 5 μm column, flow rate 4 mL/min, 20% (0.1% ammonia/MeOH)/$CO_2$) $t_R$ 5.05 min, 90% enantiomeric excess. Other analytical data consistent with Example 132. The following examples were prepared by methods analogous to Example 1 or Example 52, substituting appropriate starting materials and intermediates where necessary:

Also, the following chiral resolutions were performed and individual enantiomers or diastereomers progressed to final Examples by methods analogous to Example 1 or Example 52, substituting appropriate starting materials and intermediates where necessary:

Example 85 Intermediate→Example 103 and Example 104 (Alternative Route 2)

Example 85 intermediate racemic trans ester methyl 3-(N-(4-chloro-5-cyano-2-((2-methoxycyclopentyl)oxy)phenyl) sulfamoyl)-4-cyclopropylbenzoate (105 mg) was purified on Unichiral CND-5H column (4.6×250 mm), eluting with 90% n-hexane/10% ethanol/0.1% TFA (1 mL/min), 25° C., 254 nm UV detection. Appropriate fractions were pooled and reduced in vacuo to give Peak 1 (51 mg), RT 13.18 min (99.8%) and Peak 2 (45 mg), RT 15.48 min (99.9%). Peak 1 ester was progressed to give trans diastereomer D1 (Example 103) and Peak 2 ester was progressed to give trans diastereomer D2 (Example 104).

Example 84 Intermediate 4 Example 116 and Example 117

Example 84 intermediate racemic trans aniline 5-amino-2-chloro-4-((2-ethynylcyclopentyl)oxy)benzonitrile (150 mg) was purified on Unichiral CMD-5H column (4.6×250 mm), eluting with 90% n-hexane/10% ethanol (1 mL/min), 25° C., 254 nm UV detection. Appropriate fractions were pooled and reduced in vacuo to give Peak 1 (55 mg), RT 13.10 min (96.3%) and Peak 2 (46 mg), RT 23.69 min (98.7%). Peak 1 aniline was progressed to give trans diastereomer D1 (Example 116) and Peak 2 aniline was progressed to give trans diastereomer D2 (Example 117).

Example 126 and Example 127

Racemic cis acid 3-(N-(4-chloro-5-cyano-2-((2-ethynylcyclopentyl)oxy)phenyl)sulfamoyl)-4-cyclopropylbenzoic acid (131 mg) was purified on Unichiral CMD-5H column (4.6×250 mm), eluting with 60% n-hexane/40% isopropanol/0.1% TFA (1 mL/min), 25° C., 254 nm UV detection. Appropriate fractions were pooled and reduced in vacuo to give Peak 1 (Example 126, cis diastereomer D1, 31 mg), RT 6.99 min (100%) and Peak 2 (Example 127, cis diastereomer D2, 22 mg), RT 10.79 min (99.3%).

Example 118 to Give Example 128 and Example 129

Example 118 racemic trans acid 3-(N-(4-chloro-5-cyano-2-(2-hydroxycyclobutoxy)phenyl)sulfamoyl)-4-cyclopropylbenzoic acid (150 mg) was purified on Unichiral CMD-5H column (4.6×250 mm), eluting with 70% n-hexane/30% ethanol (1 mL/min), 25° C., 254 nm UV detection. Appropriate fractions were pooled and reduced in vacuo to give Peak 1 (Example 128, trans diastereomer D1, 47 mg), RT 8.48 min (97.0%) and Peak 2 (Example 129, trans diastereomer D2, 49 mg), RT 10.51 min (99.6%).

Example 113 Intermediate 4 Example 135 and Example 136

Example 113 intermediate racemic cis aniline 5-amino-2-chloro-4-(2-hydroxycyclobutoxy)benzonitrile (213 mg)

was purified on Unichiral CMD-5H column (4.6×250 mm), eluting with 80% n-hexane/20% ethanol (1 mL/min), 25° C., 254 nm UV detection. Appropriate fractions were pooled and reduced in vacuo to give Peak 1 (73 mg), RT 12.49 min (99.8%) and Peak 2 (82 mg), RT 14.58 min (99.8%). Peak 1 aniline was progressed to give cis diastereomer D1 (Example 135) and Peak 2 aniline was progressed to give cis diastereomer D2 (Example 136).

Example 119 Intermediate 4 Example 138 and Example 139

Example 119 intermediate racemic trans ester methyl 3-(N-(4-chloro-5-cyano-2-(2-methoxycyclobutoxy)phenyl) sulfamoyl)-4-cyclopropylbenzoate (182 mg) was purified on Unichiral CNZ-5H column (4.6×250 mm), eluting with 80% n-hexane/20% ethanol/0.1% TFA (1 mL/min), 25° C., 254 nm UV detection. Appropriate fractions were pooled and reduced in vacuo to give Peak 1 (72 mg), RT 13.76 min (100%) and Peak 2 (67 mg), RT 16.49 min (99.7%). Peak 1 ester was progressed to give trans diastereomer D1 (Example 138) and Peak 2 ester was progressed to give trans diastereomer D2 (Example 139).

Example 134 Intermediate 4 Example 140 and Example 141

Example 134 intermediate racemic ester methyl 3-(N-(4-chloro-5-cyano-2-((3,3-difluorocyclopentyl)oxy)phenyl) sulfamoyl)-4-cyclopropylbenzoate (150 mg) was purified on Unichiral CND-5H column (4.6×250 mm), eluting with 90% n-hexane/10% ethanol/0.1% TFA (1 mL/min), 25° C., 254 nm UV detection. Appropriate fractions were pooled and reduced in vacuo to give Peak 1 (32 mg), RT 19.69 min (>95%) and Peak 2 (27 mg), RT 21.70 min (>95%). Peak 1 ester was progressed to give enantiomer E1 (Example 140) and Peak 2 ester was progressed to give enantiomer E2 (Example 141).

Example 102 Intermediate 4 Example 142 and Example 143

Example 102 intermediate racemic cis aniline 5-amino-2-chloro-4-((2-methoxycyclopentyl)oxy)benzonitrile (187 mg) was purified on Unichiral CMZ-5H column (4.6×250 mm), eluting with 95% n-hexane/5% ethanol (1 mL/min), 25° C., 254 nm UV detection. Appropriate fractions were pooled and reduced in vacuo to give Peak 1 (59 mg), RT 24.14 min (100%) and Peak 2 (56 mg), RT 25.64 min (98.8%). Peak 1 aniline was progressed to give cis diastereomer D1 (Example 142) and Peak 2 aniline was progressed to give cis diastereomer D2 (Example 143).

Example 137 Intermediate Example 144 and Example 145

Example 137 intermediate racemic cis aniline 5-amino-2-chloro-4-((2-methoxycyclobutyl)oxy)benzonitrile (250 mg) was purified on Unichiral CMZ-5H column (4.6×250 mm), eluting with 90% n-hexane/10% ethanol (1 mL/min), 25° C., 254 nm UV detection. Appropriate fractions were pooled and reduced in vacuo to give Peak 1 (110 mg), RT 16.56 min (98.8%) and Peak 2 (86 mg), RT 17.85 min (97.8%). Peak 1 aniline was progressed to give cis diastereomer D (Example 144) and Peak 2 aniline was progressed to give cis diastereomer 02 (Example 145).

| Example | Structure | Name/Analytical Data |
|---|---|---|
| 110 Cis racemate | 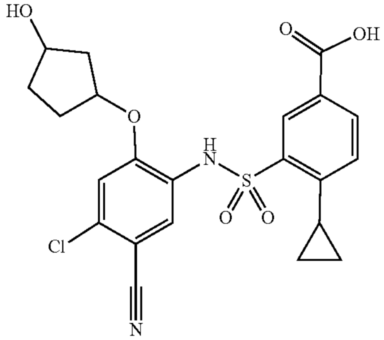 [SMILES: N#Cc1cc(NS(=O)(=O)c2cc(C(=O)O)ccc2C2CC2)c(OC2CCC(O)C2)cc1Cl] | 3-(N-(4-chloro-5-cyano-2-((cis-3-hydroxycyclopentyl)oxy)phenyl)sulfamoyl)-4-cyclopropylbenzoic acid UPLC-MS (Method 1) m/z 474.95 (M − H)$^-$ at 1.608 min. $^1$H NMR (400 MHz, DMSO-$d_6$) δ 13.22 (s, 1H), 10.09 (s, 1H), 8.30 (d, J 1.5 Hz, 1H), 7.98 (d, J = 8.2 Hz, 1H), 7.66 (s, 1H), 7.25 (s, 1H), 7.11 (d, J = 8.3 Hz, 1H), 4.88 (s, 1H), 4.50 (s, 1H), 4.07 (s, 1H), 2.75-2.59 (m, 1H), 1.99 (dt, J = 13.9, 7.1 Hz, 1H), 1.84-1.73 (m, 1H), 1.60 (ddd, J = 26.0, 11.3, 4.8 Hz, 2H), 1.46-1.30 (m, 2H), 0.98 (dd, J = 9.6, 5.0 Hz, 2H), 0.80 (s, 2H). |
| 111 Trans racemate | 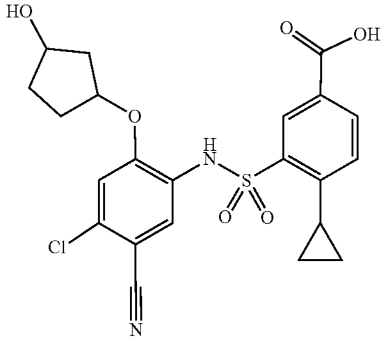 [SMILES: N#Cc1cc(NS(=O)(=O)c2cc(C(=O)O)ccc2C2CC2)c(OC2CCC(O)C2)cc1Cl] | 3-(N-(4-chloro-5-cyano-2-((trans-3-hydroxycyclopentyl)oxy)phenyl)sulfamoyl)-4-cyclopropylbenzoic acid UPLC-MS (Method 1) m/z 474.95 (M − H)$^-$ at 1.695 min. $^1$H NMR (400 MHz, DMSO-$d_6$) δ 13.17 (s, 1H), 10.03 (s, 1H), 8.34 (d, J = 1.6 Hz, 1H), 7.98 (dd, J = 8.2, 1.4 Hz, 1H), 7.63 (s, 1H), 7.31 (s, 1H), 7.12 (d, J = 8.3 Hz, 1H), 4.82-4.71 (m, 1H), 4.04 (p, J = 5.4 Hz, 1H), 2.68 (td, J = 8.3, 4.3 Hz, 1H), 2.15-2.06 (m, 2H), 1.76 (d, J = 6.8 Hz, 1H), 1.74-1.51 (m, 3H), 1.47 (d, J = 13.9 Hz, 1H), 1.04 (d, J = 7.0 Hz, 2H), 0.83 (dd, J = 18.0, 7.3 Hz, 2H). |

-continued

| Example | Structure | Name/Analytical Data |
|---|---|---|
| 112<br>Cis relative | 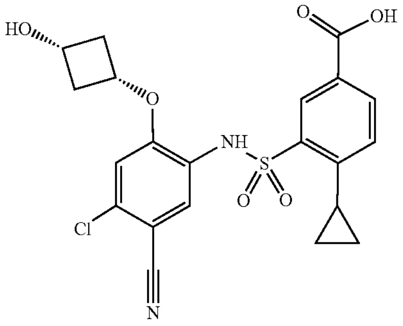 [SMILES: N#Cc1cc(NS(=O)(=O)c2cc(C(=O)O)ccc2C2CC2)c(O[C@H]2C[C@@H](O)C2)cc1Cl] | 3-(N-(4-chloro-5-cyano-2-(cis-3-hydroxycyclobutoxy)phenyl)sulfamoyl)-4-cyclopropylbenzoic acid<br>UPLC-MS (Method 2) m/z 461.05 (M − H)$^-$ at 3.583 min. $^1$H NMR (400 MHz, DMSO-$d_6$) δ 10.35 (s, 1H), 8.28 (s, 1H), 7.98 (d, J = 7.7 Hz, 1H), 7.65 (s, 1H), 7.12 (d, J = 8.1 Hz, 1H), 7.08 (s, 1H), 5.31 (s, 1H), 4.26-4.12 (m, 1H), 3.80-3.65 (m, 1H), 2.75 (s, 1H), 2.61 (s, 2H), 1.75-1.59 (m, 2H), 1.05 (d, J = 6.3 Hz, 2H), 0.84 (s, 2H). |
| 113<br>Cis racemate | 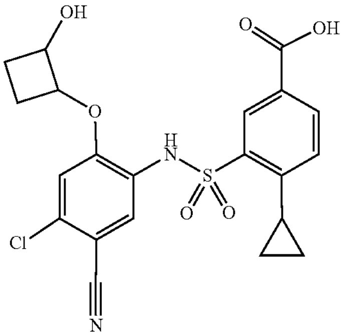 [SMILES: N#Cc1cc(NS(=O)(=O)c2cc(C(=O)O)ccc2C2CC2)c(OC2CCC2O)cc1Cl] | 3-(N-(4-chloro-5-cyano-2-(cis-2-hydroxycyclobutoxy)phenyl)sulfamoyl)-4-cyclopropylbenzoic acid<br>UPLC-MS (Method 1) m/z 460.95 (M − H)$^-$ at 1.626 min. $^1$H NMR (400 MHz, DMSO-$d_6$) δ 10.26 (s, 1H), 8.42 (s, 1H), 7.98 (d, J = 7.8 Hz, 1H), 7.65 (s, 1H), 7.17-7.02 (m, 2H), 5.42 (s, 1H), 4.76 (s, 1H), 4.25 (s, 1H), 2.68 (s, 1H), 1.98 (d, J = 12.6 Hz, 2H), 1.86 (d, J = 7.5 Hz, 1H), 1.64 (s, 1H), 1.06 (s, 2H), 0.84 (s, 1H), 0.73 (s, 1H). |
| 116<br>Trans diastereomer D1 | 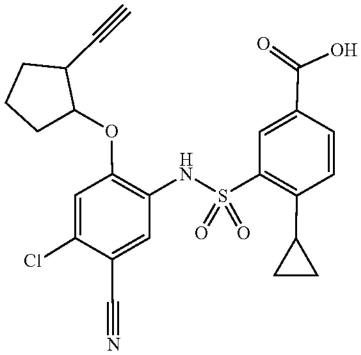 [SMILES: C#CC1CCCC1Oc1cc(Cl)c(C#N)cc1NS(=O)(=O)c1cc(C(=O)O)ccc1C1CC1] | 3-(N-(4-chloro-5-cyano-2-((trans-2-ethynylcyclopentyl)oxy)phenyl)sulfamoyl)-4-cyclopropylbenzoic acid<br>UPLC-MS (Method 2) m/z 483.00 (M − H)$^-$ at 4.147 min. Other analytical data consistent with Example 84. |
| 117<br>Trans diastereomer D2 | 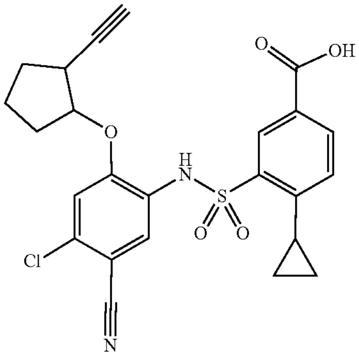 [SMILES: C#CC1CCCC1Oc1cc(Cl)c(C#N)cc1NS(=O)(=O)c1cc(C(=O)O)ccc1C1CC1] | 3-(N-(4-chloro-5-cyano-2-((trans-2-ethynylcyclopentyl)oxy)phenyl)sulfamoyl)-4-cyclopropylbenzoic acid<br>UPLC-MS (Method 2) m/z 483.05 (M − H)$^-$ at 4.161 min. Other analytical data consistent with Example 84. |

-continued

| Example | Structure | Name/Analytical Data |
|---|---|---|
| 118 Trans racemate | 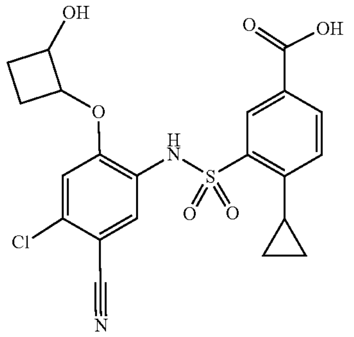 | 3-(N-(4-chloro-5-cyano-2-(trans-2-hydroxycyclobutoxy)phenyl)sulfamoyl)-4-cyclopropylbenzoic acid UPLC-MS (Method 1) m/z 460.95 (M − H)$^-$ at 1.589 min. $^1$H NMR (400 MHz, DMSO-$d_6$) δ 13.23 (s, 1H), 10.20 (s, 1H), 8.30 (d, J = 1.6 Hz, 1H), 8.00 (d, J = 8.2 Hz, 1H), 7.67 (s, 1H), 7.43 (s, 1H), 7.14 (d, J = 8.3 Hz, 1H), 5.70 (d, J = 6.7 Hz, 1H), 4.33 (q, J = 7.6 Hz, 1H), 3.64 (s, 1H), 2.73 (s, 1H), 1.92 (d, J = 7.6 Hz, 2H), 1.32 (d, J = 9.1 Hz, 1H), 1.11 (d, J = 9.6 Hz, 1H), 1.04 (d, J = 8.2 Hz, 2H), 0.84 (s, 2H). |
| 126 Cis diastereomer D1 | 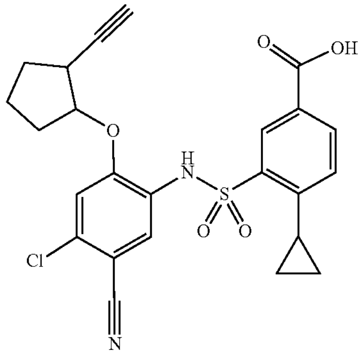 [SMILES: C#CC1CCCC1Oc1cc(Cl)c(C#N)cc1NS(=O)(=O)c1cc(C(=O)O)ccc1C1CC1] | 3-(N-(4-chloro-5-cyano-2-((cis-2-ethynylcyclopentyl)oxy)phenyl)sulfamoyl)-4-cyclopropylbenzoic acid UPLC-MS (Method 2) m/z 483.00 (M − H)$^-$ at 4.161 min. $^1$H NMR (400 MHz, DMSO-$d_6$) δ 13.26 (s, 1H), 9.89 (s, 1H), 8.36 (d, J = 1.5 Hz, 1H), 7.99 (d, J = 8.2 Hz, 1H), 7.57 (s, 1H), 7.50 (s, 1H), 7.14 (d, J = 8.2 Hz, 1H), 4.98 (s, 1H), 2.90 (s, 1H), 2.68 (s, 1H), 2.62 (d, J = 2.4 Hz, 1H), 1.89-1.79 (m, 2H), 1.71 (d, J = 12.9 Hz, 2H), 1.59 (s, 1H), 1.43 (s, 1H), 1.09-0.95 (m, 2H), 0.84 (d, J = 7.3 Hz, 2H). |
| 127 Cis diastereomer D2 | 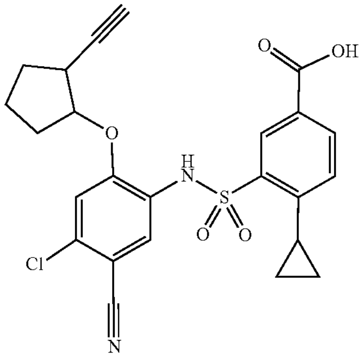 [SMILES: C#CC1CCCC1Oc1cc(Cl)c(C#N)cc1NS(=O)(=O)c1cc(C(=O)O)ccc1C1CC1] | 3-(N-(4-chloro-5-cyano-2-((cis-2-ethynylcyclopentyl)oxy)phenyl)sulfamoyl)-4-cyclopropylbenzoic acid UPLC-MS (Method 2) m/z 483.00 (M − H)$^-$ at 4.170 min. $^1$H NMR (400 MHz, DMSO-$d_6$) δ 13.23 (s, 1H), 9.89 (s, 1H), 8.36 (s, 1H), 7.99 (d, J = 8.2 Hz, 1H), 7.57 (s, 1H), 7.50 (s, 1H), 7.14 (d, J = 8.2 Hz, 1H), 4.98 (s, 1H), 2.90 (s, 1H), 2.68 (s, 1H), 2.62 (d, J = 2.2 Hz, 1H), 1.88-1.79 (m, 2H), 1.71 (d, J = 13.3 Hz, 2H), 1.59 (s, 1H), 1.43 (s, 1H), 1.07-0.97 (m, 2H), 0.84 (d, J = 6.8 Hz, 2H). |
| 128 Trans diastereomer D1 | 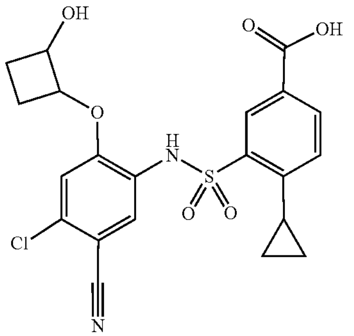 [SMILES: N#Cc1cc(NS(=O)(=O)c2cc(C(=O)O)ccc2C2CC2)c(OC2CCC2O)cc1Cl] | 3-(N-(4-chloro-5-cyano-2-(trans-2-hydroxycyclobutoxy)phenyl)sulfamoyl)-4-cyclopropylbenzoic acid UPLC-MS (Method 1) m/z 460.95 (M − H)$^-$ at 1.488 min. $^1$H NMR (400 MHz, DMSO-$d_6$) δ 13.23 (s, 1H), 10.20 (s, 1H), 8.31 (d, J = 1.5 Hz, 1H), 8.00 (d, J = 8.2 Hz, 1H), 7.67 (s, 1H), 7.43 (s, 1H), 7.14 (d, J = 8.3 Hz, 1H), 5.70 (d, J = 6.6 Hz, 1H), 4.33 (d, J = 6.4 Hz, 1H), 3.64 (s, 1H), 2.73 (s, 1H), 1.92 (d, J = 8.3 Hz, 2H), 1.38-1.27 (m, 1H), 1.11 (d, J = 8.7 Hz, 1H), 1.04 (d, J = 8.2 Hz, 2H), 0.84 (s, 2H). |

-continued

| Example | Structure | Name/Analytical Data |
|---|---|---|
| 129 Trans diastereomer D2 | 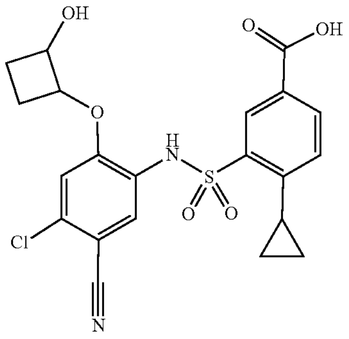 [SMILES: N#Cc1cc(NS(=O)(=O)c2cc(C(=O)O)ccc2C2CC2)c(OC2CCC2O)cc1Cl] | 3-(N-(4-chloro-5-cyano-2-(trans-2-hydroxycyclobutoxy)phenyl)sulfamoyl)-4-cyclopropylbenzoic acid UPLC-MS (Method 1) m/z 460.95 (M − H)− at 1.493 min. ¹H NMR (400 MHz, DMSO-$d_6$) δ 13.25 (s, 1H), 10.19 (s, 1H), 8.31 (d, J = 1.6 Hz, 1H), 8.00 (d, J = 9.6 Hz, 1H), 7.67 (s, 1H), 7.42 (s, 1H), 7.13 (d, J = 8.3 Hz, 1H), 5.70 (s, 1H), 4.33 (q, J = 7.7 Hz, 1H), 3.65 (s, 1H), 2.73 (s, 1H), 1.92 (d, J = 7.4 Hz, 2H), 1.32 (d, J = 9.2 Hz, 1H), 1.11 (d, J = 8.9 Hz, 1H), 1.04 (d, J = 8.2 Hz, 2H), 0.83 (s, 2H). |
| 134 | 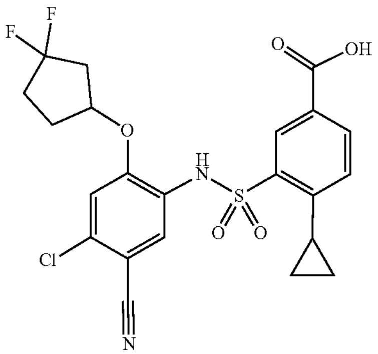 [SMILES: N#Cc1cc(NS(=O)(=O)c2cc(C(=O)O)ccc2C2CC2)c(OC2CCC(F)(F)C2)cc1Cl] | 3-(N-(4-chloro-5-cyano-2-((3,3-difluorocyclopentyl)oxy)phenyl)sulfamoyl)-4-cyclopropylbenzoic acid UPLC-MS (Method 2) m/z 494.95 (M − H)− at 4.000 min. 1H NMR (400 MHz, DMSO-d6) δ 13.24 (s, 1H), 10.24 (s, 1H), 8.36-8.32 (m, 1H), 7.98 (d, J = 8.2 Hz, 1H), 7.69 (s, 1H), 7.35 (s, 1H), 7.11 (d, J = 8.3 Hz, 1H), 4.97 (s, 1H), 2.71-2.54 (m, 2H), 2.06 (dd, J = 14.4, 7.1 Hz, 4H), 1.66 (s, 1H), 0.99 (d, J = 8.3 Hz, 2H), 0.81 (s, 2H). |
| 135 Cis diastereomer D1 | 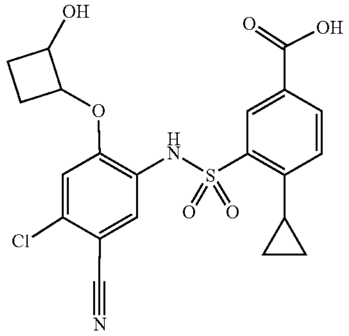 | 3-(N-(4-chloro-5-cyano-2-(cis-2-hydroxycyclobutoxy)phenyl)sulfamoyl)-4-cyclopropylbenzoic acid UPLC-MS (Method 2) m/z 460.95 (M − H)− at 3.700 min. 1H NMR (400 MHz, DMSO-d6) δ 13.27 (s, 1H), 10.25 (s, 1H), 8.46-8.39 (m, 1H), 7.98 (d, J = 8.2 Hz, 1H), 7.65 (s, 1H), 7.17-7.06 (m, 2H), 5.39 (d, J = 7.9 Hz, 1H), 4.76 (s, 1H), 4.25 (s, 1H), 2.74-2.62 (m, 1H), 2.07-1.80 (m, 3H), 1.64 (t, J = 10.5 Hz, 1H), 1.13-0.99 (m, 2H), 0.79 (dd, J = 46.8, 5.0 Hz, 2H). |
| 136 Cis diastereomer D2 | 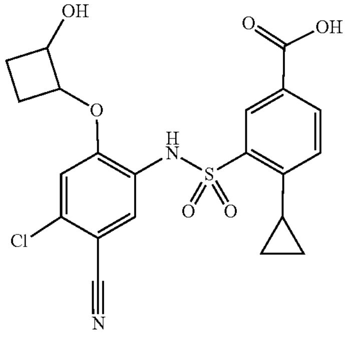 [SMILES: N#Cc1cc(NS(=O)(=O)c2cc(C(=O)O)ccc2C2CC2)c(OC2CCC2O)cc1Cl] | 3-(N-(4-chloro-5-cyano-2-(csi-2-hydroxycyclobutoxy)phenyl)sulfamoyl)-4-cyclopropylbenzoic acid UPLC-MS (Method 1) m/z 460.95 (M − H)− at 3.666 min. 1H NMR (400 MHz, DMSO-d6) δ 13.27 (s, 1H), 10.25 (s, 1H), 8.45-8.39 (m, 1H), 7.98 (d, J = 8.1 Hz, 1H), 7.65 (s, 1H), 7.16-7.07 (m, 2H), 5.39 (d, J = 8.3 Hz, 1H), 4.76 (s, 1H), 4.25 (s, 1H), 2.68 (s, 1H), 2.05-1.81 (m, 3H), 1.64 (s, 1H), 1.13-0.99 (m, 2H), 0.88-0.69 (m, 2H). |

-continued

| Example | Structure | Name/Analytical Data |
|---|---|---|
| 140 Enantiomer E1 | 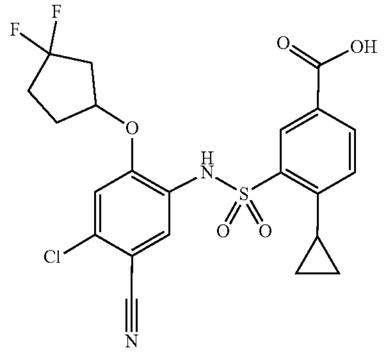 [SMILES: N#Cc1cc(NS(=O)(=O)c2cc(C(=O)O)ccc2C2CC2)c(OC2CCC(F)(F)C2)cc1Cl] | 3-(N-(4-chloro-5-cyano-2-((3,3-difluorocyclopentyl)oxy)phenyl)sulfamoyl)-4-cyclopropylbenzoic acid UPLC-MS (Method 2) m/z 495.00 (M − H)− at 4.000 min. 1H NMR (400 MHz, DMSO-d6) δ 8.34 (s, 1H), 7.99 (d, J = 8.2 Hz, 1H), 7.70 (s, 1H), 7.35 (s, 1H), 7.12 (d, J = 8.2 Hz, 1H), 4.96 (s, 1H), 2.67 (s, 1H), 2.61 (s, 1H), 2.05 (d, J = 15.5 Hz, 4H), 1.65 (s, 1H), 0.99 (d, J = 7.2 Hz, 2H), 0.81 (s, 2H). |
| 141 Enantiomer E2 | 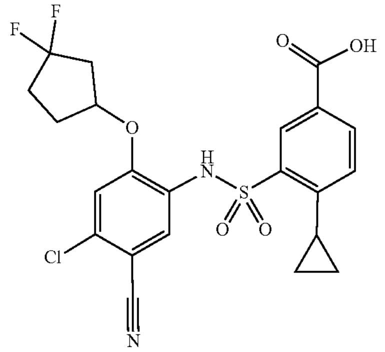 [SMILES: N#Cc1cc(NS(=O)(=O)c2cc(C(=O)O)ccc2C2CC2)c(OC2CCC(F)(F)C2)cc1Cl] | 3-(N-(4-chloro-5-cyano-2-((3,3-difluorocyclopentyl)oxy)phenyl)sulfamoyl)-4-cyclopropylbenzoic acid UPLC-MS (Method 2) m/z 494.95 (M − H)− at 4.000 min. 1H NMR (400 MHz, DMSO-d6) δ 8.33 (s, 1H), 7.98 (d, J = 8.2 Hz, 1H), 7.70 (s, 1H), 7.35 (s, 1H), 7.12 (d, J = 8.3 Hz, 1H), 4.96 (s, 1H), 2.66 (d, J = 4.1 Hz, 1H), 2.58 (d, J = 8.4 Hz, 1H), 2.05 (d, J = 15.2 Hz, 4H), 1.66 (d, J = 3.3 Hz, 1H), 0.99 (d, J = 8.1 Hz, 2H), 0.81 (s, 2H). |

Example 109: 3-(N-(4-chloro-5-cyano-2-(((1R,2R)-2-methoxycyclopentyl)oxy)phenyl)sulfamoyl)-4-cyclopropylbenzoic acid

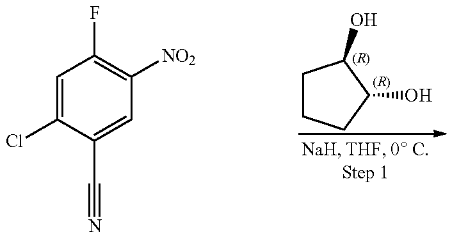

-continued

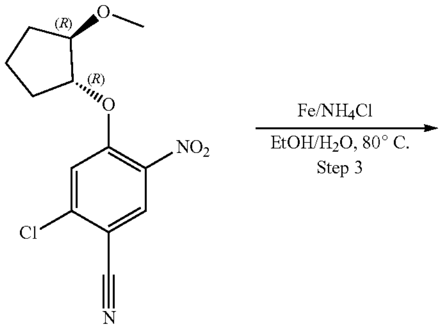

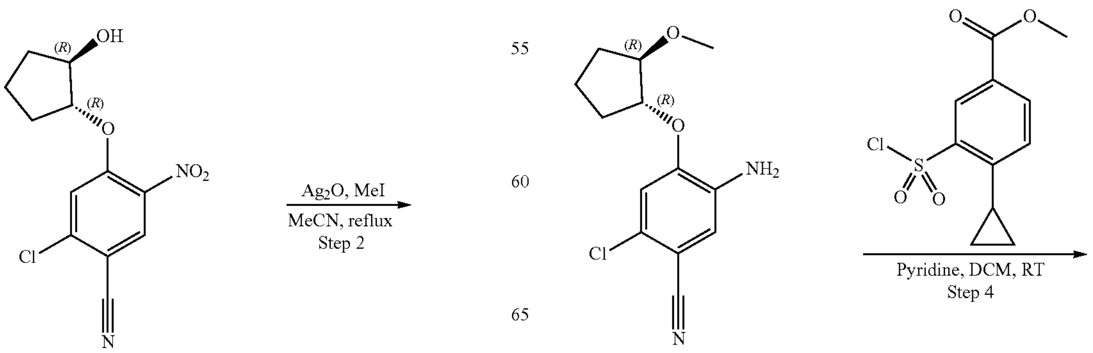

-continued

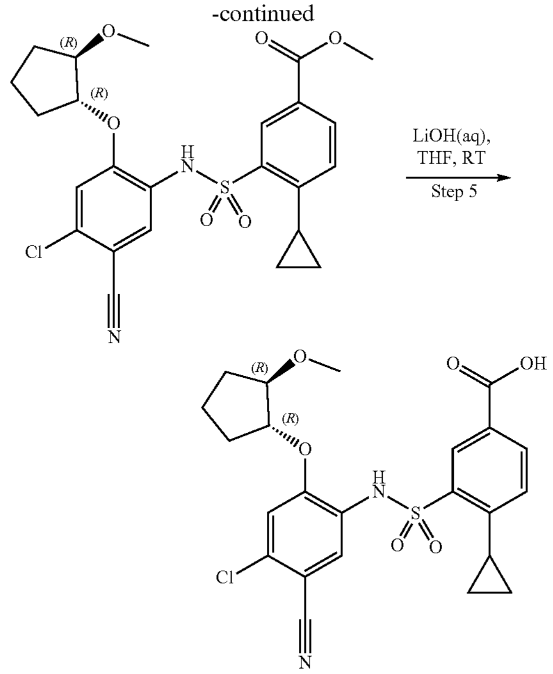

Step 2: 2-chloro-4-(((1R,2R)-2-methoxycyclopentyl)oxy)-5-nitrobenzonitrile: A mixture of 2-chloro-4-(((1R,2R)-2-hydroxycyclopentyl)oxy)-5-nitrobenzonitrile (0.141 g, 0.5 mmol), MeI (0.141 g, 1.0 mmol) and $Ag_2O$ (0.23 g, 1.0 mmol) in MeCN (5 mL) was heated at 80° C. for 12 h. The reaction mixture was filtered through celite. The filtrate was concentrated and purified by silica gel chromatography (eluting with 1/10 EtOAc/PE) to afford the title compound (0.091 g, 0.31 mmol, 62% yield) as an yellow oil. 1H NMR (400 MHz, Chloroform-d) δ 8.17 (d, J=1.4 Hz, 1H), 7.40 (d, J=1.4 Hz, 1H), 4.78-4.68 (m, 1H), 3.36 (d, J=1.4 Hz, 3H), 2.22-2.13 (m, 1H), 2.11-2.00 (m, 3H), 1.87-1.72 (m, 4H).

The experiment process for Step 1 is the same as Example 52

The experiment process for Step 3, 4 and 5 are the same as Example 1

The following examples were prepared by methods analogous to Example 109, substituting appropriate starting materials and intermediates where necessary:

| Example | Structure | Name/analytical data |
| --- | --- | --- |
| 109 | 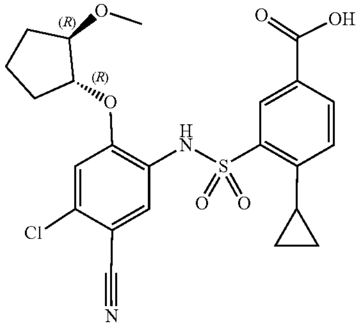 | 3-(N-(4-chloro-5-cyano-2-(((1R,2R)-2-methoxycyclopentyl)oxy)phenyl)sulfamoyl)-4-cyclopropylbenzoic acid UPLC-MS (Method 1) m/z 489.00 (M − H)$^-$ at 1.958 min. Other analytical data consistent with Example 103. |
| 102<br>Cis racemate | 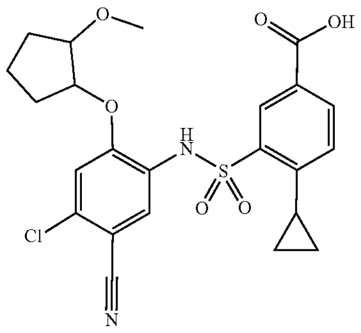 [SMILES: COC1CCCC1Oc1cc(Cl)c(C#N)cc1NS(=O)(=O)c1cc(C(=O)O)ccc1C1CC1] | 3-(N-(4-chloro-5-cyano-2-((cis-2-methoxycyclopentyl)oxy)phenyl)sulfamoyl)-4-cyclopropylbenzoic acid UPLC-MS (Method 2) m/z 489.00 (M − H)- at 4.033 min. 1H NMR (400 MHz, DMSO-d6) δ 13.22 (s, 1H), 9.92 (s, 1H), 8.35 (s, 1H), 7.99 (d, J = 8.2 Hz, 1H), 7.57 (s, 1H), 7.45 (s, 1H), 7.13 (d, J = 8.3 Hz, 1H), 4.84-4.77 (m, 1H), 3.78-3.65 (m, 1H), 3.07 (s, 3H), 2.73-2.59 (m, 1H), 1.81-1.68 (m, 2H), 1.65-1.48 (m, 3H), 1.44-1.32 (m, 1H), 1.07-0.94 (m, 2H), 0.87-0.74 (m, 2H). |

-continued

| Example | Structure | Name/analytical data |
|---|---|---|
| 119 Trans racemate | 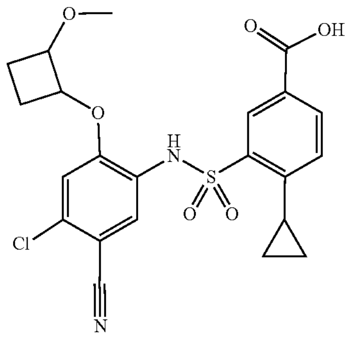 [SMILES: COC1CCC1Oc1cc(Cl)c(C#N)cc1NS(=O)(=O)c1cc(C(=O)O)ccc1C1CC1] | 3-(N-(4-chloro-5-cyano-2-(trans-2-methoxycyclobutoxy)phenyl)sulfamoyl)-4-cyclopropylbenzoic acid UPLC-MS (Method 2) m/z 475.00 (M − H)⁻ at 3.994 min. ¹H NMR (400 MHz, DMSO-$d_6$) δ 13.25 (s, 1H), 10.23 (s, 1H), 8.30 (d, J = 1.6 Hz, 1H), 8.05-7.96 (m, 1H), 7.72 (s, 1H), 7.29 (s, 1H), 7.16 (d, J = 8.3 Hz, 1H), 4.54 (q, J = 7.7 Hz, 1H), 3.46 (q, J = 8.0 Hz, 1H), 3.11 (s, 3H), 2.78-2.68 (m, 1H), 2.11-2.00 (m, 1H), 1.93 (q, J = 9.5 Hz, 1H), 1.35-1.24 (m ,1H), 1.06-1.00 (m, 2H), 0.98-0.85 (m, 2H), 0.84-0.76 (m, 1H). |
| 124 Cis/Trans mixture | 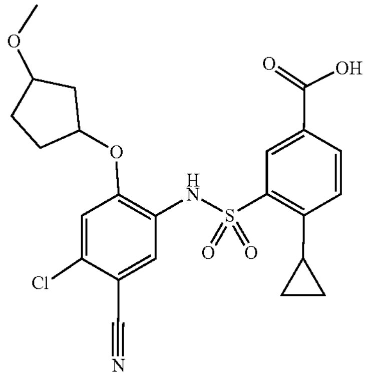 [SMILES: COC1CCC(Oc2cc(Cl)c(C#N)cc2NS(=O)(=O)c2cc(C(=O)O)ccc2C2CC2)C1] | 3-(N-(4-chloro-5-cyano-2-((3-methoxycyclopentyl)oxy)phenyl)sulfamoyl)-4-cyclopropylbenzoic acid UPLC-MS (Method 1) m/z 489.00 (M − H)⁻ at 1.756 min. ¹H NMR (400 MHz, DMSO-$d_6$) δ 13.22 (s, 1H), 9.98 (s, 1H), 8.33 (d, J = 1.8 Hz, 1H), 7.98 (dd, J = 8.3, 1.8 Hz, 1H), 7.65 (s, 1H), 7.31 (s, 1H), 7.11 (d, J = 8.3 Hz, 1H), 4.75 (s, 1H), 3.68 (s, 1H), 3.16 (s, 3H), 2.66 (s, 1H), 2.28-2.18 (m, 1H), 1.69 (s, 2H), 1.55 (d, J = 4.8 Hz, 2H), 1.40 (d, J = 14.1 Hz, 1H), 1.01 (dd, J = 8.2, 2.5 Hz, 2H), 0.81 (d, J = 4.4 Hz, 2H). |
| 137 Cis racemate | 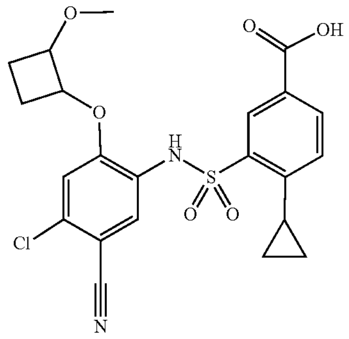 [SMILES: COC1CCC1Oc1cc(Cl)c(C#N)cc1NS(=O)(=O)c1cc(C(=O)O)ccc1C1CC1] | 3-(N-(4-chloro-5-cyano-2-(cis-2-methoxycyclobutoxy)phenyl)sulfamoyl)-4-cyclopropylbenzoic acid UPLC-MS (Method 1) m/z 475.00 (M − H)⁻ at 1.716 min. 1H NMR (400 MHz, DMSO-d6) δ 13.20 (s, 1H), 10.13 (s, 1H), 8.37-8.29 (m, 1H), 7.98 (d, J = 8.3 Hz, 1H), 7.62 (s, 1H), 7.20 (s, 1H), 7.13 (d, J = 8.3 Hz, 1H), 4.73 (d, J = 4.6 Hz, 1H), 4.07 (d, J = 5.0 Hz, 1H), 2.97 (s, 3H), 2.72 (s, 1H), 2.00-1.82 (m, 4H), 1.10-0.97 (m, 2H), 0.87-0.80 (m, 2H). |
| 138 Trans diastereomer D1 | 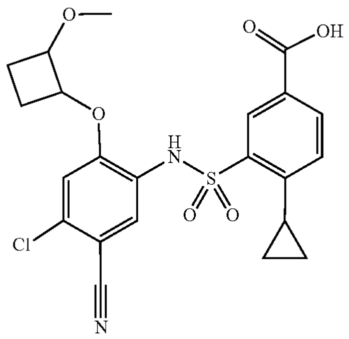 [SMILES: COC1CCC1Oc1cc(Cl)c(C#N)cc1NS(=O)(=O)c1cc(C(=O)O)ccc1C1CC1] | 3-(N-(4-chloro-5-cyano-2-(trans-2-methoxycyclobutoxy)phenyl)sulfamoyl)-4-cyclopropylbenzoic acid UPLC-MS (Method 1) m/z 475.00 (M − H)– at 1.750 min. 1H NMR (400 MHz, DMSO-d6) δ 13.25 (s, 1H), 10.23 (s, 1H), 8.30 (d, J = 1.5 Hz, 1H), 8.01 (d, J = 6.9 Hz, 1H), 7.72 (s, 1H), 7.28 (s, 1H), 7.16 (d, J = 8.3 Hz, 1H), 4.54 (q, J = 7.3 Hz, 1H), 3.46 (q, J = 7.8 Hz, 1H), 3.11 (s, 3H), 2.78-2.67 (m, 1H), 2.06 (q, J = 9.4 Hz, 1H), 1.93 (q, J = 9.6 Hz, 1H), 1.37-1.23 (m, 1H), 1.07-0.97 (m, 2H), 0.98-0.89 (m, 1H), 0.83-0.76 (m, 2H). |

-continued

| Example | Structure | Name/analytical data |
|---|---|---|
| 139 Trans diastereomer D2 | 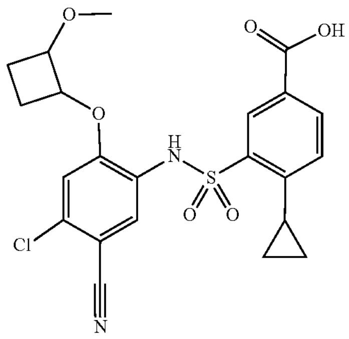 [SMILES: COC1CCC1Oc1cc(Cl)c(C#N)cc1NS(=O)(=O)c1cc(C(=O)O)ccc1C1CC1] | 3-(N-(4-chloro-5-cyano-2-(trans-2-methoxycyclobutoxy)phenyl)sulfamoyl)-4-cyclopropylbenzoic acid Analytical data consistent with Example 138. |
| 142 Cis diastereomer D1 | 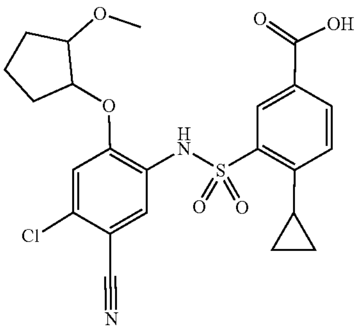 [SMILES: COC1CCCC1Oc1cc(Cl)c(C#N)cc1NS(=O)(=O)c1cc(C(=O)O)ccc1C1CC1] | 3-(N-(4-chloro-5-cyano-2-((cis-2-methoxycyclopentyl)oxy)phenyl)sulfamoyl)-4-cyclopropylbenzoic acid Analytical data consistent with Example 102. |
| 143 Cis diastereomer D2 | 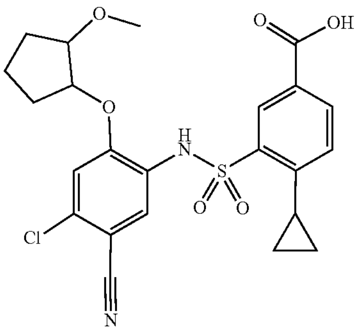 [SMILES: COC1CCCC1Oc1cc(Cl)c(C#N)cc1NS(=O)(=O)c1cc(C(=O)O)ccc1C1CC1] | 3-(N-(4-chloro-5-cyano-2-((cis-2-methoxycyclopentyl)oxy)phenyl)sulfamoyl)-4-cyclopropylbenzoic acid Analytical data consistent with Example 102. |
| 144 Cis diastereomer D1 | 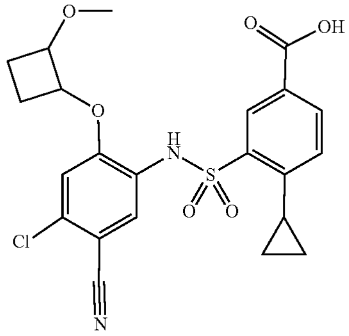 [SMILES: COC1CCC1Oc1cc(Cl)c(C#N)cc1NS(=O)(=O)c1cc(C(=O)O)ccc1C1CC1] | 3-(N-(4-chloro-5-cyano-2-(cis-2-methoxycyclobutoxy)phenyl)sulfamoyl)-4-cyclopropylbenzoic acid UPLC-MS (Method 1) m/z 475.00 (M − H)− at 1.616 min. 1H NMR (400 MHz, DMSO-d6) δ 10.15 (s, 1H), 8.33 (s, 1H), 7.98 (d, J = 7.6 Hz, 1H), 7.62 (s, 1H), 7.19 (s, 1H), 7.13 (d, J = 8.2 Hz, 1H), 4.76-4.70 (m, 1H), 4.10-4.04 (m, 1H), 2.98 (s, 3H), 2.77-2.68 (m, 1H), 2.03-1.78 (m, 4H), 1.09-0.96 (m, 2H), 0.87-0.77 (m, 2H). |

-continued

| Example | Structure | Name/analytical data |
|---|---|---|
| 145 Cis diastsereomer D2 | 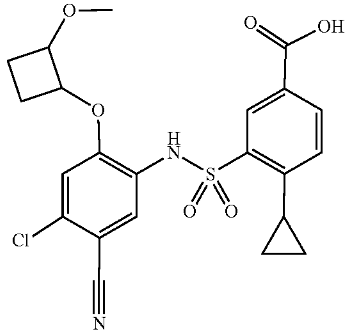 [SMILES: COC1CCC1Oc1cc(Cl)c(C#N)cc1NS(=O)(=O)c1cc(C(=O)O)ccc1C1CC1] | 3-(N-(4-chloro-5-cyano-2-(cis-2-methoxycyclobutoxy)phenyl)sulfamoyl)-4-cyclopropylbenzoic acid Analytical data consistent with Example 144 |

Biological Investigations

The following assays can be used to illustrate the commercial utilities of the compounds according to the present invention.

Biological Assay 1: ERAP1 Mediated Hydrolysis of an Amide Substrate Measured in a Biochemical System Materials and Solutions

- 1× Assay buffer (AB): 25 mM Bis-tris propane, 0.05% w/v
- Hydroxypropylmethylcellulose pH 7.75 made with Optima grade water
- Decapeptide WRVYEKC(Dnp)ALK-acid (where Dnp is Dinitrophenyl maleimide) (10-mer)
- L-Leucine 7-amido-4-methylcoumarin (L-AMC)
- Purified ERAP1(37-941)-10His (ERAP1)

Assay Procedure:

12.5 μL ERAP1 enzyme in 1×AB was combined with 250 nL test compound in DMSO. 12.5 μL of either 240 μM L-AMC in 1×AB or 100 μM 10-mer in 1×AB was added to the reaction and incubated at 23° C. for 1 h. For detection, plates were read at excitation 365 nm and emission 442 nm (L-AMC) or excitation 279 nm and emission 355 nm (10-mer). Compound $IC_{50}$ was determined using a 4-parameter equation. The results for selected compounds according to the invention are shown in Table 1.

OVA Antigen Presentation Assay

The cellular effect of representative compounds according to the invention on antigen presentation can be measured by assessing their effect on the presentation of an ovalbumin-specific peptide (SIINFEKL) to T-cells, as previously described [Reeves et al, (2014) *Proc. Natl. Acad. Sci. USA* 111; 17594-17599]. Briefly, SiHa cells are transiently transfected with plasmids encoding mouse H2Kb and an ER-targeted N-terminally extended precursor peptide derived from ovalbumin (MRYMILGLLALAAVCSAAIVMKSIINFEHL) using Lipofectamine 3000. The cells are harvested 6 h post-transfection and transfected SiHa cells are plated compounds across a 12-point concentration response curve to quantify ERAP1 inhibitor $IC_{50}$. SiHa cells are cultured in the presence of compound for 48 h. Subsequently, B3Z cells [Karttunen et al, (1992) *Proc. Natl. Acad. Sci. USA* 89; 6020-6024] are added to the cell culture for 4 h; the B3Z T-cell hybridoma encodes a TCR recognizing specifically the SIINFEHL/H2Kb complex at the cell surface, which upon activation, triggers a signalling cascade leading to the transcription of the LacZ gene that is under the control of the IL-2 promoter. Intracellular β-galactosidase activity as a readout of T-cell activation is measured by quantifying the conversion of chlorophenored-β-D-galacto-pyrannoside (CPRG) to chlorophenol red by measuring absorbance at 570 nm.

Immunopeptidomics

The effect of representative compounds according to the invention on global antigen processing can be determined using an unbiased proteomics pipeline as described by Purcell and colleagues [Purcell et al, (2019) Nat Protoc. 14; 1687-1707]. Briefly, 500 million SiHa cells are treated with compound for 24 h or siRNA for 72 hours and then harvested, lysed and MHC-bound peptides isolated by immunoaffinity capture. The peptides are eluted using 10% (v/v) acetic acid and separated from the MHC-1 and β2-microglobulin proteins by HPLC before analysis by LC-MS/MS.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

| Activity of selected compounds according to the invention | |
|---|---|
| 1 | HIGH |
| 2 | LOW |
| 3 | LOW |
| 4 | MEDIUM |
| 5 | LOW |
| 6 | MEDIUM |
| 7 | LOW |
| 8 | HIGH |
| 9 | HIGH |
| 10 | HIGH |
| 11 | HIGH |
| 12 | HIGH |
| 13 | MEDIUM |
| 14 | LOW |
| 15 | LOW |
| 16 | HIGH |
| 17 | HIGH |
| 18 | HIGH |
| 19 | MEDIUM |
| 20 | HIGH |
| 21 | MEDIUM |
| 22 | HIGH |

TABLE 1-continued

| Activity of selected compounds according to the invention | |
|---|---|
| 23 | HIGH |
| 24 | HIGH |
| 25 | HIGH |
| 26 | MEDIUM |
| 27 | HIGH |
| 28 | MEDIUM |
| 29 | HIGH |
| 30 | MEDIUM |
| 31 | MEDIUM |
| 32 | MEDIUM |
| 33 | HIGH |
| 34 | HIGH |
| 35 | HIGH |
| 36 | MEDIUM |
| 37 | MEDIUM |
| 38 | LOW |
| 39 | MEDIUM |
| 40 | MEDIUM |
| 41 | HIGH |
| 42 | HIGH |
| 43 | LOW |
| 44 | HIGH |
| 45 | MEDIUM |
| 46 | MEDIUM |
| 47 | HIGH |
| 48 | HIGH |
| 49 | MEDIUM |
| 50 | HIGH |
| 51 | HIGH |
| 52 | LOW |
| 53 | MEDIUM |
| 54 | MEDIUM |
| 55 | MEDIUM |
| 56 | HIGH |
| 57 | HIGH |
| 58 | HIGH |
| 59 | HIGH |
| 60 | HIGH |
| 61 | HIGH |
| 62 | HIGH |
| 63 | HIGH |
| 64 | HIGH |
| 65 | MEDIUM |
| 66 | LOW |
| 67 | LOW |
| 68 | MEDIUM |
| 69 | HIGH |
| 70 | HIGH |
| 71 | HIGH |
| 72 | HIGH |
| 73 | HIGH |
| 74 | HIGH |
| 75 | MEDIUM |
| 76 | HIGH |
| 77 | HIGH |
| 78 | HIGH |
| 79 | HIGH |
| 80 | HIGH |
| 81 | HIGH |
| 82 | HIGH |
| 83 | HIGH |
| 84 | HIGH |
| 85 | HIGH |
| 86 | HIGH |
| 87 | HIGH |
| 88 | HIGH |
| 89 | HIGH |
| 90 | HIGH |
| 91 | MEDIUM |
| 92 | HIGH |
| 93 | MEDIUM |
| 94 | HIGH |
| 95 | LOW |
| 96 | HIGH |
| 97 | HIGH |
| 98 | HIGH |
| 99 | HIGH |
| 100 | HIGH |
| 101 | LOW |
| 102 | HIGH |
| 103 | HIGH |
| 104 | LOW |
| 105 | HIGH |
| 106 | HIGH |
| 107 | HIGH |
| 108 | HIGH |
| 109 | HIGH |
| 110 | HIGH |
| 111 | MEDIUM |
| 112 | LOW |
| 113 | HIGH |
| 114 | HIGH |
| 115 | HIGH |
| 116 | LOW |
| 117 | HIGH |
| 118 | HIGH |
| 119 | HIGH |
| 120 | HIGH |
| 121 | HIGH |
| 122 | MEDIUM |
| 123 | HIGH |
| 124 | HIGH |
| 125 | HIGH |
| 126 | HIGH |
| 127 | LOW |
| 128 | HIGH |
| 129 | LOW |
| 130 | MEDIUM |
| 131 | HIGH |
| 132 | MEDIUM |
| 133 | MEDIUM |
| 134 | HIGH |
| 135 | LOW |
| 136 | HIGH |
| 137 | HIGH |
| 138 | HIGH |
| 139 | LOW |
| 140 | HIGH |
| 141 | HIGH |
| 142 | HIGH |
| 143 | MEDIUM |
| 144 | HIGH |
| 145 | MEDIUM |

$IC_{50}$ vs Decapeptide WRVYEKC(Dnp)ALK-acid (where Dnp is Dinitrophenyl maleimide) (10-mer); High (<1 nM), Medium (>1 nM to <5 nM), Low (>5 nM).

REFERENCES

1. Serwold et al, (2002), ERAAP customizes peptides for MHC class I molecules in the endoplasmic reticulum; Nature: 419, p 480.
2. Snyder et al, (2014), Genetic Basis for Clinical Response to CTLA-4 Blockade in Melanoma; NEJM: 371, p 2189.
3. Van Allen et al, (2015), Genomic correlates of response to CTLA-4 blockade in metastatic melanoma; Science: 348, p 124.
4. James et al, (2013), Induction of Protective Antitumor Immunity through Attenuation of ERAAP Function; J Immunol: 190, p 5839.
5. Niranjana et al, (2016), ERAAP Shapes the Peptidome Associated with Classical and Nonclassical MHC Class I Molecules; J Immunol: 197, p 1035.
6. Pepelyayeva et al, (2018), ERAP1 deficient mice have reduced Type 1 regulatory T cells and develop skeletal and intestinal features of Ankylosing Spondylitis; Sci. Reports: 8: p 12464.
7. Cifaldi et al, (2015), ERAP1 Regulates Natural Killer Cell Function by Controlling the Engagement of Inhibitory Receptors, Cancer Res.: 75, p 824.

8. Steinbach et al, (2017), ERAP1 overexpression in HPV-induced malignancies: A possible novel immune evasion mechanism, Oncoimmunol: 6, e1336594.

9. Kim et al, (2011), Human cytomegalovirus microRNA miR-US4-1 inhibits CD8+ T cell responses by targeting the aminopeptidase ERAP1, Nat. Immunol.: 12, p 984.

10. Tenzer et al, (2009), Antigen processing influences HIV-specific cytotoxic T lymphocyte immunodominance, Nat. Immunol.: 10, p 636.

11. Reeves et al, (2018), The role of polymorphic ERAP1 in autoinflammatory disease, Biosci. Rep.: 29, p 38.

12. Chen et al, (2014), Silencing or inhibition of endoplasmic reticulum aminopeptidase 1 (ERAP1) suppresses free heavy chain expression and Th17 responses in ankylosing spondylitis, Ann Rheum Dis: 75, p 916.

13. Sheehan, N J (January 2004). "The ramifications of HLA-B27". *Journal of the Royal Society of Medicine.* 97 (1): 10-4.

14. Smith, JA (January 2015). "Update on ankylosing spondylitis: current concepts in pathogenesis". *Current allergy and asthma reports.* 15 (1): 489.

15. Kuiper J J W, Mutis T, de Jager W, de Groot-Mijnes J D, Rothova A (2011). "Intraocular interleukin-17 and proinflammatory cytokines in HLA-A29-associated birdshot chorioretinopathy". *Am J Ophthalmol.* 152 (2): 177-182

16. Kuiper J J W, Emmelot M E, Rothova A, Mutis T (2013). "Interleukin-17 production and T helper 17 cells in peripheral blood mononuclear cells in response to ocular lysate in patients with birdshot chorioretinopathy". *Mol Vis.* 19: 2606-14

17. Kuiper J J W, van Setten J, Ripke S, Van't Slot R, Mulder F, Missotten T, Baarsma G S, Francioli L C, Pulit S L, de Kovel C G, Ten Dam-van Loon N, den Hollander A I, Huis In Het Veld P, Hoyng C B, Cordero-Coma M, Martin J, Llorenç V, Arya B, Thomas D, Bakker S C, Ophoff R A, Rothova A, de Bakker P I, Mutis T, Koeleman B P (2014). "A genome-wide association study identifies a functional ERAP2 haplotype associated with birdshot chorioretinopathy". *Hum Mol Genet.* 23 (22): 6081-6087

18. Evans et al (2011), Interaction between ERAP1 and HLA-B27 in ankylosing spondylitis implicates peptide handling in the mechanism for HLA-B27 in disease susceptibility. Nat Genet. 10; 43(8):761-7

19. Conde-Jaldon et al (2014), Epistatic interaction of ERAP1 and HLA-B in Behçet disease: a replication study in the Spanish population. PloS One. 14; 9(7)

20. Kuiper et al (2018), Functionally distinct ERAP1 and ERAP2 are a hallmark of HLA-A29-(Birdshot) Uveitis. Hum Mol Genet. Doi: 10.1093/hmg/ddy319

21. Strange et al (2010), A genome-wide association study identifies new psoriasis susceptibility loci and an interaction between HLA-C and ERAP1. Nat Genet.; 42(11): 985-90.

The invention claimed is:

1. A compound of formula (I), or a pharmaceutically acceptable salt or hydrate thereof,

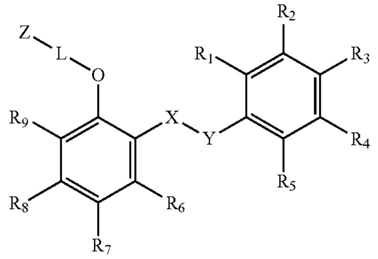

(I)

wherein:

the group X—Y is —$NHSO_2$—;

Z is a monocyclic or polycyclic cycloalkyl group or a monocyclic or polycyclic heterocycloalkyl group, each of which is optionally substituted by one or more groups selected from haloalkyl, alkyl, alkenyl, alkynyl and —$(CR_{16}R_{17})_mR_{18}$, where m is 0 to 6;

L is a direct bond or a group $(CR_{14}R_{15})_n$, where n is 1 or 2;

$R_1$ is selected from H, Cl, F, CN and alkyl;

$R_2$ is selected from COOH and a tetrazolyl group;

$R_3$ is selected from H, halo, alkoxy and alkyl;

$R_4$ is selected from H and halo;

$R_5$ is selected from H, alkyl, haloalkyl, $SO_2$-alkyl, Cl, alkoxy, OH, CN, hydroxyalkyl, alkylthio, heteroaryl, cycloalkyl, heterocycloalkyl and haloalkoxy;

$R_6$ is H;

$R_7$ is selected from H, CN, haloalkyl, halo, $SO_2$-alkyl, $SO_2NR_{12}R_{13}$, heteroaryl, $CONR_{10}R_{11}$ and alkyl, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is selected from H, alkyl and halo;

$R_{10}$, $R_{11}$, $R_{12}$ and $R_{13}$ are each independently selected from H and alkyl;

$R_{14}$ and $R_{15}$ are each independently selected from H, halo and alkyl;

$R_{16}$ and $R_{17}$ are each independently selected from H, halo, haloalkyl and alkyl; and each $R_{18}$ is independently selected from OH, CN, alkoxy and halo.

2. The compound according to claim 1, wherein L is a direct bond; $(CH_2)_n$ and n is 1 or 2; or CH(Me).

3. The compound according to claim 1, wherein Z is a 3- to 7-membered monocyclic cycloalkyl or a 3- to 7-membered monocyclic heterocycloalkyl group, each of which is optionally substituted.

4. The compound according to claim 1, wherein Z is a 4-membered monocyclic cycloalkyl or a 4-membered monocyclic heterocycloalkyl group, each of which is optionally substituted.

5. The compound according to claim 1, wherein Z is a 5-membered monocyclic cycloalkyl or a 5-membered monocyclic heterocycloalkyl group, each of which is optionally substituted.

6. The compound according to claim 1, wherein Z is an optionally substituted polycyclic cycloalkyl group or an optionally substituted polycyclic heterocycloalkyl group, wherein said polycyclic group is fused, unfused, bridged or spirocyclic.

7. The compound according to claim 6, wherein Z is a bicyclic cycloalkyl or a bicyclic heterocycloalkyl group, each of which is fused, unfused, bridged or spirocyclic, and each of which is optionally substituted.
8. The compound according to claim 1, wherein Z is selected from:
Z-1
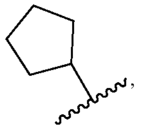
Z-2
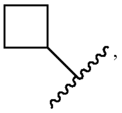
Z-3
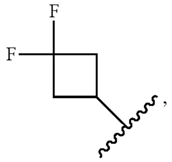
Z-4
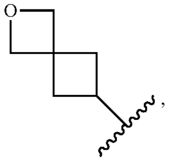
Z-5
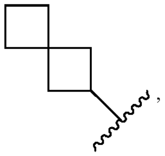
Z-6
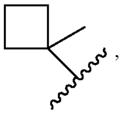
Z-7
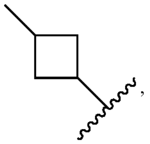
Z-8
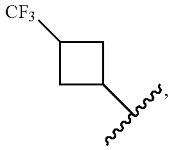
Z-9
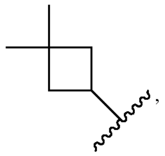
-continued
Z-10
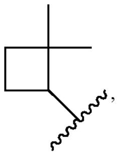
Z-11
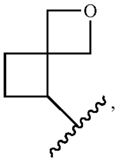
Z-12
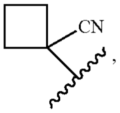
Z-13
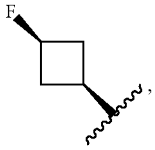
Z-14
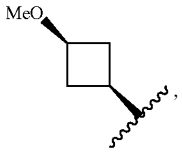
Z-15
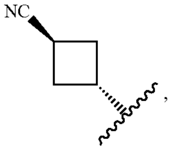
Z-16
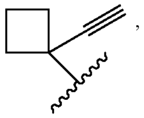
Z-17
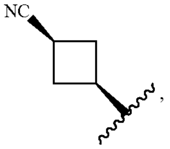
Z-18
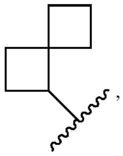
Z-19
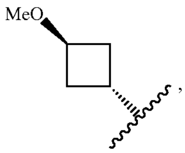

-continued
Z-20
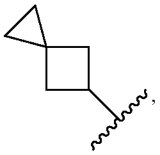
Z-21
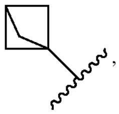
Z-22
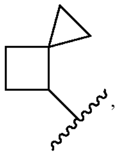
Z-23
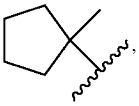
Z-24
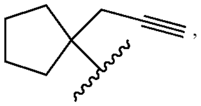
Z-25
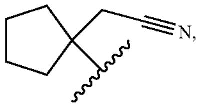
Z-26
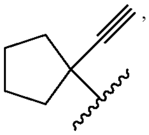
Z-27
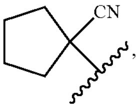
Z-28
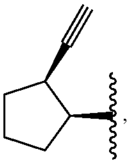
Z-29
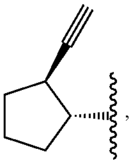
Z-30
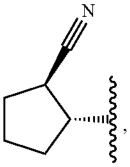
-continued
Z-31
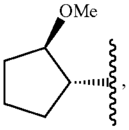
Z-32
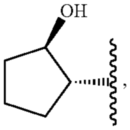
Z-33
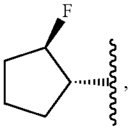
Z-34
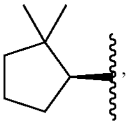
Z-35
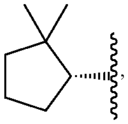
Z-36
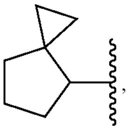
Z-37
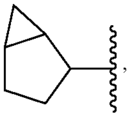
Z-38
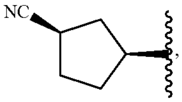
Z-39
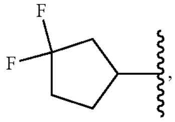
Z-40
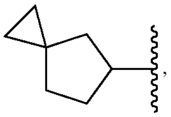
Z-41
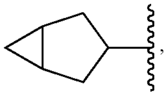
Z-42
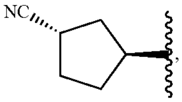

-continued
Z-63
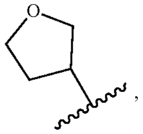
Z-64
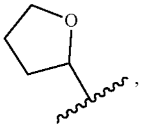
Z-65
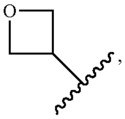
Z-66
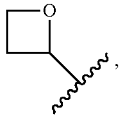
Z-67
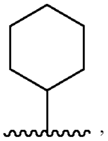
Z-72
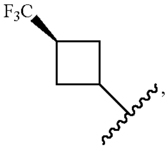
Z-75
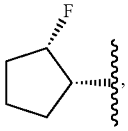
Z-76
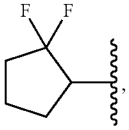
Z-77
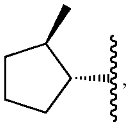
Z-78
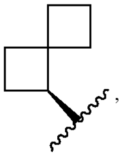
Z-79
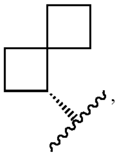
-continued
Z-80
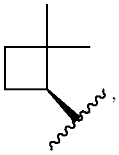
Z-81
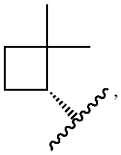
Z-82
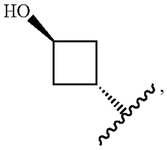
Z-83
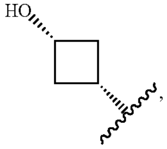
Z-84
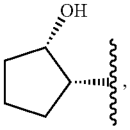
Z-85
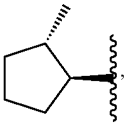
Z-86
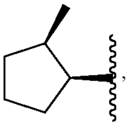
Z-87
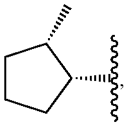
Z-88
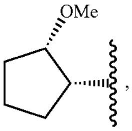
Z-89
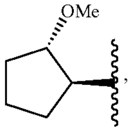

-continued
Z-90
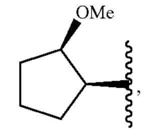
Z-91
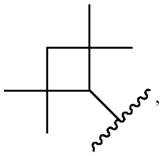
Z-92
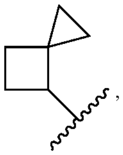
Z-93
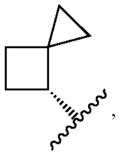
Z-94
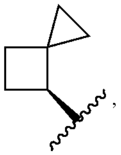
Z-95
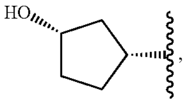
Z-96
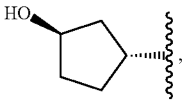
Z-97
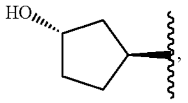
Z-98
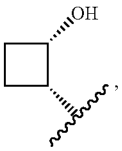
Z-99
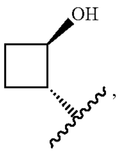
-continued
Z-100
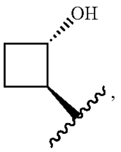
Z-101
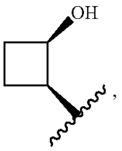
Z-102
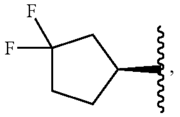
Z-103
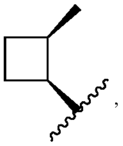
Z-104
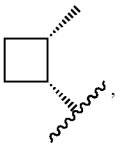
Z-105
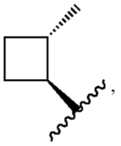
Z-106
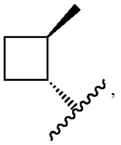
Z-107
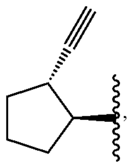
Z-108
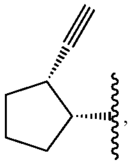
Z-109
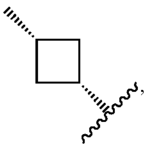

-continued
Z-110
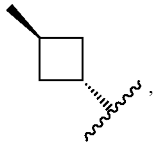
Z-111
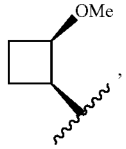
Z-112
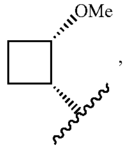
Z-113
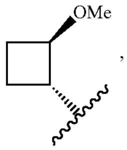
Z-114
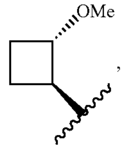
Z-115
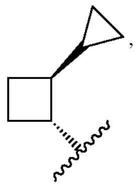
Z-116
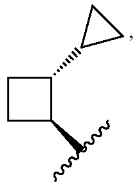
Z-117
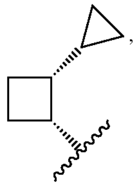
Z-118
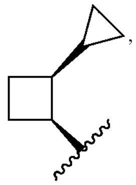
-continued
Z-119
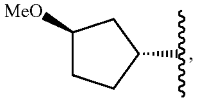
Z-120
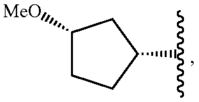
Z-121
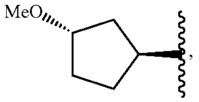
Z-122
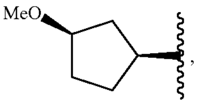
Z-123
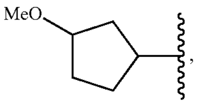
Z-124
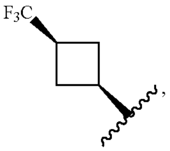
Z-125
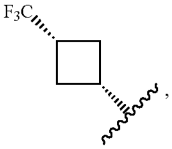
Z-126
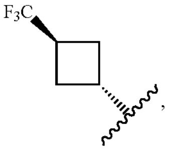
Z-127
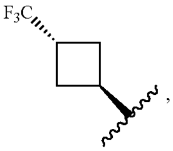
Z-128
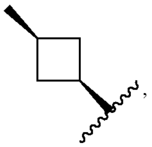
Z-129
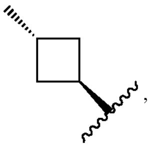

-continued
Z-130
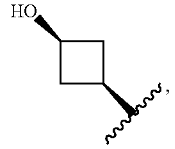
Z-131
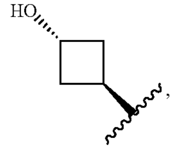
Z-132
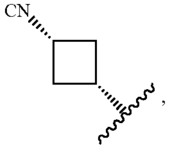
Z-133
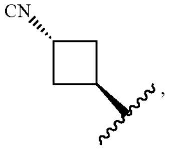
Z-134
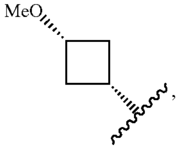
Z-135
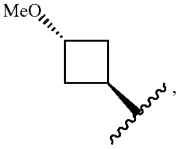
Z-136
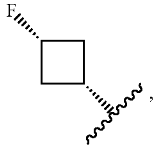
Z-137
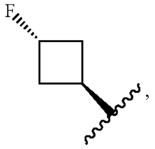
Z-138
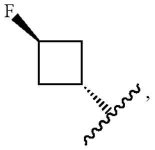
Z-139
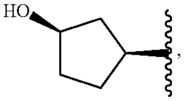
-continued
Z-140
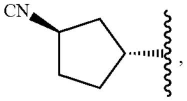
Z-141
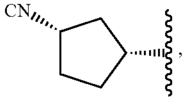
Z-142
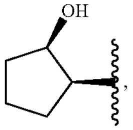
Z-143
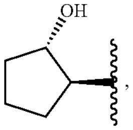
Z-144
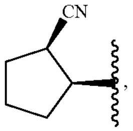
Z-145
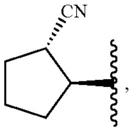
Z-146
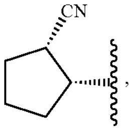
Z-147
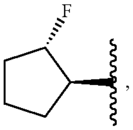
Z-148
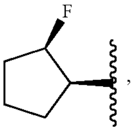
Z-149
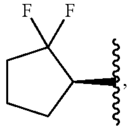
Z-150
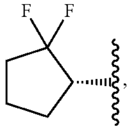

-continued
Z-151
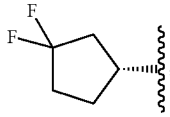,
Z-152
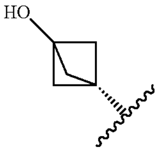 and
Z-153
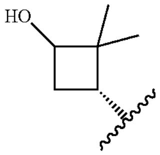.
9. The compound according to claim 1, wherein L-Z is selected from:
Z-43
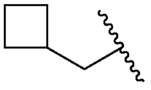,
Z-44
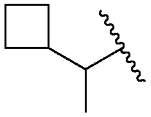,
Z-45
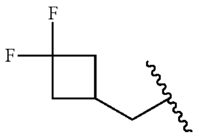,
Z-46
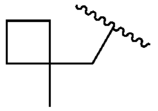,
Z-47
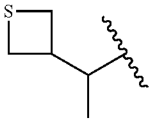,
Z-48
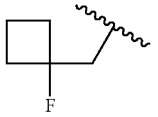,
Z-49
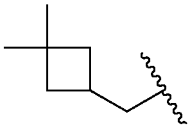,
Z-50
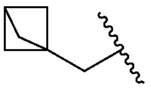,
-continued
Z-51
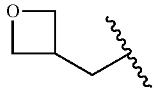,
Z-52
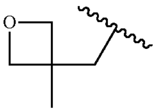,
Z-53
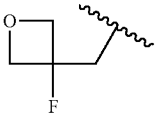,
Z-54
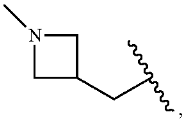,
Z-55
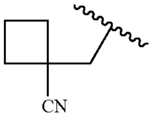,
Z-56
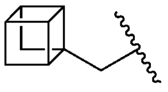,
Z-57
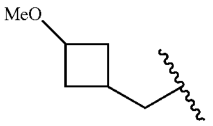,
Z-58
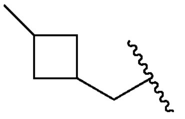,
Z-59
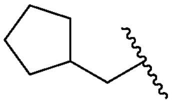,
Z-60
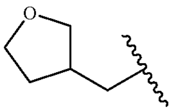,
Z-61
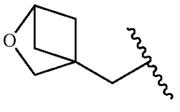,
Z-62
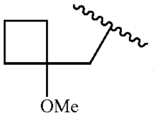, -continued

Z-68

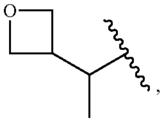,

Z-69

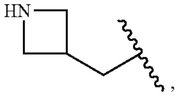,

Z-70

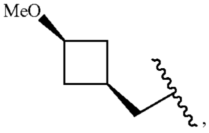,

Z-71

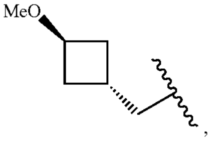,

Z-73

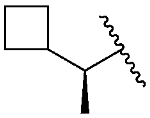 and

Z-74

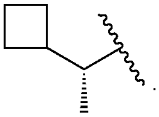.

10. The compound according to claim 1, wherein $R_2$ is COOH.

11. The compound according to claim 1, wherein $R_4$ is selected from H and F.

12. The compound according to claim 1, wherein $R_5$ is selected from alkyl, alkoxy and cycloalkyl.

13. The compound according to claim 1, wherein $R_5$ is cyclopropyl.

14. The compound according to claim 1, wherein $R_7$ is selected from H, CN, haloalkyl, Cl, F, $SO_2$-alkyl, $CONR_{10}R_{11}$, heteroaryl and alkyl, wherein the heteroaryl group is selected from pyrazol-3-yl, pyrazol-4-yl, pyrazol-5-yl, isothiazol-3-yl, isothiazol-4-yl, isothiazol-5-yl, 1,2,4-triazol-5-yl, tetrazol-1-yl, tetrazol-5-yl, isoxazol-3-yl, isoxazol-4-yl and isoxazol-5-yl, each of which is optionally substituted by one or more substituents selected from alkyl, halo, alkoxy, CN, haloalkyl and OH.

15. The compound according to claim 1, wherein $R_7$ is CN.

16. The compound according to claim 1, wherein $R_8$ is Cl.

17. The compound according to claim 1, wherein $R_9$ is H.

18. The compound according to claim 1, wherein $R_1$ is H.

19. The compound according to claim 1, wherein $R_1$, $R_3$, $R_4$ and $R_9$ are all H.

20. The compound according to claim 1, wherein:

X—Y is NH—$SO_2$;

$R_1$ is H;

$R_2$ is COOH;

$R_3$ is H or F;

$R_4$ is H or F;

$R_5$ is selected from OMe, cyclopropyl and Et;

$R_6$ is H;

$R_7$ is selected from CN, tetrazol-1-yl, isothiazol-5-yl and 5-methyl-isoxazol-4-yl;

$R_8$ is selected from H, Cl and F; and $R_9$ is selected from H, Me, Cl and F.

21. The compound according to claim 1, which is of formula (Ia):

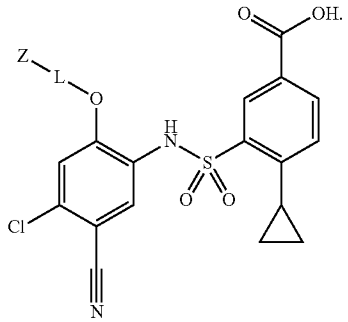.

(Ia)

22. The compound according to claim 1, which is selected from the following:

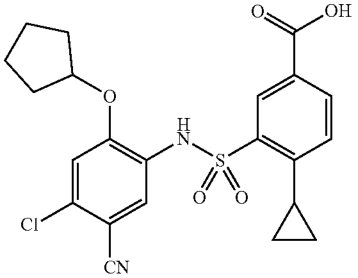

(1)

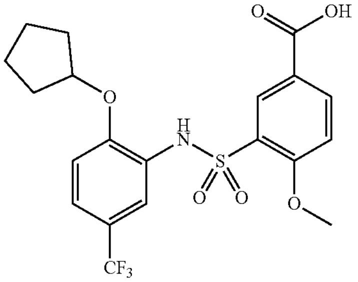

(2)

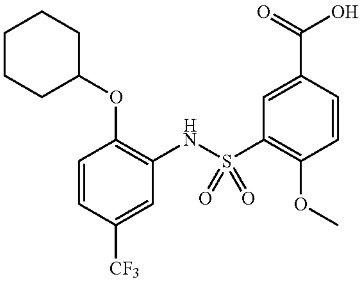

(3)

-continued
(4)
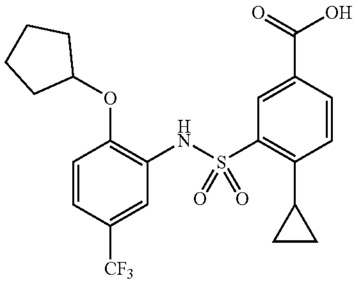
(5)
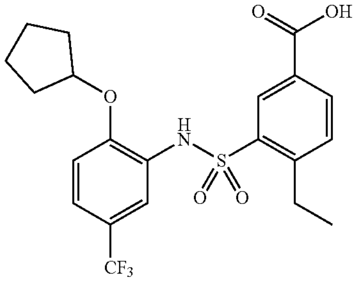
(6)
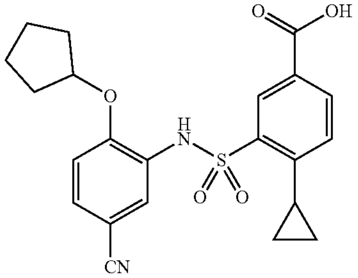
(7)
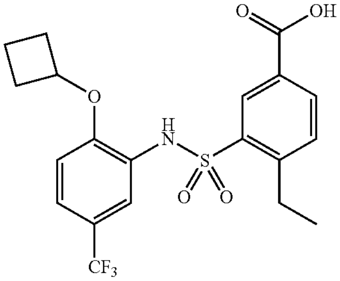
(8)
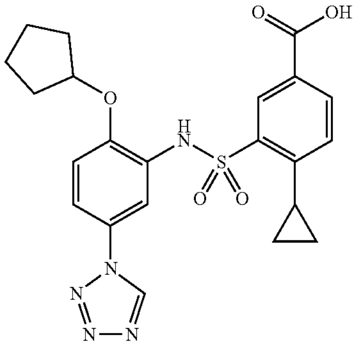
-continued
(9)
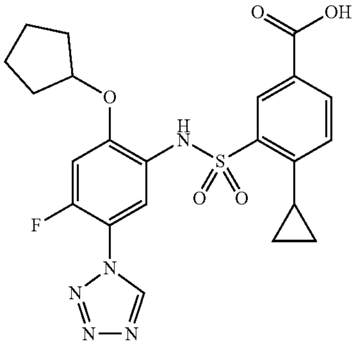
(10)
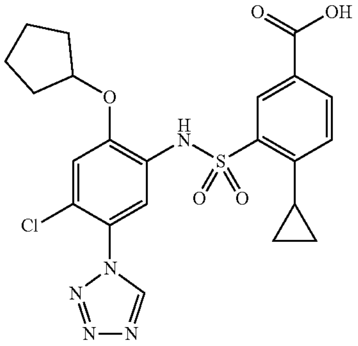
(11)
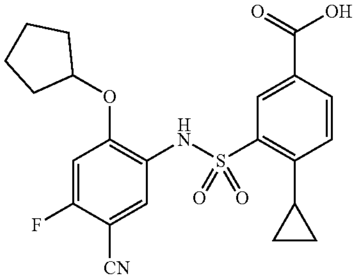
(12)
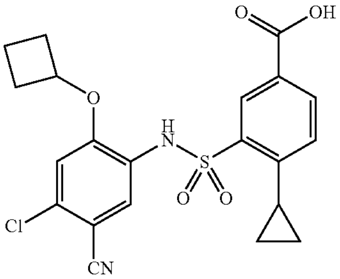
(13)
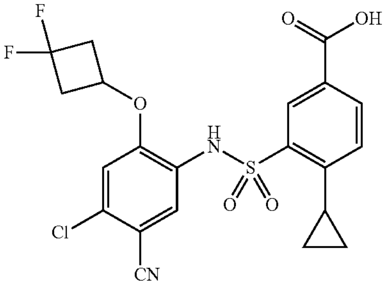

-continued
(14)
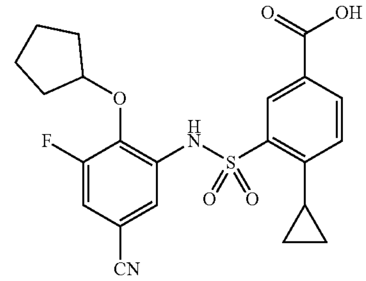
(15)
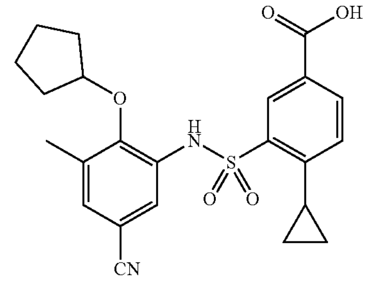
(16)
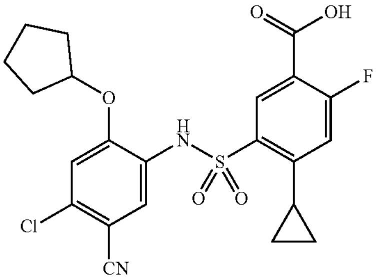
(17)
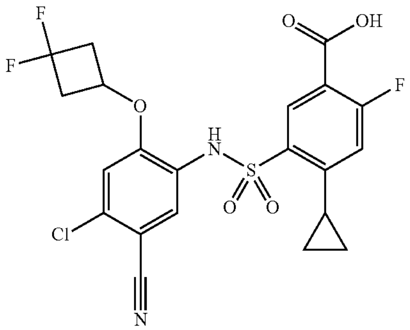
(18)
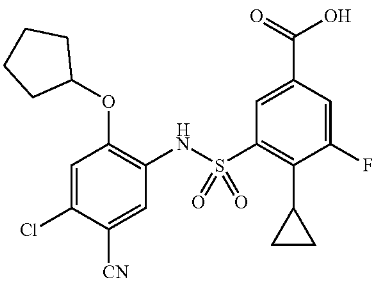
-continued
(19)
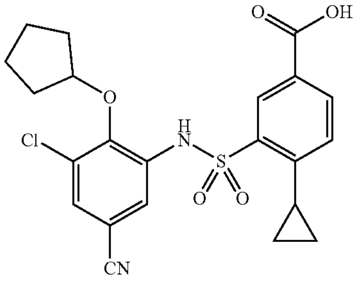
(20)
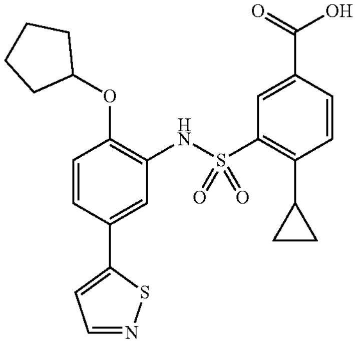
(21)
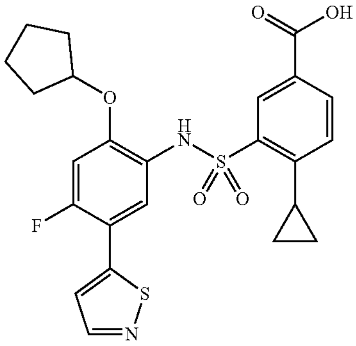
(22)
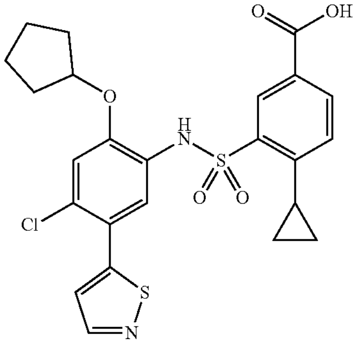

-continued
(23)
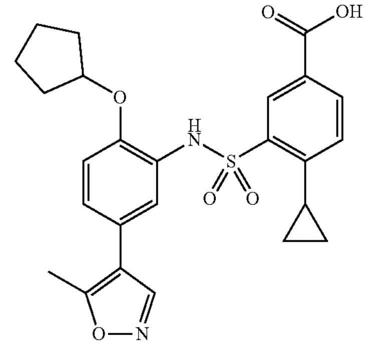
(24)
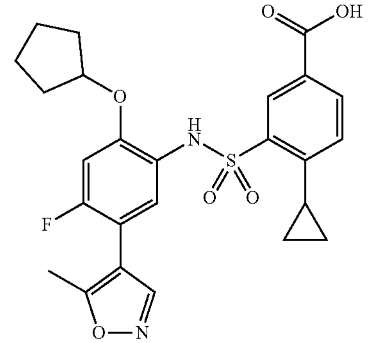
(25)
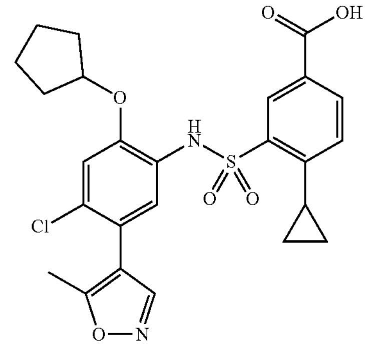
(26)
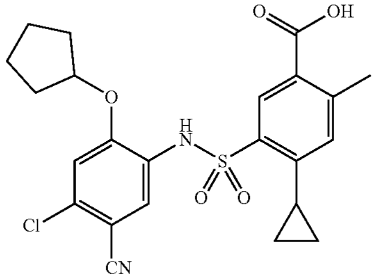
(27)
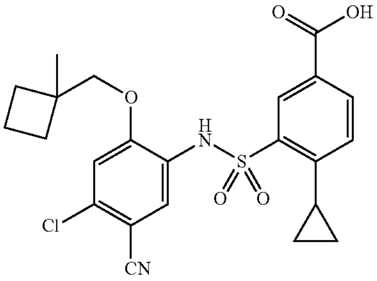
-continued
(28)
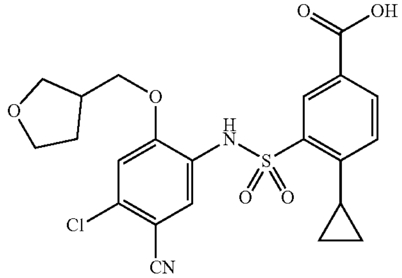
(29)
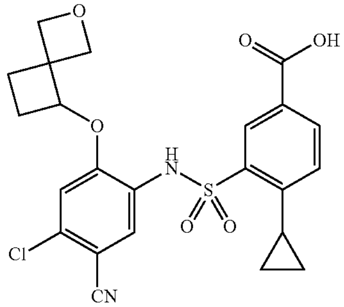
(30)
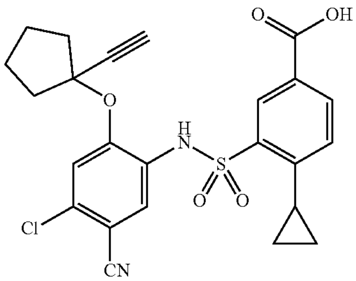
(31)
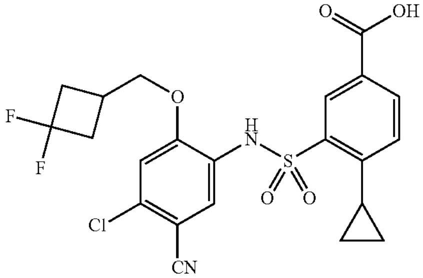
(32)
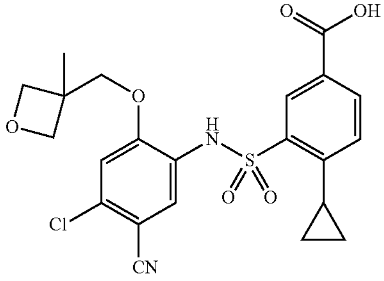

-continued
(33)
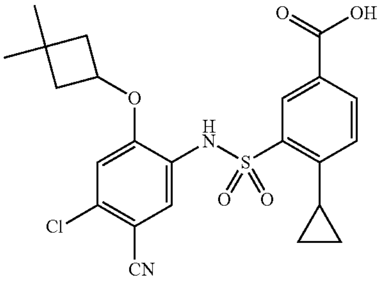
(34)
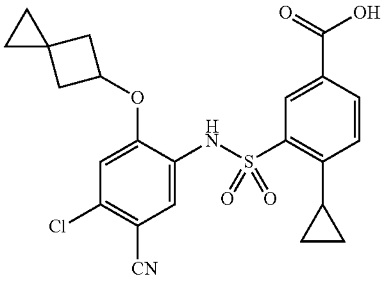
(35)
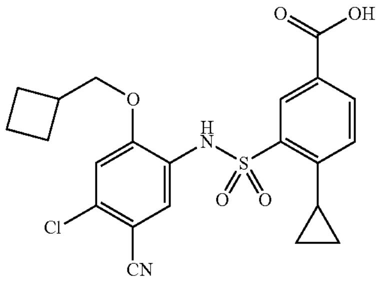
(36)
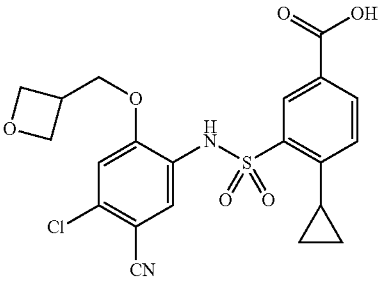
(37)
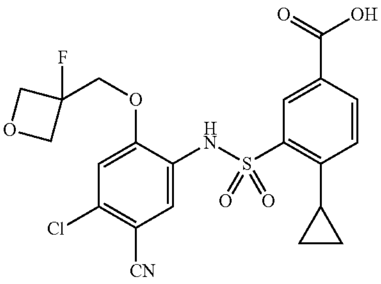
-continued
(38)
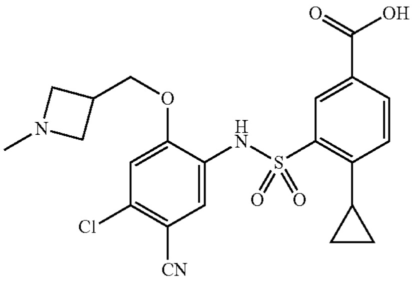
(39)
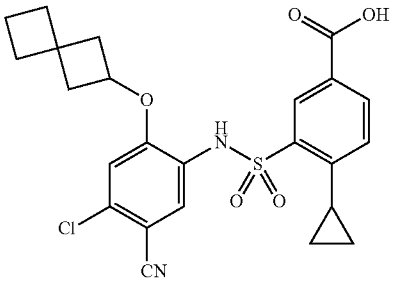
(40)
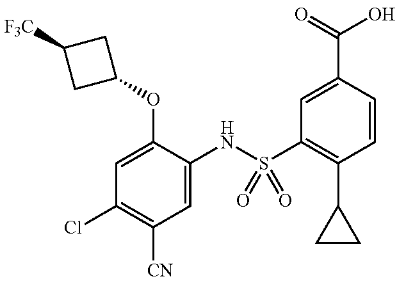
Trans relative
(41)
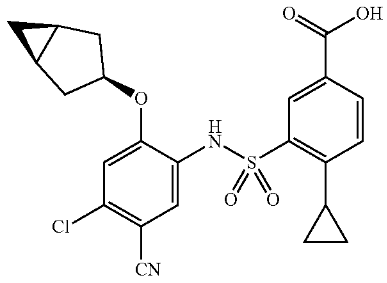
Cis relative
(42)
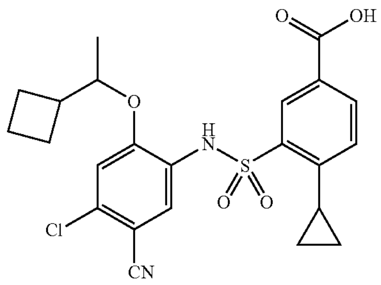

(43)
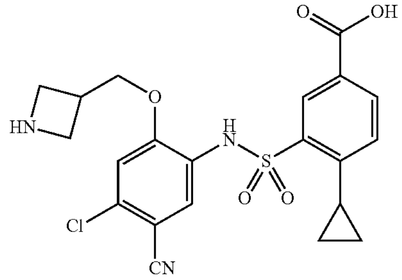
(44)
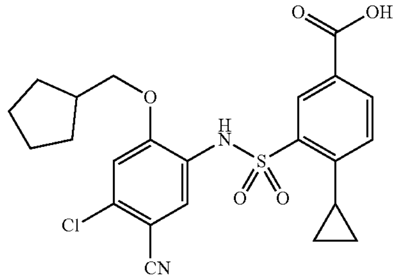
(45)
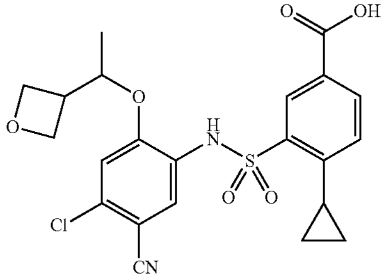
(46)
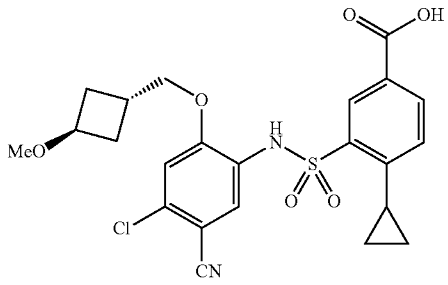
Trans relative
(47)
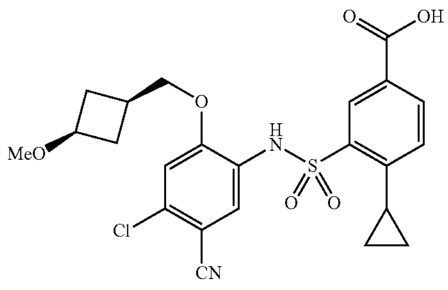
Cis relative
(48)
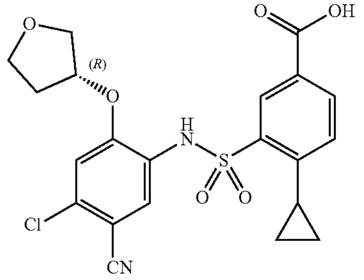
(49)
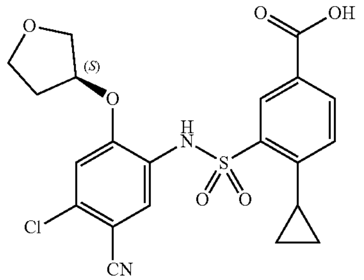
(50)
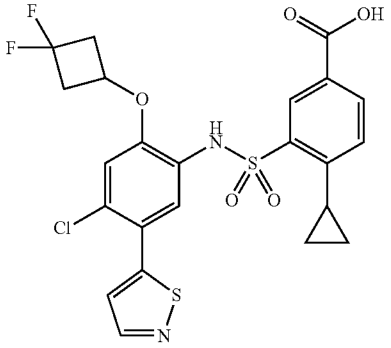
(51)
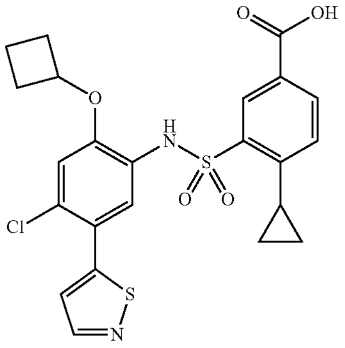
(52)
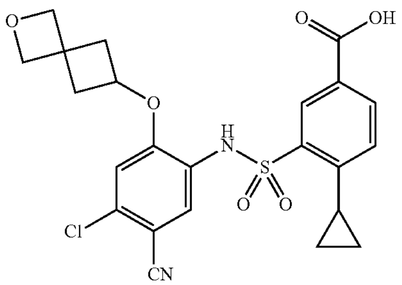

-continued
(53)
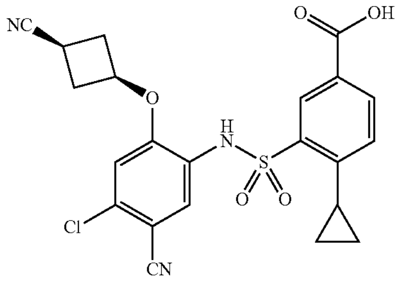
Cis relative
(54)
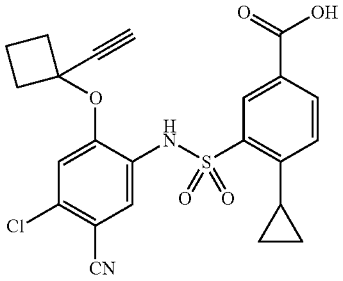
(55)
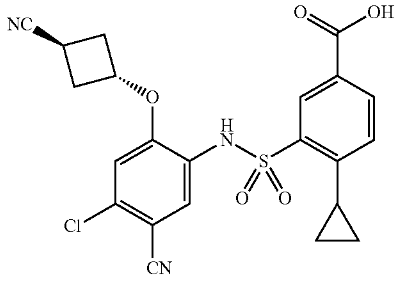
Trans relative
(56)
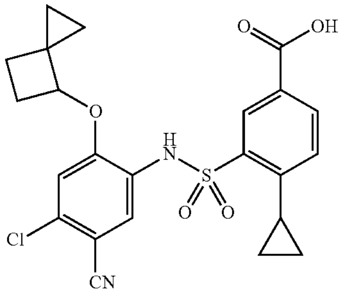
(57)
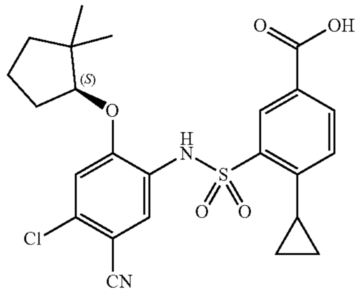
-continued
(58)
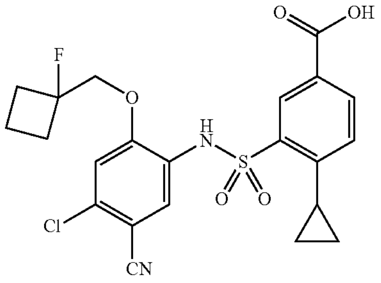
(59)
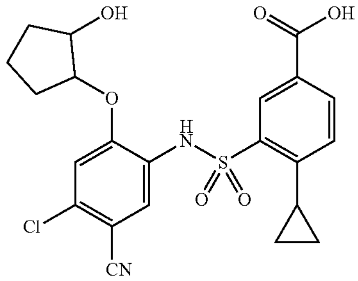
Trans racemate
(60)
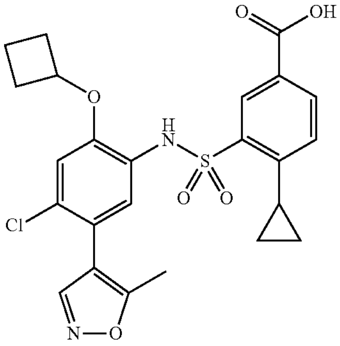
(61)
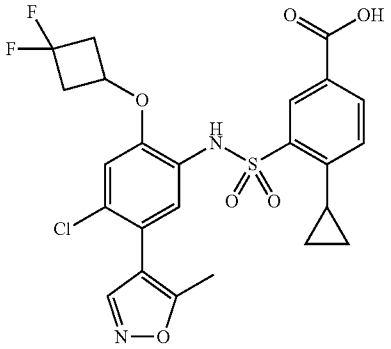
(62)
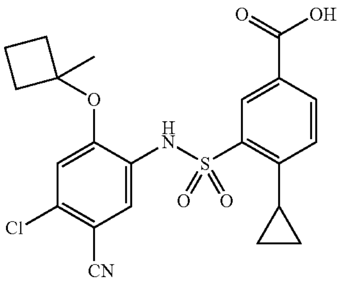

-continued
(63)
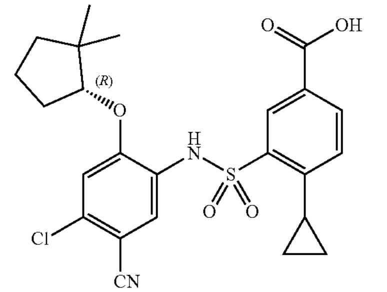
(64)
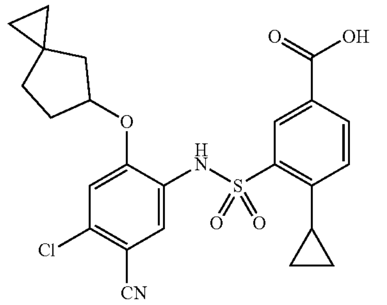
(65)
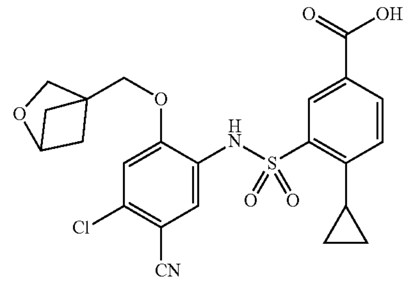
(66)
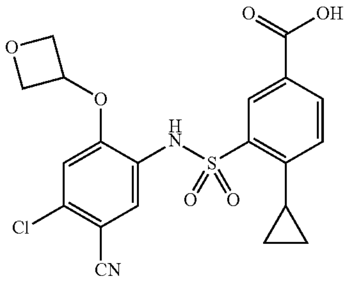
(67)
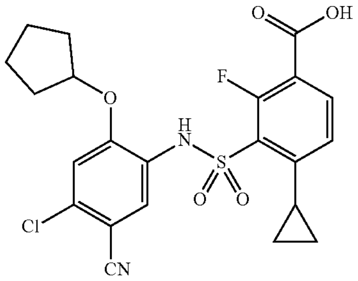
-continued
(68)
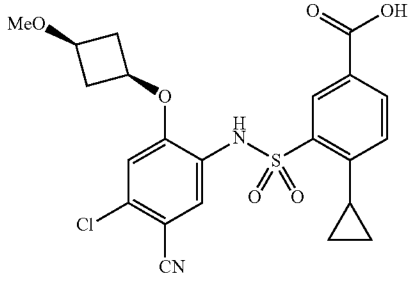
Cis relative
(69)
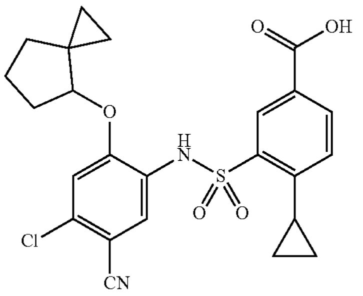
(70)
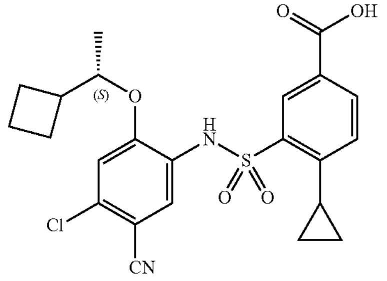
(71)
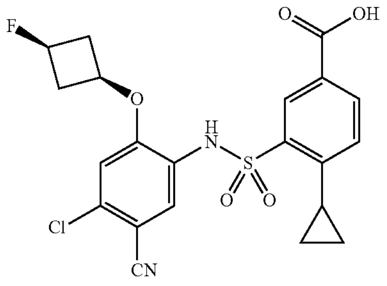
Cis relative
(72)
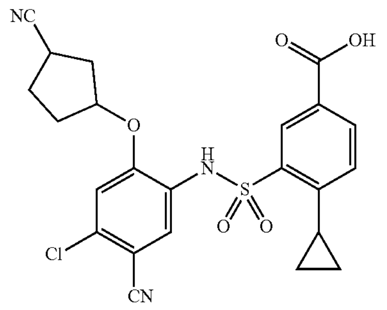
Trans racemate -continued
(73)
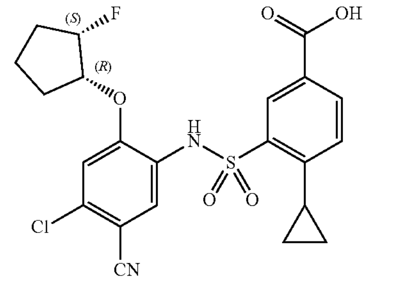
(74)
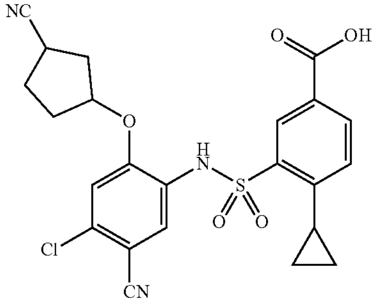
(75)
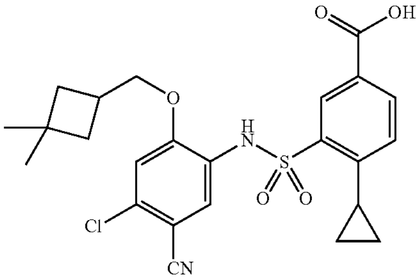
(76)
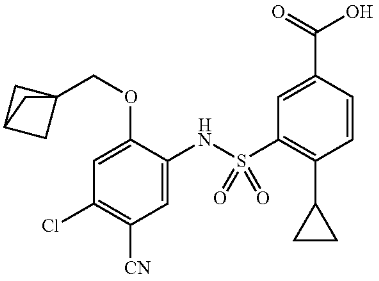
(77)
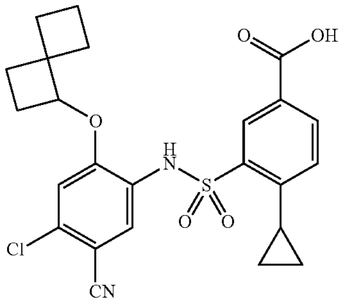
-continued
(78)
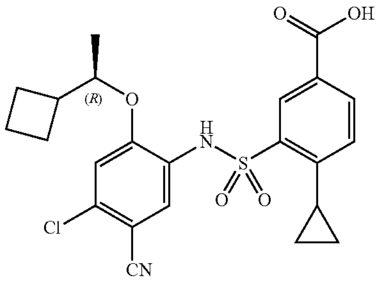
(79)
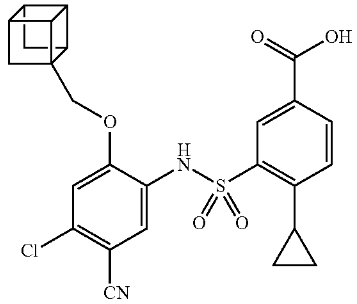
(80)
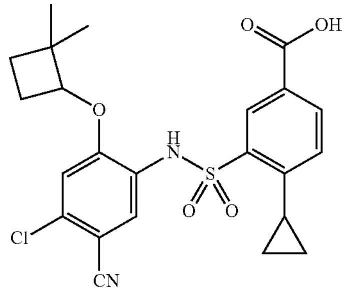
(81)
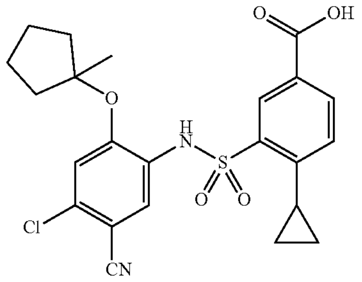
(82)
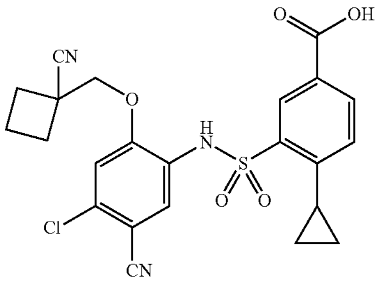

(83)
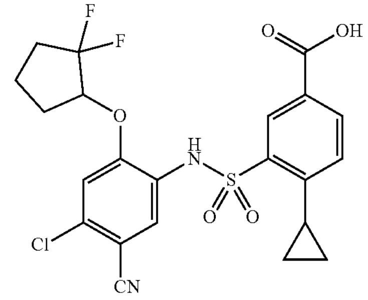
(84)
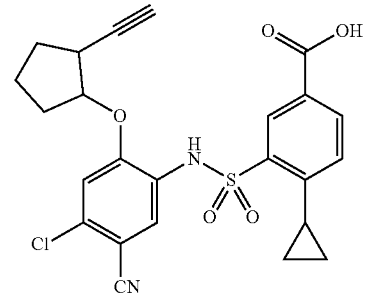
Trans racemate
(85)
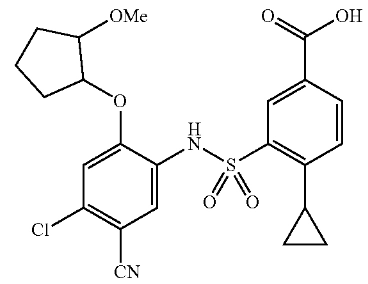
Trans racemate
(86)
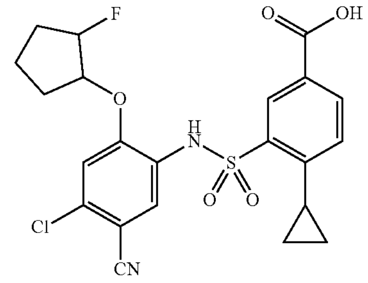
Trans racemate
(87)
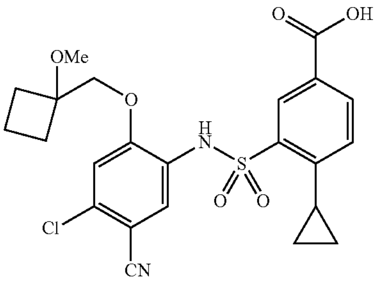
(88)
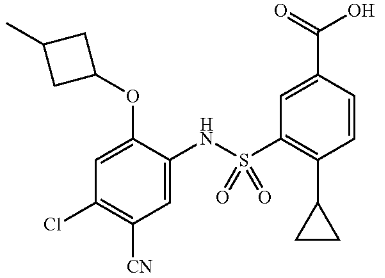
Cis/Trans
(89)
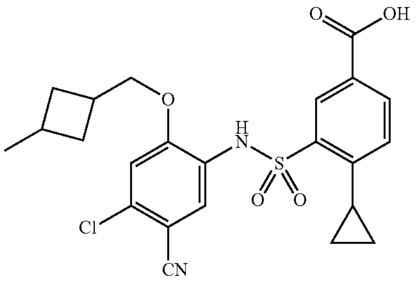
Cis/Trans
(90)
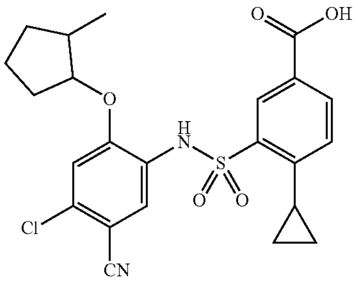
Trans racemate
(91)
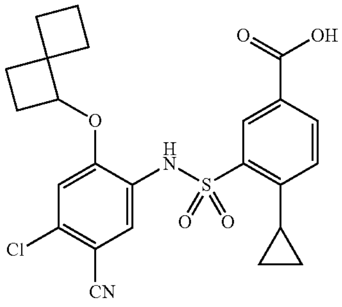
Enantiomer E1

-continued
(92)
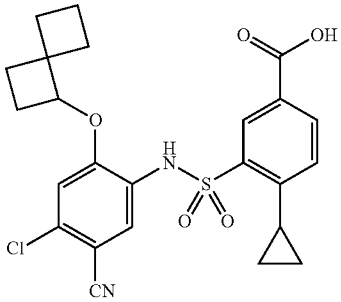
Enantiomer E2
(93)
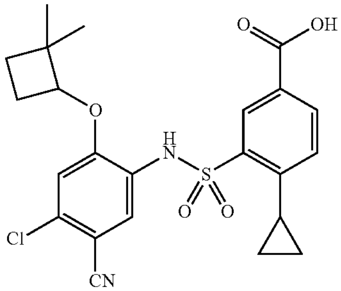
Enantiomer E1
(94)
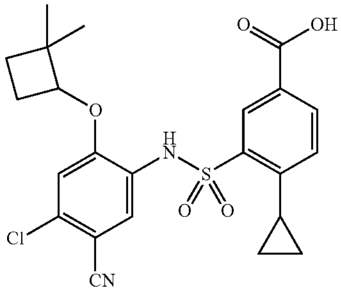
Enantiomer E2
(95)
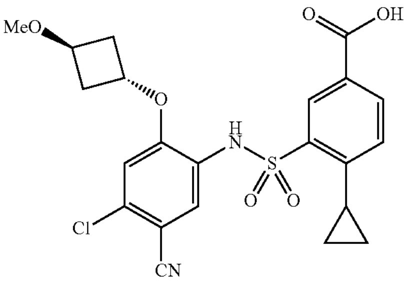
Trans relative
-continued
(96)
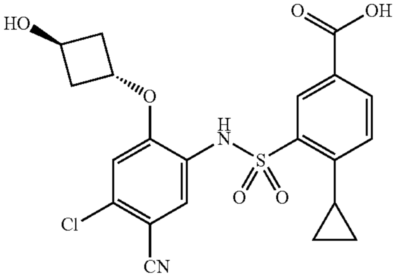
Trans relative
(97)
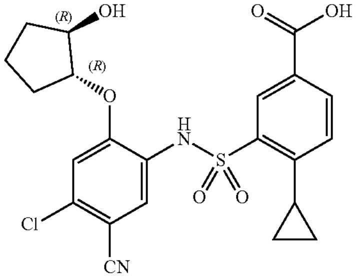
(98)
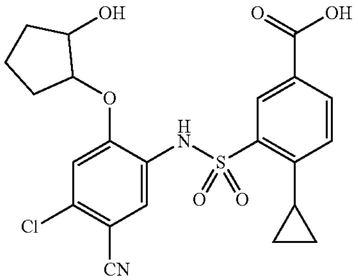
Cis racemate
(99)
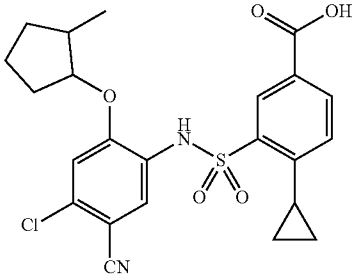
Trans diastereomer D1
(100)
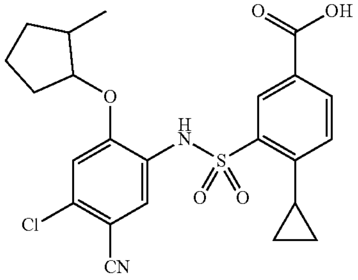
Trans diastereomer D2

-continued
(101)
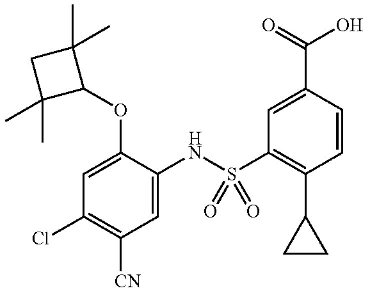
(102)
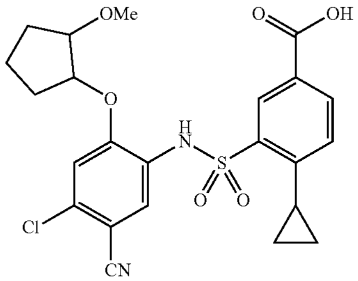
Cis racemate
(103)
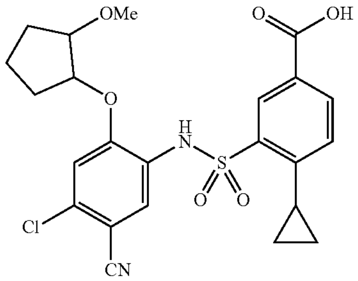
Trans diastereomer D1
(104)
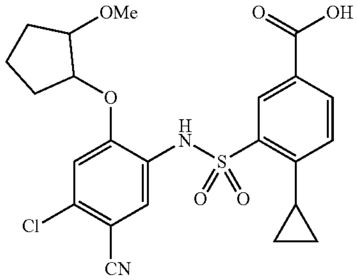
Trans diastereomer D2
(105)
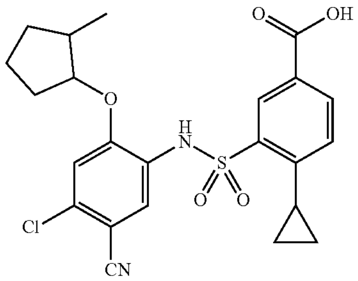
Cis racemate
-continued
(106)
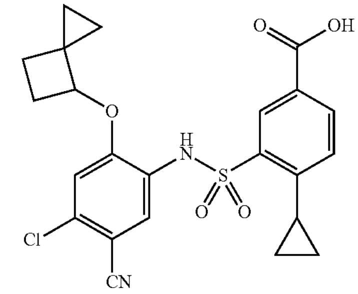
Enantiomer E1
(107)
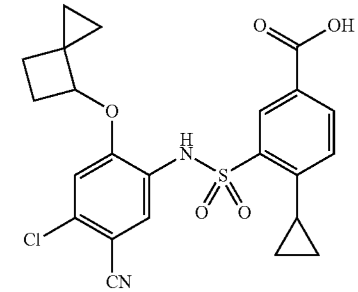
Enantiomer E2
(108)
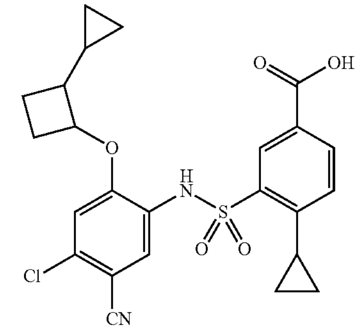
Cis/Trans
(109)
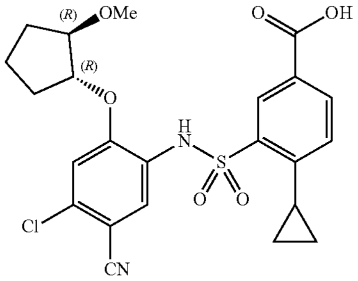

-continued
(110)
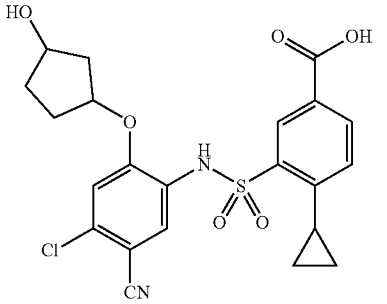
Cis racemate
(111)
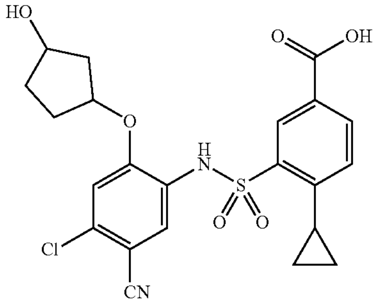
Trans racemate
(112)
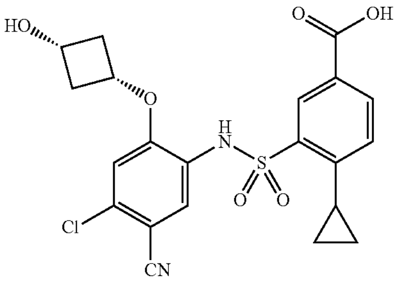
Cis relative
(113)
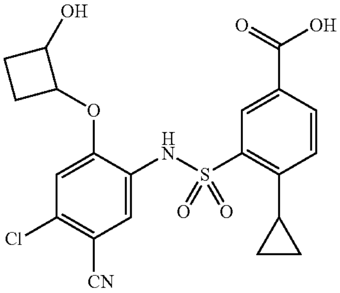
Cis racemate
-continued
(114)
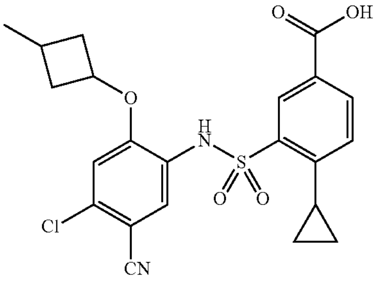
Diastereomer D1
(115)
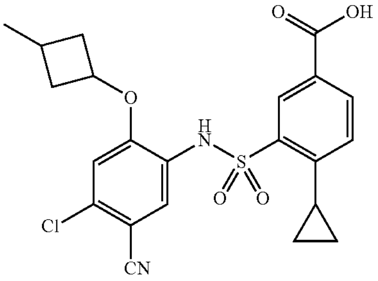
Diastereomer D2
(116)
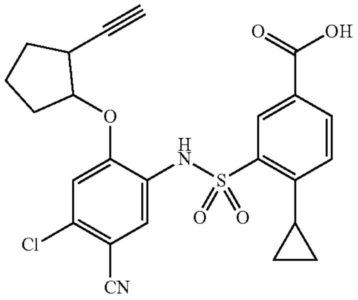
Trans diastereomer D1
(117)
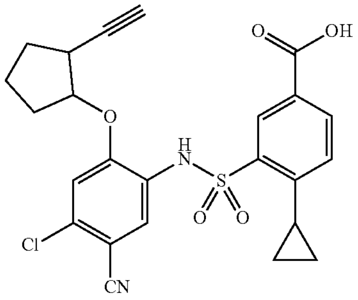
Trans diastereomer D2

-continued
(118)
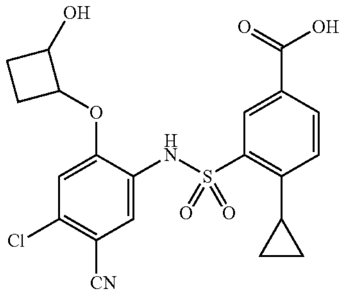
Trans racemate
(119)
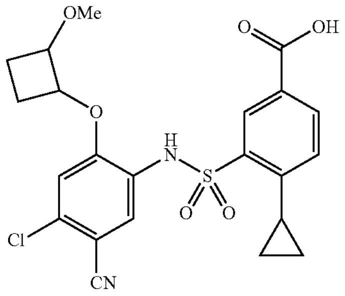
Trans racemate
(120)
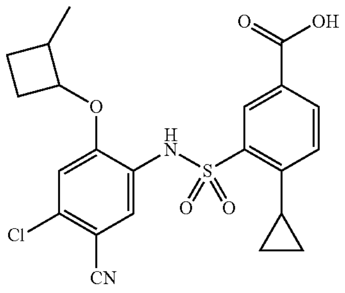
Diastereomer D1
(121)
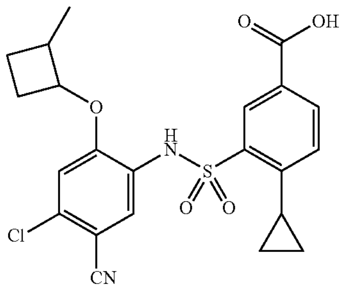
Diastereomer D2
-continued
(122)
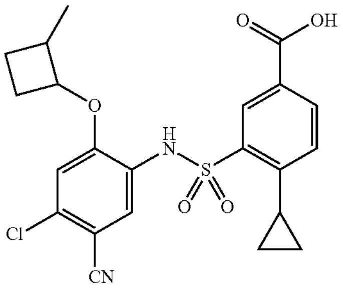
Diastereomer D3
(123)
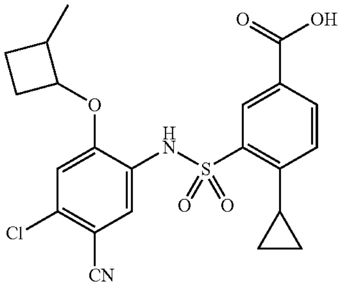
Diastereomer D4
(124)
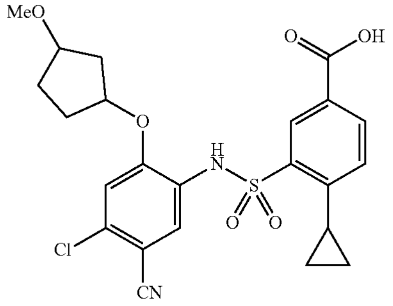
Cis/Trans
(125)
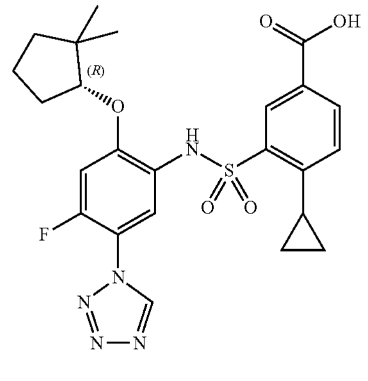

-continued
(126)
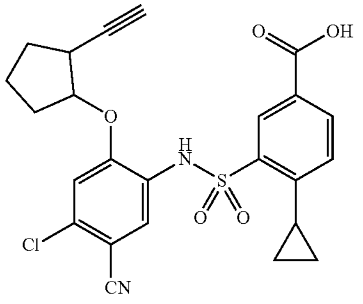
Cis diastereomer D1
(127)
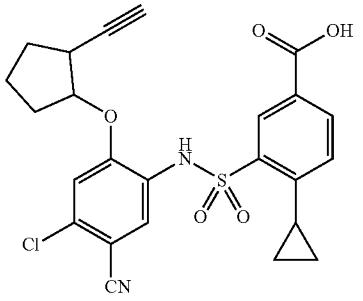
Cis diastereomer D2
(128)
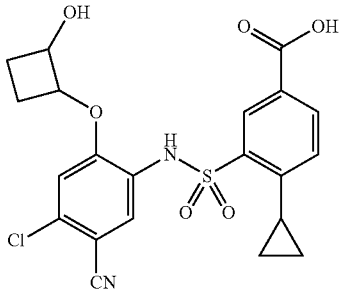
Trans diastereomer D1
(129)
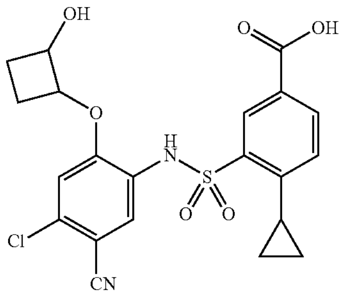
Trans diastereomer D2
-continued
(130)
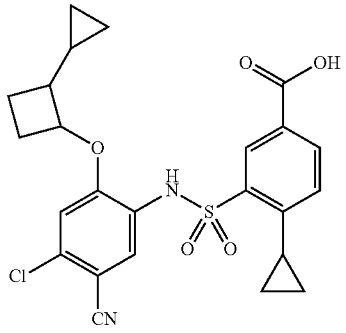
Diastereomer D1
(131)
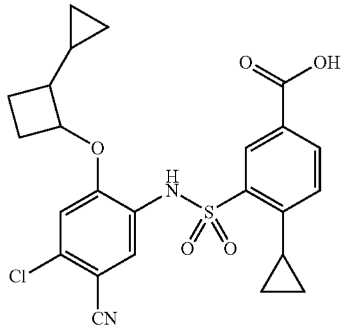
Diastereomer D2
(132)
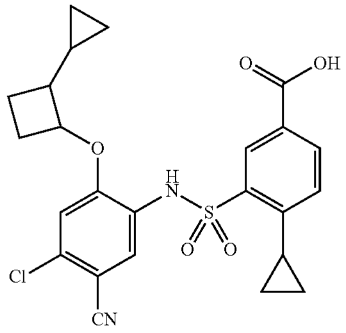
Diastereomer D3
(133)
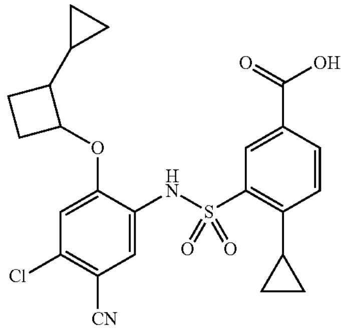
Diastereomer D4

-continued
(134)
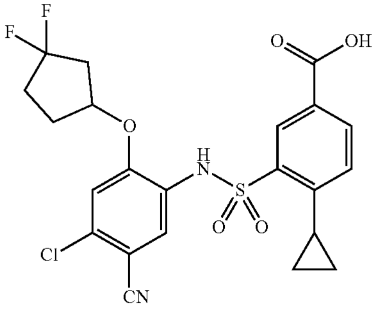
(135)
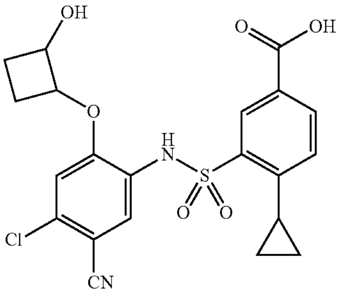
Cis diastereomer D1
(136)
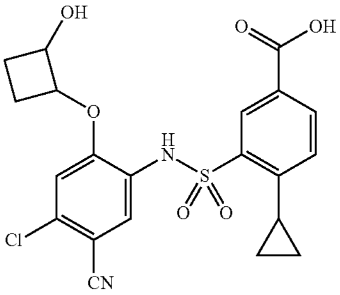
Cis diastereomer D2
(137)
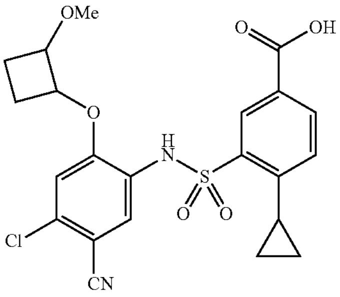
Cis racemate
-continued
(138)
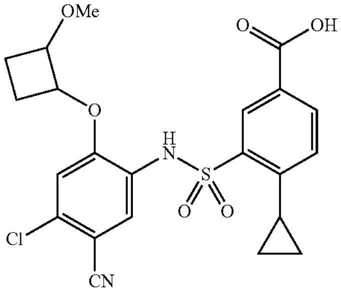
Trans diastereomer D1
(139)
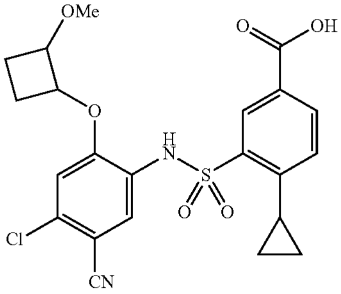
Trans diastereomer D2
(140)
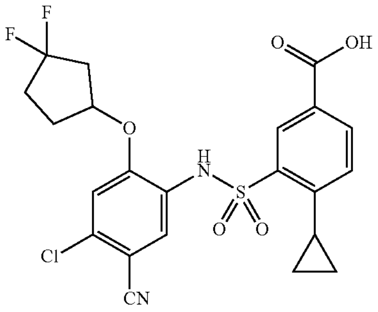
Enantiomer E1
(141)
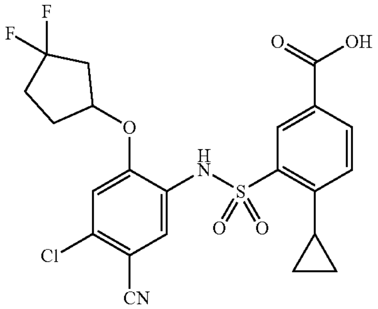
Enantiomer E2

-continued (142)

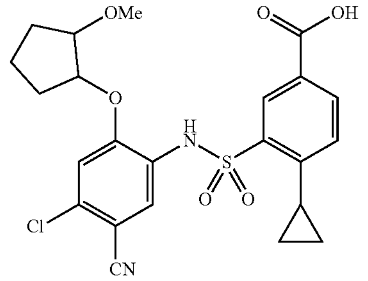

Cis diastereomer D1

(143)

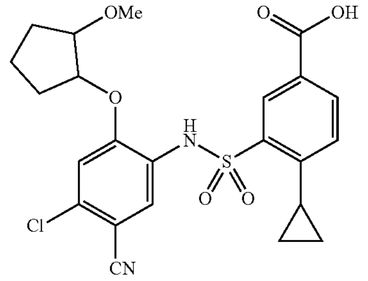

Cis diastereomer D2

(144)

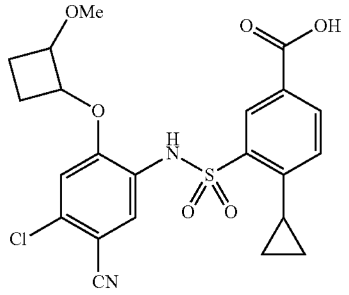

Cis diastereomer D1

(145)

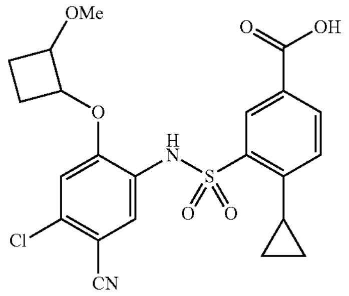

Cis diastereomer D2

-continued (146)

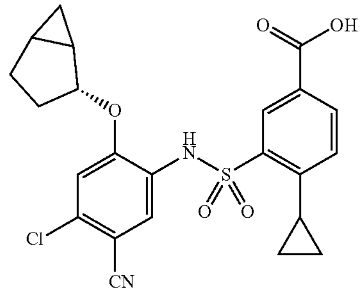

(147)

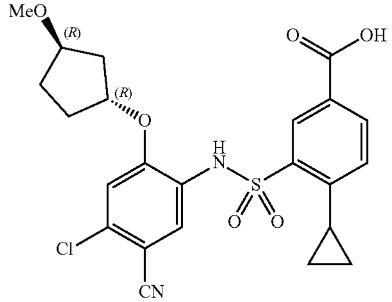

(148)

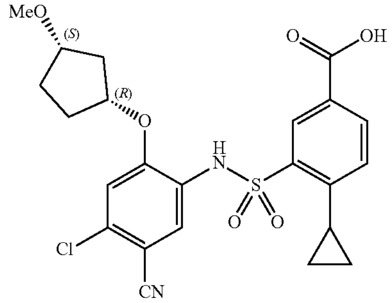

(149)

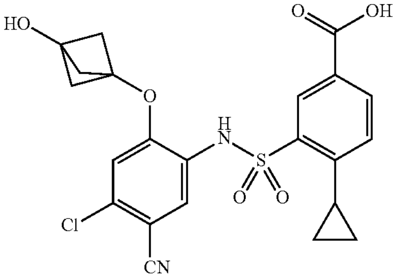

(150)

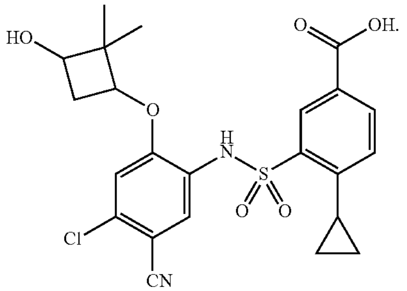

or a pharmaceutically acceptable salt or hydrate thereof.

23. A pharmaceutical composition comprising the compound of formula (I) as defined in claim 1 admixed with a pharmaceutically acceptable excipient, diluent or carrier, and optionally one or more additional active agents.

24. A method of treating or preventing a disorder selected from a proliferative disorder, an immune disorder, a viral disorder and an inflammatory disorder in a subject in need thereof, said method comprising administering to the subject a therapeutically effective amount of the compound according to claim 1.

25. The method according to claim 24 wherein the disorder is a proliferative disorder selected from cancer.

26. An in vitro or in vivo method for producing an antigen-presenting cell which presents a neo-antigen, comprising contacting antigen-presenting cell with a compound of formula (I) as defined in claim 1 to induce a neo-antigen in said antigen-presenting cell.

27. An immunogenic composition comprising an antigen-presenting cell obtained or obtainable by the method according to claim 26.

28. A method of treating or preventing cancer in a subject in need thereof, said method comprising administering to the subject a therapeutically effective amount of an immunogenic composition according to claim 27.

29. The method according to claim 24, wherein said compound is used in combination with an immunotherapy.

30. The method according to claim 24, wherein the disorder is an immune disorder selected from ankylosing spondylitis, Behcet's disease, psoriasis and birdshot chorioretinopathy.

31. The method according to claim 24, wherein the disorder is an inflammatory disorder.

32. The method according to claim 24, wherein the viral disorder is an infectious viral disease selected from HIV, HPV, CMV and HCV.

33. A combination comprising a compound according to claim 1 and a further active agent.

34. The method according to claim 24, wherein the disorder is a proliferative disorder selected from leukemia.

* * * * *